United States Patent
Yamanaka et al.

(10) Patent No.: US 10,398,515 B2
(45) Date of Patent: Sep. 3, 2019

(54) MEDICAL MANIPULATOR AND INITIALIZATION METHOD FOR MEDICAL MANIPULATOR

(71) Applicant: OLYMPUS CORPORATION, Tokyo (JP)

(72) Inventors: Noriaki Yamanaka, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 419 days.

(21) Appl. No.: 15/134,629

(22) Filed: Apr. 21, 2016

(65) Prior Publication Data

US 2016/0228203 A1    Aug. 11, 2016

Related U.S. Application Data

(63) Continuation of application No. PCT/JP2014/078358, filed on Oct. 24, 2014.

(30) Foreign Application Priority Data

Oct. 24, 2013 (JP) .................................. 2013-221543

(51) Int. Cl.
*A61B 1/00* (2006.01)
*A61B 1/05* (2006.01)
(Continued)

(52) U.S. Cl.
CPC ............ *A61B 34/30* (2016.02); *A61B 1/0002* (2013.01); *A61B 1/00006* (2013.01);
(Continued)

(58) Field of Classification Search
CPC ......... A61B 34/30; A61B 34/70; A61B 90/13; A61B 1/00006; A61B 1/0002;
(Continued)

(56) References Cited

U.S. PATENT DOCUMENTS 7,386,365 B2    6/2008 Nixon
7,831,292 B2 *  11/2010 Quaid .................... A61B 34/20
                                                   345/156
(Continued)

FOREIGN PATENT DOCUMENTS

EP      2108327 A1    10/2009
EP    2 130 479 A1    12/2009
(Continued)

OTHER PUBLICATIONS

Extended Supplementary European Search Report dated May 23, 2017 in European Patent Application No. 14 85 5322.5.
(Continued)

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A medical manipulator includes an insertion portion, an arm portion, a light irradiation section irradiating a luminous flux having an optical axis parallel to an arm axial line, an imaging section imaging a locus of an optical image, a rotational movement portion rotating the arm portion around a reference axial line, and an initialization control unit performing initialization control to aligning the arm portion with the reference axial line, in which the initialization control unit includes: a locus acquisition control section controlling the light irradiation section, the rotational movement portion, and the imaging section to acquire a locus of the luminous flux, a convergence determination section computing a diameter of the locus and determines whether or not the diameter of the locus has converged, a driving amount correction section obtaining a driving amount of the first redundant joint and performs driving, and a convergence operation control section.

22 Claims, 64 Drawing Sheets

(51) Int. Cl.
*A61B 1/06* (2006.01)
*A61B 1/018* (2006.01)
*A61B 34/20* (2016.01)
*A61B 34/00* (2016.01)
*A61B 34/30* (2016.01)
*A61B 90/13* (2016.01)
*B25J 9/16* (2006.01)
*A61B 17/00* (2006.01)

(52) U.S. Cl.
CPC .......... *A61B 1/00149* (2013.01); *A61B 1/018* (2013.01); *A61B 1/05* (2013.01); *A61B 1/0676* (2013.01); *A61B 34/70* (2016.02); *A61B 90/13* (2016.02); *B25J 9/1692* (2013.01); *A61B 2017/00725* (2013.01); *A61B 2034/2055* (2016.02); *A61B 2034/301* (2016.02); *A61B 2034/306* (2016.02); *G05B 2219/39048* (2013.01)

(58) Field of Classification Search
CPC ....... A61B 1/00149; A61B 1/018; A61B 1/05; A61B 1/0676; B25J 9/1692
USPC ........ 600/102, 103, 113, 114, 117, 118, 145, 600/146, 147, 148, 149, 150, 151, 152, 600/160
See application file for complete search history.

(56) References Cited

U.S. PATENT DOCUMENTS

| | | | | |
|---|---|---|---|---|
| 9,492,240 | B2 * | 11/2016 | Itkowitz | A61B 34/37 |
| 2009/0088634 | A1 * | 4/2009 | Zhao | B25J 9/1689 |
| | | | | 600/427 |
| 2009/0187288 | A1 | 7/2009 | Shimada et al. | |
| 2009/0292165 | A1 * | 11/2009 | Sugiyama | A61B 34/71 |
| | | | | 600/106 |
| 2010/0217075 | A1 * | 8/2010 | Shigeta | A61B 1/00009 |
| | | | | 600/104 |
| 2011/0252912 | A1 | 10/2011 | Nakagiri et al. | |
| 2012/0307027 | A1 * | 12/2012 | Popovic | B25J 9/1697 |
| | | | | 348/65 |
| 2015/0065793 | A1 * | 3/2015 | Diolaiti | A61B 1/00009 |
| | | | | 600/102 |

FOREIGN PATENT DOCUMENTS

| | | |
|---|---|---|
| JP | H08-090464 A | 4/1996 |
| JP | H10-146316 A | 6/1998 |
| JP | 2003-245367 A | 9/2003 |
| JP | 2005-296379 A | 10/2005 |
| JP | 2007-260298 A | 10/2007 |
| JP | 2012-223871 A | 11/2012 |
| WO | WO 2007/145327 A1 | 12/2007 |
| WO | WO 2008/093455 A1 | 8/2008 |
| WO | WO 2011/083374 A1 | 7/2011 |

OTHER PUBLICATIONS

International Search Report dated Dec. 2, 2014 issued in PCT/JP2014/078358.

Namba, Shunsuke et al., "Endoscopic Instrument Interface with Touch Panel Using Visual Servoing", Transactions of Japanese Society for Medical and Biological Engineering, vol. 46, No. 6, Japanese Society for Medical and Biological Engineering (2008), pp. 595-605.

* cited by examiner

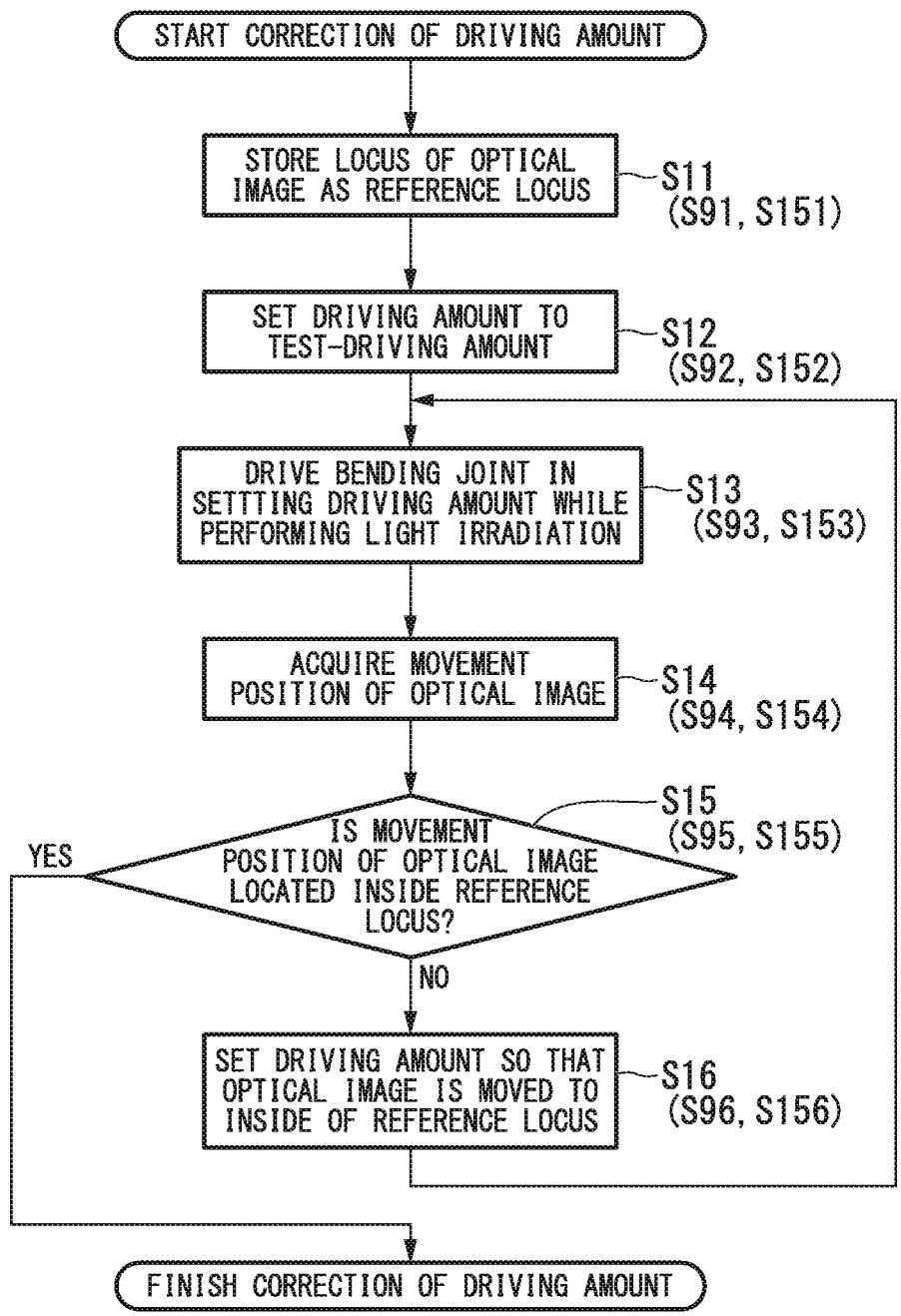

MEDICAL MANIPULATOR AND INITIALIZATION METHOD FOR MEDICAL MANIPULATOR

This application is a continuation application based on PCT Patent Application No. PCT/JP2014/078358, filed Oct. 24, 2014, claiming priority based on Japanese Patent Application No. 2013-221543, filed Oct. 24, 2013, the content of which is incorporated herein by reference.

BACKGROUND OF THE INVENTION

Field of the Invention

The present invention relates to a medical manipulator and an initialization method for the medical manipulator.

Description of the Related Art

In the related art, devices as medical manipulators employing various configurations or control methods are known. For example, a master-slave type medical manipulator which includes a master manipulator being operated by an operator, and a slave manipulator performing on the basis of a signal transmitted from the master manipulator are known.

As such a medical manipulator, a manipulator having a configuration in which a treatment portion performing treatment on a treatment target part is provided at a distal end of a movable arm, and a proximal end portion of the movable arm is held in a channel of a distal end portion of an endoscope.

The movable arm has a configuration in which, for example, a plurality of arms are connected to each other via joints including bending joints for changing angles between arms adjacent to each other.

In such a medical manipulator, an image of the front side is displayed on a display section by the endoscope, and an operator performs a procedure through a remote control while observing a display screen.

In order to easily perform the procedure, a driving command value for an arm portion, an operation amount or an operation direction of the arm portion in a body cavity, and a positional relationship with respect to a treatment target in the body cavity preferably accurately correspond to each other.

For example, Japanese Unexamined Patent Application, First Publication No. 2005-296379 discloses a treatment tool for an endoscope and a treatment tool system for an endoscope in which light being guided from a light source to a distal end of a treatment portion by using light guide means is emitted from an emission portion as guiding light for positioning the treatment portion, and the treatment portion is positioned while a position of a beam spot formed on a target part or the vicinity thereof by the guiding light is checked.

Solution to Problem

A medical manipulator according to a first aspect of the present invention includes an insertion portion configured to be inserted into the body; an arm portion in which a plurality of arms are connected to each other via joints including bending joints which change an angle between arms adjacent to each other; a support portion supporting the arm portion at a distal end part of the insertion portion; a light irradiation section irradiating a luminous flux having an optical axis parallel to an axial line of the arm from an irradiation port disposed at an arm which is closer to a distal end than the bending joint in the arm portion; an imaging section provided at the distal end part of the insertion portion or the support portion and images a locus of an optical image based on the luminous flux; a movement portion including at least one of a rotational movement portion which rotates a supported part of the arm portion supported at the support portion around a reference axial line which is along a longitudinal direction of the insertion portion, and an advance/retract movement portion which advances or retracts the supported part along the reference axial line; and an initialization control unit performing initialization control for forming a reference state in which the arm of the arm portion is aligned with the reference axial line, wherein the initialization control unit includes: a locus acquisition control section controlling the light irradiation section, the movement portion, and the imaging section so as to move the arm portion while irradiating the luminous flux and to acquire the locus; a convergence determination amount calculation portion computing a predetermined physical quantity for determining a convergence state of the locus on the basis of the locus; and a driving amount correction section that corrects a driving amount of the bending joint on the basis of the physical quantity computed by the convergence determination amount calculation portion.

According to a second aspect of the present invention, in the first aspect, the medical manipulator may further include a convergence determination section that determines that the locus has converged in a case where a computed value of the physical quantity is the smallest.

According to a third aspect of the present invention, in the second aspect, the medical manipulator may further include a convergence operation control section that performs control for repeatedly performing operations of the locus acquisition control section, the convergence determination amount calculation portion, the convergence determination section, and the driving amount correction section until the convergence determination section determines that the locus has converged, and the driving amount correction section may obtain a driving amount of the bending joint which causes the physical quantity to be smaller in a case where the convergence determination section determines that the locus has not converged, and drives the bending joint by the driving amount.

According to the medical manipulator of a fourth aspect of the present invention, in the third aspect, the initialization control unit may further include an arm portion information storage section that stores configuration information of the arm portion including information of a presence or absence of a redundant joint in the bending joint, and information of an offset amount which is a distance between the axial line of the arm provided with the irradiation port and the optical axis, and the initialization control unit may control operations of the locus acquisition control section, the convergence determination amount calculation portion, the convergence determination section, and the driving amount correction section on the basis of the configuration information of the arm portion.

According to the medical manipulator of a fifth aspect of the present invention, in the fourth aspect, in a case where the arm portion supported at the support portion is not provided with a redundant joint, and the offset amount is 0 or has a positive value in a direction perpendicular to a bent plane of the bending joint, the locus acquisition control section may perform rotational movement of the arm portion by using the rotational movement portion or advance-retract movement of the arm portion by using the advance/retract movement portion, and the convergence operation control section performs control for repeatedly performing operations of the locus acquisition control section, the convergence determination amount calculation portion, the convergence determination section, and the driving amount correction section on all the bending joints.

According to the medical manipulator of a sixth aspect of the present invention, in the fourth aspect, in a case where the movement portion includes the rotational movement portion and the advance/retract movement portion, the arm portion supported at the support portion is not provided with a redundant joint, and the offset amount has a positive value in a direction perpendicular to a bent plane of the bending joint, the locus acquisition control section may perform rotational movement of the arm portion by using the rotational movement portion or advance-retract movement of the arm portion by using the advance/retract movement portion, the convergence determination section may determine whether or not a first convergence state in which the physical quantity has converged in a case where the rotational movement portion rotationally moves the arm portion occurs, the convergence determination section may determine whether or not a second convergence state in which the physical quantity has converged in a case where the advance/retract movement portion advances or retracts the arm portion occurs, and the convergence determination section may determine that the locus has converged in a case where both of the first convergence state and the second convergence state occurs; the convergence operation control section may perform control for repeatedly performing a convergence operation in which a first convergence operation and a second convergence operation are performed on all of the bending joints until the convergence determination section determines that the locus has converged, the first convergence operation and the second convergence operation may be performed on one of the bending joints, the first convergence operation in which rotational movement of the arm portion may be performed by the rotational movement portion, and the bending joint may be driven by the driving amount correction section until the first convergence state determined to occur by the convergence determination portion, and the second convergence operation in which advance-retract movement of the arm portion may be performed by the advance/retract movement portion, and the bending joint may be driven by the driving amount correction section until the second convergence state is determined to occur by the convergence determination portion.

According to the medical manipulator of a seventh aspect of the present invention, in the fourth aspect, in a case where the movement portion includes the rotational movement portion and the advance/retract movement portion, the arm portion supported at the support portion is not provided with a redundant joint, and the offset amount has a positive value in a direction parallel to a bent plane of the bending joint, the locus acquisition control section may perform at least one of rotational movement of the arm portion by using the rotational movement portion and advance-retract movement of the arm portion by using the advance/retract movement portion, the convergence determination section may determine whether or not a first convergence state occurs in which the physical quantity has converged in a case where the rotational movement portion rotationally moves the arm portion, and may determine whether or not a second convergence state occurs in which the physical quantity has converged in a case where the advance/retract movement portion advances or retracts the arm portion, the convergence determination section may determine that the locus has converged in a case where both of the first convergence state and the second convergence state are determined to occur, the convergence operation control section may perform, on one of the bending joints, a convergence operation in which a first convergence operation and a second convergence operation are performed until the convergence determination section determines that the locus has converged, the first convergence operation in which rotational movement of the arm portion by using the rotational movement portion and advance-retract movement of the arm portion by using the advance/retract movement portion is performed, and the bending joint is driven by the driving amount correction section according to a change amount of the physical quantity and a change direction of the physical quantity until the first convergence state is determined to occur by the convergence determination portion, and the second convergence operation in which advance-retract movement of the arm portion are performed by the advance/retract movement portion, and the bending joint is driven by the driving amount correction section until the second convergence state is determined to occur by the convergence determination portion, and the convergence operation may be performed on all of the bending joints until the convergence determination section determines that the locus has converged.

According to the medical manipulator of an eighth aspect of the present invention, in the fourth aspect, wherein, in a case where the movement portion includes the rotational movement portion and the advance/retract movement portion, the arm portion supported at the support portion includes redundant joints, and the offset amount is 0, the locus acquisition control section may perform rotational movement of the arm portion by using the rotational movement portion or advance-retract movement of the arm portion by using the advance/retract movement portion, the convergence determination section may determine whether or not a first convergence state in which the physical quantity has converged in a case where the rotational movement portion rotationally moves the arm portion occurs, the convergence determination section may determine whether or not a second convergence state in which the physical quantity has converged in a case where the advance/retract movement portion advances or retracts the arm portion occurs, and the convergence determination section may determine that the locus has converged in a case where both of the first convergence state and the second convergence state are determined to occur, and when one of the redundant joints adjacent to each other is referred to as a first redundant joint, and the other redundant joint is referred to as a second redundant joint, the convergence operation control section may perform a first convergence operation in which rotational movement of the arm portion by using the rotational movement portion is performed while fixing an angle of the second redundant joint, and the first redundant joint may be driven in a driving amount of the first redundant joint obtained by the driving amount correction section until the convergence determination section determines the first convergence state occurs, the convergence operation control section may consecutively perform a second convergence operation in which advance-retract movement of the arm portion by using the advance/retract movement portion is performed while fixing an angle of the first redundant joint, and the second redundant joint may be driven in a driving amount of the second redundant joint obtained by the driving amount correction section until the convergence determination section determines the second convergence state occurs, and the convergence operation control section may perform control for repeatedly performing the first convergence operation and the second convergence operation in this order until the convergence determination section determines the convergence operation control section during the second convergence operation.

According to the medical manipulator of a ninth aspect of the present invention, in the fourth aspect, in a case where the movement portion includes the rotational movement portion and the advance/retract movement portion, the arm portion supported at the support portion includes redundant joints, and the offset amount is 0, the locus acquisition control section may perform rotational movement of the arm portion by using the rotational movement portion or advance-retract movement of the arm portion by using the advance/retract movement portion, the convergence determination section may determine whether or not a first convergence state occurs in which the physical quantity has converged in a case where the rotational movement portion rotationally moves the arm portion, and may determine whether or not a second convergence state occurs in which the physical quantity has converged in a case where the advance/retract movement portion advances or retracts the arm portion, and the convergence determination section may determine that the locus has converged in a case where both of the first convergence state and the second convergence state are determined to occur, and when one of the redundant joints adjacent to each other is referred to as a first redundant joint, and the other redundant joint is referred to as a second redundant joint, the convergence operation control section may perform a parallelization operation in which the optical axis is set parallel to the reference axial line by driving the first redundant joint by a driving amount of the first redundant joint, the first redundant joint is driven by the driving amount obtained by the driving amount correction section until the convergence determination section determines the second convergence state occurs, and a linearization operation in which driving amounts for bending the first redundant joint and the second redundant joint at the same angle in directions reverse to each other by rotational movement of the arm portion by using the rotational movement portion so as to reduce a distance between the optical axis and the reference axial line thereby the physical quantity becoming smaller are obtained by the driving amount correction section until the first convergence state is determined to occur by the convergence determination section, and the first redundant joint and the second redundant joint are respectively driven by the driving amounts.

According to the medical manipulator of a tenth aspect of the present invention, in the fourth aspect, in a case where the movement portion may include the rotational movement portion and the advance/retract movement portion, the arm portion supported at the support portion includes redundant joints, and the offset amount has a positive value in a direction parallel to a bent plane of the bending joint, the locus acquisition control section may perform rotational movement of the arm portion by using the rotational movement portion or advance-retract movement of the arm portion by using the advance/retract movement portion, the convergence determination section may determine whether or not a first convergence state in which the physical quantity has converged in a case where the rotational movement portion rotationally moves the arm portion occurs, the convergence determination section may determine whether or not a second convergence state occurs in which the physical quantity has converged in a case where the advance/retract movement portion advances or retracts the arm portion, and the convergence determination section may determine that the locus has converged in a case where both of the first convergence state and the second convergence state are determined to occur, and wherein, when one of the redundant joints adjacent to each other is referred to as a first redundant joint, and the other redundant joint is referred to as a second redundant joint, the driving amount correction section may calculate driving amounts of the first redundant joint and the second redundant joint, the driving amounts of the first redundant joint and the second redundant joint in which the first redundant joint and the second redundant joint are aligned with the reference axial line by deviating the optical axis by the offset amount on the basis of the offset amount in a case where the optical axis is aligned with the reference axial line, the convergence operation control section may consecutively perform a first convergence operation in which rotational movement of the arm portion by using the rotational movement portion is performed while fixing an angle of the second redundant joint, and the first redundant joint is driven by the driving amount of the first redundant joint obtained by the driving amount correction section until the first convergence state is determined to occur by the convergence determination section, the convergence operation may consecutively perform a second convergence operation in which advance-retract movement of the arm portion by using the advance/retract movement portion is performed while fixing an angle of the first redundant joint, and the second redundant joint is driven by the driving amount of the second redundant joint obtained by the driving amount correction section until the second convergence state is determined to occur by the convergence determination section, the convergence operation may consecutively perform an optical axis alignment operation in which the optical axis is aligned with the reference axial line by repeatedly performing the first convergence operation and the second convergence operation until the convergence determination section determines that the locus has converged, and the convergence operation may consecutively perform control for performing an arm axial line alignment operation in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other in a state in which the optical axis is aligned with the reference axial line are calculated on the basis of the offset amount by the driving amount correction section and the first redundant joint and the second redundant joint are respectively driven by the driving amounts According to the medical manipulator of an eleventh aspect of the present invention, in the fourth aspect, in a case where the movement portion includes the rotational movement portion and the advance/retract movement portion, the arm portion supported at the support portion includes redundant joints, and the offset amount has a positive value in a direction parallel to a bent plane of the bending joint, the locus acquisition control section may perform rotational movement of the arm portion by using the rotational movement portion or advance-retract movement of the arm portion by using the advance/retract movement portion, the convergence determination section may determine whether or not a first convergence state occurs in which the physical quantity has converged in a case where the rotational movement portion rotationally moves the arm portion, the convergence determination section may determine whether or not a second convergence state occurs in which the physical quantity has converged in a case where the advance/retract movement portion advances or retracts the arm portion, and the convergence determination section may determine that the locus has converged in a case where both of the first convergence state and the second convergence state are determined to occur, and wherein, when one of the redundant joints adjacent to each other is referred to as a first redundant joint, and the other redundant joint is referred to as a second redundant joint, the convergence operation control section may perform a parallelization operation in which advance-retract movement of the arm portion by using the advance/retract movement portion is performed while fixing an angle of the second redundant joint, and the first redundant joint is driven by the driving amount of the first redundant joint obtained by the driving amount correction section until the second convergence state is determined to occur by the convergence determination section thereby the optical axis is set parallel to the reference axial line, the convergence operation control section may perform control for performing an optical axis alignment operation in which rotational movement of the arm portion by using the rotational movement portion is performed, driving amounts for bending the first redundant joint and the second redundant joint are bent at the same angle in directions reverse to each other such that a distance between the optical axis and the reference axial line become smaller and the physical quantity is further reduced are obtained by the driving amount correction section until the first convergence state is determined to occur by the convergence determination section, and the first redundant joint and the second redundant joint are respectively driven by the driving amounts thereby the optical axis is aligned with the reference axial line, and the convergence operation control section may perform control for performing an arm axial line alignment operation in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other in a state in which the optical axis is aligned with the reference axial line are calculated on the basis of the offset amount by the driving amount correction section, and the first redundant joint and the second redundant joint are respectively driven by the driving amounts According to the medical manipulator of a twelfth aspect of the present invention, in any one of fourth to eleventh aspects, the arm portion may include an arm information supply section that is attachably and detachably provided at a driving section driving the bending joint or the support portion, and transmit the configuration information to the initialization control unit.

According to the medical manipulator of a thirteenth aspect of the present invention, in any one of first to twelfth aspects, the physical quantity may include any one of a diameter of the locus, a deviation amount of the optical image, an area surrounded by the locus, and a length of the locus.

According to the medical manipulator of a fourteenth aspect of the present invention, in the thirteenth aspect, the physical quantity may be the diameter of the locus in a case where rotational movement is performed by the movement portion, and may be the deviation amount of the optical image in a case where advance and retract movement is performed by the movement portion.

According to the medical manipulator of a fifteenth aspect of the present invention, in any one of first to fourteenth aspects, the initialization control unit may include a backlash measurement control section driving the bending joint to perform a bending operation in which the bending joint reciprocates in a predetermined angle range while irradiating the luminous flux from the light irradiation section, and measuring a backlash amount of the bending joint on the basis of a relationship between a position of the optical image imaged by the imaging section and a driving command value of the bending joint, and the driving amount correction section may correct the driving amount by using the backlash amount.

According to a sixteenth aspect of the present invention, an initialization method for a medical manipulator including an arm portion in which a plurality of arms are connected to each other via joints including bending joints which change an angle between arms adjacent to each other and the arm portion supported by a support portion of a distal end of an insertion portion configured to be inserted into the body, the method comprising: a locus acquisition step of irradiating a luminous flux having an optical axis parallel to an axial line of the arm from an irradiation port disposed at an arm which is closer to a distal end than the bending joint in the arm portion, performing at least one of rotational movement in which a supported part of the arm is rotated around a reference axial line which is along a longitudinal direction of the insertion portion, and an advance/retract movement in which the supported part is advanced or retracted along the reference axial line, and acquiring a locus of an optical image based on the luminous flux; a convergence determination amount calculation step of computing a predetermined physical quantity for determining a convergence state of the locus on the basis of the locus; and a driving amount correction step of correcting a driving amount of the bending joint on the basis of the physical quantity computed in the convergence determination amount calculation step.

According to the initialization method for a medical manipulator of a seventeenth aspect of the present invention, in the sixteenth aspect, the initialization method for a medical manipulator may further include a convergence determination step of determining that the locus has converged in a case where a computed value of the physical quantity is the smallest after the convergence determination amount calculation step.

According to the initialization method for a medical manipulator of an eighteenth aspect of the present invention, in the seventeenth aspect, the driving amount correction step may be calculating a driving amount of the bending joint which causes the physical quantity to be further reduced, and driving the bending joint with the driving amount, and repeatedly executing the locus acquisition step, the convergence determination amount calculation step, the convergence determination step, and the driving amount correction step until the locus is determined to be converged in the convergence determination step According to the initialization method for a medical manipulator of a nineteenth aspect of the present invention, in the eighteenth aspect, the initialization method for a medical manipulator may further include an operation setting step of acquiring configuration information of the arm portion which includes information of the presence or absence of a redundant joint in the bending joint, and information of an offset amount which is a distance between the axial line of the arm provided with the irradiation port and the optical axis, and setting operations in the locus acquisition step, the convergence determination amount calculation step, the convergence determination step, and the driving amount correction step on the basis of the configuration information of the arm portion, before initially starting the locus acquisition step.

According to the initialization method for a medical manipulator of a twentieth aspect of the present invention, in the eighteenth or nineteenth aspect, in a case where the arm portion supported at the support portion is not provided with a redundant joint, and an offset amount which is a distance between the axial line of the arm provided with the irradiation port and the optical axis is 0 or has a positive value in a direction perpendicular to a bent plane of the bending joint, the locus acquisition step may perform the rotational movement or the advance-retract movement of the arm portion, and may repeatedly execute the locus acquisition step, the convergence determination amount calculation step, the convergence determination step, and the driving amount correction step in this order on all the bending joints.

According to the initialization method for a medical manipulator of a twenty-first aspect of the present invention, in the eighteenth or nineteenth aspect, in a case where the arm portion supported at the support portion is not provided with a redundant joint, and an offset amount which is a distance between the axial line of the arm provided with the irradiation port and the optical axis has a positive value in a direction perpendicular to a bent plane of the bending joint, the locus acquisition step may perform the rotational movement or the advance-retract movement of the arm portion, and the convergence determination step may determine in a case where the locus acquisition step in which the arm portion is rotationally moved is executed whether or not a first convergence state in which the physical quantity has converged occurs, the convergence determination step may determine in a case where the locus acquisition step in which the arm portion is advanced or retracted is executed whether or not a second convergence state in which the physical quantity has converged occurs, and the convergence determination step may determine that the locus has converged in a case where both of the first convergence state and the second convergence state are determined to occur, wherein the initialization method may further includes: a first convergence step which includes the locus acquisition step in which rotational movement of the arm portion is performed, the convergence determination amount calculation step, the convergence determination step, and the driving amount correction step which is executed until the first convergence state is determined to occur in the convergence determination step, and which is completed in a case where the first convergence state is determined to occur in the convergence determination step; and a second convergence step which includes the locus acquisition step in which advance-retract movement of the arm portion is performed, the convergence determination amount calculation step, the convergence determination step, and the driving amount correction step which is executed until the second convergence state is determined to occur in the convergence determination step, and which is completed in a case where the second convergence state is determined to occur in the convergence determination step, and wherein the first convergence step and the second convergence step may be executed in this order or a reverse order, initialization of a single bending joint is completed in a case where the locus is determined to be converged in any one of the convergence determination step, and the above respective steps are executed on all of the bending joints.

According to the initialization method for a medical manipulator of a twenty-second aspect of the present invention, in the eighteenth or nineteenth aspect, in a case where the arm portion supported at the support portion is not provided with a redundant joint, and an offset amount which is a distance between the axial line of the arm provided with the irradiation port and the optical axis has a positive value in a direction parallel to a bent plane of the bending joint, at least one of rotational movement and advance-retract movement of the arm portion may be performed in the locus acquisition step, and the convergence determination step may determine whether or not a first convergence state in which the physical quantity has converged in a case where the locus acquisition step in which the arm portion is rotationally moved is executed occurs, may determine whether or not a second convergence state occurs in which the physical quantity has converged in a case where the locus acquisition step in which the arm portion is advanced or retracted is executed, and may determine that the locus has converged in a case where both of the first convergence state and the second convergence state are determined to occur, wherein the initialization method may further include: a first convergence step which includes the locus acquisition step in which rotational movement and advance-retract movement of the arm portion are performed, the convergence determination amount calculation step in which respective physical quantities are computed on the basis of loci acquired through the rotational movement and the advance-retract movement, the convergence determination step, and the driving amount correction step which is executed until the first convergence state is determined to occur in the convergence determination step and in which a driving amount is corrected on the basis of a change amount and a change direction of a physical quantity, and which is completed in a case where the first convergence state is determined to occur in the convergence determination step; and a second convergence step which includes the locus acquisition step in which advance-retract movement of the arm portion is performed, the convergence determination amount calculation step, the convergence determination step, and the driving amount correction step which is executed until the second convergence state is determined to occur in the convergence determination step, and which is completed in a case where the second convergence state is determined to occur in the convergence determination step, and wherein the first convergence step and the second convergence step may be executed in this order, initialization of a single bending joint is completed in a case where the locus is determined to be converged in the convergence determination step, and the above respective steps are executed on all of the bending joints.

According to the initialization method for a medical manipulator of a twenty-third aspect of the present invention, in the eighteenth or nineteenth aspect, in a case where the arm portion supported at the support portion includes redundant joints, and an offset amount which is a distance between the axial line of the arm provided with the irradiation port and the optical axis is 0, rotational movement or advance-retract movement of the arm portion may be performed in the locus acquisition step, and the convergence determination step may determine whether or not a first convergence state in which the physical quantity has converged in a case where the locus acquisition step in which the arm portion is rotationally moved is executed occurs, may determine whether or not a second convergence state in which the physical quantity has converged in a case where the locus acquisition step in which the arm portion is advanced or retracted is executed occurs, and may determine that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method may further include: a first convergence step which includes the locus acquisition step in which rotational movement of the arm portion is performed while fixing an angle of the second redundant joint, the convergence determination amount calculation step, the convergence determination step, and the driving amount correction step in which a driving amount of the first redundant joint is corrected, and which is completed in a case where the first convergence state is determined to occur in the convergence determination step; and a second convergence step which includes the locus acquisition step in which advance-retract movement of the arm portion is performed while fixing an angle of the first redundant joint, the convergence determination amount calculation step, the convergence determination step, and the driving amount correction step in which a driving amount of the second redundant joint is corrected, and which is completed in a case where the second convergence state is determined to occur in the convergence determination step, and wherein the first convergence step and the second convergence step may be repeatedly executed in this order, initialization of a pair of redundant joints is completed in a case where the locus is determined to be converged in the convergence determination step of the second convergence step, and the above respective steps may be executed on all of the redundant joints.

According to the initialization method for a medical manipulator of a twenty-fourth aspect of the present invention, in the eighteenth or nineteenth aspect, in a case where the arm portion supported at the support portion includes redundant joints, and an offset amount which is a distance between the axial line of the arm provided with the irradiation port and the optical axis is 0, rotational movement or advance-retract movement of the arm portion is performed in the locus acquisition step, and the convergence determination step determines whether or not a first convergence state in which the physical quantity has converged in a case where the locus acquisition step in which the arm portion is rotationally moved is executed occurs, determines whether or not a second convergence state in which the physical quantity has converged in a case where the locus acquisition step in which the arm portion is advanced or retracted is executed occurs, and determines that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method further includes: a parallelization step which includes the locus acquisition step in which advance-retract movement of the arm portion is performed while fixing an angle of the second redundant joint, the convergence determination amount calculation step, the convergence determination step, and the driving amount correction step in which a driving amount of the first redundant joint is corrected, and which is completed in a case where the second convergence state is determined to occur in the convergence determination step such that the optical axis is set parallel to the reference axial line; and a linearization step which includes the locus acquisition step in which rotational movement of the arm portion is performed, the convergence determination amount calculation step, the convergence determination step, and the driving amount correction step in which driving amounts for bending the first redundant joint and the second redundant joint at the same angle in directions reverse to each other such that a distance between the optical axis and the reference axial line is reduced thereby the physical quantity become smaller are obtained, and the first redundant joint and the second redundant joint are respectively driven by the driving amounts, and which is completed in a case where the first convergence state is determined to occur in the convergence determination step, and wherein the parallelization step and the linearization step are executed in this order, initialization of a pair of redundant joints is completed in a case where the locus is determined to be converged in the convergence determination step, and the above respective steps are executed on all of the redundant joints.

According to the initialization method for a medical manipulator of a twenty-fifth aspect of the present invention, in the eighteenth or nineteenth aspect, in a case where the arm portion supported at the support portion includes redundant joints, and an offset amount which is a distance between the axial line of the arm provided with the irradiation port and the optical axis has a positive value in a direction parallel to a bent plane of the bending joint, in the locus acquisition step, rotational movement or advance-retract movement of the arm portion may be performed in the locus acquisition step, and the convergence determination step may determine whether or not a first convergence state in which the physical quantity has converged in a case where the locus acquisition step in which the arm portion is rotationally moved is executed occurs, may determine whether or not a second convergence state in which the physical quantity has converged in a case where the locus acquisition step in which the arm portion is advanced or retracted is executed occurs, and may determine that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method may further include: a first convergence step which includes the locus acquisition step in which rotational movement of the arm portion is performed while fixing an angle of the second redundant joint, the convergence determination amount calculation step, the convergence determination step, and the driving amount correction step in which a driving amount of the first redundant joint is corrected, and which is completed in a case where the first convergence state is determined to occur in the convergence determination step; and a second convergence step which includes the locus acquisition step in which advance-retract movement of the arm portion is performed while fixing an angle of the first redundant joint, the convergence determination amount calculation step, the convergence determination step, and the driving amount correction step in which a driving amount of the second redundant joint is corrected, and which is completed in a case where the second convergence state is determined to occur in the convergence determination step; an optical axis alignment step in which the first convergence step and the second convergence step are performed in this order, and which is completed in a case where the locus is determined to be converged in the convergence determination step such that the optical axis is aligned with the reference axial line; and an arm axial line alignment step in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other from a state in which the optical axis is aligned with the reference axial line are calculated on the basis of the offset amount, and the first redundant joint and the second redundant joint are respectively driven by the driving amounts, and wherein the first convergence step, the second convergence step, the optical axis alignment step, and the arm axial line alignment step may be executed in this order and initialization of a pair of redundant joints is completed, and the respective steps are executed on all of the redundant joints.

According to the initialization method for a medical manipulator of a twenty-sixth aspect of the present invention, in the eighteenth or nineteenth aspect, in a case where the arm portion includes redundant joints, and an offset amount which is a distance between the axial line of the arm provided with the irradiation port and the optical axis has a positive value in a direction parallel to a bent plane of the bending joint, rotational movement or advance-retract movement of the arm portion may be performed in the locus acquisition step, and the convergence determination step may determine whether or not a first convergence state in which the physical quantity has converged in a case where the locus acquisition step in which the arm portion is rotationally moved is executed occurs, may determine whether or not a second convergence state in which the physical quantity has converged in a case where the locus acquisition step in which the arm portion is advanced or retracted is executed occurs, and may determine that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method may further include: a parallelization step which includes the locus acquisition step advance-retract movement of the arm portion is performed while fixing an angle of the second redundant joint, the convergence determination amount calculation step, the convergence determination step, and the driving amount correction step in which a driving amount of the first redundant joint is corrected, and which is completed in a case where the second convergence state is determined to occur in the convergence determination step such that the optical axis is set parallel to the reference axial line; an optical axis alignment step which includes the locus acquisition step in which rotational movement of the arm portion is performed, the convergence determination amount calculation step, the convergence determination step, and the driving amount correction step in which driving amounts for bending the first redundant joint and the second redundant joint at the same angle in directions reverse to each other such that a distance between the optical axis and the reference axial line is reduced such that the physical quantity become smaller are obtained, and the first redundant joint and the second redundant joint are respectively driven by the driving amounts, and which is completed in a case where the first convergence state is determined to occur in the convergence determination step thereby the optical axis is aligned with the reference axial line; and an arm axial line alignment step in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other from a state in which the optical axis is aligned with the reference axial line are calculated on the basis of the offset amount, and the first redundant joint and the second redundant joint are respectively driven by the driving amounts, and wherein the parallelization step, the optical axis alignment step, and the arm axial line alignment step may be executed in this order and initialization of a pair of redundant joints is completed, and the respective steps are executed on all of the redundant joints.

According to the initialization method for a medical manipulator of a twenty-seventh aspect of the present invention, in any one of the sixteenth to twenty-sixth aspects, the physical quantity may include any one of a diameter of the locus, a deviation amount of the optical image, an area surrounded by the locus, and a length of the locus.

According to the initialization method for a medical manipulator of a twenty-eighth aspect of the present invention, in the twenty-seventh aspect, the physical quantity may be the diameter of the locus in a case where rotational movement is performed in the locus acquisition step, and the physical quantity may be the deviation amount of the optical image in a case where advance-retract movement is performed in the locus acquisition step.

According to a twenty-ninth aspect of the present invention, in any one of the sixteenth to twenty-eighth aspects, the initialization method for a medical manipulator may further include a backlash measurement step of driving the bending joint so as to perform a bending operation in which the bending joint reciprocates in a predetermined angle range while irradiating the luminous flux from the irradiation port, and measuring a backlash amount of the bending joint on the basis of a relationship between a position of the optical image and a driving command value of the bending joint, prior to the locus acquisition step which is initially executed, and wherein, the driving amount may be corrected by using the backlash amount in the driving amount correction step.

Advantageous Effects of Invention

According to the medical manipulators and the methods of initializing the medical manipulators in the above-described respective aspects, since the arm portion is moved while irradiating a luminous flux from the arm portion, and the bending joint of the arm portion can be initialized by driving the bending joint so that a locus of an optical image of the luminous flux converges, it is possible to achieve an effect in which an intuitive operation of the arm portion can be realized.

BRIEF DESCRIPTION OF THE DRAWINGS

FIG. 10 is a flowchart illustrating a flow of a driving amount correction step in the initialization method for the medical manipulator according to the first embodiment of the present invention.

DETAILED DESCRIPTION OF THE PREFERRED EMBODIMENTS

Figure 1:
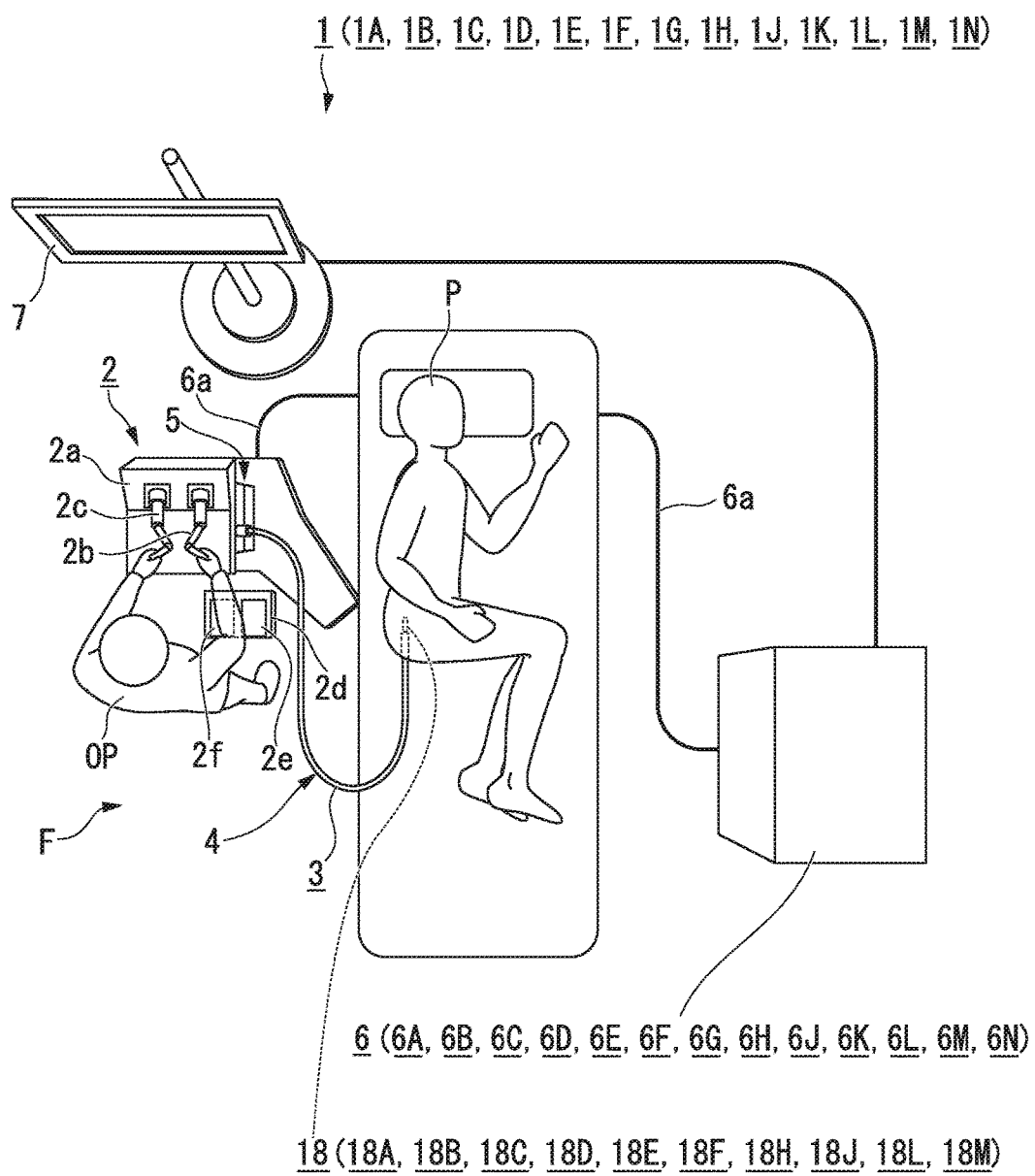
FIG. 1 is a schematic system configuration diagram of a medical manipulator of a first embodiment of the present invention.

Hereinafter, embodiments of the present invention will be described with reference to the accompanying drawings.

Throughout all the drawings, the same reference numerals are given to similar or corresponding members even in a case of different embodiments, and common description will be omitted.

First Embodiment

A medical manipulator of a first embodiment of the present invention will be described.

Figure 2:
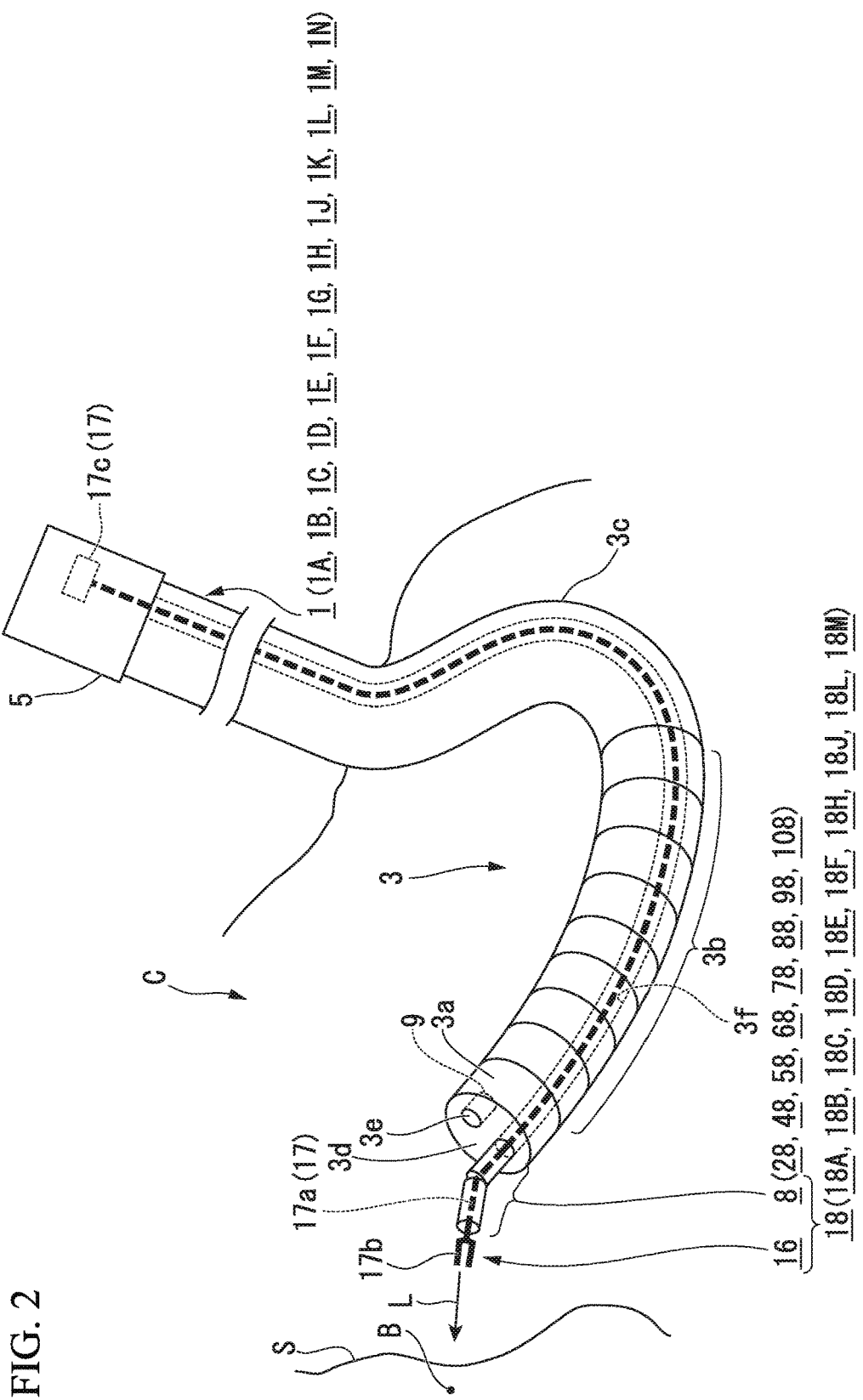
FIG. 2 is a schematic perspective view illustrating configurations of main portions of the medical manipulator according to the first embodiment of the present invention.
Figure 3A:
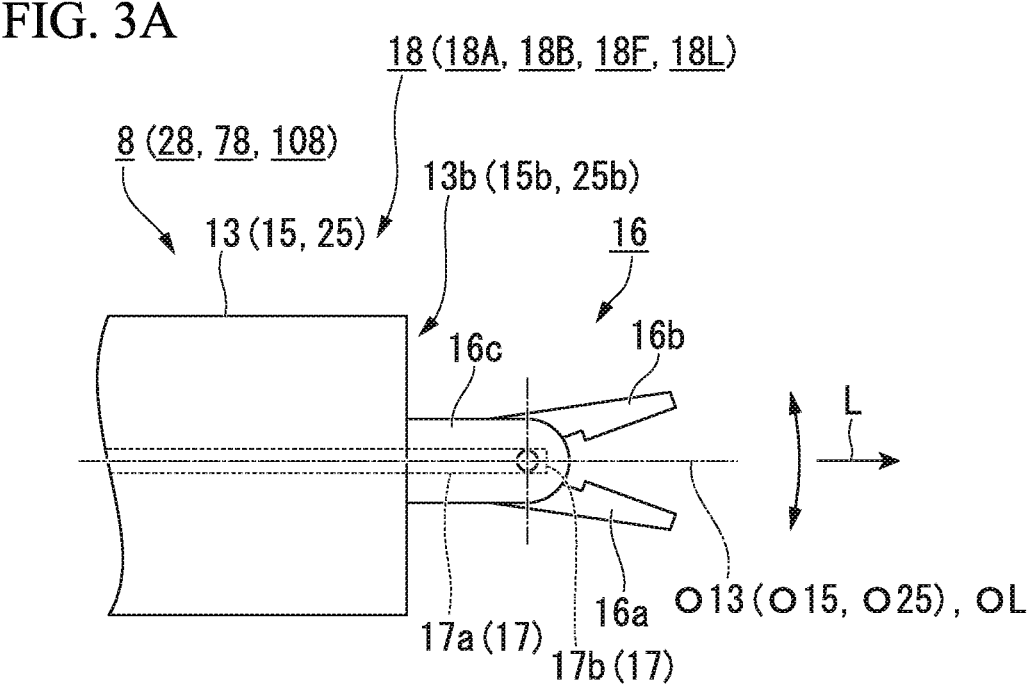
FIG. 3A is a schematic front view for explaining an arrangement of a light irradiation section of the medical manipulator according to the first embodiment of the present invention.
Figure 3B:
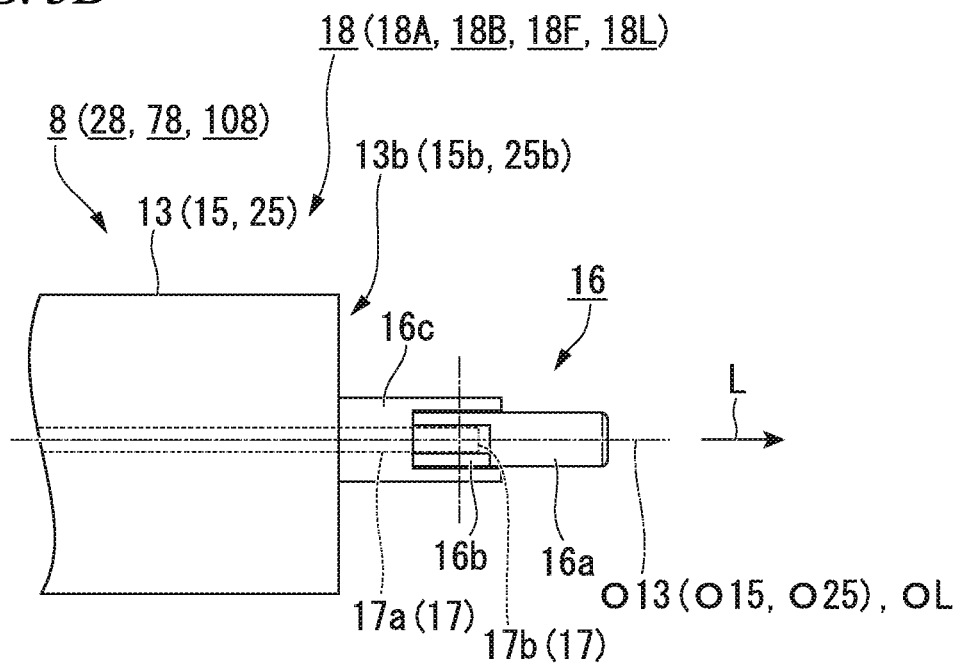
FIG. 3B is a schematic plan view for explaining the arrangement of the light irradiation section of the medical manipulator according to the first embodiment of the present invention.
Figure 4A:
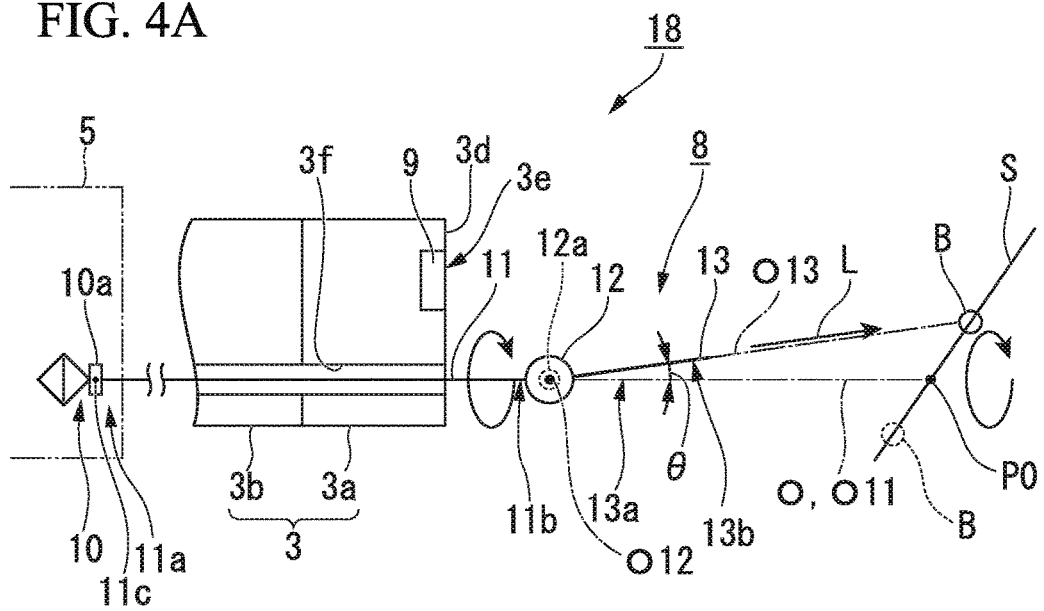
FIG. 4A is a schematic diagram illustrating a configuration of an arm portion of the medical manipulator according to the first embodiment of the present invention.

FIG. 1 is a schematic system configuration diagram of a medical manipulator of the first embodiment of the present invention. FIG. 2 is a schematic perspective view illustrating configurations of main portions of the medical manipulator according to the first embodiment of the present invention. FIGS. 3A and 3B are schematic front view and plan view for explaining an arrangement of a light irradiation section of the medical manipulator according to the first embodiment of the present invention. FIG. 4A is a schematic diagram illustrating a configuration of an arm portion of the medical manipulator according to the first embodiment of the present invention.

Figure 4B:
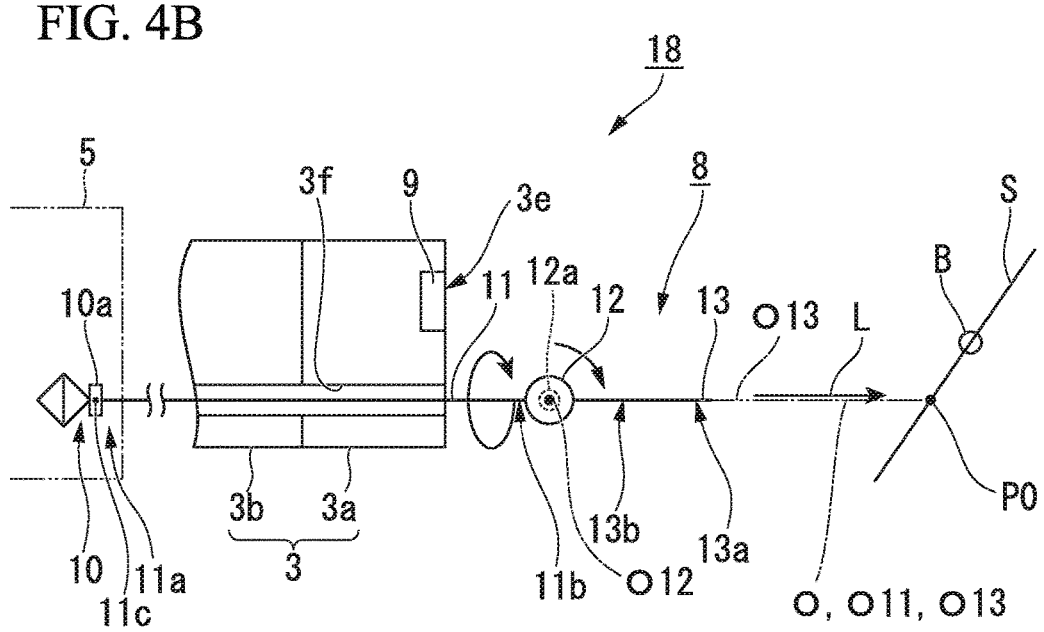
FIG. 4B is an operation explanatory diagram illustrating a configuration of the arm portion of the medical manipulator according to the first embodiment of the present invention.
Figure 5:
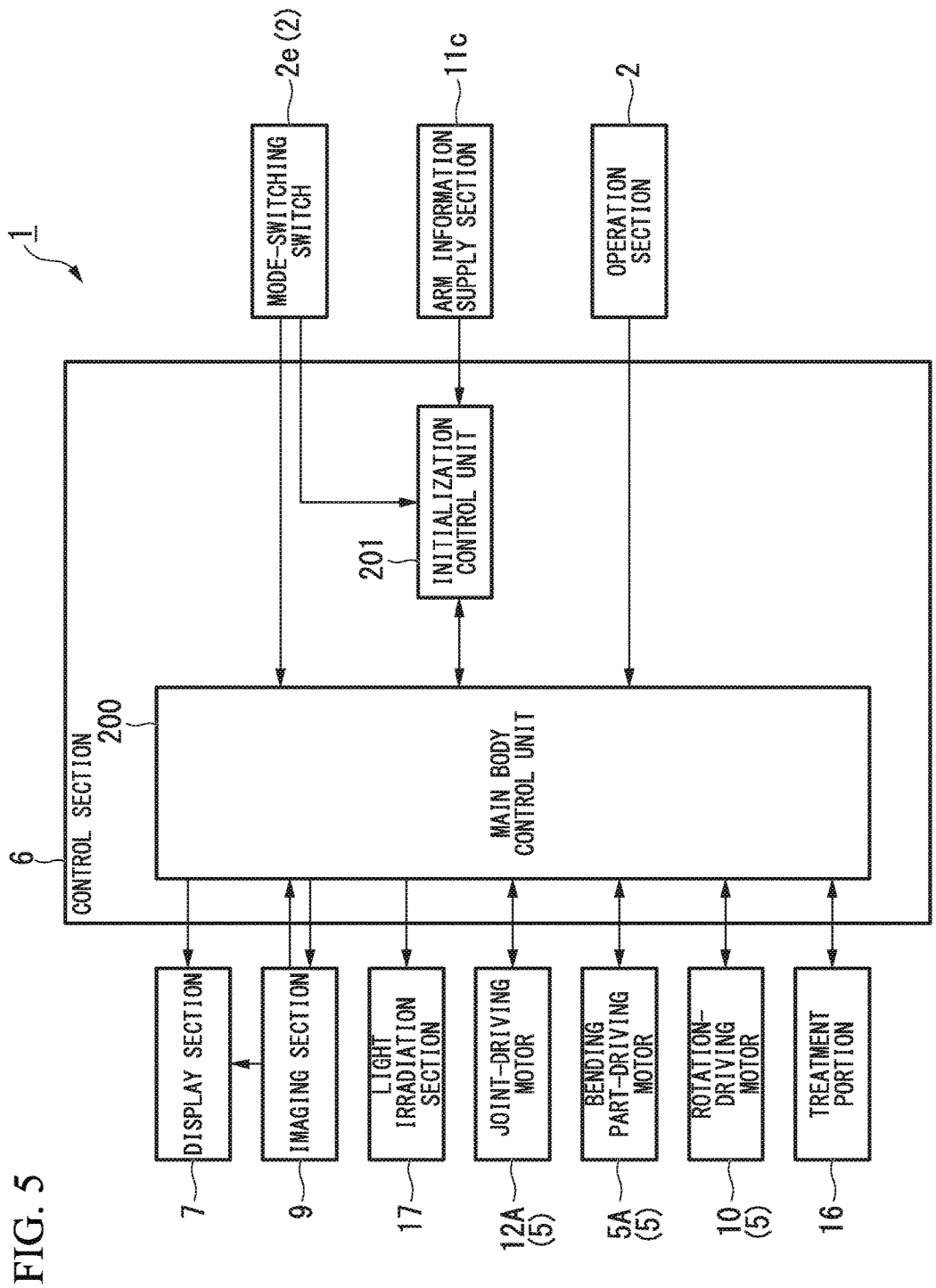
FIG. 5 is a functional block diagram illustrating a major functional configuration of a control section of the medical manipulator according to the first embodiment of the present invention.
Figure 6:
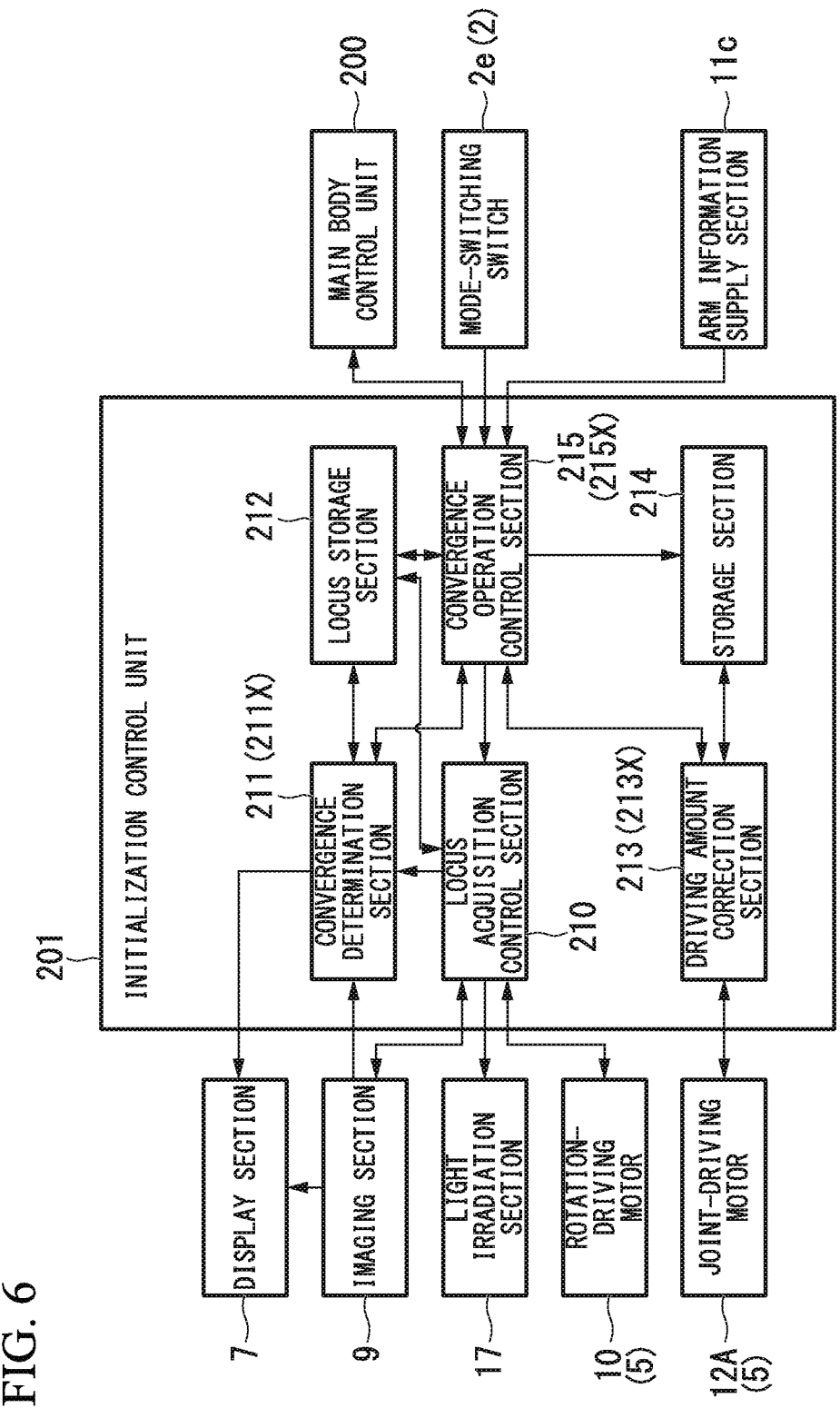
FIG. 6 is a functional block diagram illustrating a functional configuration of initialization control of the medical manipulator according to the first embodiment of the present invention.

FIG. 4B is an operation explanatory diagram illustrating a configuration of the arm portion of the medical manipulator according to the first embodiment of the present invention. FIG. 5 is a functional block diagram illustrating a major functional configuration of a control section of the medical manipulator according to the first embodiment of the present invention. FIG. 6 is a functional block diagram illustrating a functional configuration of initialization control of the medical manipulator according to the first embodiment of the present invention.

In addition, each drawing is a schematic diagram, and a shape, a dimension, or the like is exaggerated for better understanding (this is also the same for the subsequent drawings).

As illustrated in FIG. 1, a surgery support robot 1 which is the medical manipulator according to the present embodiment is a master-slave type endoscope system, and includes an operation section 2 which is operated by an operator OP; an endoscope 4 provided with a flexible insertion portion 3 inserted into the body of a patient P, for example, a smooth organ such as the colon and a surgery instrument 18 which will be described later; a driving section 5 which performs driving such as an operation of inserting the insertion portion 3 of the endoscope 4, an operation of curving a distal end of the insertion portion 3, an operation of twisting the insertion portion 3, and driving of the surgery instrument 18 on a proximal end side of the insertion portion 3; a control section 6 which controls an operation of the surgery support robot 1; and a display section 7 which is electrically connected to the control section 6 and configured to display an image acquired by the endoscope 4 so as to be seen by the operator OP during an operation with the operation section 2.

The operation section 2 includes a pair of operation arms 2b and 2c attached to an operation table 2a, and a foot switch 2d disposed on a surface F of a floor.

The operation arms 2b and 2c have an articulated structure. The operation arm 2b is used to operate to be curved a curved portion at a distal end of the insertion portion 3 to be bent, The operation arm 2c is used to operate the surgery instrument 18 (refer to FIG. 2) which will be described later, provided at a distal end of the endoscope 4.

The foot switch 2d includes a mode-switching switch 2e for switching a control mode of the control section 6, and a confirmation switch 2f for inputting a confirmation instruction or the like by the operator OP.

In the present embodiment, the control mode includes a treatment operation mode for operating the surgery instrument 18 and the endoscope 4, and an initialization mode for initializing an arm portion 8 which will be described later.

FIG. 2 illustrates the insertion portion 3 which is inserted into the body cavity C inside the body of the patient P.

The insertion portion 3 is so-called flexible, and includes a distal end rigid part 3a (support portion) provided on a distal end side in an insertion direction, a bending part 3b which is provided more proximal side than the distal end rigid part 3a and can be operated to be curved by the operation section 2, and a flexible tube part 3c which is provided more proximal side than the bending part 3b and is flexible.

A channel 3f consists of a hole part or a tubular part into which the surgery instrument 18 is slidably inserted from the proximal end to the distal end is provided inside the insertion portion 3.

Although a specific configuration of the bending part 3b is not illustrated, for example, the bending part includes a plurality of joint rings which are connected so as to be rotationally moved to each other, and an operation wire which is inserted into the joint rings and of which a distal end is fixed to the joint ring on the most distal end side and a proximal end is connected to a driving motor or the like in the driving section 5.

A light receiving window 3e for capturing an image of the front side of the distal end rigid part 3a is provided on a distal end surface 3d of the distal end rigid part 3a, and an imaging section 9 which captures an image of the front side of the distal end rigid part 3a through the light receiving window 3e is disposed into the distal end rigid part 3a facing the light receiving window 3e.

A configuration of the imaging section 9 is not particularly limited. A configuration in which an imaging element (not illustrated) and an imaging element such as a CCD are combined with each other is employed as an example.

The imaging section 9 is communicably connected to the control section 6 via a wiring (not illustrated), and performs an imaging operation and also sends a video signal to the control section 6 in response to a control signal from the control section 6.

The wiring (not illustrated) of the imaging section 9 is inserted into the insertion portion 3, extends to the proximal end side of the insertion portion 3, and is inserted into a wiring cable 6a via the driving section 5 and is connected to the control section 6.

In the distal end rigid part 3a, an opening on the distal end side of the channel 3f is formed in a region adjacent to the light receiving window 3e, and a distal end part of the arm portion 8 constituting the surgery instrument 18 along with a treatment portion 16 is provided so as to be capable of protruding toward the front side of the distal end surface 3d.

The channel 3f is a rigid cylindrical hole which is also used as a bearing part of the arm portion 8 inserted into the channel 3f, and is formed in a flexible tubular shape inside the bending part 3b and the flexible tube part 3c.

The channel 3f linearly extends in the distal end rigid part 3a, and, hereinafter, a central axis thereof will be referred to as a reference axial line O.

A direction of the reference axial line O may employ a direction as necessary as long as the direction is substantially along a longitudinal direction of the distal end side of the insertion portion 3 (including a case of being completely along the longitudinal direction). In the present embodiment, as an example, the reference axial line O is perpendicular to the distal end surface 3d, and is thus parallel to the longitudinal direction of the distal end side of the insertion portion 3. In addition, in the present embodiment, the reference axial line O is parallel to an imaging optical axis of the imaging section 9. For this reason, the reference axial line O has a constant positional relationship on an imaging screen of the imaging section 9.

The surgery instrument 18 can be advanced or retracted inside the channel 3f, for example, the treatment portion 16 and the arm portion 8 can be stored inside the insertion portion 3 when the insertion portion 3 is inserted into the body cavity C.

Hereinafter, unless otherwise mentioned, as illustrated in FIG. 2, a description is made based on a positional relationship in a state in which the treatment portion 16 and the arm portion 8 protrude from the distal end surface 3d corresponding to a condition when used in the body cavity C.

The treatment portion 16 is a device portion for treating a treatment target, and is provided as an example of an end effector of the arm portion 8. The treatment portion 16 may employ an appropriate treatment tool as necessary. Examples of the treatment portion 16 may include a member extending in a rod shape or a hook shape for pressing the biological tissue, a tube member such as an injection needle, gripping forceps in which a plurality of treatment tool pieces are combined with each other, a member which cuts or cauterizes a biotissue through conduction, a laser treatment tool which cuts or cauterizes a biotissue with laser light, and a clip for stopping the bleeding or extending a tissue. In addition, instead of the treatment portion 16, an enlargement endoscope for observing a treatment target in detail or a camera for acquiring a stereoscopic shape may be provided as an end effector for the purposes other than treatment.

In the present embodiment, as an example of the treatment portion 16, gripping forceps as illustrated in FIGS. 3A and 3B are employed. In other words, the treatment portion 16 includes a support member 16c fixed to an arm distal end 13b which is the most distal end portion of the arm portion 8, and treatment tool pieces 16a and 16b which are supported at the support member 16c so as to be rotationally moved.

Proximal end sides of the treatment tool pieces 16a and 16b are connected to operation members (not illustrated) formed of, for example, wires, in order to open and close distal ends of the treatment tool pieces 16a and 16b. The operation members are inserted into the arm portion 8 and the insertion portion 3 and are connected to the driving section 5.

As schematically illustrated in FIG. 4A, the arm portion 8 includes a first arm 11 (arm), a first joint 12 (bending joint) connected to an arm distal end 11b of the first arm 11, and a second arm 13 (arm) which is connected to the first arm 11 via the first joint 12 so as to be bent, from the proximal end side supported at the distal end rigid part 3a toward the distal end side.

The first arm 11 is schematically illustrated as a straight line in FIGS. 4A and 4B, but is a cylindrical member which is slidably inserted into the channel 3f. Only the arm distal end 11b of the first arm 11 is formed of a rigid member extending straight. However, a portion of the first arm 11 located more proximal side than the arm distal end 11b of the first arm 11 is flexible so as to be curved along bending part 3b and a curved state of the channel 3f inside the flexible tube part 3c.

The arm distal end 11b of the first arm 11 is supported by the channel 3f of the distal end rigid part 3a so as to be rotated around the reference axial line O. In FIGS. 4A and 4B, the arm distal end 11b is schematically illustrated to protrude still further toward the distal end side than the distal end surface 3d but may not protrude.

For this reason, the arm distal end 11b linearly extends along an arm axial line O11 which is the same axis as the reference axial line O.

As mentioned above, the distal end rigid part 3a constitutes a support portion which supports the arm portion 8 at the distal end of the insertion portion 3.

An arm proximal end 11a of the first arm 11 is attachably and detachably fixed to a rotation-driving motor 10 (a rotational movement portion or a movement portion) which is fixed to the driving section 5 via a connection portion 10a.

An arm information supply section 11c which directly or indirectly sends configuration information of the arm portion 8 to the control section 6 is provided at the arm proximal end 11a.

Here, the configuration information of the arm portion 8 is information of a configuration of the arm portion 8 which is required in an operation of initializing the arm portion 8 and will be described later, and includes, for example, the number of joints, the type of joint or arrangement thereof, information of the presence or absence of a redundant joint, and information of an offset amount will be described later. In a case where the redundant joint is included, information for specifying joints forming the redundant joint is included.

The information of an offset amount includes information of the magnitude of an offset and information of an offset direction. The offset direction also includes differentiation between a "rotary shaft direction offset" and a "curved plane direction offset".

Examples of a configuration of the arm information supply section 11c may be as follows: a configuration of mechanically readable transmission code such as an uneven part; a configuration of writing the transmission code to a wireless tag and electromagnetically transmitting it; and a configuration of converting the transmission code to an optical reading code and providing an information display for displaying it. The transmission code is consisted of a configuration information itself or consisting of an identification number, an identification code, or a serial number or the like of the arm portion corresponding to the configuration information of the arm portion 8.

In the present embodiment, as an example, the mechanically readable configuration is employed.

The rotation-driving motor 10 is a motor which rotates the first arm 11 around a central axial line thereof, and is electrically connected to the control section 6 via a wiring (not illustrated).

The rotation-driving motor 10 may rotate the arm proximal end 11a of the first arm 11 at least once around, for example, may be configured to rotate the arm proximal end around once or more in one direction, and may be configured to rotate the arm proximal end by a half turn or more in two directions.

The rotation-driving motor 10 in the present embodiment constitutes a rotational movement portion which rotates the arm proximal end 11a of the first arm 11 which is a supported part of the arm portion 8 supported at the distal end rigid part 3a, around the reference axial line O which is substantially along the longitudinal direction of the insertion portion 3.

The connection portion 10a is a member by which the arm proximal end 11a of the first arm 11 is attachably and detachably connect to the rotation-driving member 10 such that the arm axial line O11 is located at the same axis as the reference axial line O. In the present embodiment, a sensor which reads the configuration information of the arm portion 8 on the basis of a mechanical uneven structure in accordance with a configuration of the above-described arm information supply section 11c during installation of the first arm 11 is provided. The read configuration information is sent to the control section 6 via a wire (not illustrated).

A configuration of the first joint 12 is not particularly limited as long as the first joint is a bending joint which connects the arm distal end 11b of the first arm 11 to an arm proximal end 13a of the second arm 13.

In the present embodiment, a rotary joint having a rotation body, which is coupled to a front end of the arm proximal end 11a via a pin so as to be capable of rotating around a first rotary shaft O12, is employed. A pulley 12a which transmits a rotation driving force from the proximal end side is provided at the rotation body of the first joint 12 on the same axis as that of the first rotary shaft O12.

A driving wire (driving force transmission wire material) (not illustrated) extending from the driving section 5 is wound around the pulley 12a. For example, the driving wire is routed inside the insertion portion 3 (the first arm 11) in a state of being inserted into, a coil sheath, and is connected to the driving section 5 (a joint-driving motor 12A which will be described later) on the proximal end side. For this reason, the pulley 12a and the rotation body to which the pulley 12a is fixed are rotated by pushing and pulling the driving wire in the longitudinal direction of the insertion portion 3 (the first arm 11) by the driving section 5 (the joint-driving motor 12A which will be described later).

The rotation body provided with the pulley 12a is connected to the second arm 13.

The first joint 12 is connected to the arm tip end 11b of the first arm 11 such that the first rotary shaft O12 is perpendicular to the arm axial line O11 and the reference axial line O.

The second arm 13 is a member extending along an arm axial line O13 (an axial line of the arm), and is schematically illustrated as a straight line in FIGS. 4A and 4B. In the present embodiment, as an example, a cylindrical member in which the arm axial line O13 is in a central axial line is employed.

An arm proximal end 13a of the second arm 13 is connected to the first joint 12 such that the second arm 13 can rotate around the first rotary shaft O12 such that the second arm 13 can rotate around the first rotary shaft O12 at an intersection between the arm axial line O11 and the first rotary shaft O12.

For this reason, the arm axial line O13 can be aligned in a positional relationship of the same axis with the arm axial line O11 by adjusting a driving amount of the first joint 12.

As illustrated in FIGS. 3A and 3B, an optical fiber 17a is disposed inside the arm portion 8 which having the above configuration.

A fiber end surface 17b (irradiation port) of a distal end of the optical fiber 17a is disposed such that a fiber axis is aligned with the arm axial line O13 and is exposed between the treatment tool pieces 16a and 16b in a state in which the treatment portion 16 is opened.

As illustrated in FIG. 2, a proximal end side of the optical fiber 17a extends to the driving section 5 through the arm portion 8 and the insertion portion 3 and is connected to a laser light source 17c provided inside the driving section 5.

For this reason, a laser luminous flux emitted from the laser light source 17c is guided through the optical fiber 17a, and is applied forward from the fiber end surface 17b as a laser luminous flux L (luminous flux). An optical axis OL of the laser luminous flux L is aligned on the same axis with the arm axial line O13.

The laser luminous flux L may be any one of a divergent luminous flux, a convergent luminous flux, and a parallel luminous flux as long as, when the laser luminous flux is projected onto an inner wall S of the body cavity C, an optical image is formed in an image captured by the imaging section 9, a central position of the optical image can be acquired, and a locus of the optical image moving in accordance with movement of the arm portion 8 can be acquired. That is, as long as an optical image having a spot diameter in which an irradiation region of the laser luminous flux L is sufficiently smaller than an imaging region is formed, the spot diameter may change depending on an irradiation location or a movement destination.

In the present embodiment, as an example, a configuration is employed in which a condensing lens (not illustrated) is provided at the distal end of the optical fiber 17a, and can emit a substantially parallel luminous flux (including a case of a parallel luminous flux). If the laser luminous flux L is a parallel luminous flux, a spot diameter of an optical image is unlikely to change even if a distance from the inner wall S changes when the laser luminous flux is projected onto the inner wall S of the body cavity C. In addition, since a luminance reduction is slight, a spot center is easily calculated.

With the above-described configuration, the optical fiber 17a and the laser light source 17c constitutes a light irradiation section 17 which applies a luminous flux having an optical axis parallel to the axial line of the arm from the irradiation port disposed in the arm closer to the distal end than the bending joint.

Here, the bending joint, the arm, the irradiation port, the axial line of the arm, the optical axis, and the luminous flux respectively correspond to the first joint 12, the second arm 13, the fiber end surface 17b, the arm axial line O13, the optical axis OL, and the laser luminous flux L.

If a distance between the axial line of the arm provided with the irradiation port and the optical axis is defined as an "offset amount", in the present embodiment, since the arm axial line O13 is the same axis with the optical axis OL, the offset amount is 0.

In addition, since the optical axis OL matches the gripping center of the treatment portion 16, the laser luminous flux L is a marker indicating a treatment target part which comes into contact with the front of the treatment portion 16.

Next, a functional configuration of the control section 6 will be described.

As illustrated in FIG. 5, the control section 6 includes a main body control unit 200 and an initialization control unit 201 (initialization control unit).

The main body control unit 200 controls a treatment operation performed by the surgery support robot 1, and is communicably connected to the imaging section 9, the light irradiation section 17, the joint-driving motor 12A, the treatment portion 16, the rotation-driving motor 10, a bending part-driving motor 5A, and the initialization control unit 201.

Here, the joint-driving motor 12A is a motor supplying a rotation driving force to the first joint 12, and the bending part-driving motor 5A is a motor provided inside the driving section 5 and controlling a curving operation of the bending part 3b. The joint-driving motor 12A and the bending part-driving motor 5A constitutes a part of the driving section 5 along with the rotation-driving motor 10.

A description of a specific configuration of the main body control unit 200 will be omitted, and can control an operation of each device portion or can acquire various information in order to perform treatment through remote control by using the treatment portion 16.

In addition, if a notification that initialization of the arm portion 8 has been completed is sent from the initialization control unit 201 will be described later, the main body control unit performs control for setting a rotating angle position of the first joint 12 to an origin position of driving.

Control on the light irradiation section 17 performed by the main body control unit 200 includes control of turning-on, turning-off, and a light amount of the laser luminous flux L corresponding to the operator OP's operation on the operation section 2.

Consequently, the operator OP can recognize a positional relationship between a treatment target part and the treatment portion 16 while viewing a position of a beam spot B (refer to FIG. 2) of the laser luminous flux L in an image on the display section 7.

Control on the joint-driving motor 12A, the rotation-driving motor 10, and the treatment portion 16 performed by the main body control unit 200 includes control for moving the treatment portion 16 by changing a curved state of the arm portion 8 or opening and closing the treatment portion 16 in response to the operator OP's operation on the operation section 2.

The initialization control unit 201 is a device portion which controls initialization of the arm portion 8 and includes, as illustrated in FIG. 6, a locus acquisition control section 210, a convergence determination section 211 (convergence determination amount calculation portion), a locus storage section 212, a driving amount correction section 213, a storage section 214, and a convergence operation control section 215. The initialaization of the arm portion 8 is configured to form a reference state in which the second arm 13 is aligned along the reference axial line O.

The locus acquisition control section 210 controls the light irradiation section 17, the rotation-driving motor 10, and the imaging section 9 so as to perform such that the arm portion 8 is rotationally moved by the rotation-driving motor 10 while irradiating the laser luminous flux L from the light irradiation section 17, a locus of an optical image of the laser luminous flux L is imaged by the imaging section 9, and a locus of the optical image which is a locus of the center of the optical image is acquired through image processing.

The locus of the optical image is acquired as a closed curve by rotating the rotation-driving motor 10 once around or more.

The locus acquisition control section 210 is communicably connected to each of the light irradiation section 17, the rotation-driving motor 10, the imaging section 9, and the convergence operation control section 215.

The image sent from the imaging section 9 is stored in the locus storage section 212 and is appropriately read by the locus acquisition control section 210 as necessary in image processing for acquiring a locus of the optical image.

As an example of the image processing for acquiring a locus, there is a method in which an optical image is sampled, coordinates of passing points are acquired on the basis of the center of the sampled optical light images, and a locus is acquired by using a plurality of passing points, or a method in which strip-shaped images obtained through scanning of optical images are sequentially acquired, and a locus is acquired on the basis of a central position of a width of the optical image perpendicular to a scanning direction of a width perpendicular to a movement direction.

The locus of an optical image acquired in the above-described way is sent to the locus storage section 212 and is stored in the locus storage section 212. In addition, a locus image is generated and sent to the display section 7 and the image is displayed on the display section 7 as necessary.

The convergence determination section 211 computes a diameter of the locus which is a physical quantity for determining a locus convergence state on the basis of the locus acquired by the locus acquisition control section 210 and determines convergence of the locus. The convergence determination section 211 is communicably connected to each of the imaging section 9, the locus storage section 212, the display section 7, and the convergence operation control section 215.

In the convergence determination in the present embodiment, it is determined that convergence occurs if the diameter of the locus is equal to or smaller than a determination threshold value which is set in advance. The determination threshold value is set to an appropriate value close to 0 in advance by taking into consideration an alignment limit of the arm axial lines O11 and O13 caused by a manufacturing error of the arm portion 8 or a calculation error in the locus of an optical image.

Information of the convergence determination result by the convergence determination section 211 and information of the diameter of the locus are sent to the convergence operation control section 215, and the convergence determination result is sent to the display section 7 and is displayed on the display section 7 as necessary. In addition, the convergence determination section 211 includes a storage region, and configured to store the information of the diameter of the locus in a time series.

The locus storage section 212 stores data of the locus analyzed by the convergence determination section 211 in a time series. For this reason, the convergence determination section 211 can refer to a change in the locus in a time series as necessary.

In a case where the convergence determination section 211 determines that the locus does not converge, the driving amount correction section 213 calculates a driving amount of the first joint 12 which becomes a smaller diameter of the locus on the basis of the diameter of the locus computed by the convergence determination section 211, and drives the first joint 12 in this driving amount.

The driving amount correction section 213 is communicably connected to each of the joint-driving motor 12A, the storage section 214, and the convergence operation control section 215.

Here, the driving amount includes information of a rotating angle and a rotating direction of the first joint 12.

The calculated driving amount is stored in a time series in the storage section 214, and is also converted into a driving command value for the joint-driving motor 12A and is sent to the joint-driving motor 12A.

A specific method of obtaining a driving amount will be described in a description of an operation will be described later.

The storage section 214 stores the driving amount obtained by the driving amount correction section 213 and also stores the configuration information of the arm portion 8 sent via the convergence operation control section 215. For this reason, the storage section 214 constitutes an arm portion information storage unit which stores the configuration information of the arm portion 8.

The stored configuration information in the present embodiment is, for example, information that "the number of bending joints is one", "there is no redundant joint", and "an offset amount is 0" according to the configuration of the arm portion 8.

The convergence operation control section 215 performs control for repeatedly performing operations of the locus acquisition control section 210, the convergence determination section 211, and the driving amount correction section 213 until the convergence determination section 211 determines that a locus converges when an initialization mode is input via the mode-switching switch 2e.

In addition, the convergence operation control section 215 reads the configuration information of the arm portion 8 transmitted from the arm information supply section 11c and stores the configuration information in the storage section 214 when the arm portion 8 is connected to the connection portion 10a.

Further, if the convergence determination section 211 determines that the locus converges, the convergence operation control section 215 notifies the main body control unit 200 that the initialization is completed.

The convergence operation control section 215 is communicably connected to the mode-switching switch 2e, the locus acquisition control section 210, the convergence determination section 211, the locus storage section 212, the driving amount correction section 213, the arm information supply section 11c, the storage section 214, and the main body control unit 200.

The device configuration of the control section 6 described above is constituted of a computer including a CPU, memories, input and output interfaces, external storage devices, and the like, and thus a control program or a calculation program for performing the above-described control or calculation is executed.

Next, an operation of the surgery support robot 1 will be described focusing on an initialization method for the medical manipulator according to the present embodiment.

Figure 7:
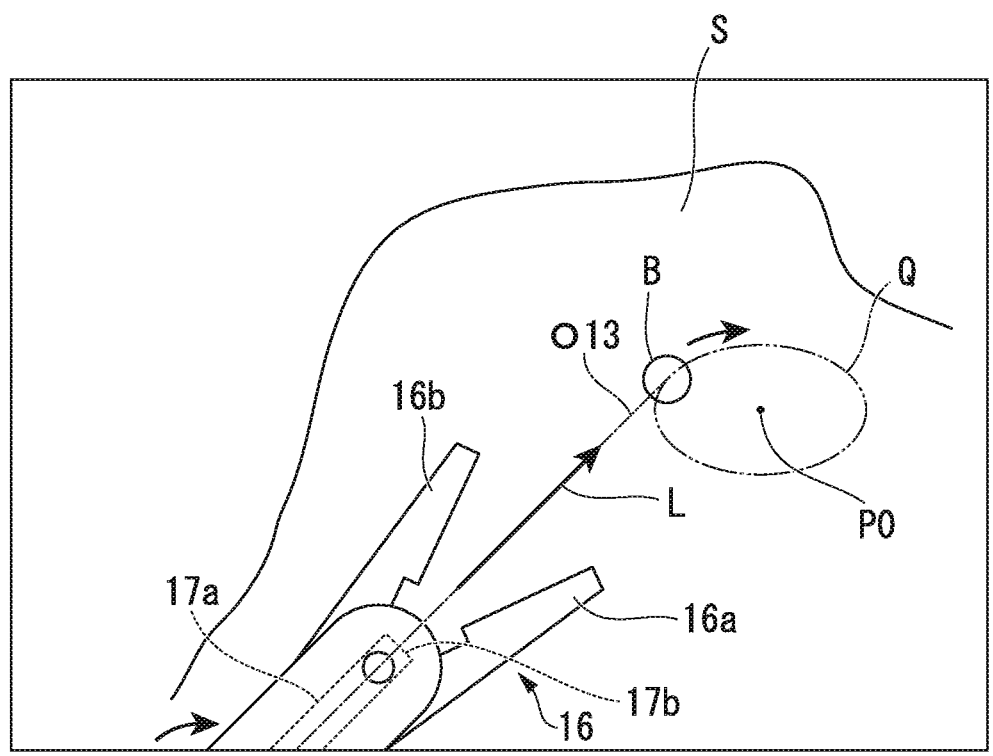
FIG. 7 is a schematic diagram illustrating an example of an image displayed on a display section of the medical manipulator according to the first embodiment of the present invention.
Figure 8:
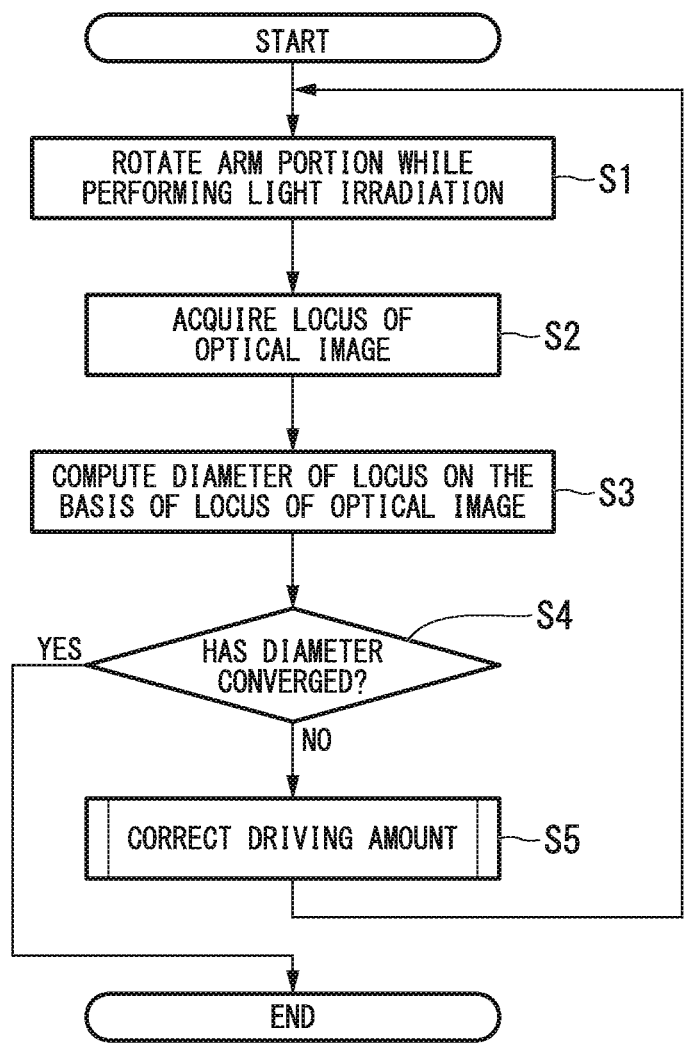
FIG. 8 is a flowchart illustrating a flow of an initialization method for the medical manipulator according to the first embodiment of the present invention.
Figure 9A:
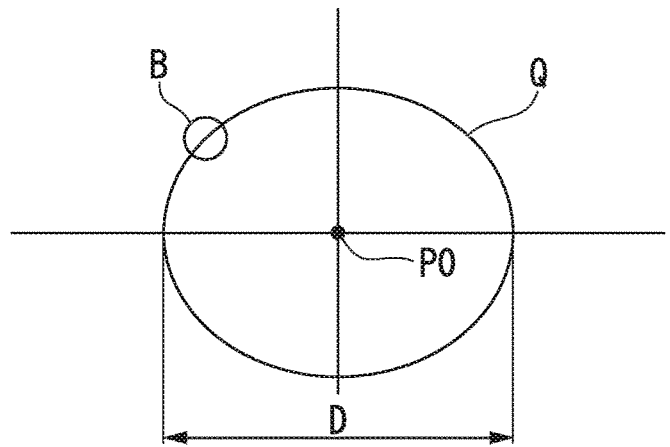
FIG. 9A is a schematic diagram illustrating an example of a locus of an optical image in the initialization method for the medical manipulator according to the first embodiment of the present invention.
Figure 9B:
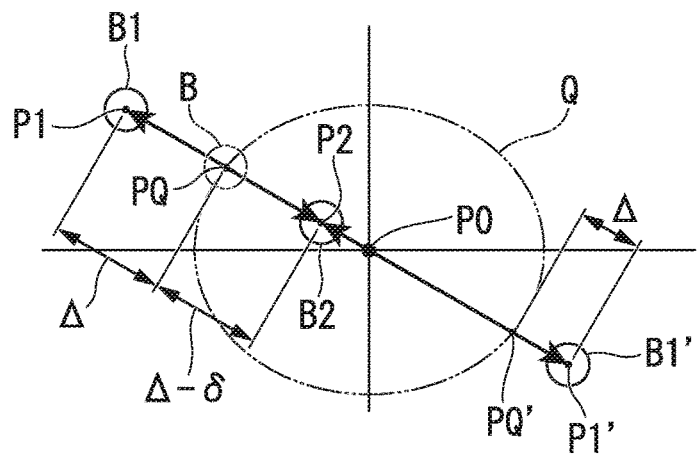
FIG. 9B is a schematic diagram illustrating an example of a locus of an optical image in the initialization method for the medical manipulator according to the first embodiment of the present invention.
Figure 9C:
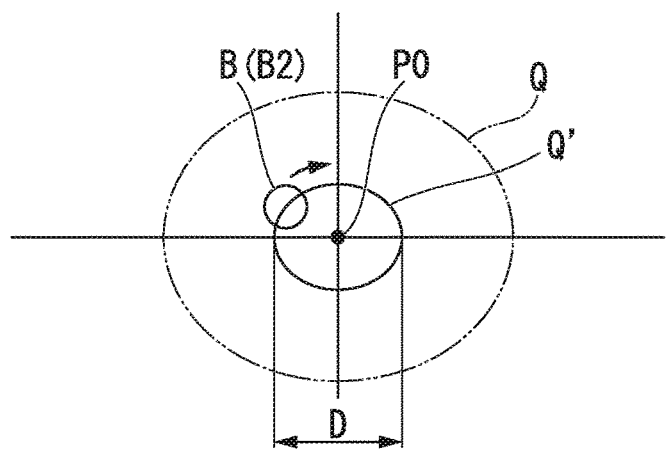
FIG. 9C is a schematic diagram illustrating an example of a locus of an optical image in the initialization method for the medical manipulator according to the first embodiment of the present invention.

FIG. 7 is a schematic diagram illustrating an example of an image displayed on the display section of the medical manipulator according to the first embodiment of the present invention. FIG. 8 is a flowchart illustrating a flow of an initialization method for the medical manipulator according to the first embodiment of the present invention. FIGS. 9A, 9B and 9C are schematic diagrams illustrating examples of a locus of optical image in the initialization method for the medical manipulator according to the first embodiment of the present invention. FIG. 10 is a flowchart illustrating a flow of a driving amount correction step in the initialization method for the medical manipulator according to the first embodiment of the present invention.

In a case where treatment is performed by the surgery support robot 1 of the present embodiment, as illustrated in FIG. 1, for example, the insertion portion 3 on the distal end side of the endoscope 4 is inserted into, for example, a smooth organ such as the colon of the patient P, and the surgery instrument 18 are disposed in the body cavity C along with the insertion portion 3. In this case, as illustrated in FIG. 7, an image of the front side of the imaging section 9, captured by the imaging section 9 is displayed on the display section 7.

In addition, the operator OP switches a control mode of the surgery support robot 1 to an initialization mode by using the mode-switching switch 2e (refer to FIG. 1) prior to treatment.

Consequently, in the control section 6, control performed by the main body control unit 200 is temporarily stopped, and the treatment portion 16 is opened so as not to block the laser luminous flux L.

In the initialization control unit 201, the convergence operation control section 215 starts operation control, and the initialization method for the medical manipulator according to the present embodiment is performed as follows, thereby the arm portion 8 is initialized.

The initialization method for the medical manipulator according to the present embodiment includes a locus acquisition step, a convergence determination amount calculation step, a convergence determination step, and a driving amount correction step, and is performed by repeatedly performing the locus acquisition step, the convergence determination amount calculation step, the convergence determination step, and the driving amount correction step until it is determined that the locus of an optical image of the laser luminous flux L converges.

These steps are executed by executing steps S1 to S5 illustrated in FIG. 8 according to the flow shown in FIG. 8.

In step S1, the arm portion 8 is rotated while performing irradiation with light.

This step is executed when a control signal is sent from the convergence operation control section 215 to the locus acquisition control section 210, and control of the locus acquisition control section 210 is started.

The locus acquisition control section 210 turns on the laser light source 17c of the light irradiation section 17. Consequently, as illustrated in FIG. 7, a laser luminous flux L is emitted from the fiber end surface 17b along the arm axial line O13 and irradiates the inner wall S, and thus a dot-like beam spot B (optical image) is formed on the inner wall S.

Next, the locus acquisition control section 210 sends a control signal to the rotation-driving motor 10 and a rotation of the rotation-driving motor 10 is started.

Through the above operation, step S1 is completed.

Next, step S2 is executed. In this step, a locus of the optical image is acquired.

The locus acquisition control section 210 acquires an image captured by the imaging section 9 while rotating the rotation-driving motor 10 at least once around, and acquires a locus by performing image processing on the image.

In this step, a state of a rotating angle of the first joint 12 is unclear, and an angle between the first arm 11 and the second arm 13 is also unclear. For this reason, the first arm 11 and the second arm 13 are in a state in which the arm axial line O13 of the second arm 13 is not aligned with the reference axial line O (referred to as a "bent state" of the arm portion 8) as illustrated in FIG. 4A, or a state in which the arm axial line is aligned with the reference axial line O (hereinafter, referred to as an "aligned state" of the arm portion 8) as illustrated in FIG. 4B.

In the bent state of the arm portion 8, the beam spot B is rotationally moved centering on a point P0 on the inner wall S at which the reference axial line O intersects the inner wall S. At this time, a rotation radius of the beam spot B changes depending on an angle θ of the arm axial line O13 to the reference axial line O, and depending on a distance of the first joint 12 from the first rotary shaft O12 to the inner wall S. However, since the beam spot B returns to an origin position if the rotation-driving motor 10 is rotated around once or more, the beam spot draws a substantially circular closed curve Q (including a case of a circular closed curve) as illustrated in FIG. 9A.

However, since the angle θ is 0 in the aligned state of the arm portion 8, the beam spot B converges to substantially a single point (including a case of a single point) on the point P. Here, as a case where the beam spot does not completely converge to a single point, for example, there is a case where an axis is deviated due to manufacturing errors of the first arm 11 and the second arm 13, or an error occurs in image processing.

Hereinafter, a description will be made assuming that a locus of the beam spot B is acquired as illustrated in FIG. 9A.

If the acquisition of the locus is completed, the locus acquisition control section 210 stops the rotation of the rotation-driving motor 10, stores an image of the closed curve Q in the locus storage section 212, and displays the image on the display section 7 as necessary.

In addition, the convergence operation control section 215 is notified that step S2 has been completed.

Through the operation, step S2 is completed.

The above steps S11 and S2 constitute the locus acquisition step of the present embodiment in which the laser luminous flux L having the optical axis OL parallel to the arm axial line O13 is emitted from the fiber end surface 17b disposed at the second arm 13 closer to the distal end than the first joint 12 in the arm portion 8, a rotation movement in which the arm proximal end 11a which is a supported part of the arm is rotated around the reference axial line O is performed, and the locus of the beam spot B based on the laser luminous flux L is acquired.

Next, step S3 is executed. This step is a step of calculating a diameter of the locus on the basis of the locus of the optical image.

The convergence operation control section 215 sends a control signal for starting acquisition of the locus to the convergence determination section 211.

The convergence determination section 211 reads the latest locus data acquired by the locus acquisition control section 210 from the locus storage section 212, performs an image processing, and computes a diameter of the closed curve Q. In the present embodiment, as an example, a diameter D (refer to FIG. 9A) which is the maximum diameter is computed. The computed diameter D is stored in a storage region of the convergence determination section 211 as a computation result.

A method of computing a diameter of the locus is not particularly limited. For example, there may be a method in which a distance between respective points of a locus on an image captured by the imaging section 9 is computed as the number of pixels, and the maximum distance is used as a diameter.

In addition, a diameter may be calculated by using a length of an arc or a formula of an area on the basis of a length or an area of a locus. As a method of calculating an area of a region surrounded by a locus, there may be a method in which an area is determined by connecting point sequences of an optical image in an image to each other and counting the number of pixels inside a boundary thereof. As a length of the locus may be determined by calculating a distance between adjacent points of optical images forming the locus as the number of pixels and using a sum of distances between the points.

Through the above-described operation, step S3 is completed.

Next, step S4 is executed. This step is a step of determining whether or not the diameter computed in step S3 has converged.

The convergence determination section 211 determines that the diameter does not converge in a case where the diameter D of the closed curve Q is larger than a determination threshold value, and sends information of the determination result and information of the diameter of the locus to the convergence operation control section 215 and displays the information on the display section 7 as necessary.

The notified convergence operation control section 215 finishes step S4 and proceeds to step S5.

The convergence determination section 211 determines that the diameter has converged in a case where the diameter D of the closed curve Q is equal to or smaller than the determination threshold value, and sends information of the determination result and information of the diameter of the locus to the convergence operation control section 215 and displays the information on the display section 7 as necessary.

The notified convergence operation control section 215 turns off the laser luminous flux L, and notifies the main body control unit 200 that the initialization of the arm portion 8 has been completed. Through the operation, the initialization of the arm portion 8 is finished.

The main body control unit 200 sets a rotating angle position of the first joint 12 at the time of receiving the notification of initialization completion, to an origin position of driving. Consequently, if a control signal for return to the origin is sent from the main body control unit 200 to the first joint 12, the reference state in which the arm axial line O11 of the first arm 11 and the arm axial line O13 of the second arm 13 are aligned with the reference axial line O is recreated.

Step S3 constitutes the convergence determination amount calculation step of the present embodiment in which a diameter of a locus is computed on the basis of the locus of the beam spot B as a predetermined physical quantity for determining a convergence state of the locus.

Step S4 constitutes the convergence determination step of the present embodiment in which, it is determined that the locus has converged in a case where a value of the computed physical quantity is the smallest after the convergence determination amount calculation step.

In addition, the convergence determination section 211 is a convergence determination section of the present embodiment which determines that the locus has converged in a case where a value of the computed physical quantity is the smallest, and is also used as a convergence determination amount calculation portion of the present embodiment which computes a diameter of the locus on the basis of the locus of the beam spot B.

Step S5 constitutes the driving amount correction step of the present embodiment, and is executed by steps S11 to S16 illustrated in FIG. 10 according to the flow shown in FIG. 10.

Step S11 is a step of storing the closed curve Q which is the locus of the beam spot B used for the determination in step S4 as a reference locus.

The convergence operation control section 215 reads the image data of the closed curve Q which is the locus of the beam spot B used for the determination in step S4 from the locus storage section 212, and sends the image data to the driving amount correction section 213 and also sends a control signal for starting the driving amount correction step executed by the driving amount correction section 213.

The driving amount correction section 213 stores the image data of the closed curve Q in a storage region of the driving amount correction section 213 as a reference locus.

Through the operation, step S11 is completed.

Next, step S12 is executed. This step sets a driving amount of the first joint 12 to a test-driving amount.

As the test-driving amount, a predetermined driving angle and a predetermined direction are set in advance and are stored in the storage section 214.

The driving amount correction section 213 reads the test-driving amount from the storage section 214, and sets the test-driving amount to a driving amount for driving the joint-driving motor 12A.

Through the operation, step S12 is completed.

Next, step S13 is executed. In this step, the first joint 12 is driven in the set driving amount while light irradiation is performed.

In this step, since the laser light source 17c is turned on, the convergence operation control section 215 sends a control signal for driving the first joint 12 in the set driving amount, to the driving amount correction section 213. At this time, a position of the rotation-driving motor 10 is fixed.

The driving amount correction section 213 sends a driving command value corresponding to the set driving amount to the first joint 12. Consequently, the first joint 12 is driven.

Therefore, the second arm 13 is rotated around the first rotary shaft O12, accordingly, the optical axis OL of the laser luminous flux L is rotated, thereby, a position of the beam spot B on the inner wall S is moved.

For example, as illustrated in FIG. 9B, the position of the beam spot B is moved to a position of a beam spot B1.

After the driving is completed, the convergence operation control section 215 sends a control signal for acquiring an image from the imaging section 9 and calculating a moved position (the position of the beam spot B1) of the beam spot B, to the locus acquisition control section 210. The locus acquisition control section 210 calculates coordinates of a point P1 corresponding to the position of the beam spot B1 and sends the coordinates to the convergence operation control section 215.

The convergence operation control section 215 sends the coordinates of the point P1 to the driving amount correction section 213.

Through the operation, step S14 is completed.

Next, step S15 is executed. This step determines whether the moved position of the optical image is located inside the reference locus or not.

The driving amount correction section 213 performs determination by comparing the coordinates of the point P1 with the coordinates of the closed curve Q as the reference locus.

In a case where the coordinates of the point P1 are located inside the closed curve Q, if rotational movement is performed in the set driving amount by the rotation-driving motor 10, a diameter of the locus is reduced, thereby the locus comes close to convergence.

Therefore, step S15 is completed, and the flow proceeds to step S1 of FIG. 8 and steps S1 to S5 are repeatedly executed.

In a case where the coordinates of the point P1 are located outside the closed curve Q (including a case where the coordinates are located on the closed curve Q), if rotational movement is performed in the set driving amount by the rotation-driving motor 10, a diameter of the locus is increased, thereby the locus becomes distant from convergence.

Therefore, the flow proceeds to step S16.

In the example illustrated in FIG. 9A, since the point P1 is located outside the closed curve Q, the flow proceeds to step S16.

Step S16 is a step of setting a driving amount such that an optical image is moved to the inside of the reference locus.

The driving amount correction section 213 calculates the shortest distance P1PQ ($=\Delta$) from the beam spot B1 to the closed curve Q on a straight line which connects the central point P1 of the beam spot B1 to the central point P0 of the closed curve Q, and sets a driving amount to $2\Delta-\delta$ (where $0<\delta<\Delta$) in order to move the beam spot B1 in an opposite direction to the previous movement direction.

If driving is performed again in such a driving amount, the beam spot B1 is moved from the point P1 to a point P2 in the same manner as a beam spot B2 in FIG. 9B and is moved to the inside of the closed curve Q.

For example, also in a case of a beam spot B1' which is moved to the outside of the closed curve Q after crossing the closed curve Q in the previous drive, the beam spot is moved to the inside of the closed curve Q in the same manner by using a distance P1'PQ' ($=\Delta$).

Through the operation, step S16 is completed.

After step S16 is completed, the flow proceeds to step S13, and steps S13 to S16 are repeatedly executed. In the repeated execution, for example, as illustrated in FIG. 9C, if the beam spot B1 is moved to the inside of the closed curve Q in the same manner as the beam spot B2, it is determined that the beam spot B1 is located inside the closed curve Q in step S15 so that step S5 is completed, thereby the flow proceeds to step S1 of FIG. 8.

As mentioned above, steps S11 to S16 constitute the driving amount correction step in which, in a case where it is determined that the locus does not converge in the convergence determination step, a driving amount for the bending joint which becomes a smaller diameter on the basis of a diameter computed in the convergence determination amount calculation step, and the bending joint is driven by the driving amount.

In the repeated steps S11 to S16, as illustrated in FIG. 9C, the beam spot B draws a closed curve Q' with a small diameter inside the closed curve Q, thereby a diameter of the closed curve Q' is reduced.

Through the repetition, since the angle θ of the first joint 12 with respect to the reference axial line O is corrected so as to gradually become 0, a diameter of the locus of the beam spot B is equal to or smaller than the determination threshold value so that the aligned state of the arm portion 8 is formed.

As mentioned above, according to the initialization method for the medical manipulator according to the present embodiment, the arm portion 8 is initialized to a reference state of being aligned with the reference axial line O in a state in which the arm portion 8 is inserted into the body cavity C. The reference state can be recreated as necessary by setting an origin in this state by the main body control unit 200.

In the reference state, since a position of the treatment portion 16 at the distal end of the arm portion 8 is located at a constant position within the imaging region of the imaging section 9, a relationship between a movement position and a driving amount has a predetermined relationship when operating the arm portion 8 while viewing an image captured by the imaging section 9. For this reason, control can be started from a state in which a position and orientation of the arm portion 8 is known, accordingly, an intuitive operation can be performed.

That is, since control of a position and orientation of the arm portion 8 can be started from a well-known state, the position and orientation of the arm portion 8 can be calculated on the basis of a displacement amount of a driving force transmission wire such as the driving wire or the like at each time point during the operation by starting the control from a state where a position and orientation of the arm portion 8 are known. Consequently, since a correspondence relationship between a position and orientation of the operation arm 2c handled by the operator and the position and orientation of the arm portion 8 is acquired, an operation can intuitively perform.

In addition, an operation is possible to reliably performed without applying an unnecessary load to the joints of the arm portion 8 or the driving wire by limiting a driving amount of the driving force transmission wire such as the driving wire or the like in order to prevent the driving force transmission wire such as the driving wire or the like from driving at over than a bendable angle of each joint of the arm portion 8, or prevent an interference with the endoscope or other treatment tools.

Further, according to the initialization method for the medical manipulator according to the present embodiment, it is possible to accurately perform initialization even if an encoder for positioning is not provided in the joint. For this reason, it is possible to simplify and miniaturize a configuration of the joint.

First Modified Example

Next, a description a medical manipulator and an initialization method for the medical manipulator of a first modified example of the present embodiment will be described.

Figure 11A:
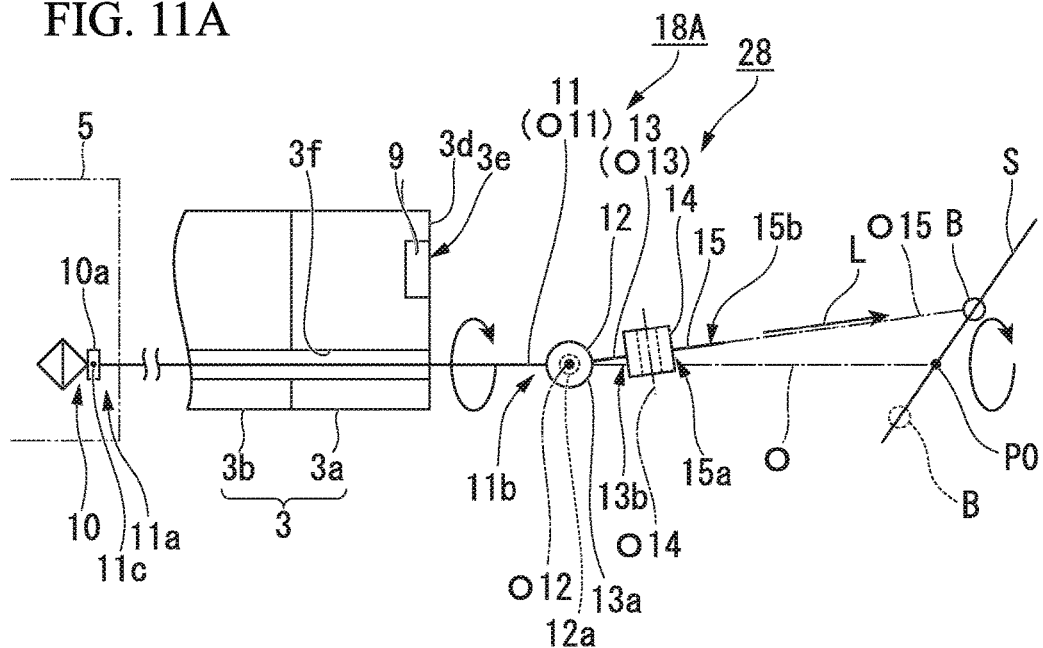
FIG. 11A is a schematic diagram of a front view illustrating configurations of main portions of a medical manipulator of a first modified example of the first embodiment of the present invention.
Figure 11B:
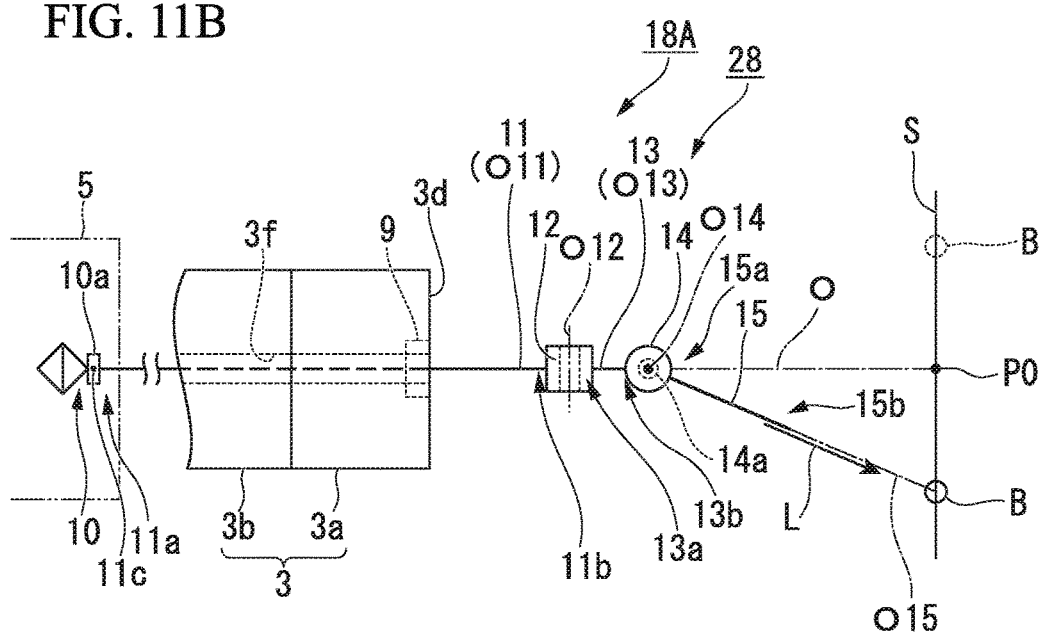
FIG. 11B is an operation explanatory diagram illustrating configurations of the main portions of the medical manipulator of the first modified example of the first embodiment of the present invention.
Figure 12:
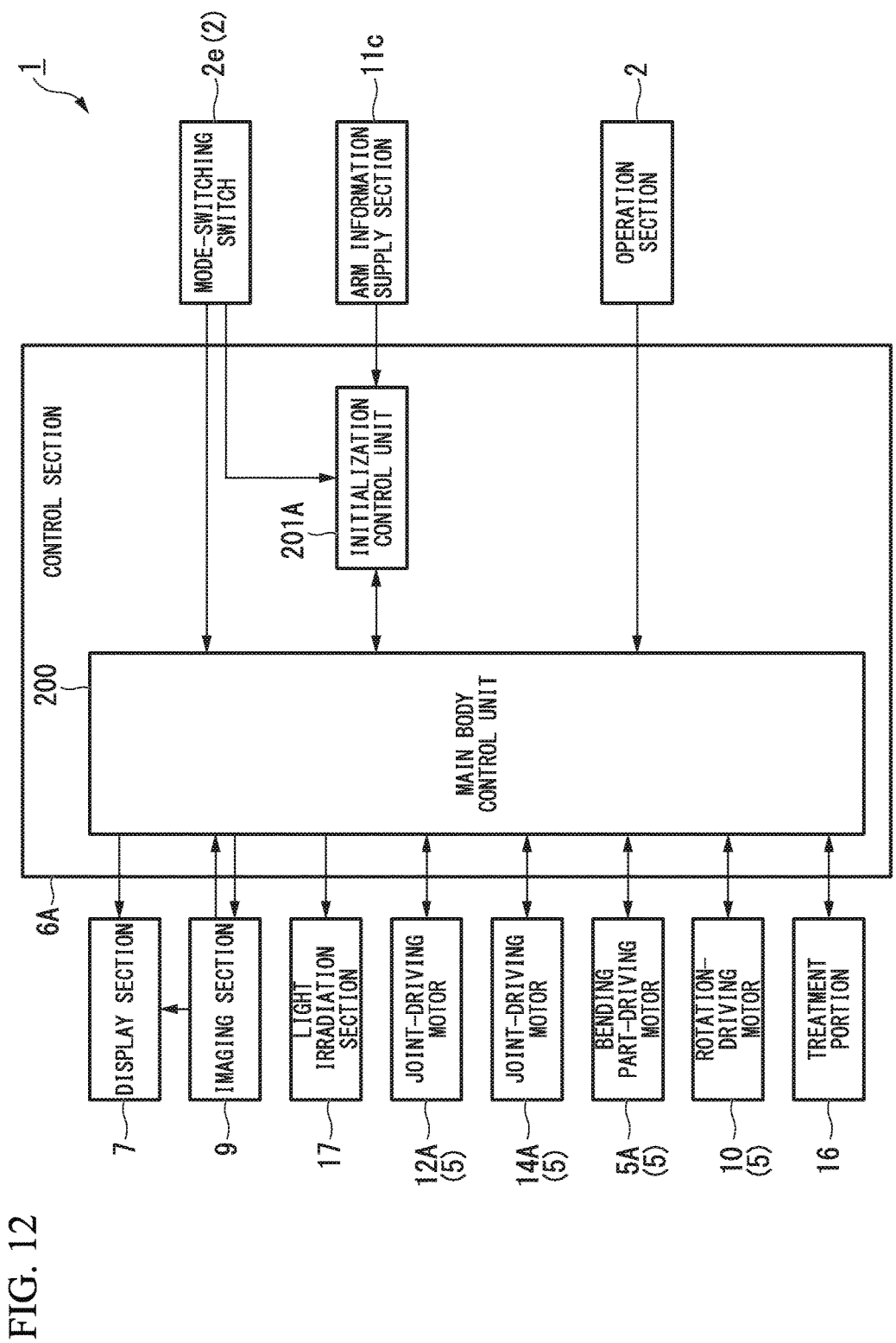
FIG. 12 is a functional block diagram illustrating a major functional configuration of a control section of the medical manipulator of the first modified example of the first embodiment of the present invention.
Figure 13:
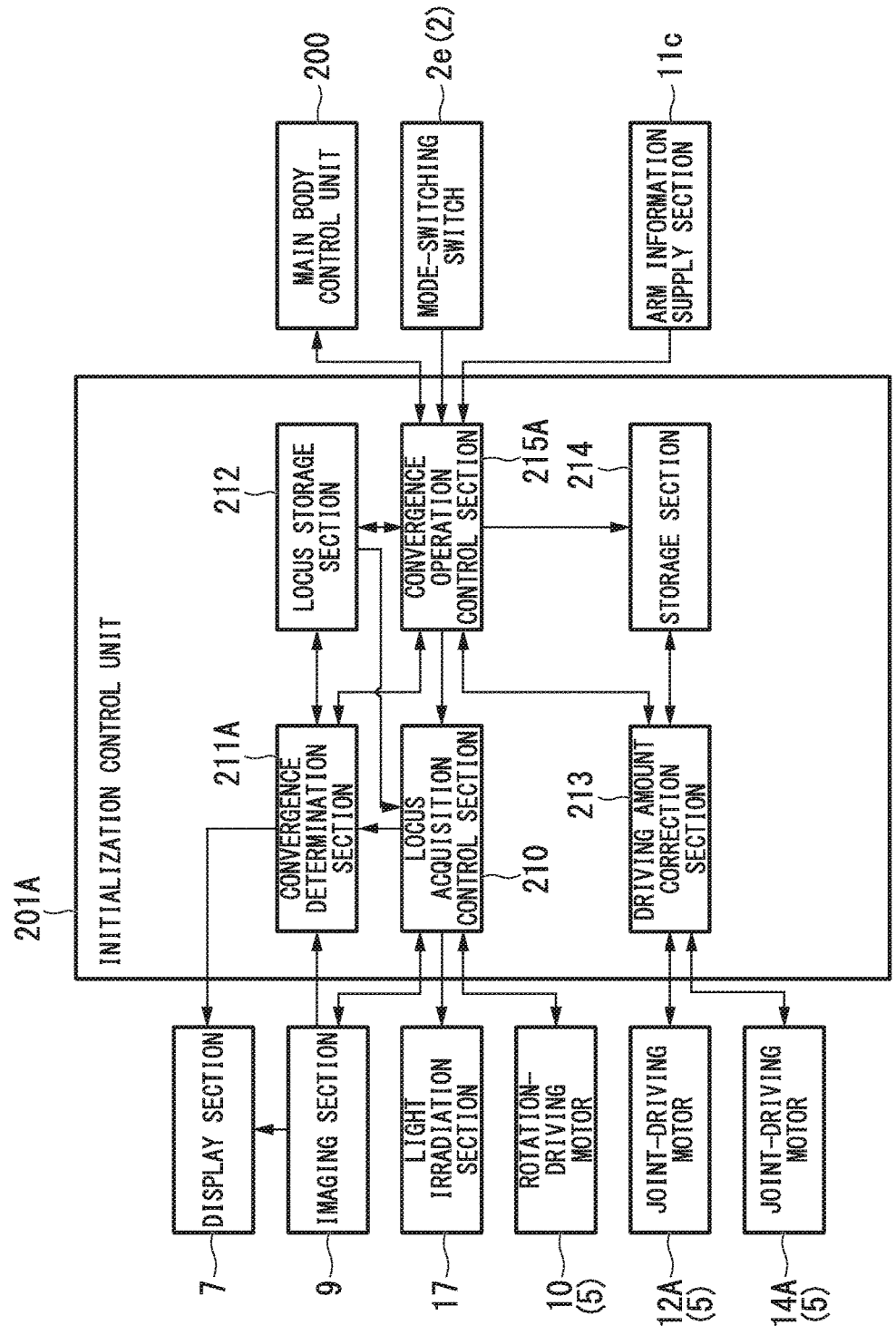
FIG. 13 is a functional block diagram illustrating a functional configuration of an initialization control unit of the medical manipulator of the first modified example of the first embodiment of the present invention.

FIGS. 11A and 11B are respectively a schematic diagram in a front view and an operation explanatory diagram illustrating configurations of main portions of the medical manipulator of the first modified example of the first embodiment of the present invention. FIG. 12 is a functional block diagram illustrating a major functional configuration of a control section of the medical manipulator of the first modified example of the first embodiment of the present invention. FIG. 13 is a functional block diagram illustrating a functional configuration of an initialization control unit of the medical manipulator of the first modified example of the first embodiment of the present invention.

As illustrated in FIG. 1, a surgery support robot 1A (medical manipulator) of the present modified example includes a surgery instrument 18A and a control section 6A instead of the surgery instrument 18 and the control section 6 of the above-described first embodiment.

Hereinafter, a description will be made focusing on differences from the first embodiment.

As main portions are schematically illustrated in FIGS. 11A and 11B, the surgery instrument 18A includes an arm portion 28 in which a second joint 14 (bending joint) and a third arm 15 (arm) are connected in this order to the arm distal end 13b of the arm portion 8 instead of the arm portion 8 of the first embodiment.

A position of the treatment portion 16 and the fiber end surface 17b of the arm portion 8 are changed to an arm distal end 15b of the third arm 15 with the same positional relationship as in the first embodiment as illustrated in FIGS. 3A and 3B in the present modified example.

As illustrated in FIGS. 11A and 11B, the second joint 14 is a rotary joint having a rotation body which is rotated around a second rotary shaft O14. A pulley 14a (refer to FIG. 11B) which transmits a rotation driving force from the proximal end side is provided at the rotation body of the second joint 14 on the same axis as that of the second rotary shaft O14.

A driving wire (driving force transmission wire) (not illustrated) which extends from the driving section 5 and inserted through the first arm 11, the first joint 12, and the second arm 13 is wound around the pulley 14a.

The driving wire is routed inside the insertion portion 3 (the first arm 11) in a state of being inserted into, for example, a coil sheath or the like, and is connected to the driving section 5 (a joint-driving motor 14A will be described later) on a proximal end side. For this reason, the pulley 14a and the rotation body to which the pulley 14a is fixed are configured to be rotated by pushing and pulling the driving wire in the longitudinal direction of the insertion portion 3 (the first arm 11) by the driving section 5 (the joint-driving motor 14A which will be described later).

The rotation body provided with the pulley 14a is connected to the third arm 15.

However, as illustrated in FIG. 11B, the second joint 14 is connected to the arm distal end 13b of the second arm 13 with a positional relationship of being perpendicular to the reference axial line O and the first rotary shaft O12. For this reason, the first joint 12 and the second joint 14 are not in a redundant relationship with each other.

The third arm 15 is a member extending along an arm axial line O15 (an axial line of the arm). In the present embodiment, as an example, a cylindrical member in which the arm axial line O15 is in a central axial line is employed.

An arm proximal end 15a of the third arm 15 is connected to the second joint 14 such that the third arm 15 can rotate around the second rotary shaft O14 at an intersection between the arm axial line O13 and the second rotary shaft O14.

For this reason, the arm axial line O15 can be aligned in a positional relationship of the same axis with the arm axial line O13 by adjusting a driving amount of the second joint 14.

As illustrated in FIGS. 3A and 3B, the optical fiber 17a and the treatment portion 16 of the present modified example are provided at the arm distal end 15b of the third arm 15 in the same positional relationship as at the arm distal end 13b of the second arm 13 of the first embodiment.

On the basis of the configuration of the arm portion 28, the arm information supply section 11c of the present modified example transmits configuration information of the arm portion 28 that "the number of bending joints is two", "there is no redundant joint", and "an offset amount is 0".

As illustrated in FIG. 12, the control section 6A is different from the control section 6 of the first embodiment in that an initialization control unit 201A (initialization control unit) is provided instead of the initialization control unit 201 of the first embodiment, and the main body control unit 200 is connected to the joint-driving motor 14A and is also capable of driving the joint-driving motor 14A.

Here, the joint-driving motor 14A is a motor for supplying a rotation driving force to the second joint 14. The joint-driving motor 14A is provided in the driving section 5, and constitutes a part of the driving section 5 in the same manner as the joint-driving motor 12A.

The initialization control unit 201A, as illustrated in FIG. 13, is different from the initialization control unit 201 of the first embodiment in that a convergence operation control section 215A and a convergence determination section 211A (convergence determination amount calculation portion) are provided instead of the convergence operation control section 215 and the convergence determination section 211 of the first embodiment, and the driving amount correction section 213 is connected to the joint-driving motor 14A and is also configured to correct a driving amount of the joint-driving motor 14A.

Control performed by the convergence operation control section 215A and the convergence determination section 211A will be described in descriptions of operations thereof.

Next, an operation of the surgery support robot 1A will be described focusing on an initialization method for the medical manipulator of the present modified example.

Figure 14:
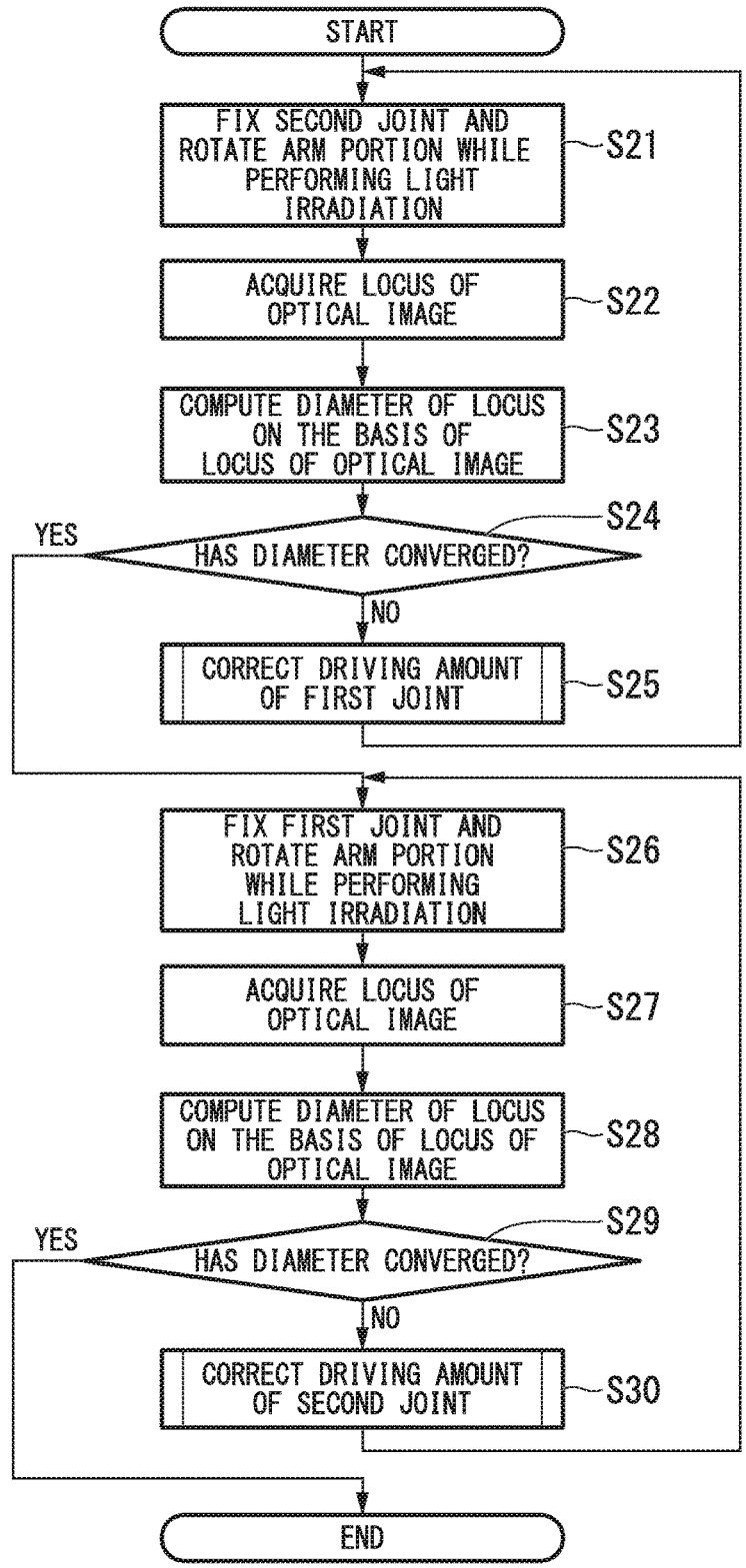
FIG. 14 is a flowchart illustrating a flow of an initialization method for the medical manipulator of the first modified example of the first embodiment of the present invention.

FIG. 14 is a flowchart illustrating a flow of an initialization method for the medical manipulator of the first modified example of the first embodiment of the present invention.

The surgery support robot 1A of the present modified example is different from the surgery support robot 1 of the first embodiment includes the arm portion 8 having only the first joint 12, the surgery support robot 1A of the present modified example is configured such that the arm portion 28 has the first joint 12 and the second joint 14 and the arm portion 28 can be bent in two-axis directions perpendicular to each other. Therefore, the method of initializing the arm portion 28 will be described focusing on differences from the first embodiment.

In the same manner as in the first embodiment, the initialization method for the medical manipulator of the present modified example includes a locus acquisition step, a convergence determination amount calculation step, a convergence determination step, and a driving amount correction step, and is performed by repeatedly performing the locus acquisition step, the convergence determination amount calculation step, the convergence determination step, and the driving amount correction step until a determination that a locus of an optical image using the laser luminous flux L converges.

These steps are executed by executing steps S21 to S30 illustrated in FIG. 14 according to the flow shown in FIG. 14.

Steps S21 to S25 are steps of aligning the arm axial line O13 with the reference axial line O by correcting a driving amount of the first joint 12 in the same manner as in the first embodiment while a driving amount of the second joint 14 is fixed.

Even in a case where the second arm 13 and the third arm 15 are bent by the second joint 14 as illustrated in FIG. 11B, the arm axial lines O13 and O15 are aligned on a straight line when viewed from the direction along the first rotary shaft O12 as illustrated in FIG. 11A. For this reason, as long as a driving amount of the second joint 14 is fixed, the beam spot B rotates while drawing a closed curve on the inner wall S when the rotation-driving motor 10 is rotated.

Therefore, the arm axial lines O11, O13 and O15 can be aligned with each other when viewed from the direction along the first rotary shaft O12 by executing the same steps as in the first embodiment are executed.

Steps S21 and S22 are the same as steps S1 and S2 of the first embodiment and constitute the locus acquisition step of the present modified example.

Step S23 is the same as step S3 of the first embodiment except for being executed by the convergence determination section 211A.

Step S24 is a step of determining whether or not the diameter computed in step S23 has converged.

However, in the present modified example, if the arm axial line O15 is bent with respect to the arm axial line O13, a locus of the beam spot B draws a closed curve centering on the point P0 even if the arm axial lines O13 and O15 are aligned with each other when viewed from the direction along the first rotary shaft O12. Since a diameter of the closed curve changes depending on an angle of the second joint 14, convergence cannot be determined in terms of an absolute value of the diameter.

The convergence determination section 211A has a determination threshold value of a diameter change width instead of a determination threshold value of a diameter absolute value as a determination threshold value. Alternatively, since a driving amount for driving the arm joint such that the beam spot B is located inside a closed curve of a locus is reduced according to convergence, the convergence determination section has a determination threshold value of the driving amount.

In addition, the convergence determination section 211A calculates a diameter change amount by comparing the diameter D of the closed curve Q computed in the same manner as in the first embodiment in step S23 with a latest value stored in the storage region, and compares the change amount with the determination threshold value. The latest value may be one value, but two or more values may be used in order to more reliably determine convergence.

In a case where the diameter change amount is larger than the determination threshold value, it is determined that the diameter does not converge, and information of the determination result and information of the diameter of the locus are sent to the convergence operation control section 215A and the information are displayed on the display section 7 as necessary.

The notified convergence operation control section 215 finishes step S24 and proceeds to step S25.

The convergence determination section 211A determines that the diameter has converged in a case where the diameter change amount is equal to or smaller than the determination threshold value, and sends information of the determination result and information of the diameter of the locus to the convergence operation control section 215A and the information are displayed on the display section 7 as necessary.

According to the convergence determination section 211A, it is possible to determine a convergence state in both a case that the diameter D of the closed curve Q converges to a constant value and a case that the diameter D converges to one point such as the point P0.

The notified convergence operation control section 215A proceeds to step S25.

Steps S23 and S24 constitute the convergence determination amount calculation step and the convergence determination step of the present modified example.

Step S25 is the same as step S5 of the first embodiment, and is executed by correcting a driving amount of the first joint 12 while a driving amount of the second joint 14 is fixed. Specifically, steps S11 to S16 of FIG. 10 are executed.

This step constitutes the driving amount correction step of the present modified example.

In the above-described way, steps S21 to S25 are executed, and if convergence of the diameter is determined in step S24, there is a positional relationship in which the arm axial lines O11 and O13 are aligned on the reference axial line O.

Steps S26 to S30 are steps of aligning the arm axial line O15 with respect to the arm axial line O13 which has already been aligned with the reference axial line O by correcting the driving amount of the second joint 14 in the same manner as in the first embodiment while fixing a driving amount of the first joint 12.

In a case where the second arm 13 and the third arm 15 are bent by the second joint 14, if the arm axial line O13 is aligned with the reference axial line O, the arm axial line O15 is also aligned with the reference axial line O when viewed from the direction along the first rotary shaft O12. However, as illustrated in FIG. 11B, when viewed from the direction along the second rotary shaft O14, the arm axial line O15 is bent with respect to the arm axial line O13. For this reason, as long as the driving amount of the first joint 12 is fixed, the beam spot B rotates while drawing a closed curve on the inner wall S according to an angle of the second joint 14 causing such bending when the rotation-driving motor 10 is rotated.

Since the arm axial lines O11 and O13 which have already aligned with the reference axial line O can be regarded as an axial line of a single arm, the arm axial lines O11, O13 and O15 can be aligned with each other by executing the same step as in the first embodiment.

Steps S26 and S27 are the same as steps S1 and S2 of the first embodiment, and constitute the locus acquisition step of the present modified example.

Step S28 is the same as step S3 of the first embodiment except for being executed by the convergence determination section 211A.

Step S29 is a step for determining whether or not the diameter computed in step S28 has converged, and is the same as step S4 of the first embodiment except for being executed by the convergence determination section 211A and the flow proceeds to step S30 in a case where convergence is not determined.

Steps S28 and S29 constitute the convergence determination amount calculation step and the convergence determination step of the present modified example.

Step S30 is the same as step S5 of the first embodiment, and is executed by correcting a driving amount of the second joint 14 while a driving amount of the first joint 12 is fixed. Specifically, steps S11 to S16 of FIG. 10 are executed.

This step constitutes the driving amount correction step of the present modified example.

In the above-described way, the arm axial lines O11, O13 and O15 are aligned on the reference axial line O by executing the steps S26 to S30.

Through the operation, the initialization method for the medical manipulator of the present modified example is finished.

According to the surgery support robot 1A of the present modified example, since the arm portion 28 can be initialized as mentioned above, control can be started from a state in which a position and orientation of the arm portion 28 is known, accordingly, an intuitive operation can be performed.

The present modified example is an example in which, in a case where a redundant joint is not provided and an offset amount is 0, even if a plurality of bending joints are provided, initialization can be performed if the arm portion 28 has only to be rotationally moved by the rotation-driving motor 10.

Second Modified Example

Next, a medical manipulator and an initialization method for the medical manipulator of a second modified example of the present embodiment will be described.

Figure 15A:
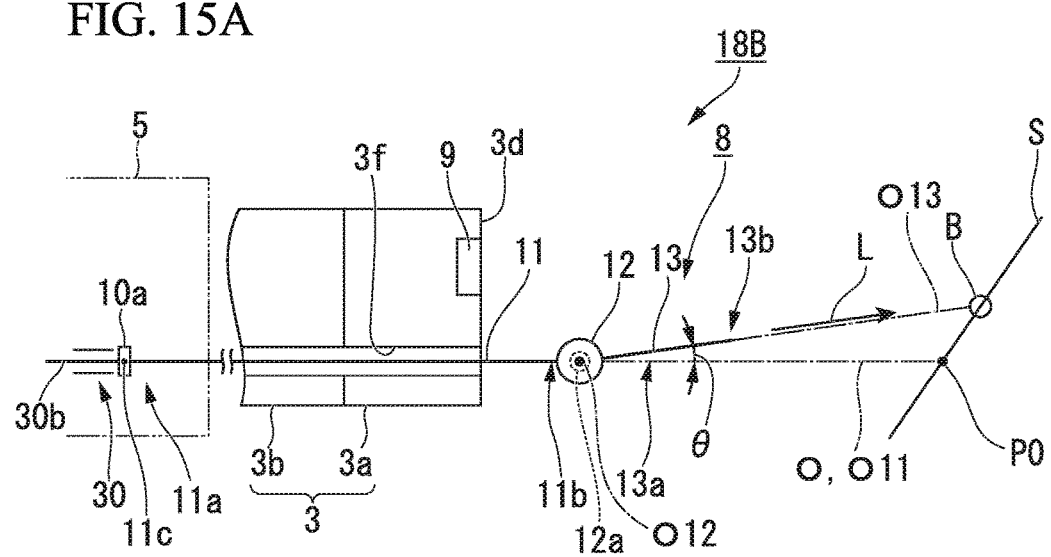
FIG. 15A is a schematic diagram of a front view illustrating configurations of main portions of a medical manipulator of a second modified example of the first embodiment of the present invention.
Figure 15B:
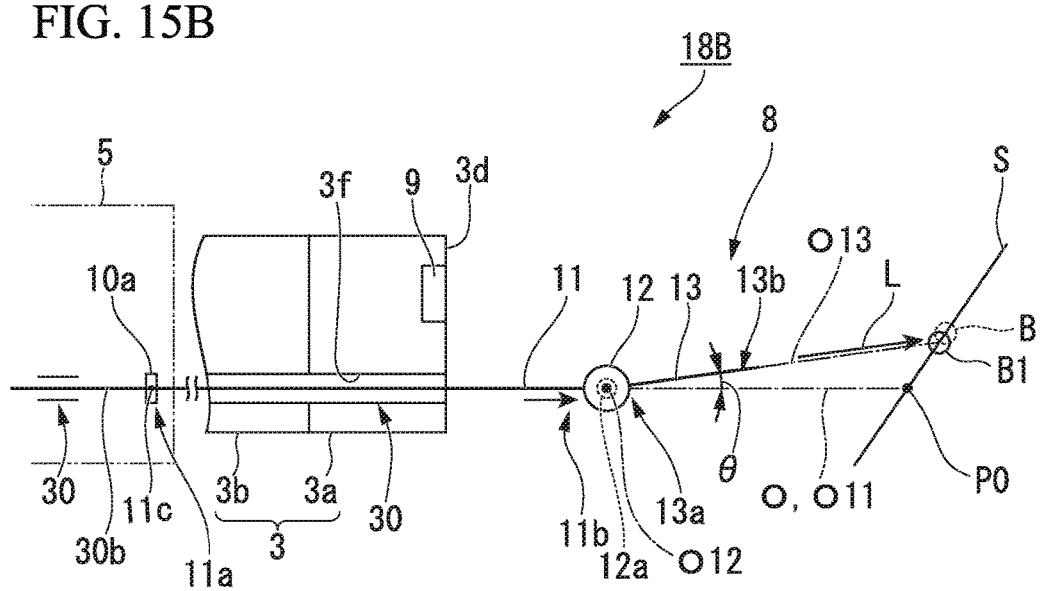
FIG. 15B is an operation explanatory diagram illustrating configurations of the main portions of the medical manipulator of the second modified example of the first embodiment of the present invention.
Figure 16:
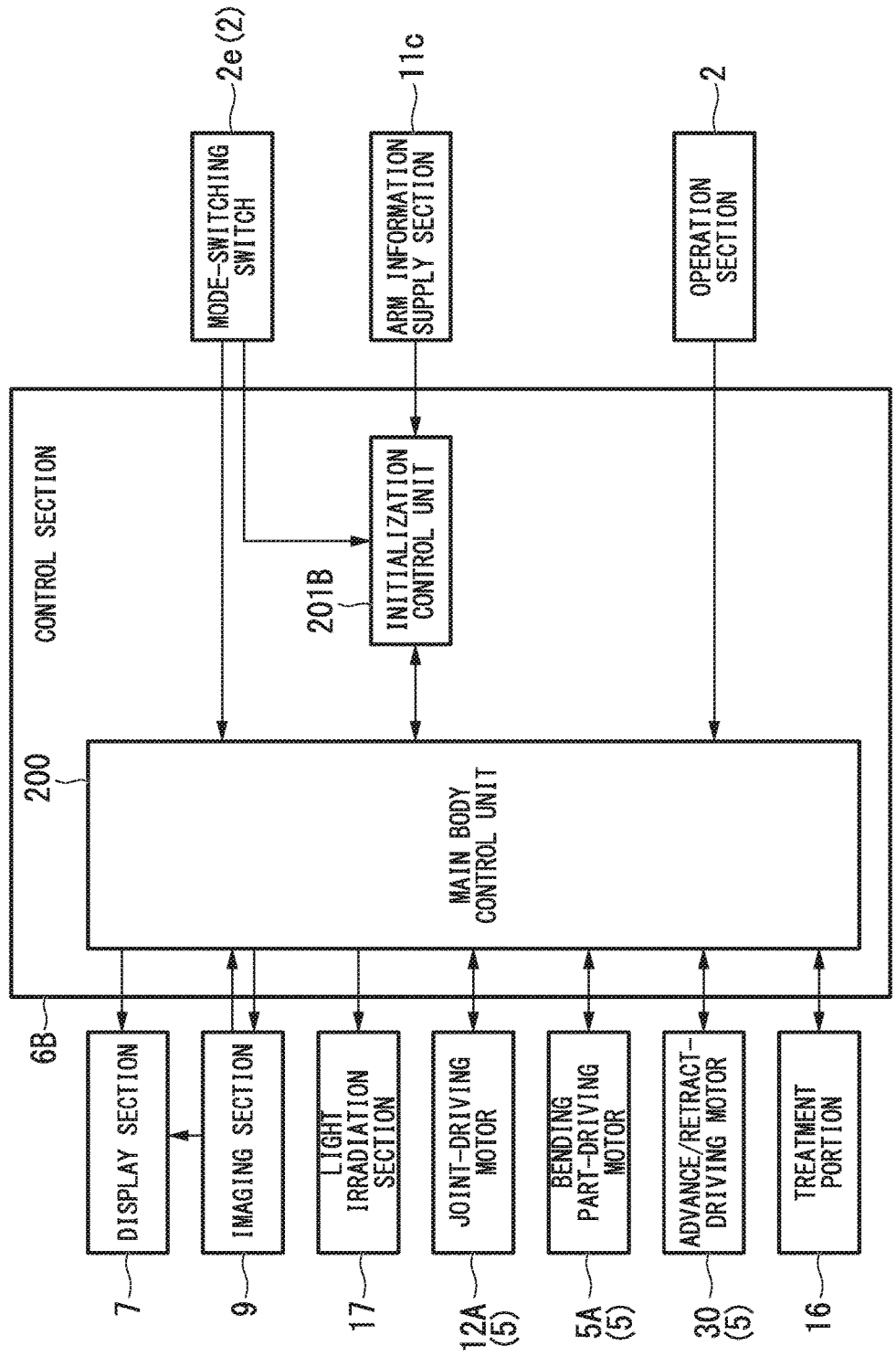
FIG. 16 is a functional block diagram illustrating a major functional configuration of a control section of the medical manipulator of the second modified example of the first embodiment of the present invention.

FIGS. 15A and 15B are respectively a schematic diagram in a front view and an operation explanatory diagram illustrating configurations of main portions of the medical manipulator of the second modified example of the first embodiment of the present invention. FIG. 16 is a functional block diagram illustrating a major functional configuration of a control section of the medical manipulator of the second modified example of the first embodiment of the present invention.

As illustrated in FIG. 1, a surgery support robot 1B (medical manipulator) of the present modified example includes a surgery instrument 18B and a control section 6B instead of the surgery instrument 18 and the control section 6 of the above-described first embodiment.

Hereinafter, a description will be made focusing on differences from the first embodiment.

As main portions are schematically illustrated in FIGS. 15A and 15B, the surgery instrument 18B includes an advance/retract-driving motor 30 (an advance/retract movement portion or a movement portion) instead of the rotation-driving motor 10 of the driving section 5 of the first embodiment.

The advance/retract-driving motor 30 is a motor which drives an advance/retract shaft 30b to advance and retracted in a shaft direction thereof on the basis of a control signal. A distal end of the advance/retract shaft 30b is connected to the arm proximal end 11a of the first arm 11 via the connection portion 10a which is the same as in the first embodiment.

Consequently, if the advance/retract-driving motor 30 is driven, the entire first arm 11 advances or retracts along the channel 3f. As a result, the arm distal end 11b of the first arm 11 configured to advance and retract along the reference axial line O of the channel 3f at the distal end rigid part 3a.

For this reason, the arm distal end 11b of the first arm 11 is supported at the distal end rigid part 3a so as to advance and retract on the reference axial line O. When advance-retract movement is performed, the arm axial line O11 of the first arm 11 is disposed on the same axis as the reference axial line O.

The advance/retract-driving motor 30 of the present modified example constitutes an advance/retract movement portion which moves the arm proximal end 11a of the first arm 11 along the reference axial line O which is substantially along the longitudinal direction of the insertion portion 3. The arm proximal end 11a of the first arm 11 is a supported part of the arm portion 8 supported at the distal end rigid part 3a.

As illustrated in FIG. 16, the control section 6B is different from the control section 6 of the first embodiment in that an initialization control unit 201B is provided instead of the initialization control unit 201 of the first embodiment, and the main body control unit 200 is connected to the advance/retract-driving motor 30 and is also capable of driving the advance/retract-driving motor 30.

Figure 17:
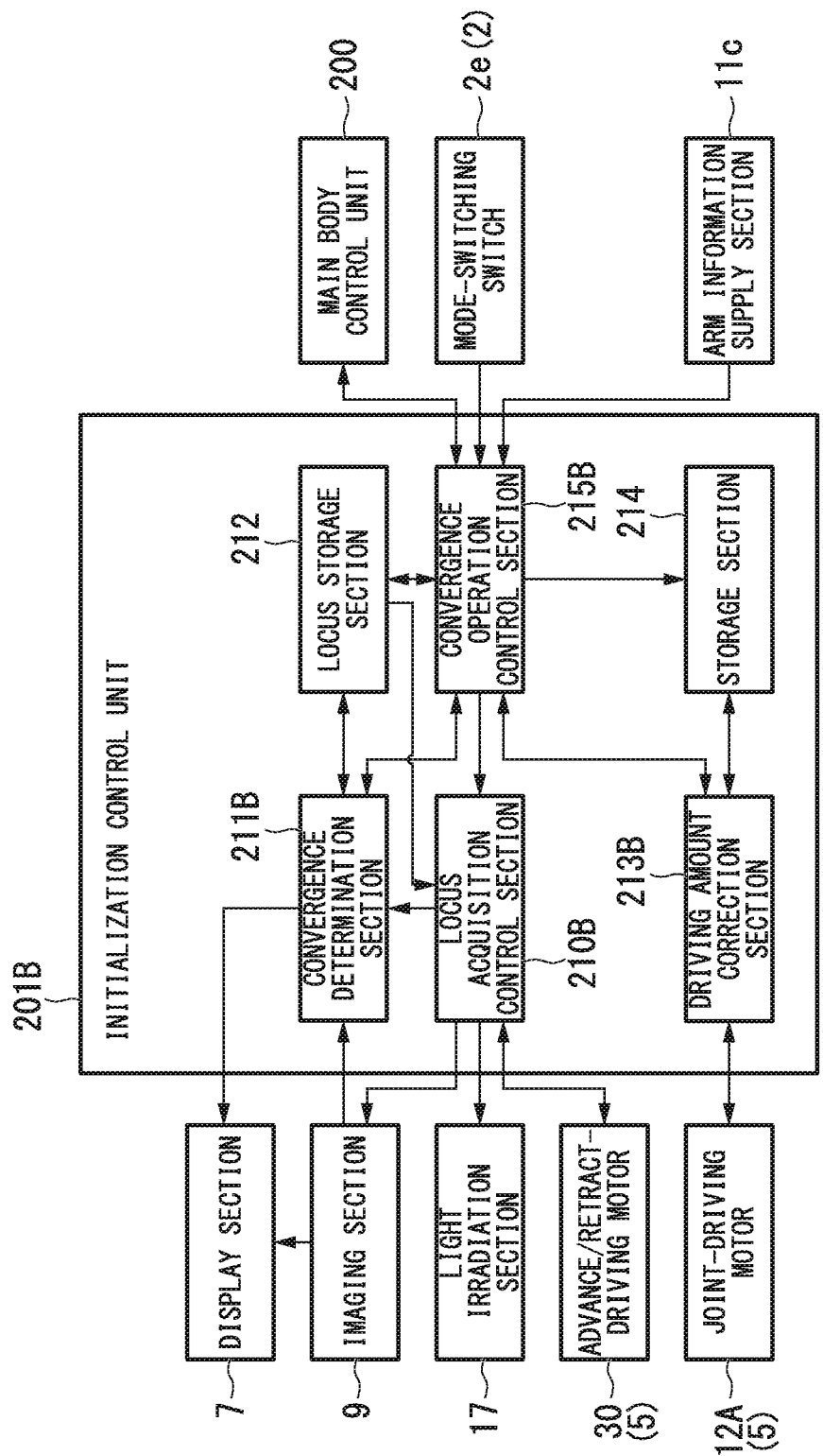
FIG. 17 is a functional block diagram illustrating a functional configuration of initialization control of the medical manipulator of the second modified example of the first embodiment of the present invention.

As illustrated in FIG. 17, the initialization control unit 201B is different from the initialization control unit 201 of the first embodiment in that a convergence operation control section 215B, a convergence determination section 211B (convergence determination amount calculation portion), and a driving amount correction section 213B are provided instead of the convergence operation control section 215, the convergence determination section 211, and the driving amount correction section 213 of the first embodiment.

Control performed by the convergence operation control section 215B, the convergence determination section 211B, and the driving amount correction section 213B will be described in descriptions of operations thereof.

Next, an operation of the surgery support robot 1B will be described focusing on an initialization method for the medical manipulator of the present modified example.

Figure 18:
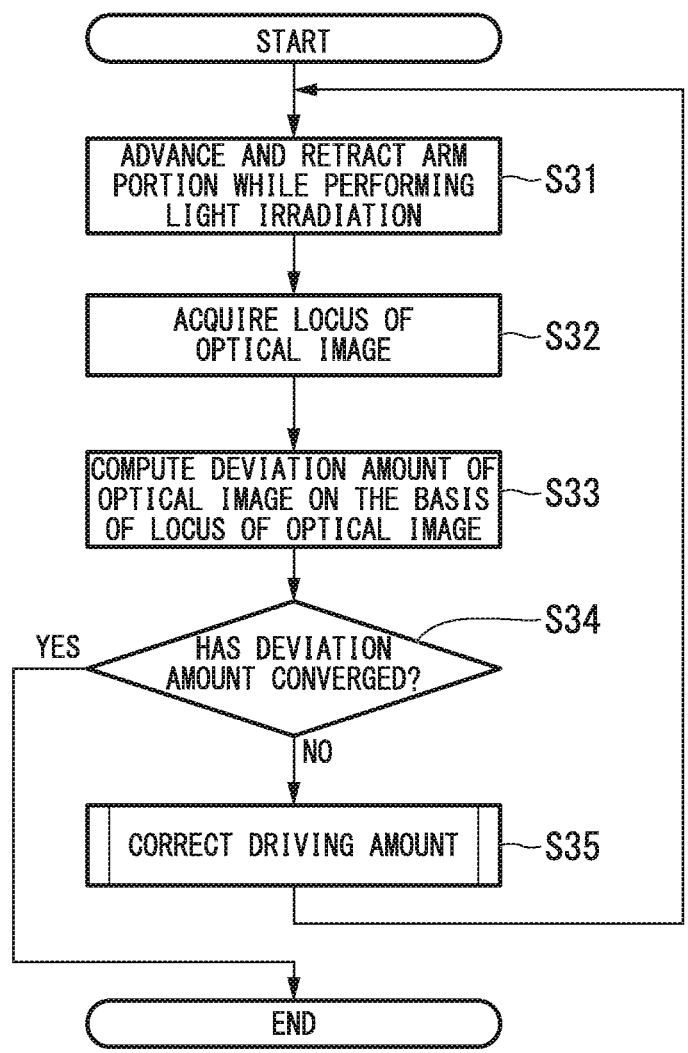
FIG. 18 is a flowchart illustrating a flow of an initialization method for the medical manipulator of the second modified example of the first embodiment of the present invention.
Figure 19A:
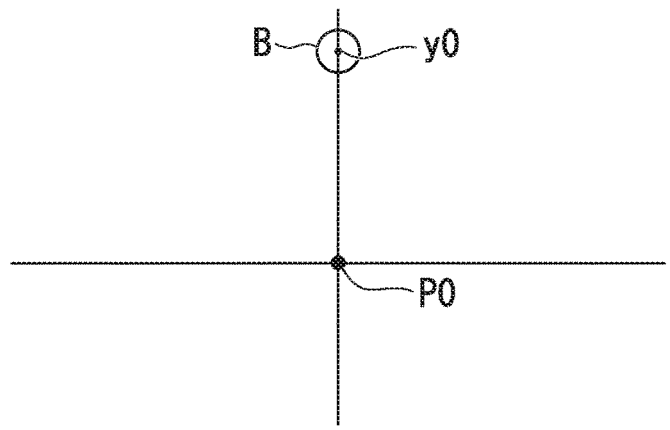
FIG. 19A is a schematic diagram illustrating an example of a locus of an optical image in the initialization method for the medical manipulator of the second modified example of the first embodiment of the present invention.
Figure 19B:
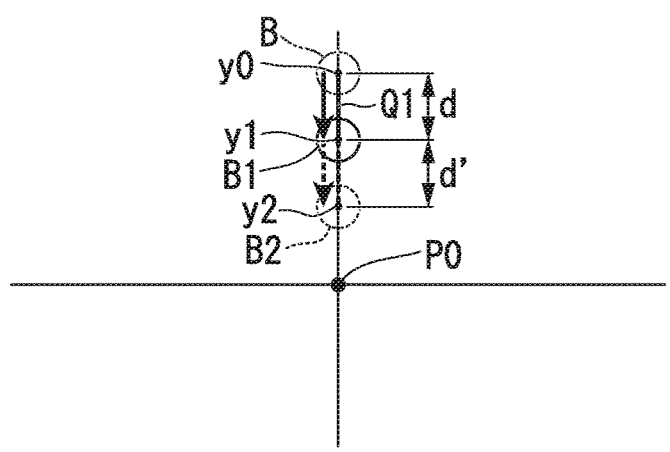
FIG. 19B is a schematic diagram illustrating an example of a locus of an optical image in the initialization method for the medical manipulator of the second modified example of the first embodiment of the present invention.
Figure 19C:
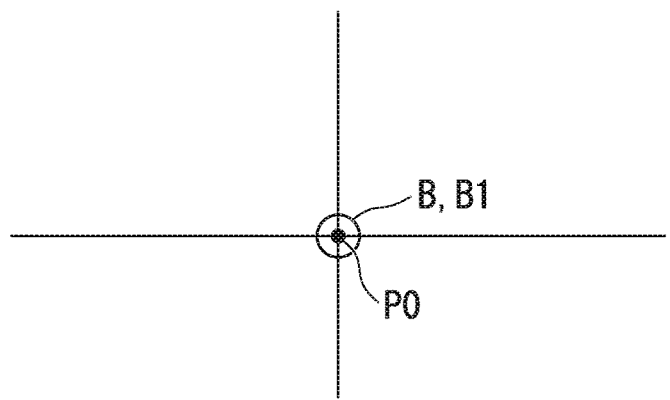
FIG. 19C is a schematic diagram illustrating an example of a locus of an optical image in the initialization method for the medical manipulator of the second modified example of the first embodiment of the present invention.
Figure 20:
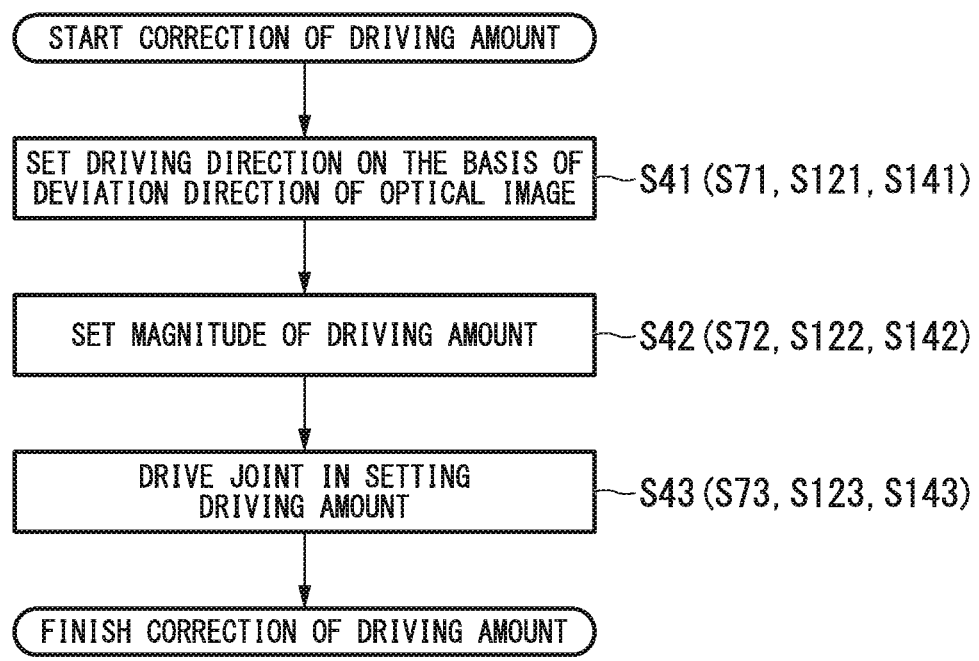
FIG. 20 is a flowchart illustrating a flow of a driving amount correction step in the initialization method for the medical manipulator of the second modified example of the first embodiment of the present invention.

FIG. 18 is a flowchart illustrating a flow of an initialization method for the medical manipulator of the second modified example of the first embodiment of the present invention. FIGS. 19A, 19B and 19C are schematic diagrams illustrating examples of loci of optical images in the initialization method for the medical manipulator of the second modified example of the first embodiment of the present invention. FIG. 20 is a flowchart illustrating a flow of a driving amount correction step in the initialization method for the medical manipulator of the second modified example of the first embodiment of the present invention.

The surgery support robot 1B of the present modified example is only different from the first embodiment in that the surgery support robot 1B of the present modified example performs advance/retract movement by the advance/retract-driving motor 30 in an initialization operation, instead of the surgery support robot 1 of the first embodiment which performs rotational movement by the rotation-driving motor 10 Therefore, the method of initializing the arm portion 8 will be described focusing on differences from the first embodiment.

In the same manner as in the first embodiment, the initialization method for the medical manipulator of the present modified example includes a locus acquisition step, a convergence determination amount calculation step, a convergence determination step, and a driving amount correction step, and is performed by repeatedly performing the locus acquisition step, the convergence determination step, and the driving amount correction step until it is determined that a locus of an optical image using the laser luminous flux L converges.

These steps are executed by executing steps S31 to S35 illustrated in FIG. 18 according to the flow shown in FIG. 18.

In step S31, the arm portion 8 is advanced or retracted while performing a light irradiation.

In this step, a control signal is sent from the convergence operation control section 215B to a locus acquisition control section 210B, and the locus acquisition control section 210B starts control.

The locus acquisition control section 210B turns on the laser light source 17c of the light irradiation section 17 in the same manner as in the first embodiment.

Next, the locus acquisition control section 210B sends a control signal to the advance/retract-driving motor 30, and starts driving of the advance/retract-driving motor 30 such that the advance/retract shaft 30b is moved by a predetermined distance in a predefined direction.

Through the operation, step S31 is completed.

Next, step S32 is executed. This step is a step of acquiring, a locus of an optical image.

The locus acquisition control section 210B acquires an image captured by the imaging section 9 while the arm portion 8 is moved in step S31, performs image processing on the image, and acquires a locus.

Although there is a difference in that the locus is substantially linearly formed in the present modified example, but a method of acquiring a locus may be employ the same acquisition method as in the locus acquisition control section 210 of the first embodiment.

In this step, a state of a rotating angle of the first joint 12 is unclear, and an angle between the first arm 11 and the second arm 13 is also unclear. For example, as illustrated in FIG. 15A, supposing that the arm axial line O13 is in a state of being bent with an angle θ with respect to the reference axial line O.

In such a state in which the arm portion 8 is bent, as illustrated in FIG. 19A, the beam spot B is projected onto a position of a point y0 which is far upward on the screen of the imaging section 9 from the point P0 on the inner wall S. In this case, as illustrated in FIG. 15B, if the advance/retract shaft 30b is advanced toward the inner wall S side, the beam spot B comes close to the point P0 like a beam spot B1.

In this case, as illustrated in FIG. 19B, the locus acquisition control section 210B acquires a linear locus Q1 which is directed from the top toward the lower side from the point y0 to a point y1.

Hereinafter, as an example, a case where the advance/retract shaft 30b is advanced will be described, but in a case where the advance/retract shaft 30b is retracted, the beam spot B moves in a reverse direction, and thus all directions may be reversed.

If acquisition of the locus is completed, the locus acquisition control section 210B stores the locus Q1 in the locus storage section 212 and displays the locus on the display section 7 as necessary.

In addition, the convergence operation control section 215B is notified that step S32 has been completed.

Through the operation, step S32 is completed.

The above steps S31 and S32 constitute the locus acquisition step of the present modified example in which the laser luminous flux L having the optical axis OL parallel to the arm axial line O13 is emitted from the fiber end surface 17b disposed at the second arm 13 closer to the distal end than the first joint 12 in the arm portion 8, an advance-retract movement in which the arm proximal end 11a which is a supported part of the arm is advanced or retracted along the reference axial line O is performed, and the locus of the beam spot B based on the laser luminous flux L is acquired.

Next, step S33 is executed. This step is a step of calculating a deviation amount of the locus of the optical image which is a physical quantity for determining a convergence state of the locus on the basis of the locus of the optical image.

The convergence operation control section 215B sends a control signal for starting acquisition of the locus to the convergence determination section 211B.

The convergence determination section 211B reads the latest locus data acquired by the locus acquisition control section 210B from the locus storage section 212, performs an image processing, and computes a length d (refer to FIG. 19B) of the locus Q1 as the magnitude of the deviation amount of the optical image.

Central positions of the optical image before and after moving may be represented by coordinates in the pixel unit on the image, and a distance therebetween may be computed as the deviation amount of the optical image.

The computed length d is stored in the storage region of the convergence determination section 211 along with a movement direction of the beam spot B.

Through the operation, step S33 is completed.

Next, step S34 is executed. This step is a step of determining whether or not the deviation amount computed in step S33 has converged.

If the arm axial line O13 is aligned with the reference axial line O, as illustrated in FIG. 19C, the movement amount d becomes 0 regardless of an advance-retract movement amount.

For this reason, the convergence determination section 211B determines that the deviation amount has converged in a case where the length d, which is the magnitude of the deviation amount of the beam spot B, is equal to or less than a predefined determination threshold value. The determination threshold value is set to an appropriate value close to 0 in advance by taking into consideration an alignment limit of the arm axial lines O11 and O13 caused by a manufacturing error of the arm portion 8 or a calculation error in a locus of an optical image.

The convergence determination section 211B determines that the deviation amount does not converge in a case where the length d of the locus Q1 is more than the determination threshold value, and sends information of the determination result and information of the magnitude of the deviation amount to the convergence operation control section 215B, and displays the information on the display section 7 as necessary.

The notified convergence operation control section 215B finishes the step S34 and proceeds to step S35.

The convergence determination section 211B determines that the deviation amount has converged in a case where the length d of the locus Q1 is equal to or less than the determination threshold value, and sends information of the determination result and information of the diameter of the locus to the convergence operation control section 215 and displays the information on the display section 7 as necessary.

The notified convergence operation control section 215B turns off the laser luminous flux L, and notifies the main body control unit 200 that the initialization of the arm portion 8 has been completed. Through the operation, the initialization of the arm portion 8 is finished.

The main body control unit 200 sets a rotating angle position of the first joint 12 at the time of receiving the notification of initialization completion, to an origin position of driving. Consequently, if a control signal for return to the origin is sent from the main body control unit 200 to the first joint 12, the reference state in which the arm axial line O11 of the first arm 11 and the arm axial line O13 of the second arm 13 are aligned with the reference axial line O is recreated.

Step S33 constitutes the convergence determination amount calculation step of the present modified example in which a deviation amount of an optical image is computed on the basis of the locus of the beam spot B as a predetermined physical quantity for determining a convergence state of the locus.

Step S34 constitutes the convergence determination step of the present modified example in which, it is determined that the locus has converged in a case where a value of the computed physical quantity is the smallest after the convergence determination amount calculation step.

Step S35 constitutes the driving amount correction step of the present modified example, and is executed by steps S41 to S43 illustrated in FIG. 20 according to the flow shown in FIG. 20.

Step S41 is a step of setting a driving direction on the basis of a deviation direction of the optical image when the locus of the optical image is acquired in step S32.

The driving amount correction section 213B sets a deviation direction of the first joint 12 on the basis of the deviation amount of the beam spot B computed by the convergence determination section 211B.

For example, supposing that the beam spot B deviates from the locus Q1 by the length d from the point y0 toward the point y1 from the top to the lower side due to movement using the advance/retract-driving motor 30 as illustrated in FIG. 19B, the arm axial line O13 is rotated counterclockwise in FIG. 15B centering on the first rotary shaft O12 as illustrated in FIG. 15B. For this reason, a driving direction of the first joint 12 is a clockwise direction in accordance with the movement direction of the beam spot B as illustrated in FIG. 15B.

Through the operation, step S41 is completed.

Next, step S42 is executed. The step is a step of setting the magnitude of a driving amount.

The magnitude of a driving amount of the first joint 12 is set to the magnitude smaller than the magnitude of a driving amount when the locus Q1 is acquired. For example, the magnitude thereof is set to the magnitude being subtracted by a predetermined amount from the magnitude of the driving amount when the locus Q1 is acquired, or the magnitude in which the magnitude of a driving amount when the locus Q1 is acquired is multiplied by a coefficient of below 1.

Through the operation, step S42 is completed.

Next, step S43 is executed. This step is a step of driving the first joint 12 with the driving amount set in step S42.

The driving amount correction section 213B sends a driving command value corresponding to the set driving amount to the first joint 12. Consequently, the first joint 12 is driven.

For example, as illustrated in FIG. 19B, the beam spot B1 located at the point y1 moves to the point y2 close to the point P0 (refer to a beam spot B2 in FIG. 19B).

Through the operation, step S43 is completed. Consequently, step S35 is completed, and the flow proceeds to step S31 of FIG. 18.

Through the repetition of executing steps S31 to S35 in the above-described manner, since the angle θ of the arm axial line O13 of the second arm 13 with respect to the reference axial line O is corrected so as to gradually become 0, a deviation amount of the beam spot B is equal to or smaller than the determination threshold value so that the aligned state of the arm portion 8 is formed.

According to the surgery support robot 1B of the present modified example, since the arm portion 8 can be initialized as mentioned above, control can be started from a state in which a position and orientation of the arm portion 8 is known, accordingly, an intuitive operation can be performed.

The present modified example is an example in which, in a case where a redundant joint is not provided and an offset amount is 0, initialization can be performed if the arm portion 8 has only to be advanced or retracted by the advance/retract-driving motor 30.

Second Embodiment

Next, a medical manipulator and an initialization method for the medical manipulator of a second embodiment of the present invention will be described.

Figure 21A:
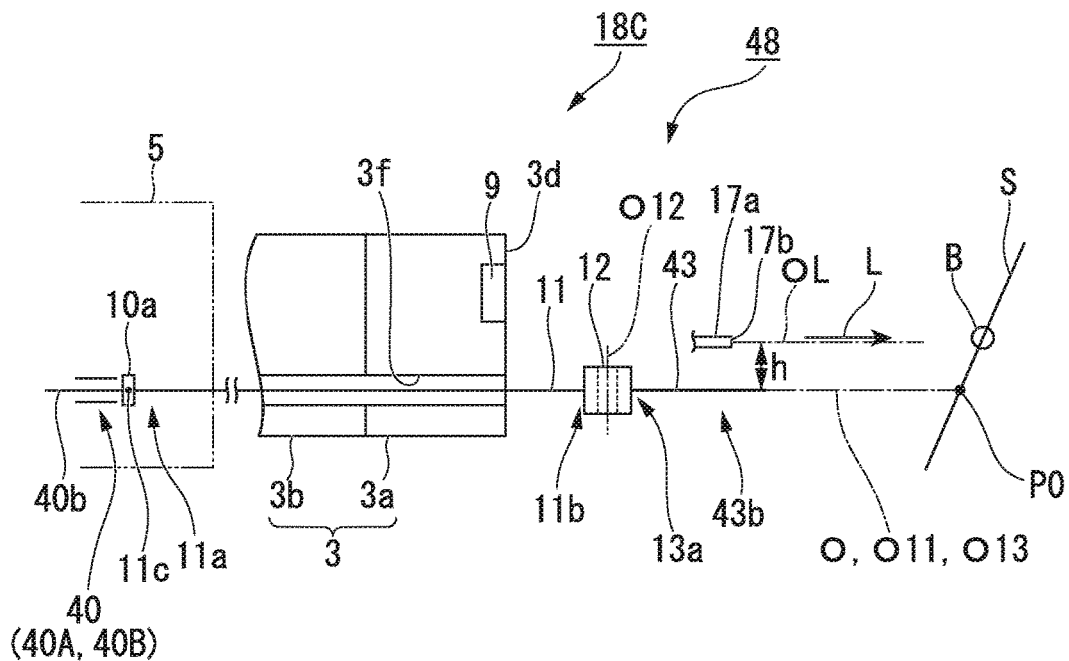
FIG. 21A is a schematic diagram in a plan view illustrating configurations of main portions of the medical manipulator of a second embodiment of the present invention.
Figure 21B:
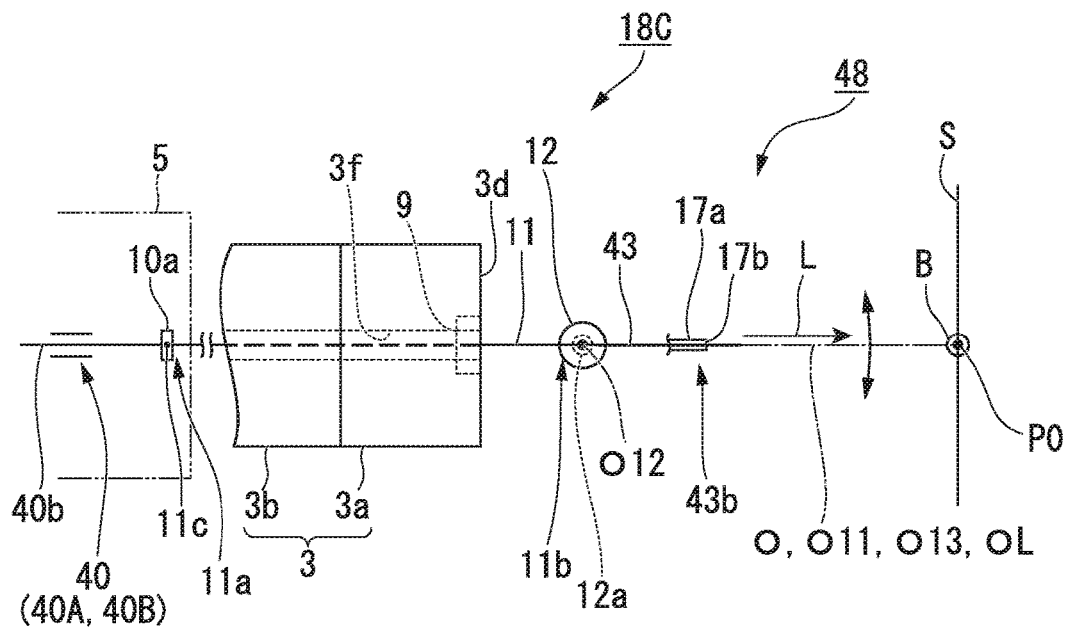
FIG. 21B is an operation explanatory diagram illustrating configurations of the main portions of the medical manipulator according to the second embodiment of the present invention.
Figure 22A:
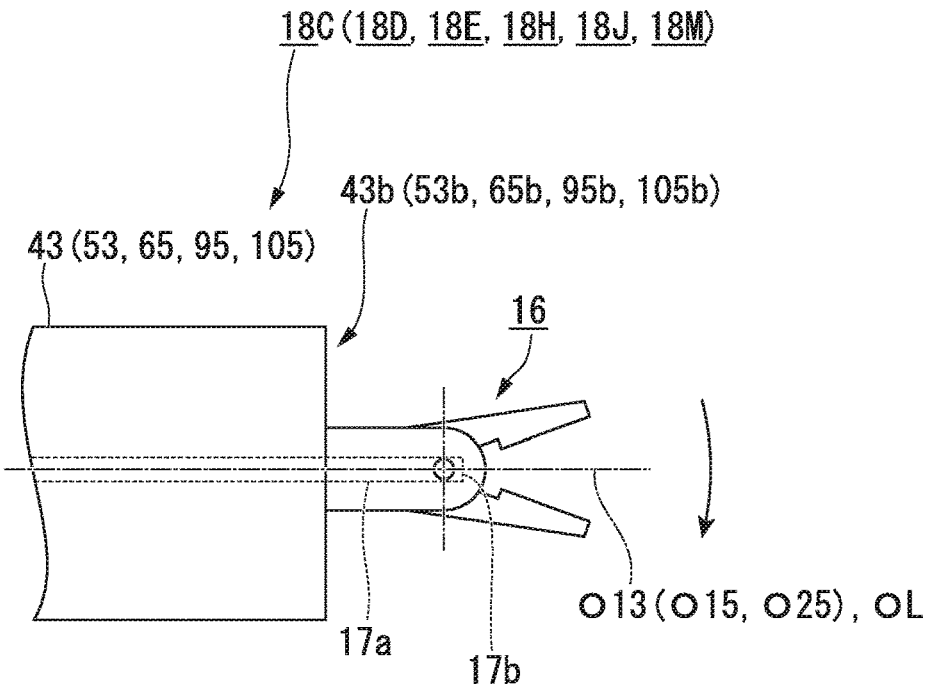
FIG. 22A is a schematic front view for explaining an arrangement of a light irradiation section of the medical manipulator according to the second embodiment of the present invention.
Figure 22B:
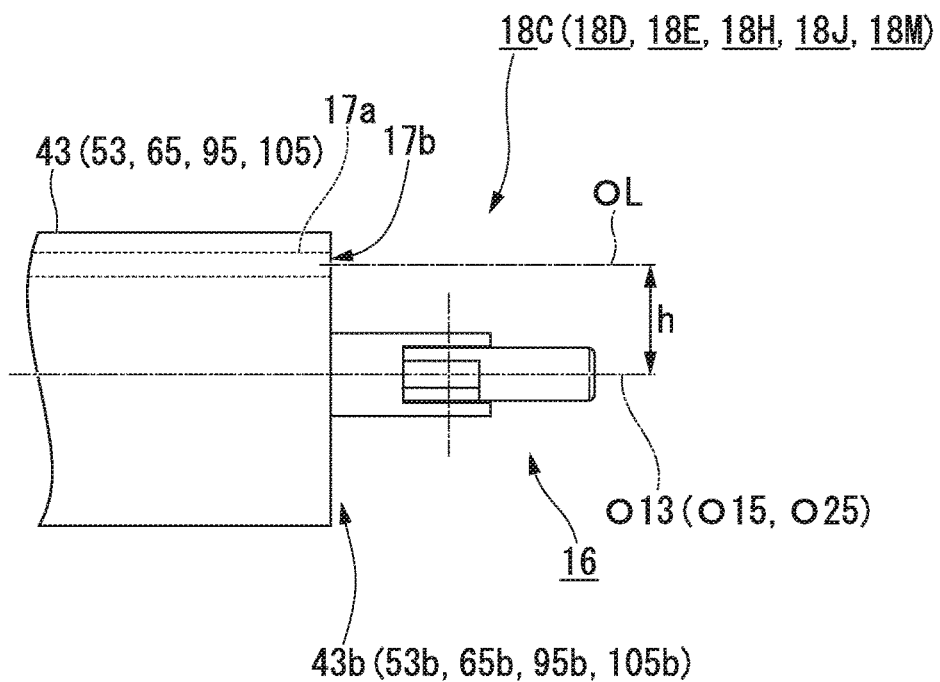
FIG. 22B is a schematic plan view for explaining the arrangement of the light irradiation section of the medical manipulator according to the second embodiment of the present invention.
Figure 23:
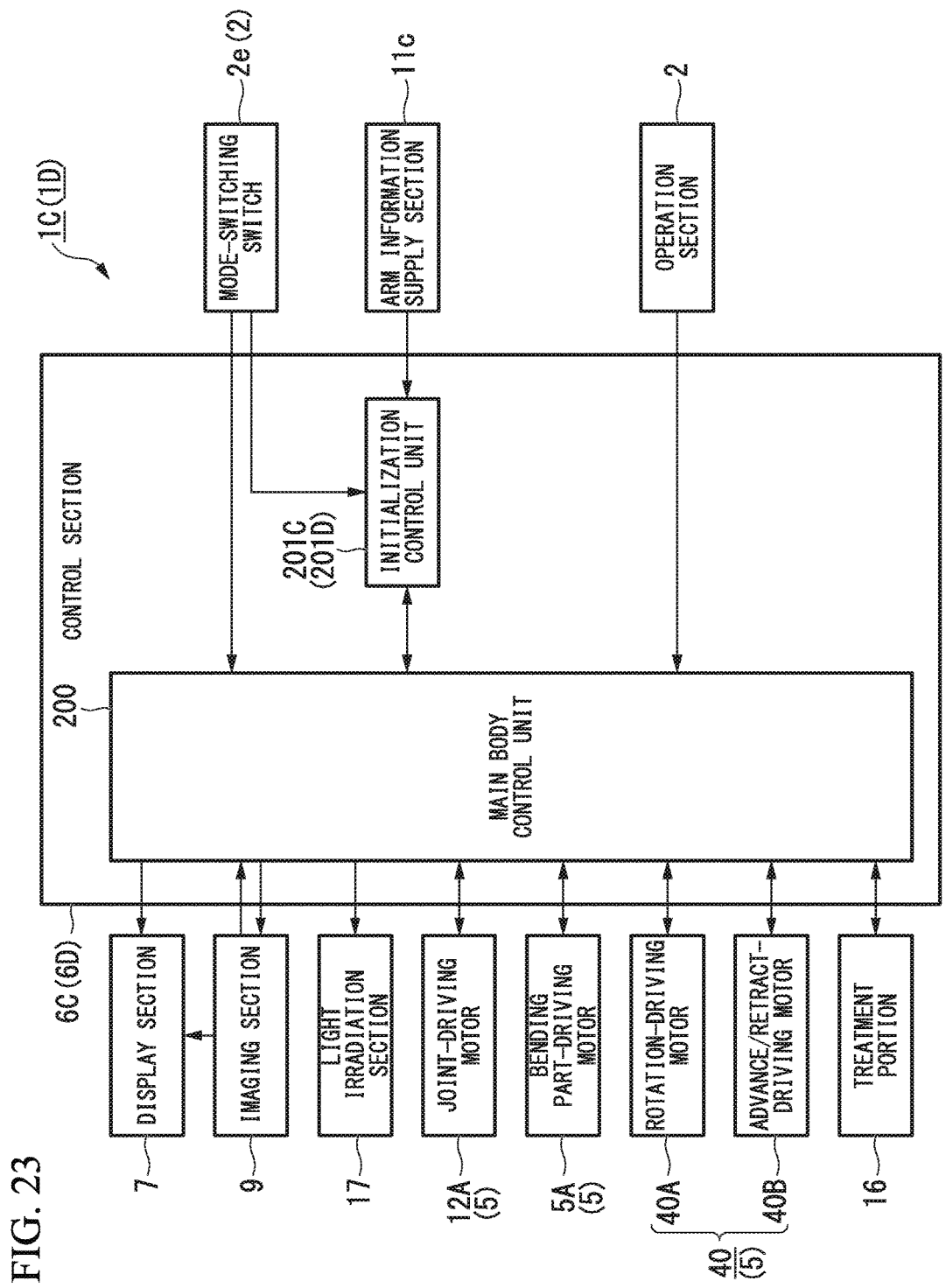
FIG. 23 is a functional block diagram illustrating a major functional configuration of a control section of the medical manipulator according to the second embodiment of the present invention.
Figure 24:
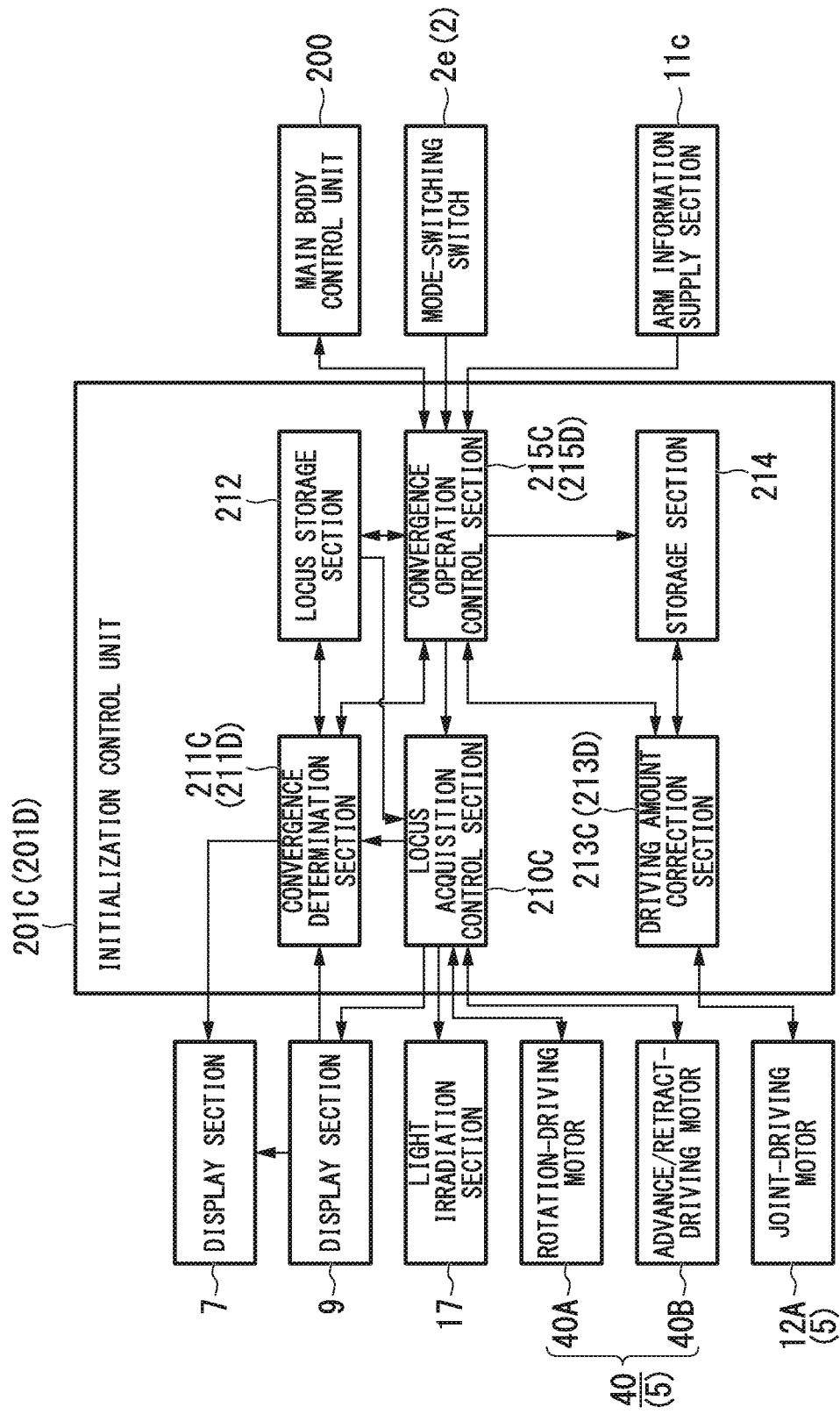
FIG. 24 is a functional block diagram illustrating a functional configuration of initialization control of the medical manipulator according to the second embodiment of the present invention.

FIGS. 21A and 21B are respectively a schematic diagram in a plan view and an operation explanatory diagram illustrating configurations of main portions of the medical manipulator of a second embodiment of the present invention. FIGS. 22A and 22B are respectively a schematic front view and plan view illustrating arrangement of a light irradiation section of the medical manipulator according to the second embodiment of the present invention. FIG. 23 is a functional block diagram illustrating a major functional configuration of a control section of the medical manipulator according to the second embodiment of the present invention. FIG. 24 is a functional block diagram illustrating a functional configuration of initialization control of the medical manipulator according to the second embodiment of the present invention.

As illustrated in FIG. 1, a surgery support robot 1C (medical manipulator) of the present modified example includes a surgery instrument 18C and a control section 6C instead of the surgery instrument 18 and the control section 6 of the above-described first embodiment.

Hereinafter, a description will be made focusing on differences from the first embodiment.

As main portions are schematically illustrated in FIGS. 21A and 21B, the surgery instrument 18C includes a movement portion 40 and an arm portion 48 instead of the rotation-driving motor 10 and the arm portion 8 of the first embodiment.

The movement portion 40 includes a movement shaft 40b, a rotation-driving motor 40A (rotational movement portion) which rotationally moves the movement shaft 40b around a central axial line thereof, and an advance/retract-driving motor 40B (an advance/retract movement portion) which advances or retracts the movement shaft 40b along the central axial line.

The connection portion 10a, which is the same as in the first embodiment, is provided at a distal end of the movement shaft 40b.

For this reason, the arm proximal end 11a of the first arm 11 is connected to the connection portion 10a, and thus at least one of rotational movement and advance-retract movement of the first arm 11 can be performed. Due to this movement, the arm distal end 11b of the first arm 11 performs at least one of rotational movement around the reference axial line O and advance-retract movement along the reference axial line O.

As mentioned above, the arm distal end 11b of the first arm 11 in the present modified example is supported at the distal end rigid part 3a so as to be rotationally moved around the reference axial line O and be advanced or retracted on the reference axial line O. The arm axial line O11 of the first arm 11 is disposed on the same axis as the reference axial line O.

The arm portion 48 includes a second arm 43 (arm) instead of the second arm 13 of the arm portion 8 of the first embodiment.

The second arm 43 is only different from the second arm 13 in that an arm distal end 43b in which the fiber end surface 17b is moved in parallel by a distance h (where h>0) and is disposed is provided instead of the arm distal end 13b of the second arm 13.

As illustrated in FIGS. 22A and 22B, the optical axis OL of the fiber end surface 17b is moved in parallel by the distance h from the arm axial line O13 in a direction perpendicular to an opening and closing direction (refer to an arrow in FIG. 22A) of the treatment portion 16. Thus, an offset amount in the arm portion 48 is h.

As illustrated in FIGS. 21A and 21B, an offset direction is a direction along the first rotary shaft O12 of the first joint 12 which is a bending joint on the proximal end side which is closest to the second arm 43.

As mentioned above, the configuration in which the optical axis OL is disposed to have an offset with respect to the arm axial line O13 is a preferable configuration, for example, in a case where the fiber end surface 17b cannot be disposed on the arm axial line O13 due to a structure or a shape of the treatment portion 16.

A case where the optical axis OL is located so as to have an offset in the direction along the first rotary shaft O12 of the first joint 12 will be hereinafter referred to as a "rotary shaft direction offset".

In contrast, a case where an offset is present in a direction perpendicular to the first rotary shaft O12, that is, in a direction (a direction parallel to a bent plane) along a plane (hereinafter, referred to as a "bent plane") which is swept due to bending movement of the arm axial line O13 will be referred to as a "bent plane direction offset".

If the term "bent plane" is used, the rotary shaft direction offset has the same meaning as an offset in a direction perpendicular to the bent plane of the first joint 12.

As an offset amount of the arm portion 48, the magnitude of the offset amount and an offset direction are transmitted to the control section 6C by the arm information supply section 11c.

On the basis of such a configuration of the arm portion 8, configuration information transmitted in the present embodiment is that "the number of bending joints is one", "there is no redundant joint", and "the magnitude of an offset amount is h, and an offset direction is the rotary shaft direction offset".

As illustrated in FIG. 23, the control section 6C is different from the control section 6 of the first embodiment in that an initialization control unit 201C is provided instead of the initialization control unit 201 of the first embodiment, and the main body control unit 200 is connected to the rotation-driving motor 40A and the advance/retract-driving motor 40B of the movement portion 40 so as to drive the motors.

As illustrated in FIG. 24, the initialization control unit 201C is different from the initialization control unit 201 of the first embodiment in that a convergence operation control section 215C, a locus acquisition control section 210C, a convergence determination section 211C (convergence determination amount calculation portion), and a driving amount correction section 213C are provided instead of the convergence operation control section 215, the locus acquisition control section 210, the convergence determination section 211, and the driving amount correction section 213 of the first embodiment.

The locus acquisition control section 210C performs the same control as in the locus acquisition control section 210 of the first embodiment in a case of acquiring a locus by using the rotation-driving motor 40A, performs the same control as in the locus acquisition control section 210B of the second modified example in a case of acquiring a locus by using the advance/retract-driving motor 40B, and switches the control in response to a control signal from the convergence operation control section 215C.

The convergence determination section 211C performs the same control as in the convergence determination section 211A of the first modified example in a case where a locus is acquired through rotational movement, performs the same control as in the convergence determination section 211B of the second modified example in a case where a locus is acquired through advance-retract movement, and switches the control in response to a control signal from the convergence operation control section 215C.

The driving amount correction section 213C is configured to perform the same control as in the driving amount correction section 213 of the first modified example in a case where a locus is acquired through rotational movement, is configured to the same control as in the driving amount correction section 213B of the second modified example in a case where a locus is acquired through advance-retract movement, and is configured to switch the control in response to a control signal from the convergence operation control section 215C.

The convergence operation control section 215C performs an operation of selecting an initialization operation using rotational movement of the arm portion 48 and an initialization operation using advance-retract movement of the arm portion 48 as necessary, so as to control operations or the like of the locus acquisition control section 210C, the convergence determination section 211C, and the driving amount correction section 213C.

Next, an operation of the surgery support robot 1C will be described focusing on an initialization method for the medical manipulator of the present modified example.

Figure 25A:
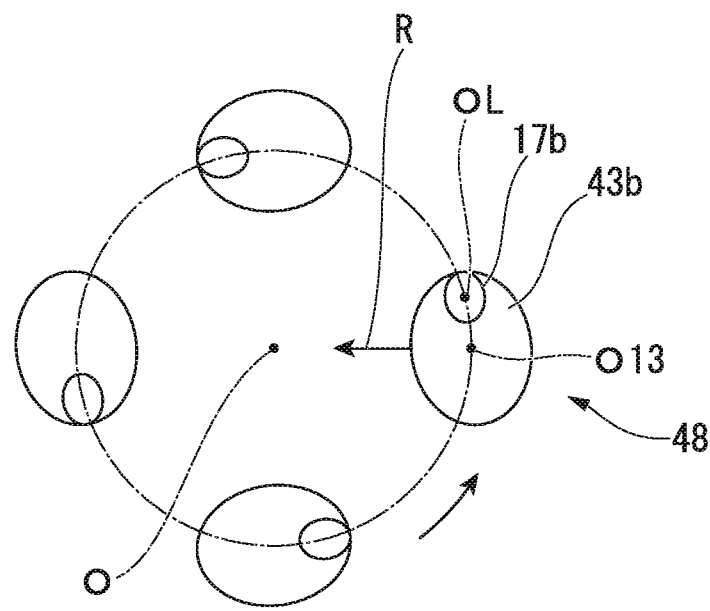
FIG. 25A is a schematic diagram for explaining an operation of initializing the medical manipulator according to the second embodiment of the present invention.
Figure 25B:
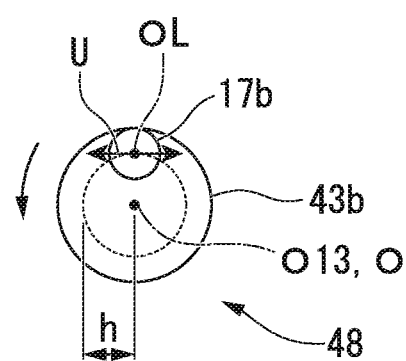
FIG. 25B is a schematic diagram for explaining an operation of initializing the medical manipulator according to the second embodiment of the present invention.

FIGS. 25A and 25B are schematic diagrams illustrating an operation of initializing the medical manipulator according to the second embodiment of the present invention. FIG. 25A is a schematic diagram in which the distal end side of the arm portion 48 is viewed from the axial line direction of the reference axial line O when the bent arm portion 48 is rotationally moved by the rotation-driving motor 40A. FIG. 25B is a schematic diagram illustrating a state in which the arm portion is aligned.

In an initialization operation, whereas the surgery support robot 1 of the first embodiment performs rotational movement using the rotation-driving motor 10, the surgery support robot 1C of the present embodiment can perform substantially the same initialization as in the first embodiment by using the rotation-driving motor 40A. In addition, the surgery support robot 1C can perform the same initialization as in the second modified example through advance-retract movement using the advance/retract-driving motor 40B.

Therefore, the method of initializing the arm portion 48 will be described focusing on differences from the first embodiment and the second modified example.

Since the optical axis OL is located in an offset state over the rotation axis, the arm portion 48 is rotationally moved in a state in which the optical axis OL is aligned with the arm axial line O13 through rotational movement of the first joint 12 when viewed from the direction along the first rotary shaft O12 as illustrated in FIG. 21B. Therefore, a locus of the beam spot B when advance-retract movement of the arm portion 48 is performed is the same as in the case of the second modified example.

Thus, by stopping the rotation-driving motor 40A and using only the advance/retract-driving motor 40B, the arm portion 48 can be initialized in the exactly the same manner as in the second modified example.

In addition, if rotational movement of the arm portion 48 is performed by stopping the advance/retract-driving motor 40B and using the rotation-driving motor 40A, as illustrated in FIG. 25A, the optical axis OL is rotated around the reference axial line O along with the arm distal end 43b in a bent state. Although not illustrated, thus, the beam spot B on the inner wall S draws the same closed curve Q as in the first embodiment.

Further, if the first joint 12 is driven to be rotationally moved in a direction of an arrow R and is thus brought into an aligned state as illustrated in FIG. 25B, the optical axis OL is rotated with the same radius as the offset amount h around the reference axial line O and the second arm 43. At this time, the first joint 12 can be rotationally moved in an illustrated arrow U direction, but since the arrow U is directed in a tangential direction of a rotation circle caused by the rotation-driving motor 40A, a diameter of the locus of the beam spot B increases even if the first joint is moved in any direction, and thus a convergence state in which the diameter is the smallest is uniquely determined.

For this reason, the closed curve Q is acquired in the same manner as in the first embodiment, a convergence determination of a change width of the diameter of the locus is performed in the same manner as in the first modified example, and thus the arm portion 48 can be initialized.

As mentioned above, the initialization operation can be performed on the arm portion 48 through both of only rotational movement and only advance-retract movement, and thus the convergence operation control section 215C selects either one thereof in response to an operation input from the operation section 2.

For example, there is a case where the arm portion 48 may be easily moved through rotational movement or a case where the arm portion 48 may be easily moved through advance-retract movement depending on a space in the body cavity C. In addition, there is a case where a highly accurate convergence determination may be performed through one of rotational movement and advance-retract movement than through the other movement depending on irregularities or inclined states of the inner wall S.

Further, the convergence operation control section 215C may perform an initialization operation through a combination of rotational movement and advance-retract movement. For example, a substantially aligned state may be formed through advance-retract movement, and then a convergence operation to achieve highly accurate alignment may be performed through rotational movement. A substantially aligned state may be formed through rotational movement, and then a convergence operation to achieve highly accurate alignment may be performed through advance-retract movement.

As mentioned above, according to the surgery support robot 1C of the present embodiment, since the arm portion 48 can be initialized in the same manner as in the first embodiment and the second modified example, control can be started from a state in which a position and orientation of the arm portion 48 is known, accordingly, an intuitive operation can be performed.

Third Modified Example

Next, a medical manipulator and an initialization method for the medical manipulator of a modified example (third modified example) of the second modified example will be described.

Figure 26:
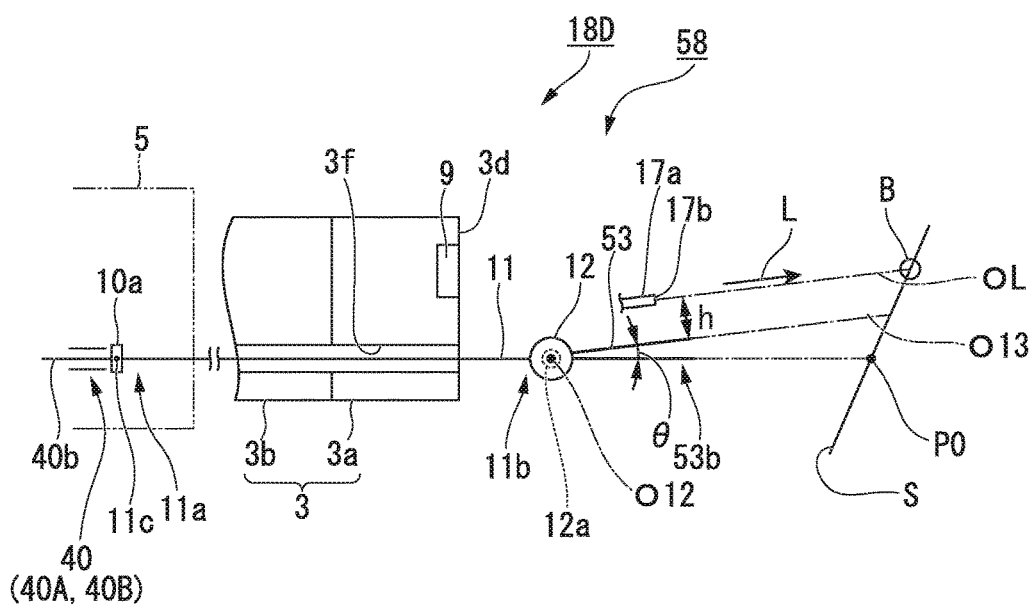
FIG. 26 is a schematic diagram of a front view illustrating configurations of main portions of a medical manipulator of a modified example (third modified example) of the second embodiment of the present invention.

FIG. 26 is a schematic diagram of a front view illustrating configurations of main portions of a medical manipulator of a modified example (third modified example) of the second embodiment of the present invention.

As illustrated in FIG. 1, a surgery support robot 1D (medical manipulator) of the present modified example includes a surgery instrument 18D and a control section 6D instead of the surgery instrument 18C and the control section 6C of the second embodiment.

Hereinafter, a description will be made focusing on differences from the second embodiment.

As main portions are schematically illustrated in FIG. 26, the surgery instrument 18D includes an arm portion 58 instead of the arm portion 48 of the second embodiment.

The arm portion 58 includes a second arm 53 (arm) instead of the second arm 43 of the arm portion 48 of the second embodiment.

The second arm 53 is only different from the second arm 43 in that an arm distal end 53b in which the fiber end surface 17b is moved in parallel by a distance h (where h>0) and a bent plane direction offset is formed with respect to the first joint 12 is provided instead of the arm distal end 43b of the second arm 43.

On the basis of the configuration of the arm portion 58, the arm information supply section 11c of the present modified example transmits configuration information that "the number of bending joints is one", "there is no redundant joint", and "the magnitude of an offset amount is h, and an offset direction is the bent plane direction offset".

As illustrated in FIG. 23, the control section 6D is different from the control section 6C of the second embodiment in that an initialization control unit 201D is provided instead of the initialization control unit 201 of the first embodiment.

As illustrated in FIG. 24, the initialization control unit 201D is different from the initialization control unit 201C of the second embodiment in that a convergence operation control section 215D and a driving amount correction section 213D are provided instead of the convergence operation control section 215C, and the driving amount correction section 213C of the second embodiment.

Control performed by the convergence operation control section 215D and the driving amount correction section 213D will be described in descriptions of operations thereof.

Next, an operation of the surgery support robot 1D will be described focusing on an initialization method for the medical manipulator of the present modified example.

Figure 27A:
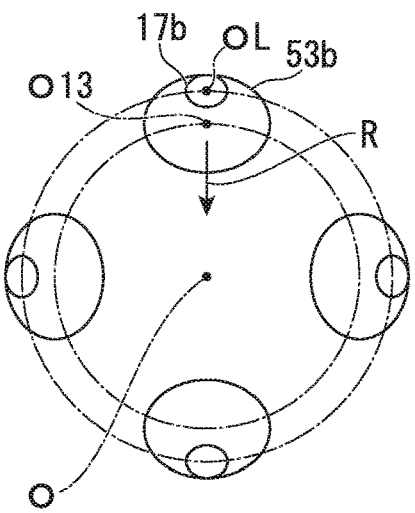
FIG. 27A is a schematic diagram for explaining a part of operation of initializing the medical manipulator of the modified example (third modified example) of the second embodiment of the present invention.
Figure 27B:
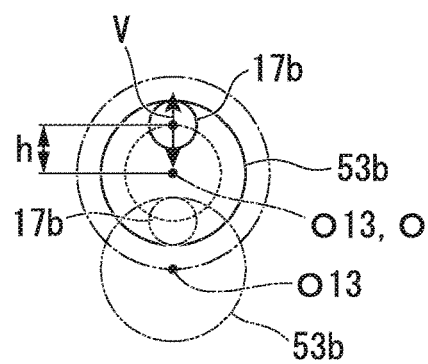
FIG. 27B is a schematic diagram for explaining a part of operation of initializing the medical manipulator of the modified example (third modified example) of the second embodiment of the present invention.
Figure 27C:
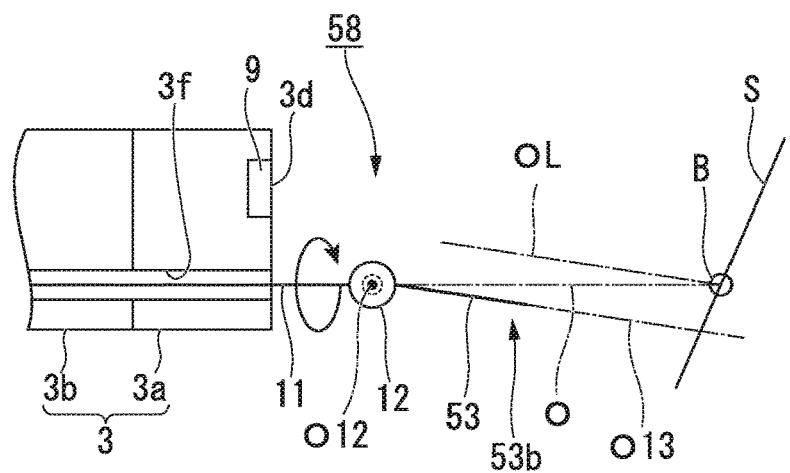
FIG. 27C is a schematic diagram for explaining a part of operation of initializing the medical manipulator of the modified example (third modified example) of the second embodiment of the present invention.
Figure 28:
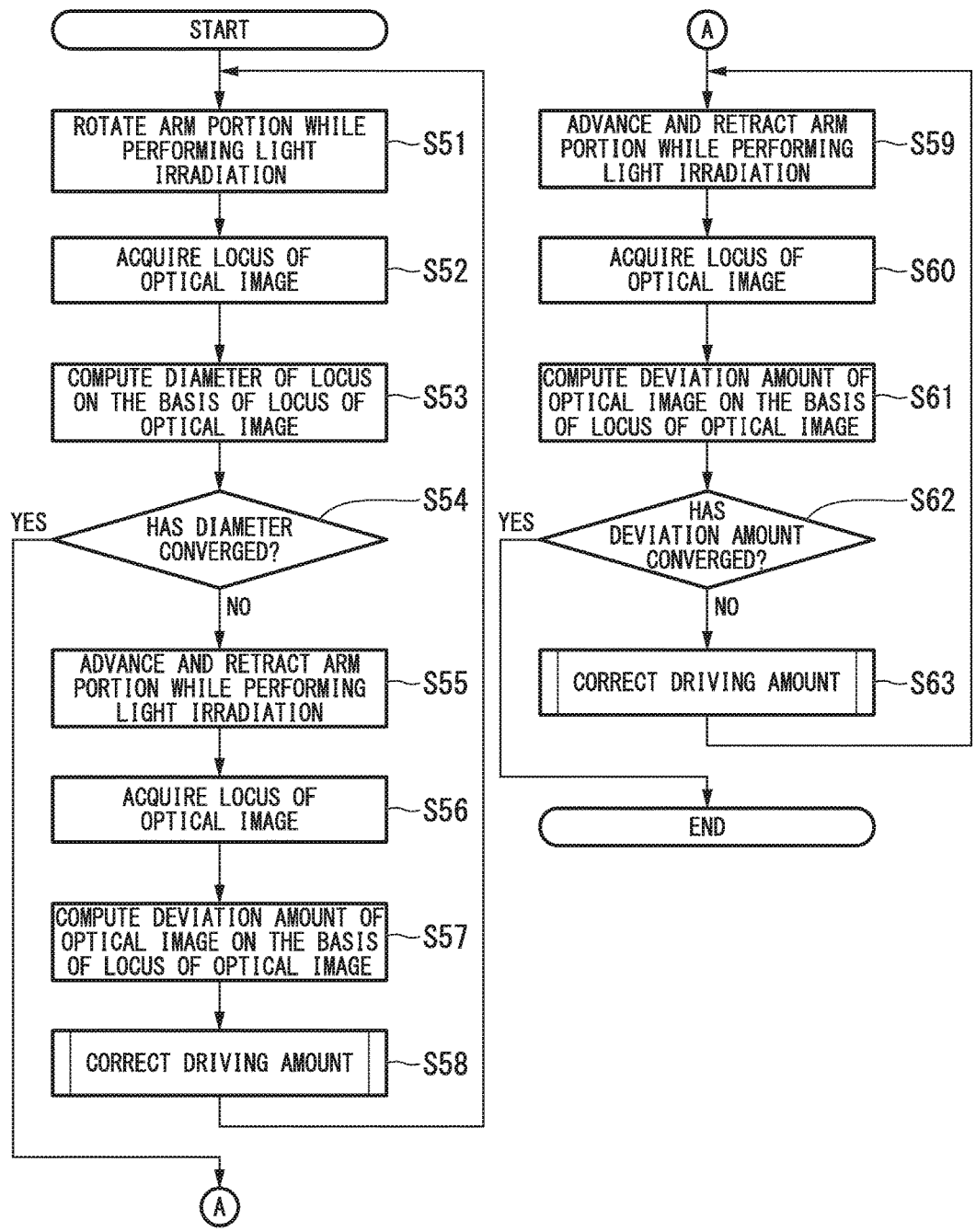
FIG. 28 is a flowchart illustrating a flow of an initialization method for a medical manipulator of the modified example (third modified example) of the second embodiment of the present invention.

FIGS. 27A, 27B and 27C are schematic diagrams illustrating a partial operation of initializing the medical manipulator of the modified example (third modified example) of the second embodiment of the present invention. FIG. 28 is a flowchart illustrating a flow of an initialization method for a medical manipulator of the modified example (third modified example) of the second embodiment of the present invention. FIGS. 29A, 29B, 29C, 29D, 29E and 29F are schematic diagrams illustrating a method of setting a driving direction after the medical manipulator of the modified example (third modified example) of the second embodiment of the present invention is rotationally moved.

In the arm portion 58 of the surgery support robot 1D of the present modified example, the optical axis OL is provided in a bent plane direction offset state with respect to the first joint 12, and thus it is necessary to combine rotational movement with advance-retract movement in an initialization operation. The reason will be described briefly.

If the advance/retract-driving motor 40B is stopped, and rotational movement of the arm portion 58 is performed by the rotation-driving motor 40A, as illustrated in FIG. 27A, the optical axis OL is rotated around the reference axial line O along with the arm distal end 53b in a bent state. However, a rotation radius of the fiber end surface 17b is different from a rotation radius of the arm distal end 53b by an offset amount h. Although not illustrated, the beam spot B on the inner wall S draws the same closed curve Q as in the first embodiment.

In addition, if the first joint 12 is driven to be rotationally moved in a direction of an arrow R and is thus brought into an aligned state as indicated by a solid line in FIG. 27B, the optical axis OL is rotated with the same diameter as the offset amount h around the reference axial line O and the second arm 53. At this time, the first joint 12 can be rotationally moved in an illustrated arrow V direction, but since the arrow V is directed in a tangential direction of a rotation circle caused by the rotation-driving motor 40A, if the first joint is rotationally moved toward the reference axial line O, a diameter of the locus is further reduced. Therefore, the beam spot B does not converge to the circle with the radius h.

As illustrated in FIG. 27C, the beam spot B converges to one point, but this state is a bent state in which the arm axial line O13 obliquely intersects the reference axial line O.

In addition, even if the locus converges to the circle with the radius h, for example, as indicated by a two-dot chain line in FIG. 27B, there is a case where the arm distal end 53b may be rotated in a constant bent state, and thus an accurate convergence determination cannot be performed.

In the present modified example, a first convergence step of realizing a first convergence state in which a diameter of a locus during rotational movement converges by combining a convergence determination using rotational movement and a convergence determination using advance-retract movement, and a second convergence step of realizing a second convergence state in which a deviation amount of an optical image during advance-retract movement in this state converges, are executed in this order.

Specifically, steps S51 to S63 illustrated in FIG. 28 are executed according to the flow shown in FIG. 28.

Steps S51 to S53 are the same as steps S1 to S3 (refer to FIG. 8) of the first embodiment.

In step S54, the convergence determination section 211D performs a convergence determination based on a diameter change width performed by the convergence determination section 211A of the first modified example in the same manner as the convergence determination section 211C of the second embodiment. In other words, step S54 is the same as step S24 (refer to FIG. 14).

In a case where the diameter has converged in this step, the flow proceeds to step S59.

In a case where the diameter has not converged, the flow proceeds to step S55.

Steps S55 to S57 are the same as steps S31 to S33 (refer to FIG. 18) of the second modified example.

Next, step S58 is executed. In this step, a driving amount of the first joint 12 is corrected on the basis of the change amount of the diameter of the locus of the beam spot B during rotational movement and the direction of the deviation amount of the beam spot B during advance-retract movement, computed by the convergence determination section 211D in steps S53 and S57. Specifically, the steps are executed by executing steps S71 to S73 illustrated in FIG. 20 according to the flow shown in FIG. 20.

The change amount of the diameter of the locus of the beam spot B during rotational movement and the direction of the deviation amount of the beam spot B during advance-retract movement, computed by the convergence determination section 211D, are sent to the convergence operation control section 215D from the convergence determination section 211D, and are sent to the driving amount correction section 213D at the time of starting step S58.

In step S71, a driving direction is set on the basis of a deviation direction of the optical image.

First, a principle of setting a driving direction in this step will be described.

Figure 29A:
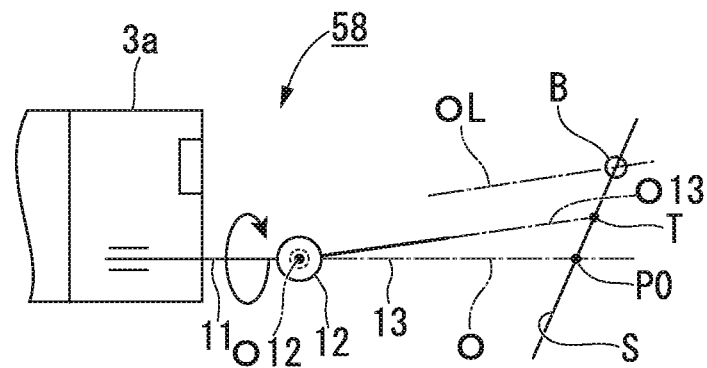
FIG. 29A is a schematic diagram for explaining a method of setting a driving direction after the medical manipulator of the modified example (third modified example) of the second embodiment of the present invention is rotationally moved.
Figure 29B:
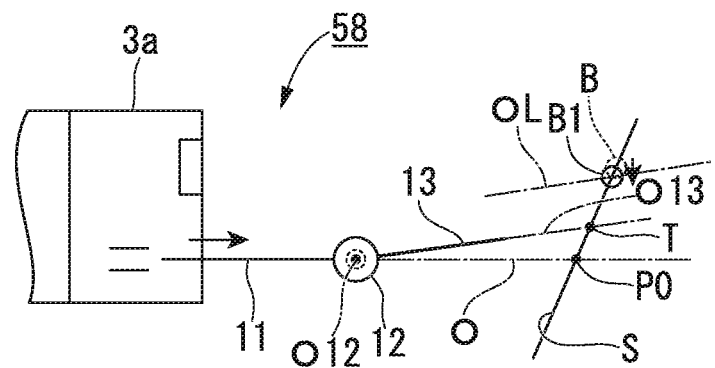
FIG. 29B is a schematic diagram for explaining a method of setting a driving direction after the medical manipulator of the modified example (third modified example) of the second embodiment of the present invention is rotationally moved.
Figure 29C:
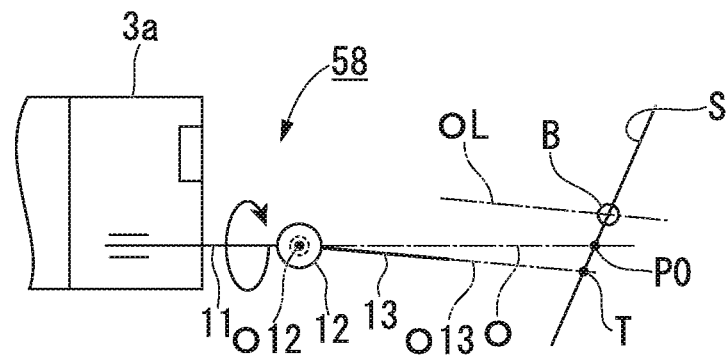
FIG. 29C is a schematic diagram for explaining a method of setting a driving direction after the medical manipulator of the modified example (third modified example) of the second embodiment of the present invention is rotationally moved.
Figure 29D:
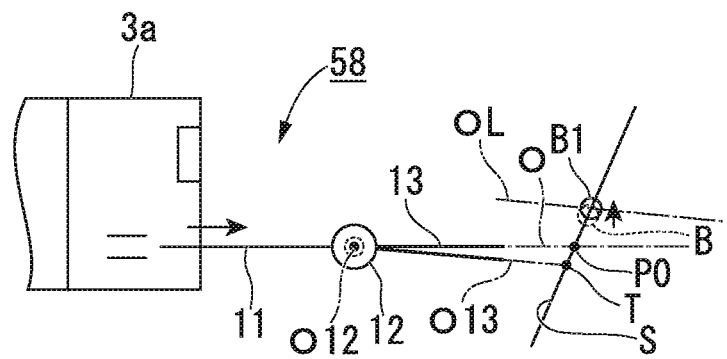
FIG. 29D is a schematic diagram for explaining a method of setting a driving direction after the medical manipulator of the modified example (third modified example) of the second embodiment of the present invention is rotationally moved.
Figure 29E:
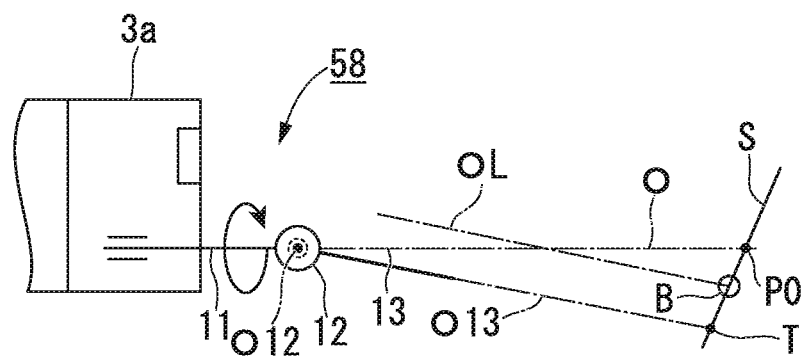
FIG. 29E is a schematic diagram for explaining a method of setting a driving direction after the medical manipulator of the modified example (third modified example) of the second embodiment of the present invention is rotationally moved.

A positional relationship between the arm portion 58 in a bent state and the beam spot B is divided into three patterns illustrated in FIGS. 29A, 29C and 29E. Hereinafter, an intersection between an extension line of the arm axial line O13 and the inner wall S will be referred to as a point T. If a diameter of a locus of the beam spot B is to be brought into a convergence state, the point T is required to match the point P0.

In the respective figures of FIG. 29, the proximal end side of the first arm 11 is illustrated to be cut so that movement is easily understood.

FIG. 29A illustrates a pattern a in which the point T is located between the point P0 and the beam spot B. If the point T is caused to come close to the point P0, the first joint 12 is required to be rotationally moved in an illustrated clockwise direction in the illustrated state.

FIG. 29C illustrates a pattern b in which the point T opposes the beam spot B with the point P0 interposed therebetween. If the point T is caused to come close to the point P0, the first joint 12 is required to be rotationally moved in an illustrated counterclockwise direction in the illustrated state.

FIG. 29E illustrates a pattern c in which the point T opposes the point P0 with the beam spot B interposed therebetween. If the point T is caused to come close to the point P0, the first joint 12 is required to be rotationally moved in an illustrated counterclockwise direction in the illustrated state.

The patterns a, b and c can be discriminated from each other by a deviation direction of a locus of an optical image through advance-retract movement of the arm portion 58.

A direction of the advance-retract movement may be either one of an advance direction and a retract direction, but a determined deviation direction is reverse thereto.

Hereinafter, as an example, a case where a determination is performed through advance of the arm portion 58 will be described.

In a case of the pattern a, if the arm portion 58 is advanced, as indicated by the beam spot B1 in FIG. 29B, the beam spot B moves in a direction of coming close to the point P0 on the inner wall S. In other words, the beam spot B moves to the illustrated lower side, and thus moves in the illustrated clockwise direction with respect to the first rotary shaft O12.

In a case of the pattern b, if the arm portion 58 is advanced, as indicated by the beam spot B1 in FIG. 29D, the beam spot B moves in a direction of becoming distant from the point P0 on the inner wall S. In other words, the beam spot B moves to the illustrated upper side, and thus moves in the illustrated counterclockwise direction with respect to the first rotary shaft O12.

Figure 29F:
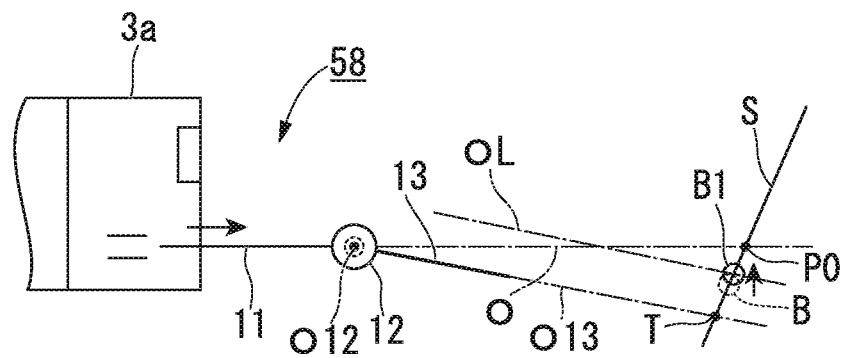
FIG. 29F is a schematic diagram for explaining a method of setting a driving direction after the medical manipulator of the modified example (third modified example) of the second embodiment of the present invention is rotationally moved.

In a case of the pattern c, if the arm portion 58 is advanced, as indicated by the beam spot B1 in FIG. 29F, the beam spot B moves in a direction of coming close to the point P0 on the inner wall S. In other words, the beam spot B moves to the illustrated upper side, and thus moves in the illustrated counterclockwise direction with respect to the first rotary shaft O12.

Therefore, in a case where the arm portion 58 is advanced, if the first joint 12 is rotationally moved so that a movement direction of the beam spot B is realized by the movement, the beam spot B can be moved so that a diameter converges.

The driving amount correction section 213D stores correspondence between a deviation direction of the beam spot B during advance-retract movement and a rotating direction of the first joint 12 as, for example, a table.

In this step, when receiving the information of the deviation direction of the beam spot B sent from the convergence determination section 211D, the driving amount correction section 213D refers to the table and sets a driving direction of the first joint 12.

Through the operation, step S71 is completed.

Next, step S72 is executed. In this step, the magnitude of a driving amount is set. The driving amount correction section 213D sets a driving amount of the first joint 12 on the basis of the deviation amount of the optical image computed in step S57 in the same manner as in step S42. In other words, in a case where the present deviation amount of the beam spot B due to an advance-retract movement is larger than the previous deviation amount of the first joint 12, a driving amount is made larger, and, in a case where the present deviation amount is smaller than the previous deviation amount, a driving amount is made smaller. The driving amount has a certain value as an initial value, and the driving amount is also reduced since the deviation amount of the beam spot B is reduced with the progress of the convergence process.

Through the operation, step S72 is completed.

Next, step S73 is executed. In this step, the first joint 12 is driven by the driving amount set in step S72.

The driving amount correction section 213D sends a driving command value corresponding to the set driving amount to the first joint 12. Consequently, the first joint 12 is driven.

Through the operation, step S73 and step S58 are completed, and the flow proceeds to step S51 of FIG. 28.

In the above-described manner, since steps S51 to S58 are repeatedly executed, correction is performed so that a diameter change width of a locus of the beam spot B is reduced, and the flow proceeds to step S59 if the convergence determination section 211D determines the first convergence state.

Steps S59 to S63 are the same as steps S31 to S35 (refer to FIG. 18) of the second modified example.

In the present modified example, the first convergence state occurs when the flow proceeds to step S59. For this reason, if the second convergence state in which a deviation amount converges is determined to occur in step S62, the convergence determination section 211D determines that the locus has converged, and finishes the initialization operation.

In the above-described manner, if steps S51 to S63 are repeatedly executed, the arm axial line O13 of the second arm 13 is aligned with the reference axial line O so that the aligned state of the arm portion 58 is formed.

The above steps S51 to S58 constitute the first convergence step which includes the locus acquisition step in which rotational movement and advance-retract movement of the arm portion are performed, the convergence determination amount calculation step, the convergence determination step, and the driving amount correction step which is executed until the first convergence state is determined to occur in the convergence determination step and in which a driving amount is corrected on the basis of a diameter change amount and a direction of a deviation amount, and which is completed in a case where the first convergence state is determined to occur in the convergence determination step. Hereinafter, operations in the first convergence step will be collectively referred to as a first convergence operation in some cases.

In the first convergence step of the present modified example, the first convergence operation in which rotational movement and advance-retract movement of the arm portion are performed by the rotational movement portion, and in which the bending joint is driven in a driving amount which is obtained so that a diameter is made smaller by the driving amount correction section until the first convergence state is determined to occur by the convergence determination section is performed.

The above steps S59 to S63 constitute the second convergence step which includes the locus acquisition step in which backward movement of the arm portion is performed, the convergence determination amount calculation step, the convergence determination step, and the driving amount correction step which is executed until the second convergence state is determined to occur in the convergence determination step, and which is completed in a case where the second convergence state is determined to occur in the convergence determination step. Hereinafter, operations in the second convergence step will be collectively referred to as a second convergence operation in some cases.

In the second convergence step of the present modified example, the second convergence operation is performed in which advance-retract movement of the arm portion is performed by the advance/retract movement portion, and the bending joint is driven in a driving amount which is obtained so that a deviation amount is made smaller by the driving amount correction section until the second convergence state is determined by the convergence determination section.

According to the surgery support robot 1D of the present modified example, since the arm portion 58 can be initialized as mentioned above, control can be started from a state in which a position and orientation of the arm portion 58 is known, accordingly, an intuitive operation can be performed.

The present modified example is an example in which, in a case where a redundant joint is not provided and an offset is given in a bent plane direction, initialization can be performed.

Fourth Modified Example

Next, a medical manipulator and an initialization method for the medical manipulator of a modified example (fourth modified example) of the second modified example will be described.

Figure 30A:
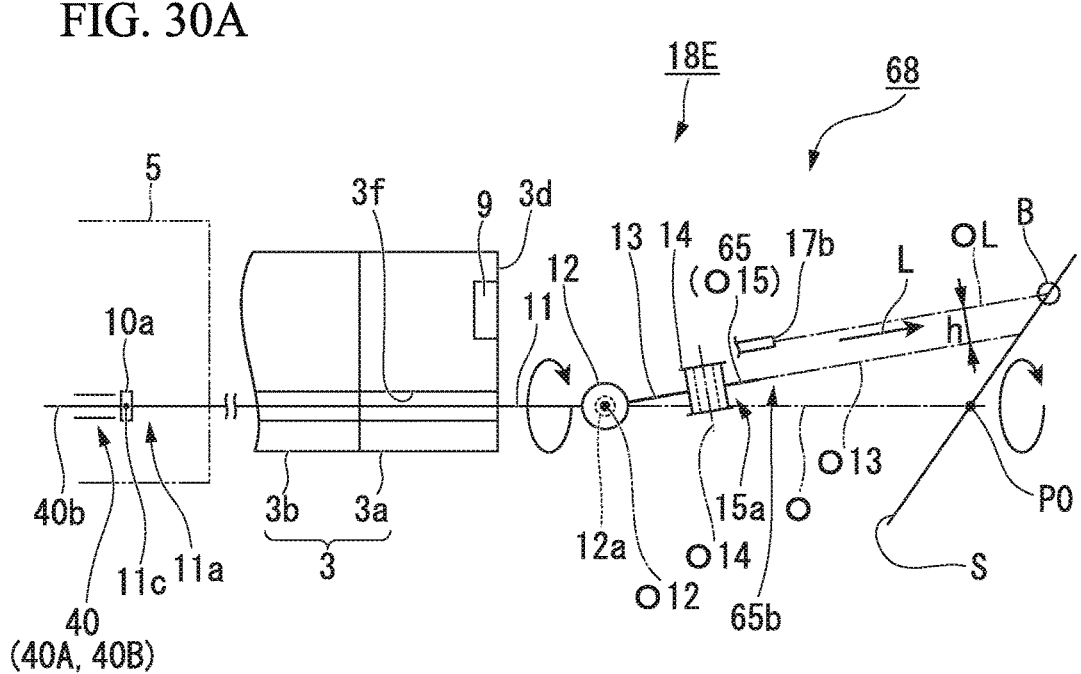
FIG. 30A is a schematic diagram of a front view illustrating configurations of main portions of a medical manipulator of a modified example (fourth modified example) of the second embodiment of the present invention.
Figure 30B:
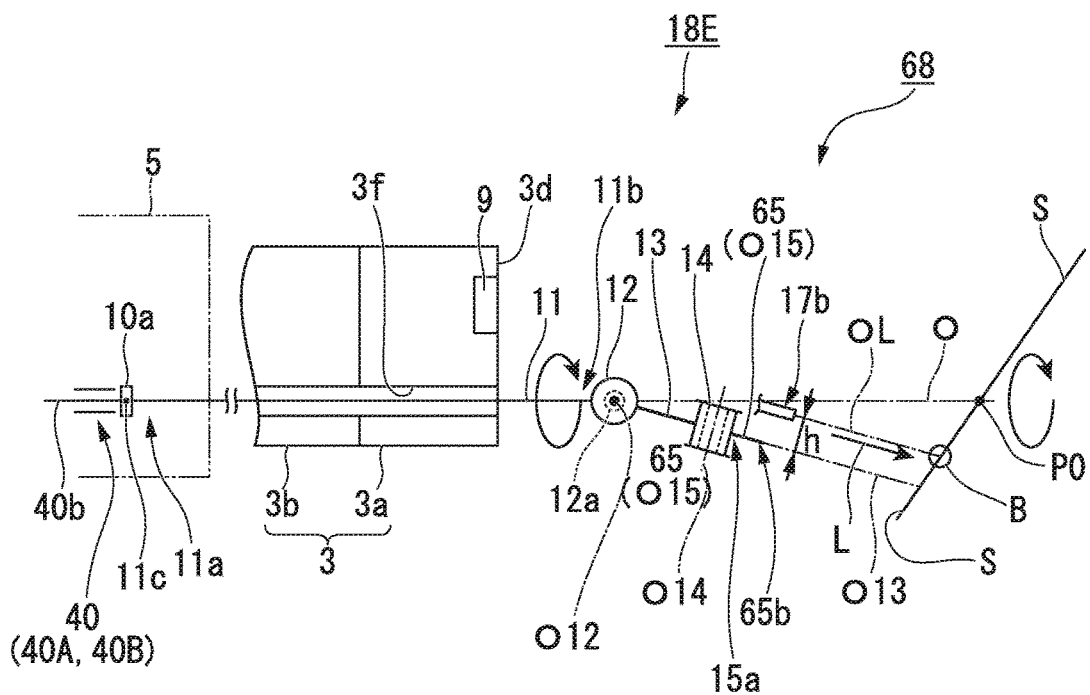
FIG. 30B is an operation explanatory diagram illustrating configurations of main portions of a medical manipulator of the modified example (fourth modified example) of of the second embodiment of the present invention.
Figure 31:
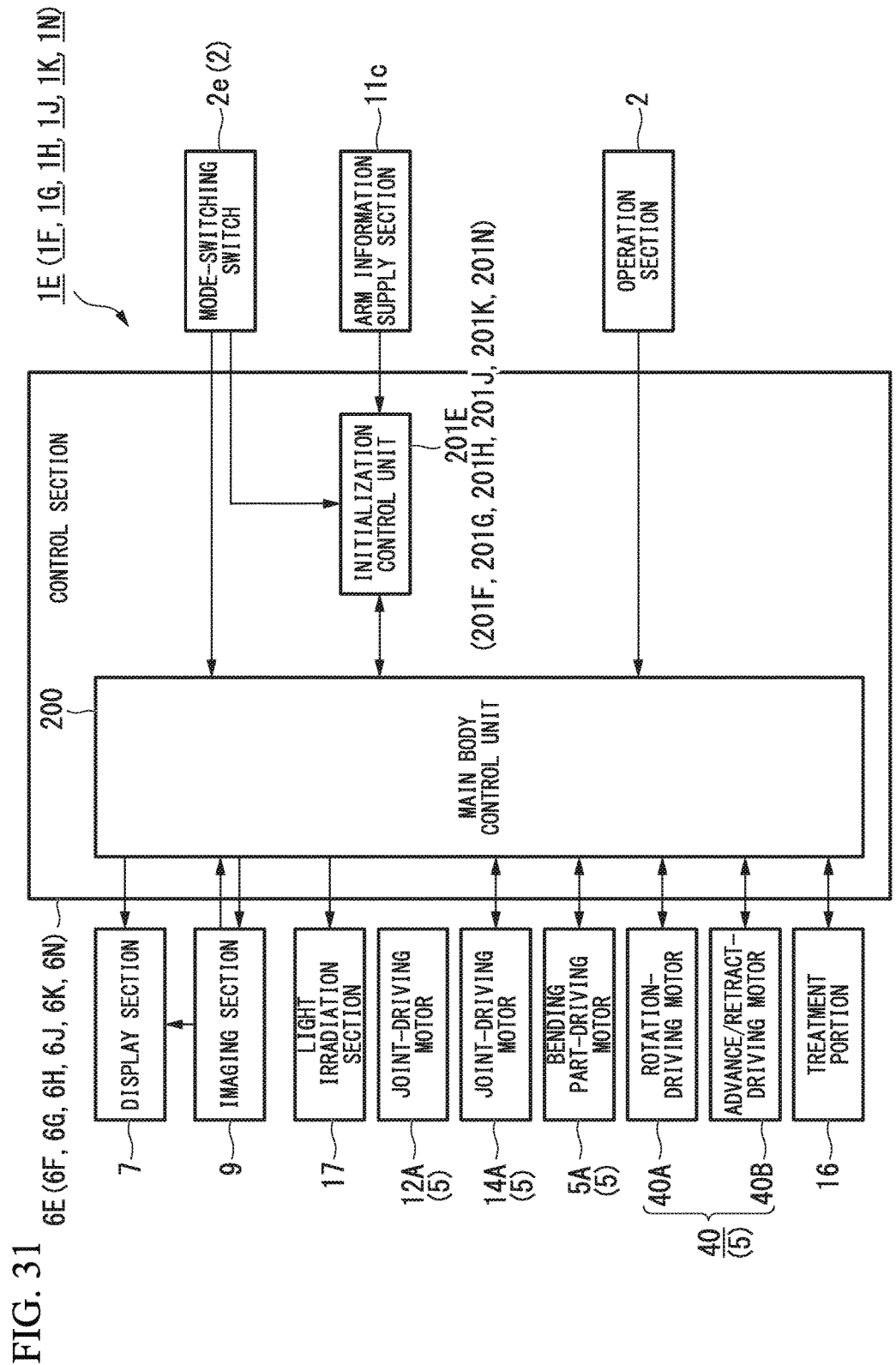
FIG. 31 is a functional block diagram illustrating a major functional configuration of a control section of the medical manipulator of the modified example (fourth modified example) of the second embodiment of the present invention.
Figure 32:
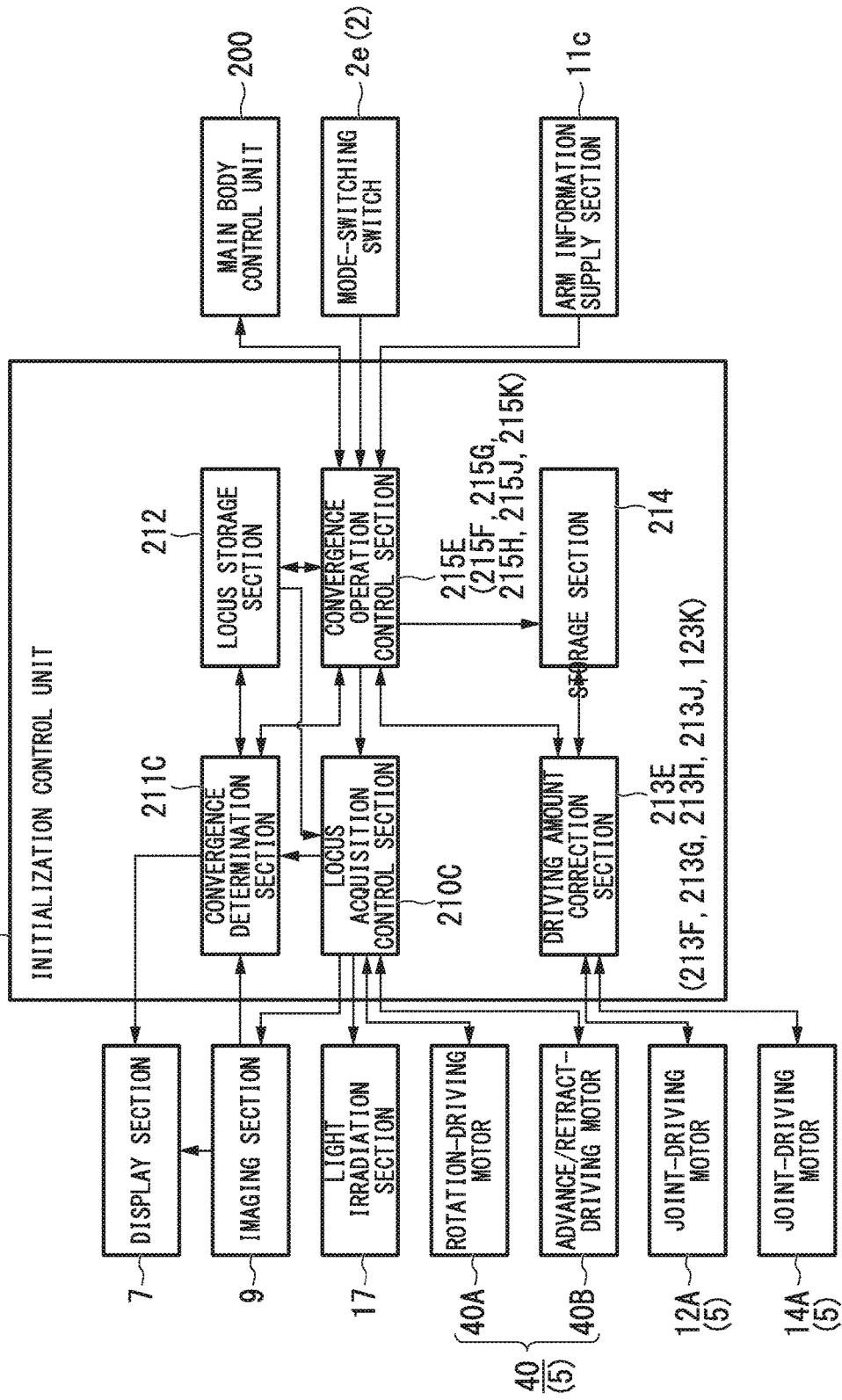
FIG. 32 is a functional block diagram illustrating a functional configuration of initialization control of the medical manipulator of the modified example (fourth modified example) of the second embodiment of the present invention.

FIGS. 30A and 30B are respectively a schematic diagram in a plan view and an operation explanatory diagram illustrating configurations of main portions of the medical manipulator of a modified example (fourth modified example) of a second embodiment of the present invention. FIG. 31 is a functional block diagram illustrating a major functional configuration of a control section of the medical manipulator of a modified example (fourth modified example) of the second embodiment of the present invention. FIG. 32 is a functional block diagram illustrating a functional configuration of initialization control of the medical manipulator of a modified example (fourth modified example) of the second embodiment of the present invention.

As illustrated in FIG. 1, a surgery support robot 1E (medical manipulator) of the present modified example includes a surgery instrument 18E and a control section 6E instead of the surgery instrument 18C and the control section 6C of the above-described second embodiment.

Hereinafter, a description will be made focusing on differences from the second embodiment.

As main portions are schematically illustrated in FIGS. 30A and 30B, the surgery instrument 18E includes an arm portion 68 instead of the arm portion 48 of the second embodiment.

The arm portion 68 includes the second arm 13 of the first modified example instead of the second arm 43 of the arm portion 48, and the second joint 14 connected to the second arm 13 in the same manner as in the first modified example, and additionally includes a third arm 65 (arm).

The third arm 65 is only different from the third arm 15 of the first modified example in that the arm distal end 15b is replaced with an arm distal end 65b.

Therefore, the arm proximal end 15a of the third arm 65 is connected to the second joint 14 in the same manner as the third arm 15 of the first modified example, and thus the arm axial line O15 of the third arm 65 can be rotationally moved around the second rotary shaft O14 centering on an intersection between the arm axial line O13 and the second rotary shaft O14.

The arm distal end 65b is one in which the treatment portion 16 and the fiber end surface 17b at the arm distal end 15b of the second embodiment are moved to have a positional relationship in which the treatment portion 16 is on the arm axial line O15 and the fiber end surface 17b is moved in parallel by a distance h and is moved to have a positional relationship forming a bent plane direction offset with respect to the second joint 14 as illustrated in FIGS. 22A and 22B.

On the basis of the configuration of the arm portion 68, the arm information supply section 11c of the present modified example transmits configuration information that "the number of bending joints is two", "there is no redundant joint", and "the magnitude of an offset amount is h, and an offset direction is the rotary shaft direction offset".

As illustrated in FIG. 31, the control section 6E is different from the control section 6C of the second embodiment in that an initialization control unit 201E (initialization control unit) is provided instead of the initialization control unit 201C of the second embodiment, and the main body control unit 200 is connected to the joint-driving motor 14A so as to drive the joint-driving motor 14A.

As illustrated in FIG. 32, the initialization control unit 201E is different from the initialization control unit 201C of the second embodiment in that a convergence operation control section 215E and a driving amount correction section 213E are provided instead of the convergence operation control section 215C and the driving amount correction section 213C of the second embodiment, and the driving amount correction section 213E is connected to the joint-driving motor 14A so as to correct a driving amount of the joint-driving motor 14A.

Control performed by the convergence operation control section 215E and the driving amount correction section 213E will be described in descriptions of operations thereof.

Next, an operation of the surgery support robot 1E will be described focusing on an initialization method for the medical manipulator of the present modified example.

Figure 33:
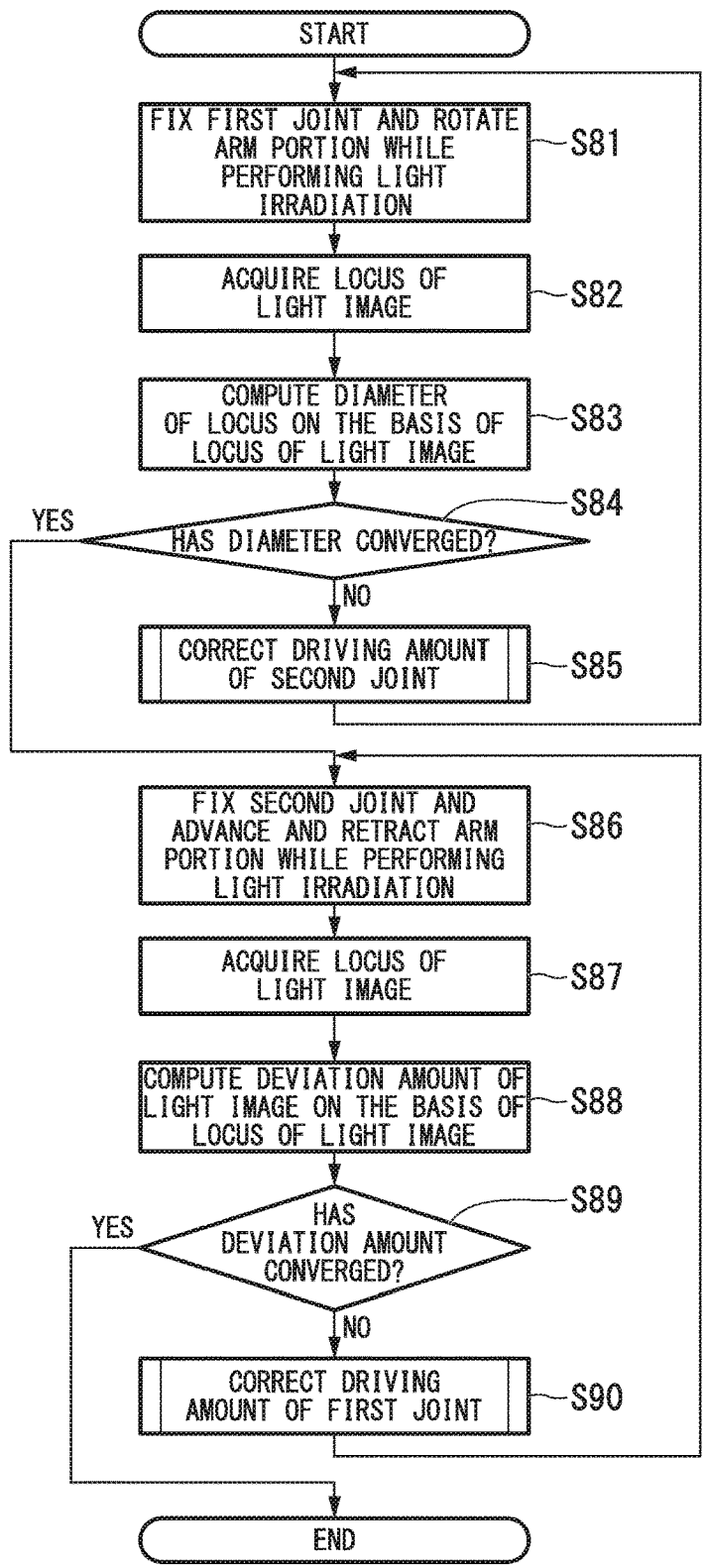
FIG. 33 is a flowchart illustrating a flow of an initialization method for the medical manipulator of the modified example (fourth modified example) of the second embodiment of the present invention.
Figure 34A:
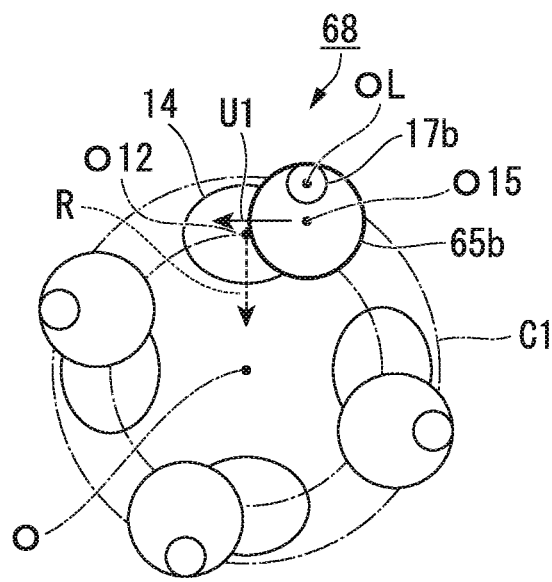
FIG. 34A is a schematic diagram for explaining an example of a convergence operation in a first joint, in the initialization method for the medical manipulator of the modified example (fourth modified example) of the second embodiment of the present invention.
Figure 34B:
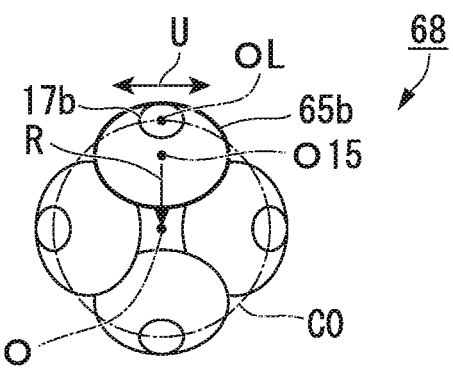
FIG. 34B is a schematic diagram for explaining an example of a convergence operation in the first joint, in the initialization method for the medical manipulator of the modified example (fourth modified example) of the second embodiment of the present invention.
Figure 34C:
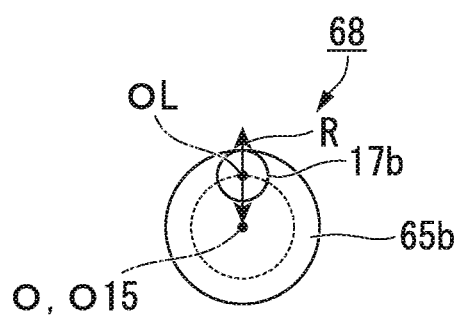
FIG. 34C is a schematic diagram for explaining an example of a convergence operation in the first joint, in the initialization method for the medical manipulator of the modified example (fourth modified example) of the second embodiment of the present invention.
Figure 35A:
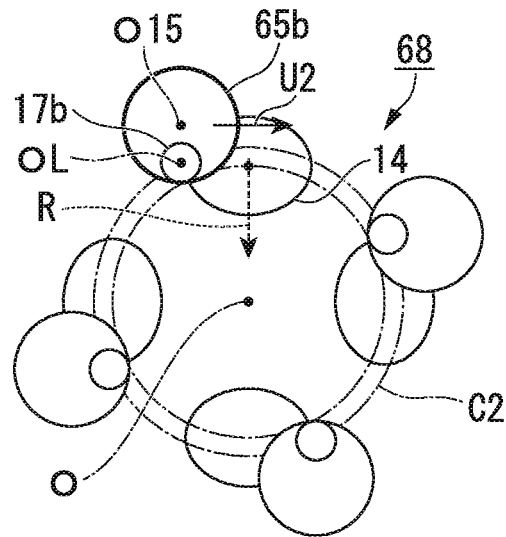
FIG. 35A is a schematic diagram for explaining an example of a convergence operation in the first joint, in the initialization method for the medical manipulator of the modified example (fourth modified example) of the second embodiment of the present invention.
Figure 35B:
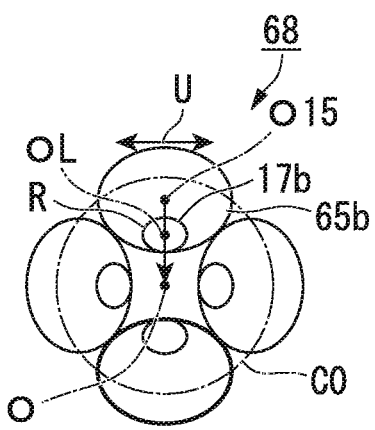
FIG. 35B is a schematic diagram for explaining an example of a convergence operation in the first joint, in the initialization method for the medical manipulator of the modified example (fourth modified example) of the second embodiment of the present invention.
Figure 35C:
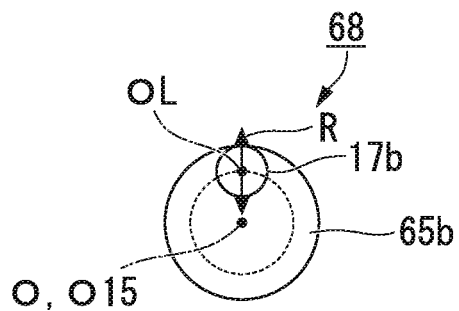
FIG. 35C is a schematic diagram for explaining an example of a convergence operation in the first joint, in the initialization method for the medical manipulator of the modified example (fourth modified example) of the second embodiment of the present invention.

FIG. 33 is a flowchart illustrating a flow of an initialization method for the medical manipulator of the modified example (fourth modified example) of the second embodiment of the present invention. FIGS. 34A, 34B and 34C are schematic diagrams illustrating examples of convergence operations in the first joint, in the initialization method for the medical manipulator of the modified example (fourth modified example) of the second embodiment of the present invention. FIGS. 35A, 35B and 35C are schematic diagrams illustrating examples of convergence operations in the first joint, in the initialization method for the medical manipulator of the modified example (fourth modified example) of the second embodiment of the present invention.

In the arm portion 68, an offset of the optical axis OL is a rotary shaft direction offset with respect to the second joint 14 being nearest positioned, but, in a case where a driving amount of the second joint 14 is fixed, and driving is performed by the first joint 12, an offset of the optical axis OL is a bent plane direction offset with respect to the first joint 12.

For this reason, in the present modified example, each of the first joint 12 and the second joint 14 is driven so as to form a state in which a locus converges, and thus initialization of the arm portion 68 is performed.

Since the rotary shaft direction offset makes a convergence operation simplified, in the present modified example, a driving amount of the second joint 14 is corrected by fixing the first joint 12 to a certain position, and then a driving amount of the first joint 12 is corrected by fixing the second joint 14 to a certain position.

Specifically, steps S81 to S90 illustrated in FIG. 33 are executed according to the flow shown in FIG. 33.

However, as described in the third modified example, in a case where of a single joint, convergence can made to occur even if there is the bent plane direction offset, and thus a driving amount may be corrected in a reverse order thereto.

Steps S81 to S85 correspond to an operation in a case where the arm portion 48 is initialized through rotational movement in the second embodiment, and an angle of the first joint 12 of the arm portion 68 is fixed. Specifically, the steps are substantially the same as steps S1 to S5 (refer to FIG. 8) of the first embodiment.

Steps S81 to S83 are the same as the above steps S1 to S3 except that the arm portion 68 is rotationally moved in a state in which an angle of the first joint 12 is fixed under the control of the convergence operation control section 215E.

In step S84, the convergence determination section 211C performs a convergence determination based on a diameter change width, performed by the convergence determination section 211A of the first modified example. In other words, step S84 is the same as the above step S24 (refer to FIG. 14).

In a case where the diameter has converged in this step, the flow proceeds to step S86.

In a case where the diameter has not converged, the flow proceeds to step S85.

Step S85 is a step which constitutes a driving amount correction step of the present modified example, and is executed by executing steps S91 to S96 which are substantially the same as steps S11 to S16 of the first embodiment according to the flow shown in FIG. 10 as illustrated in FIG. 10.

Step S91 is the same as step S11 except that the locus used for the determination in step S84 is stored as a reference locus.

Next, step S92 is executed. In this step, a driving amount of the second joint 14 is set to a test-driving amount.

As the test-driving amount, a predetermined driving angle and a predetermined direction are set in advance and are stored in the storage section 214.

The driving amount correction section 213E reads the test-driving amount from the storage section 214, and sets the test-driving amount to a driving amount for driving the joint-driving motor 14A.

Through the operation, step S92 is completed.

Next, step S93 is executed. This step is the same as step S13 except that an angle of the first joint 12 is fixed, and the second joint 14 is driven.

Steps S94 to S96 executed next are the same as steps S14 to S16.

However, in the present modified example, a configuration of the arm portion 68 is different from that in the first embodiment, and thus a movement direction of the beam spot B differs.

When the arm portion 68 is viewed from the inner wall S side along the reference axial line O during acquisition of a reference locus, the arm portion 68 is rotated as schematically illustrated in FIG. 34A in a case of being rotated in a bent state illustrated in FIG. 30A, and the arm portion 68 is rotated as schematically illustrated in FIG. 35A in a case of being rotated in a bent state illustrated in FIG. 30B.

In order to reduce a diameter of a locus of the beam spot B in this state, the second joint 14 may be moved in an illustrated arrow U1 direction in the case of FIG. 34A, and may be moved in an illustrated arrow U2 direction in the case of FIG. 35B. If the second joint 14 is rotationally moved in a reserve direction, a diameter of the locus of the substance is increased.

In other words, if the second joint 14 is rotationally moved, a rotation circle C1 (refer to FIG. 34A) and a rotation circle C2 (refer to FIG. 35A) of the fiber end surface 17b are reduced or enlarged, and thus the locus of the beam spot B is also reduced or increased.

For this reason, steps S93 to S96 are repeatedly executed, and thus the second joint 14 can be driven by a driving amount which causes a diameter of a locus of the beam spot B to be reduced in the same manner as in the first embodiment.

If it is determined that a position of the beam spot B has been moved to the inside of the reference locus in step S95, step S85 is completed, and the flow proceeds to step S81.

In the above-described manner, if steps S81 to S85 are repeatedly executed, the diameter of the locus of the beam spot B becomes the minimum so that the arm axial lines O13 and O15 are brought into an aligned state.

At this time, if the arm portion 68 is rotated by the rotation-driving motor 40A, a rotation circle of the fiber end surface 17b has the minimum diameter C0 as illustrated in FIGS. 34B and 35B.

Since a diameter of the locus of the beam spot B is the minimum according thereto, it is determined that the diameter of the locus of the beam spot B has converged in step S84, and the flow proceeds to step S86.

In such an aligned state, the second arm 13 and the third arm 65 are the same as a single arm extending along the common axial line as long as the second joint 14 is not driven. The aligned state is the same as that realized by the configuration of the arm portion 58 of the third modified example.

Steps S86 to S90 are the same as steps S59 to S63 (refer to FIG. 28) of the third modified example except that the first joint 12 is driven while fixing an angle of the second joint 14 in the arm portion 68.

If these steps are repeatedly executed, the arm portion 68 is advanced or retracted by the advance/retract-driving motor 40B from the states illustrated in FIGS. 34B and 35B, and are repeatedly driven in an illustrated R direction by the first joint 12 until a deviation amount of an optical image converges, thereby an aligned state illustrated in FIGS. 34C and 35C is formed.

In the above-described manner, the arm axial lines O13 and O15 are aligned with the reference axial line O in the arm portion 68 so that an aligned state of the arm portion 68 is formed.

According to the surgery support robot 1E of the present modified example, since the arm portion 68 can be initialized as mentioned above, control can be started from a state in which a position and orientation of the arm portion 68 is known, and thus an intuitive operation can be performed.

The present modified example is an example in which, in a case where two joints having no relationship of a redundant joint are provided, and the optical axis OL has an offset in a bent plane direction with respect to the bending joint on the distal end side, initialization can be performed.

Fifth Modified Example

Next, an initialization method for the medical manipulator of a modified example (fifth modified example) of the second modified example will be described.

Figure 36:
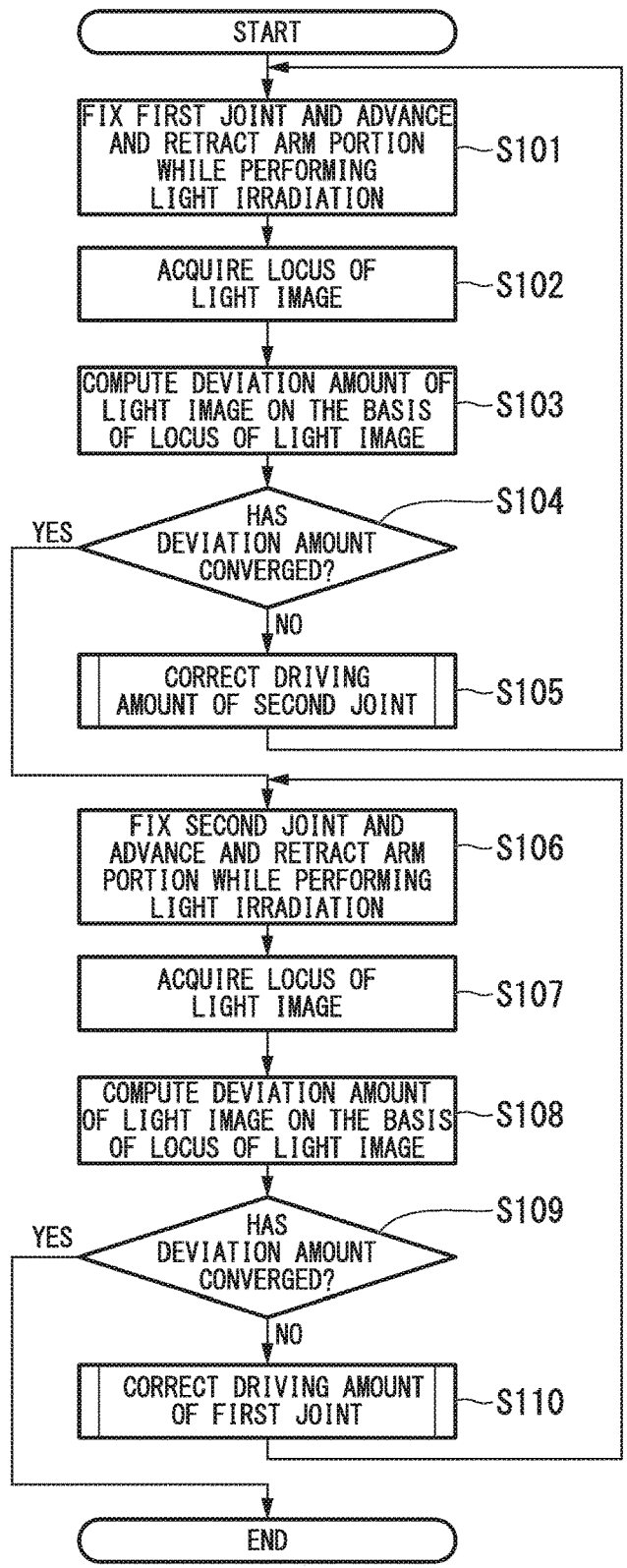
FIG. 36 is a flowchart illustrating a flow of an initialization method for a medical manipulator of a modified example (fifth modified example) of the second embodiment of the present invention.

FIG. 36 is a flowchart illustrating a flow of an initialization method for a medical manipulator of a modified example (fifth modified example) of the second embodiment of the present invention.

An initialization method for the medical manipulator of the present modified example shows an example in which the arm portion 68 of the surgery support robot 1E of the fourth modified example is initialized through only advance-retract movement using the advance/retract-driving motor 40B.

As described in the second embodiment, in a case where of a single joint, even if there is the rotary shaft direction offset, convergence can made to occur both by acquiring a locus through rotational movement and by acquiring a locus through advance-retract movement, and thus steps S81 to S85 in the fourth modified example can be replaced with a convergence operation using advance-retract movement.

A description will be made focusing on differences from the fourth modified example.

An initialization method for the medical manipulator of the present modified example is performed by executing steps S101 to S110 illustrated in FIG. 36 according to the flow shown in FIG. 36.

Steps S101 to S105 are the same as steps S86 to S90 of the fourth modified example except that an angle of the first joint 12 of the arm portion 68 is fixed, and the second joint 14 is driven.

Steps S106 to S110 are the same as steps S86 to S90 of the fourth modified example.

For this reason, although a detailed description is omitted, it can be easily understood from the above description that the steps are repeatedly executed and thus the arm portion 68 can be brought into an aligned state.

Third Embodiment

Next, a medical manipulator and an initialization method for the medical manipulator of a third embodiment of the present invention will be described.

Figure 37:
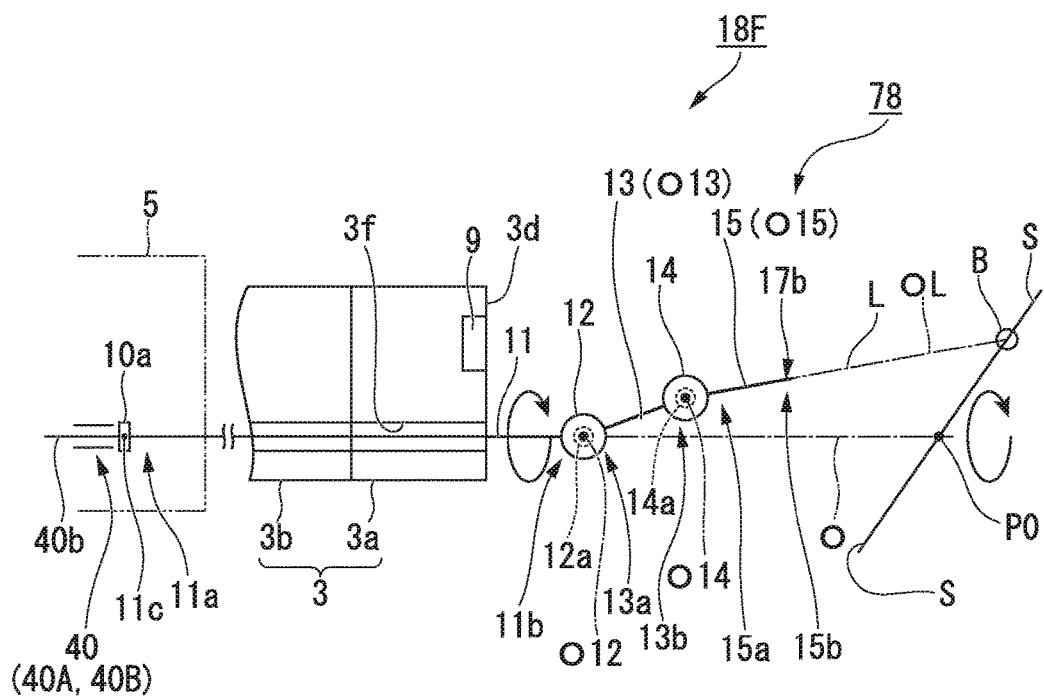
FIG. 37 is a schematic diagram of a front view illustrating configurations of main portions of a medical manipulator of a third embodiment of the present invention.
Figure 38:
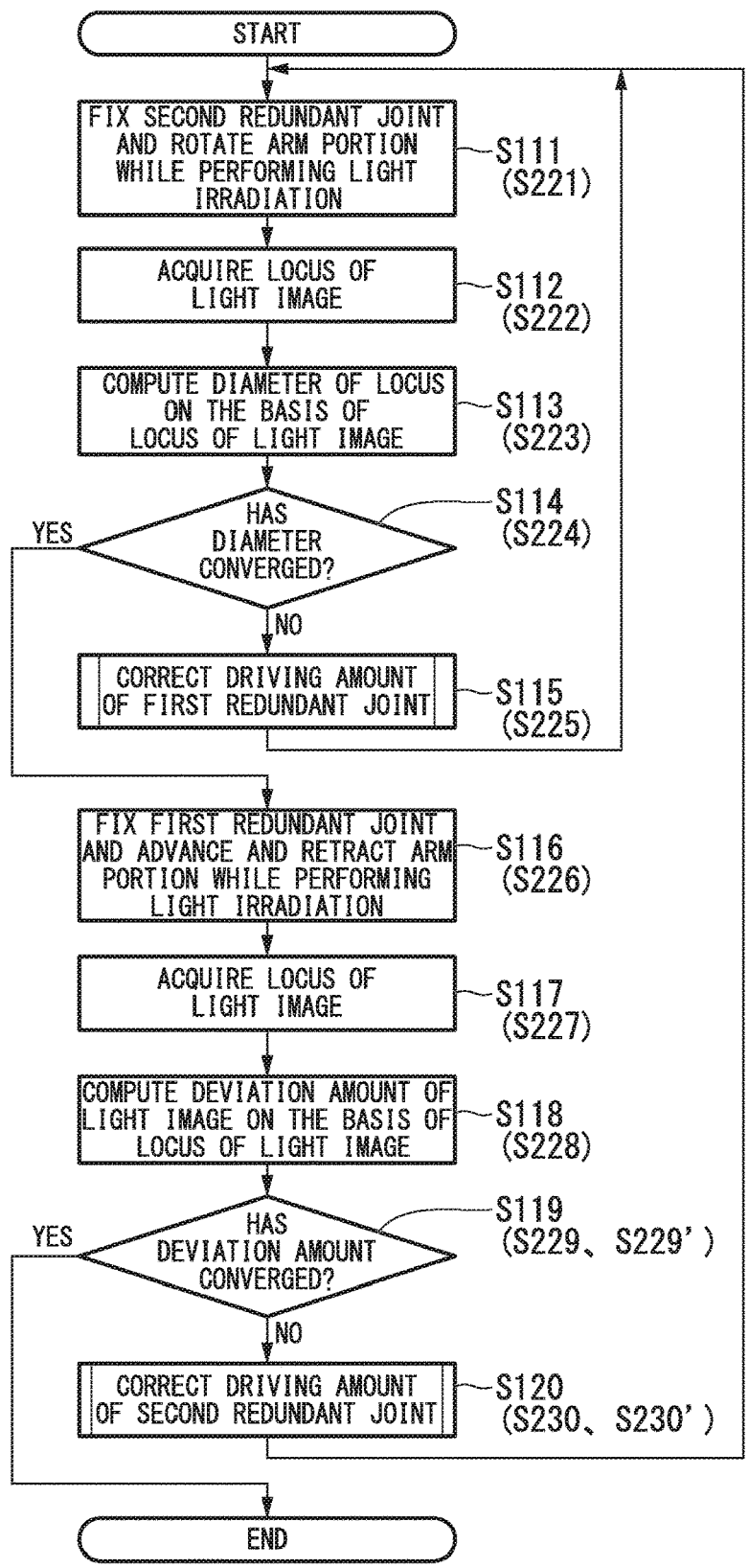
FIG. 38 is a flowchart illustrating a flow of an initialization method for the medical manipulator according to the third embodiment of the present invention.
Figure 39A:
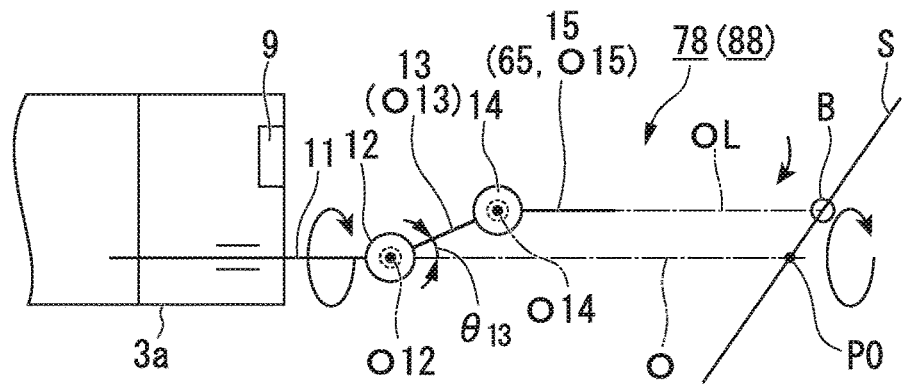
FIG. 39A is a schematic diagram for explaining an example of a convergence operation in the initialization method for the medical manipulator according to the third embodiment of the present invention.
Figure 39B:
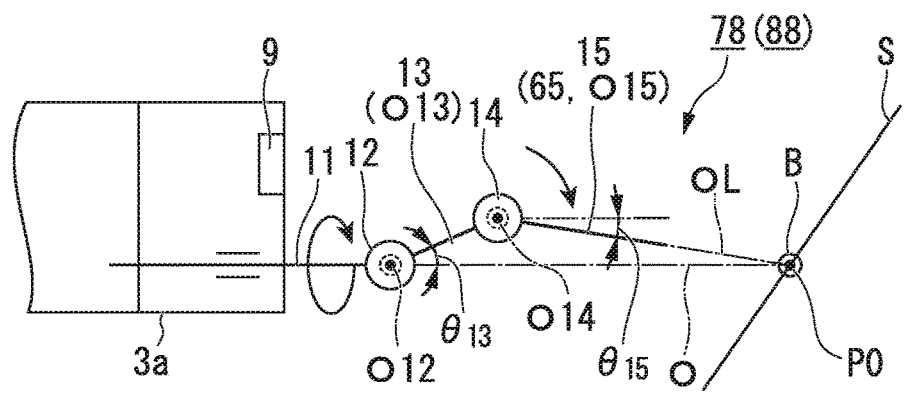
FIG. 39B is a schematic diagram for explaining an example of a convergence operation in the initialization method for the medical manipulator according to the third embodiment of the present invention.
Figure 39C:
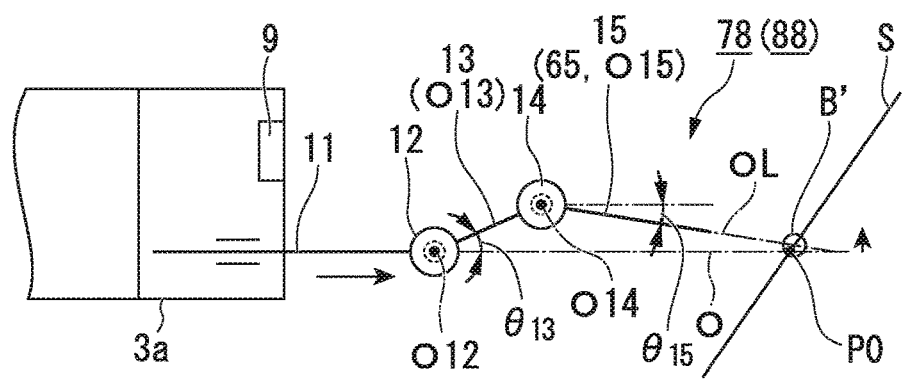
FIG. 39C is a schematic diagram for explaining an example of a convergence operation in the initialization method for the medical manipulator according to the third embodiment of the present invention.
Figure 40A:
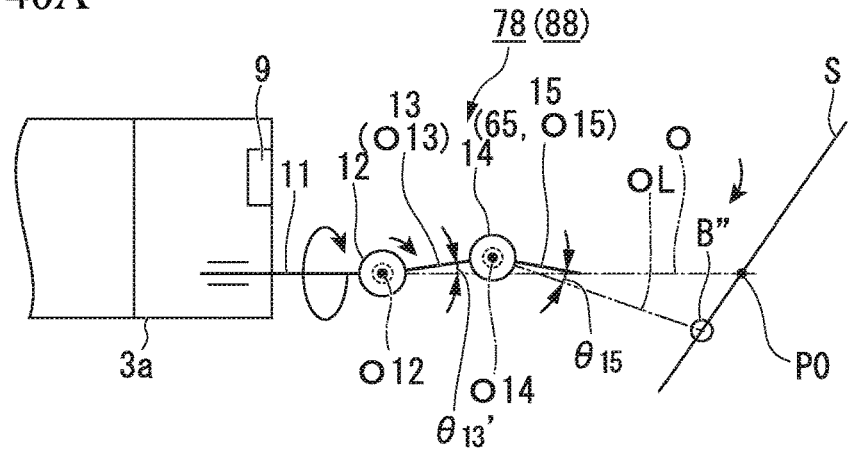
FIG. 40A is a schematic diagram for explaining an example of a converging operation performed subsequently to FIG. 39C.
Figure 40B:
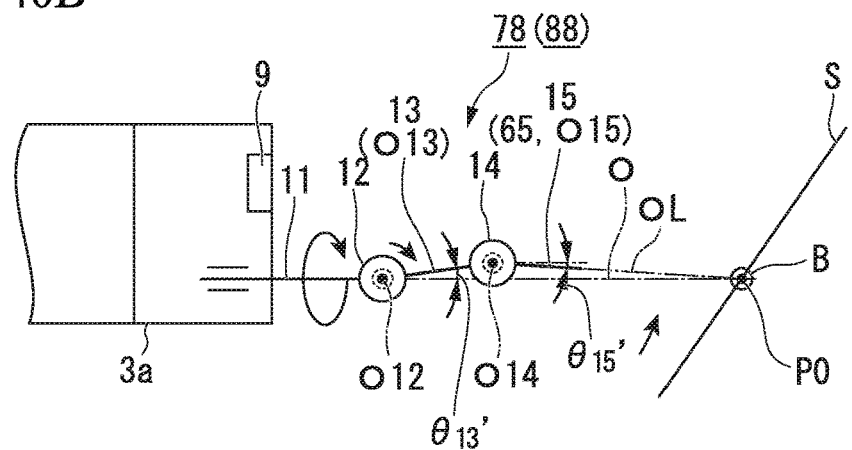
FIG. 40B is a schematic diagram for explaining an example of a converging operation performed subsequently to FIG. 39C.
Figure 40C:
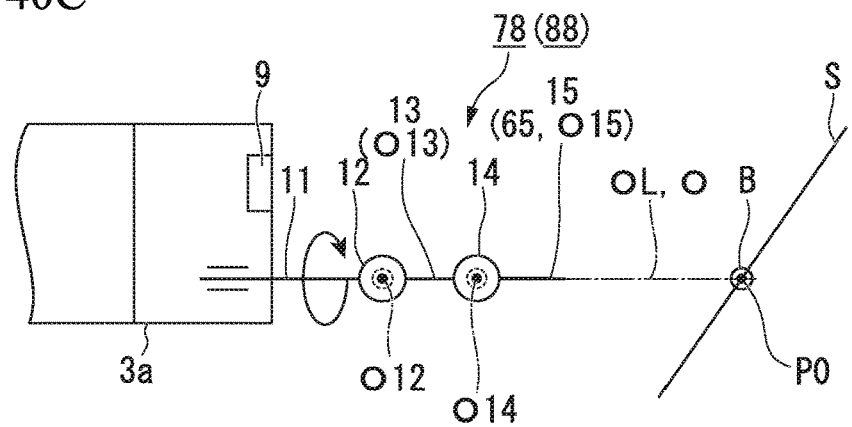
FIG. 40C is a schematic diagram for explaining an example of a converging operation performed subsequently to FIG. 39C.

FIG. 37 is a schematic diagram of a front view illustrating configurations of main portions of a medical manipulator of the third embodiment of the present invention. FIG. 38 is a flowchart illustrating a flow of an initialization method for the medical manipulator according to the third embodiment of the present invention. FIGS. 39A, 39B and 39C are schematic diagrams illustrating examples of convergence operations in the initialization method for the medical manipulator according to the third embodiment of the present invention. FIGS. 40A, 40B and 40C are schematic diagrams illustrating examples of converging operations performed subsequently to FIG. 39C.

As illustrated in FIG. 1, a surgery support robot 1F (medical manipulator) of the present embodiment includes a surgery instrument 18F and a control section 6F instead of the surgery instrument 18A and the control section 6A of the first modified example of the first modified example.

Hereinafter, a description will be made focusing on differences from the first modified example of the first modified example.

As main portions are schematically illustrated in FIG. 37, the surgery instrument 18F includes the same movement portion 40 as in the second embodiment instead of the rotation-driving motor 10 of the first modified example, and an arm portion 78 instead of the arm portion 28.

The arm portion 78 is only different from the arm portion 28 in that the second joint 14 of the arm portion 28 of the first modified example is provided so that the second rotary shaft O14 is parallel to the first rotary shaft O12.

Such a joint is referred to as a redundant joint in the present specification, and, hereinafter, in order to differentiate redundant joints from each other, in a flowchart will be described later, one redundant joint will be referred to as a first redundant joint, and the other redundant joint will be referred to as a second redundant joint. In the arm portion 78, the first joint 12 and the second joint 14 may be arbitrarily allocated to redundant joints as will be described later.

For this reason, a bent plane swept by the arm axial line O13 due to the first joint 12 and a bent plane swept by the arm axial line O15 due to the second joint 14 are the same plane (corresponding to the paper surface of FIG. 37). Consequently, the third arm 15 is moved in the bent plane when either one of the first joint 12 and the second joint 14 is driven, and has a redundant relationship with the first joint 12 and the second joint 14 in the present embodiment.

In addition, in a case where a plurality of bending joints are provided, in the present specification, joints in which the rotary shafts of the bending joints are parallel to each other when the axial lines of the respective arms of the arm portion are aligned on a straight line are referred to as redundant joints.

On the basis of the configuration of the arm portion 78, the arm information supply section 11c of the present embodiment transmits configuration information of the arm portion 78 that "the number of bending joints is two", "there is a redundant joint", and "an offset amount is 0".

As illustrated in FIG. 31, the control section 6F is different from the control section 6A of the first modified example in that an initialization control unit 201F is provided instead of the initialization control unit 201A of the first modified example, and the main body control unit 200 is connected to the rotation-driving motor 40A and the advance/retract-driving motor 40B of the movement portion 40 so as to drive the motors.

As illustrated in FIG. 32, the initialization control unit 201F is different from the initialization control unit 201A of the first modified example in that a convergence operation control section 215F, a locus acquisition control section 210C, a convergence determination section 211C, and a driving amount correction section 213F are provided instead of the convergence operation control section 215A, the locus acquisition control section 210, the convergence determination section 211A, and the driving amount correction section 213 of the first modified example.

The locus acquisition control section 210C and the convergence determination section 211C of the present embodiment are the same as the locus acquisition control section 210C and the convergence determination section 211C of the second embodiment except for being controlled in response to control signals from the convergence operation control section 215F.

A description of control performed by the convergence operation control section 215F and the driving amount correction section 213F will be made along with a description of operations thereof.

Next, an operation of the surgery support robot 1F will be described focusing on an initialization method for the medical manipulator of the present modified example.

FIG. 38 is a flowchart illustrating a flow of an initialization method for the medical manipulator according to the third embodiment of the present invention. FIGS. 39A, 39B and 39C are schematic diagrams illustrating examples of convergence operations in the initialization method for the medical manipulator according to the third embodiment of the present invention.

Since the first joint 12 and the second joint 14 have the same bent plane, even if the arm portion 78 in a bent state is rotationally moved and thus the beam spot B converges to the point P0 on the inner wall S, angles of the first joint 12 and the second joint 14 may take various values.

In addition, in a case where the arm portion 78 in a bent state is advanced and backward, an aligned state can be determined. However, in a case where a driving amount is corrected on the basis of a deviation amount of an optical image, a method of allocating driving correction amounts to two redundant joints cannot be defined if the bent state cannot be specified.

In contrast, if repeated correction is performed by advancing and retracting only one joint (refer to the second modified example), for example, in a case where correction is performed on the second joint 14, a state in which the arm axial line O15 is parallel to the reference axial line O can be obtained from the bent state illustrated in FIG. 37 as illustrated in FIG. 39A. However, in terms of the arm portion 78, this state is still a bent state. Therefore, even if the first joint 12 is advanced or retracted next by correcting a driving amount thereof convergence cannot occur other than the bent state.

Therefore, in the present embodiment, driving amounts of a pair of redundant joints are alternately corrected, rotational movement and advance-retract movement of the arm portion are alternately and repeatedly performed, thereby, an aligned state in which the first convergence state and the second convergence state occur is obtained.

Specifically, steps S111 to S120 illustrated in FIG. 38 are executed according to the flow shown in FIG. 38. Either one of the pair of redundant joints may be first driven, but, in FIG. 38, a redundant joint whose driving amount is first corrected through rotational movement of the arm portion is referred to as a first redundant joint, and a redundant joint whose driving amount is subsequently corrected through advance-retract movement of the arm portion is referred to as a second redundant joint.

Hereinafter, as an example, a case where the second joint 14 on the distal side is a first redundant joint, and the first joint 12 on the proximal side is a second redundant joint will be described.

Conversely, the first joint 12 on the proximal end side may be a first redundant joint, and the second joint 14 on the distal end side may be a second redundant joint. In this case, rotational movement of the first joint 12 on the distal end side increases a rotating radius, and thus a movement amount of the beam spot B increases.

For example, in order to further reduce a movement amount of the beam spot B for the reason such as a case where an imaging visual field of the imaging section 9 is narrow, preferably, the second joint 14 is a first redundant joint, and the first joint 12 is a second redundant joint.

Steps S111 to S115 are the same as steps S21 to S25 (refer to FIG. 14) of the first modified example except that control is performed by the convergence operation control section 215F and the driving amount correction section 213F, the first joint 12 which is a second redundant joint is fixed to a certain position, and a driving amount of the second joint 14 which is a first redundant joint is corrected.

An operation of the driving amount correction section 213F in step S115 is the same as the operation of the driving amount correction section 213F of the first modified example.

For example, if the arm portion 78 is in a bent state as illustrated in FIG. 37, by the steps are repeatedly executed several times, a driving amount of the second joint 14 is corrected so that an angle of the arm axial line O15 with respect to the reference axial line O is corrected as illustrated in FIG. 39A by repeatedly executing. As illustrated in FIG. 39B, a position of the beam spot B converges to the point P0 on the inner wall S. At this time, angles formed between the reference axial line O and the arm axial lines O13 and O15 are respectively set to O13 and O15.

Consequently, in step S114, the first convergence state is determined to occur by the convergence determination section 211C, and control of the convergence operation control section 215F proceeds to step S116.

Steps S111 to S115 constitute the first convergence step which includes the locus acquisition step in which rotational movement of the arm portion is performed in a state in which an angle of the second redundant joint is fixed, the convergence determination amount calculation step, the convergence determination step, and the driving amount correction step in which a driving amount is obtained so that a diameter is smaller and the first redundant joint is driven by the driving amount, and which is completed in a case where the first convergence state is determined to occur in the convergence determination step.

Steps S116 to S119 are the same as steps S59 to S62 (refer to FIG. 28) of the third modified example except that control is performed by the convergence operation control section 215F and the driving amount correction section 213F, an angle of the second joint 14 which is the first redundant joint of the arm portion 78 is fixed, and the first joint 12 which is the second redundant joint is driven.

For example, in step S116, the arm portion 78 is advanced toward the inner wall S by driving the advance/retract-driving motor 40B (not illustrated) of the movement portion 40 in the first convergence state illustrated in FIG. 39B as illustrated in FIG. 39C.

Consequently, in step S117, a locus in which the beam spot B is moved to a beam spot B' is acquired.

Next, in step S118, a deviation amount of the beam spot B' is computed, and information that a movement direction is an illustrated upper direction in FIG. 39C is obtained. For this reason, in step S119, it is determined that the second convergence state does not occur, and control of the convergence operation control section 215F proceeds to step S120.

Step S120 is a step which constitutes a driving amount correction step of the second redundant joint, and is executed by executing steps S121 to S123 illustrated in FIG. 20 according to the flow of FIG. 20.

The step S121 is a step of setting a driving direction on the basis of a deviation direction of the optical image.

The driving amount correction section 213F sets a deviation direction of the first joint 12 on the basis of the deviation amount of the beam spot B' computed by the convergence determination section 211C.

For example, as illustrated in FIG. 39C, in a case where the beam spot B' is moved to the illustrated upper side from the point P0 due to advance of the arm portion 78, the second joint 14 is located over the reference axial line O. For this reason, for approximation to an aligned state, the first joint 12 is preferably rotated in an illustrated clockwise direction around the first rotary shaft O12 so as to approach the second joint 14 to the reference axial line O.

The set driving direction is stored in a storage region of the driving amount correction section 213F in a time series.

Through the operation, step S121 is completed.

Next, step S122 is performed. In this step, the magnitude of a driving amount is set.

The magnitude of a driving amount of the first joint 12 is set, at first, to a predetermined value which is set in advance, and, subsequently, the driving direction stored in the storage region is referred to whenever this step is executed on a single redundant joint, and the magnitude of the driving amount is reduced when the driving direction is changed. This is because, if the driving direction is changed, this indicates that the second joint 14 has passed the reference axial line O, that is, the second arm 13 has passed an aligned state.

Through the operation, step S122 is completed.

Next, step S123 is executed. This step is a step of driving the first joint 12 by the driving amount set in step S121.

The driving amount correction section 213F sends a driving command value corresponding to the set driving amount (the magnitude and the direction) to the first joint 12. Consequently, the first joint 12 is driven.

Consequently, for example, as illustrated in FIG. 40A, an angle formed between the second arm 13 and the reference axial line O becomes θ13' (where θ13'<θ13). On the other hand, since an angle of the second joint 14 is fixed, the optical axis OL is rotated around the first rotary shaft O12, and thus a beam spot B" is moved in an illustrated lower side so that the beam spot B" is deviated relative to the point P0.

Through the operation, step S123 is completed. Consequently, step S120 of FIG. 38 is completed, and the flow proceeds to step S111.

If these steps are repeatedly executed, for example, in steps S111 to S115 executed next, a driving amount of the second joint 14 is corrected in step S115 in the bent state illustrated in FIG. 40A as illustrated in FIG. 40B, thereby, a state in which the beam spot B converges to the point P0 is obtained. At this time, angles formed between the arm axial lines O13 and O15 and the reference axial line O respectively become θ13' and θ15' (where θ15'<θ15), and thus the bent state is closer to an aligned state.

Therefore, if steps S111 to S120 are repeatedly executed, as illustrated in FIG. 40C, the arm axial lines O13 and O15 are aligned with the reference axial line O. In this case, since the second convergence state during advance-retract movement is determined in step S119, the initialization operation is completed.

Steps S116 to S120 constitute the second convergence step which includes the locus acquisition step in which advance-retract movement of the arm portion is performed in a state in which an angle of the first redundant joint is fixed, the convergence determination amount calculation step, the convergence determination step, and the driving amount correction step in which a driving amount is obtained such that a deviation amount is further reduced and the second redundant joint is driven by the driving amount, and which is completed in a case where the second convergence state is determined to occur in the convergence determination step.

In addition, steps S111 to S120 constitute a step in which the first convergence step and the second convergence step are repeatedly executed in this order, and initialization of a pair of redundant joints is completed in a case where a locus has converged in the convergence determination step of the second convergence step.

According to the surgery support robot 1F of the present embodiment, since the arm portion 78 can be initialized as mentioned above, control can be started from a state in which a position and orientation of the arm portion 78 is known, accordingly, an intuitive operation can be performed.

The present embodiment is an example of an initialization operation in a case where the redundant joints are provided, and an offset amount is 0.

According to the initialization operation of the present embodiment, since the initialization operation is performed by correcting a driving amount and by repeating a locus based on rotational movement and a locus based on advance-retract movement, the initialization operation can be performed even if a relationship between driving command values and the magnitude of a rotating amount of an actual operation in the first joint 12 and the second joint 14 is unclear. For example, in the present embodiment, the first joint 12 and the second joint 14 are driven via the driving force transmission wire material such as a driving wire inserted into the soft portion of the first arm 11, and thus an operation amount of the distal end may change relative to an operation amount of the movement portion 40. For example, a resistance load of the driving wire may change and thus the driving wire may extend. In this case, the magnitude of rotating amounts of actual operations of the first joint 12 and the second joint 14 relative to driving command values is unclear.

Sixth Modified Example

Next, a medical manipulator and an initialization method for the medical manipulator of a modified example (sixth modified example) of the third embodiment will be described.

The present modified example is a modified example of the initialization method of the third embodiment, and a surgery support robot 1G (medical manipulator) of the present embodiment includes a control section 6G instead of the control section 6F of the third embodiment as illustrated in FIG. 1.

Hereinafter, a description will be made focusing on differences from the third embodiment.

As illustrated in FIG. 31, the control section 6G includes an initialization control unit 201G instead of the initialization control unit 201F of the third embodiment. As illustrated in FIG. 32, the initialization control unit 201G includes a convergence operation control section 215G and a driving amount correction section 213G instead of the convergence operation control section 215F and the driving amount correction section 213F of the third embodiment.

Control performed by the convergence operation control section 215G and the driving amount correction section 213G will be described in descriptions of operations thereof.

Next, an operation of the surgery support robot 1G will be described focusing on an initialization method for the medical manipulator of the present modified example.

Figure 41A:
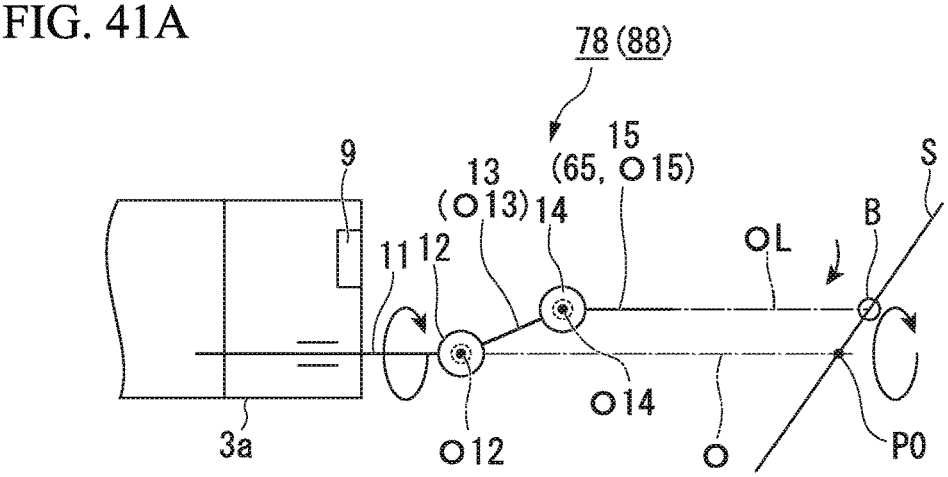
FIG. 41A is an operation explanatory diagram in an initialization method for a medical manipulator of a modified example (sixth modified example) of the third embodiment of the present invention.
Figure 41B:
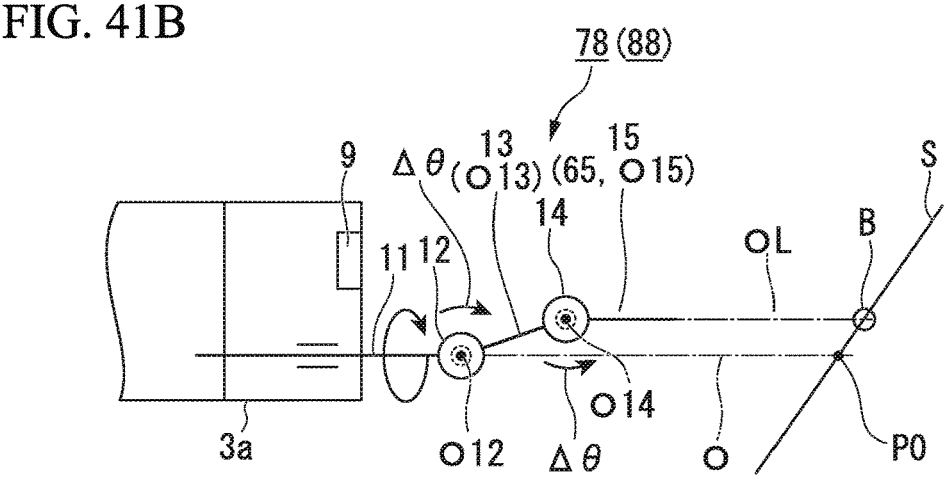
FIG. 41B is an operation explanatory diagram in the initialization method for the medical manipulator of the modified example (sixth modified example) of the third embodiment of the present invention.
Figure 41C:
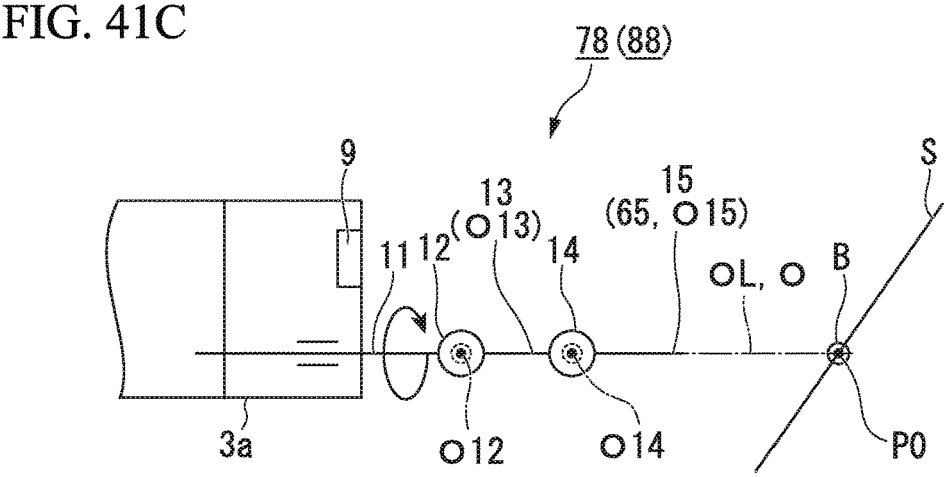
FIG. 41C is an operation explanatory diagram in the initialization method for the medical manipulator of the modified example (sixth modified example) of the third embodiment of the present invention.
Figure 42:
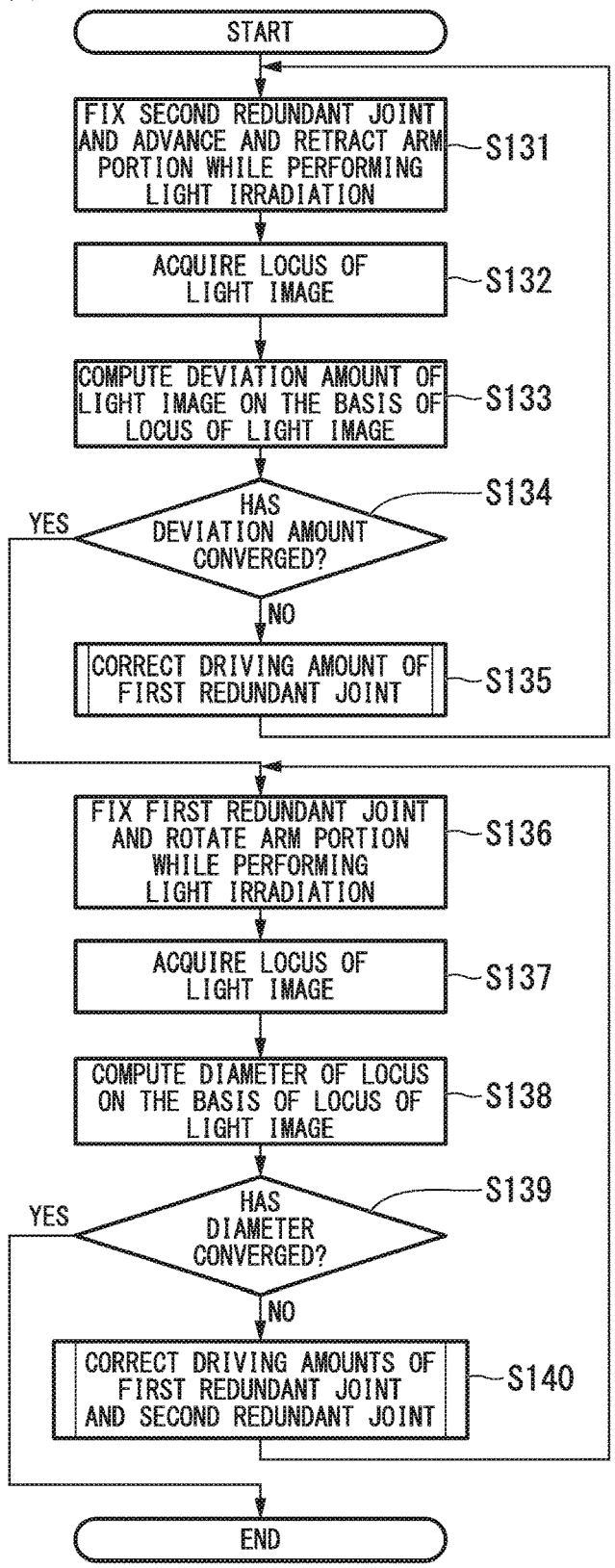
FIG. 42 is a flowchart illustrating a flow of an initialization method for the medical manipulator of the modified example (sixth modified example) of the third embodiment of the present invention.

FIGS. 41A, 41B and 41C are schematic diagrams illustrating a partial operation of initializing the medical manipulator of the modified example (sixth modified example) of the third embodiment of the present invention. FIG. 42 is a flowchart illustrating a flow of an initialization method for a medical manipulator of the modified example (sixth modified example) of the third embodiment of the present invention. FIGS. 43A, 43B, 43C and 43D are schematic diagrams illustrating a method of setting a driving direction when a driving amount of the redundant joint is corrected in the initialization method for the medical manipulator of the modified example (sixth modified example) of the third embodiment of the present invention.

In the present modified example, for example, a state (hereinafter, referred to as a "parallelized state") is formed in which the arm axial line O15 is parallel to the reference axial line O as illustrated in FIG. 41A (hereinafter, also referred to as a "parallelization operation" in some cases) from a bent state of the arm portion 78 as illustrated in FIG. 37. In addition, and thus an aligned state illustrated in FIG. 41C is formed from the parallelized state by repeatedly driving the first joint 12 and the second joint 14 at the same magnitude of driving amounts in opposite driving directions (hereinafter, referred to as a "linearization operation" in some cases).

However, the present modified example is a preferable initialization method in a case where driving command values in which the magnitudes of driving amounts are the same as each other and driving directions are different from each other, generated by the driving amount correction section 213G substantially match (also including a case of matching) such that at least the magnitudes of driving amounts of the first joint 12 and the second joint 14 is in a predetermined allowable range.

Specifically, steps S131 to S140 illustrated in FIG. 42 are executed according to the flow shown in FIG. 42.

In the present modified example, in the same manner as in the third embodiment, either one of a pair of redundant joints may be first driven, but, in FIG. 42, a redundant joint whose driving amount is first corrected in order to form a parallelized state is referred to as a first redundant joint, and a redundant joint whose angle is fixed until a linearization operation is started is referred to as a second redundant joint.

Hereinafter, as an example, a case where the second joint 14 on the distal side is a first redundant joint, and the first joint 12 on the proximal side is a second redundant joint will be described.

Steps S131 to S134 are the same as steps S116 to S119 (refer to FIG. 38) of the third embodiment except that control is performed by the convergence operation control section 215G and the driving amount correction section 213G, and a driving amount of the second joint 14 which is a first redundant joint is corrected while fixing the first joint 12 which is a second redundant joint.

An operation of the driving amount correction section 213G in step S135 is a step that, a driving amount of the second joint 14 is corrected such that the arm axial line O13 and the reference axial line O come close to a parallelized state, and a method of determining a driving direction is different from that in step S120 of the third embodiment.

Specifically, steps S141 to S143 illustrated in FIG. 20 are executed according to the flow shown in FIG. 20.

Step S141 is a step of setting a driving direction on the basis of a deviation direction of the optical image.

First, a principle of setting a driving direction in this step will be described.

A positional relationship between the arm portion 78 in a bent state and the beam spot B is divided into four patterns illustrated in FIGS. 43A, 43B, 43C and 43D.

Figure 43A:
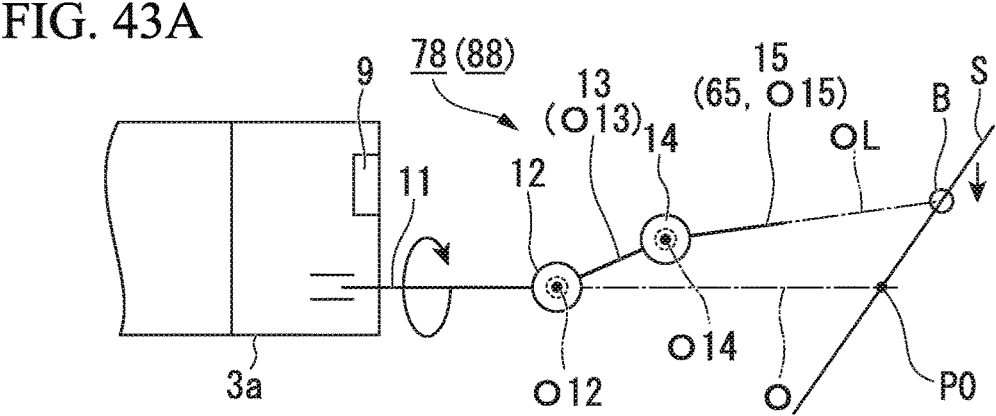
FIG. 43A is a schematic diagram for explaining a method of setting a driving direction when a driving amount of a redundant joint is corrected in the initialization method for the medical manipulator of the modified example (sixth modified example) of the third embodiment of the present invention.

FIG. 43A illustrates a case where the second joint 14 is located on an illustrated upper side with regard to the reference axial line O, and the beam spot B is located further toward an illustrated upper side than in the parallelized state. In this case, the first joint 12 is required to be rotated in an illustrated clockwise direction.

Figure 43B:
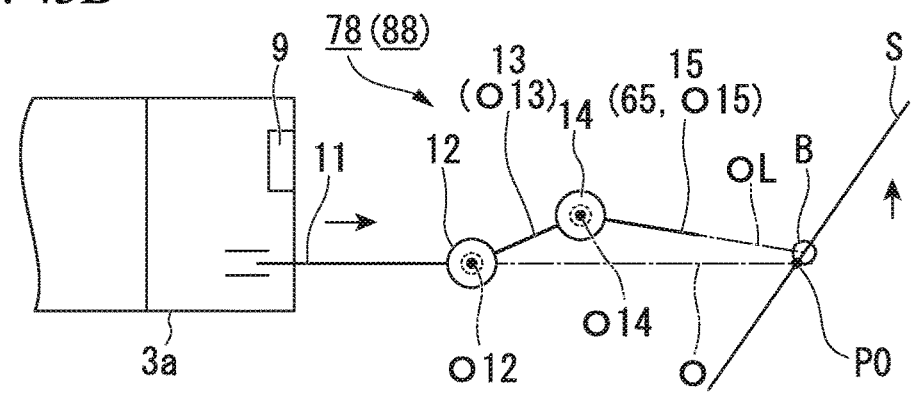
FIG. 43B is a schematic diagram for explaining a method of setting a driving direction when a driving amount of the redundant joint is corrected in the initialization method for the medical manipulator of the modified example (sixth modified example) of the third embodiment of the present invention.

FIG. 43B illustrates a case where the second joint 14 is located on an illustrated upper side with regard to the reference axial line O, and the beam spot B is located further toward an illustrated lower side than in the parallelized state. In this case, the first joint 12 is required to be rotated in an illustrated counterclockwise direction.

Figure 43C:
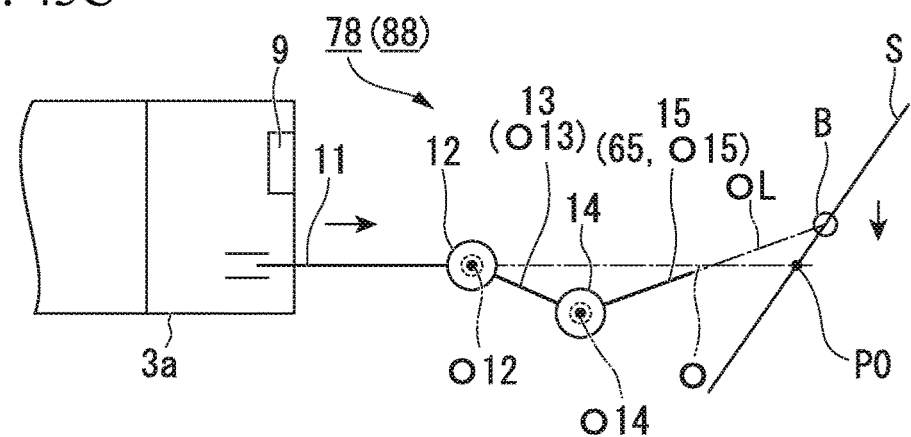
FIG. 43C is a schematic diagram for explaining a method of setting a driving direction when a driving amount of the redundant joint is corrected in the initialization method for the medical manipulator of the modified example (sixth modified example) of the third embodiment of the present invention.

FIG. 43C illustrates a case where the second joint 14 is located on an illustrated lower side with regard to the reference axial line O, and the beam spot B is located further toward an illustrated upper side than in the parallelized state. In this case, the first joint 12 is required to be rotated in an illustrated clockwise direction.

Figure 43D:
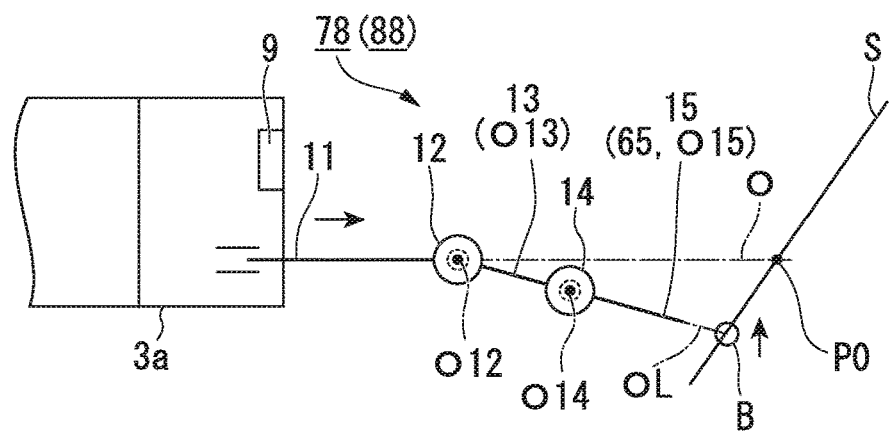
FIG. 43D is a schematic diagram for explaining a method of setting a driving direction when a driving amount of the redundant joint is corrected in the initialization method for the medical manipulator of the modified example (sixth modified example) of the third embodiment of the present invention.

FIG. 43D illustrates a case where the second joint 14 is located on an illustrated lower side with regard to the reference axial line O, and the beam spot B is located further toward an illustrated lower side than in the parallelized state. In this case, the first joint 12 is required to be rotated in an illustrated counterclockwise direction.

A driving direction for each pattern can be specified on the basis of a deviation direction of the beam spot B when the arm portion 78 is advanced or retracted by the advance/retract-driving motor 40B of the movement portion 40.

For example, in a case where the arm portion 78 is advanced toward the inner wall S, the driving direction is a direction rotating the third arm 15 along a deviation direction (illustrated vertical arrow) of the beam spot B.

In a case where the arm portion 78 is retracted, the driving direction is in a reverse direction.

The driving amount correction section 213G stores correspondence between a deviation direction of the beam spot B during advance-retract movement and a rotating direction of the second joint 14 as, for example, a table.

In this step, the driving amount correction section 213G refers to the table and sets a driving direction of the second joint 14 when receiving the information of the deviation direction of the beam spot B sent from the convergence determination section 211C.

The set driving direction is stored in a storage region of the driving amount correction section 213G in a time series.

Through the operation, step S141 is completed.

Next, step S142 is executed. This step is a step of setting the magnitude of a driving amount.

The magnitude of a driving amount of the second joint 14 is set, at first, to a predetermined value which is set in advance, and, subsequently, the driving direction stored in the storage region is referred to whenever this step is executed on a single redundant joint, and the magnitude of the driving amount is reduced when the driving direction is changed. This is because, if the driving direction is changed, this indicates that the third arm 15 has passed a parallelized state.

Through the operation, step S142 is completed.

Next, step S143 is executed. This step is a step of driving the second joint 14 by the driving amount set in step S141.

The driving amount correction section 213G sends a driving command value corresponding to the set driving amount (the magnitude and the direction) to the second joint 14. Consequently, the second joint 14 is driven.

Through the operation, step S143 is completed. Consequently, step S135 of FIG. 42 is completed, and the flow proceeds to step S131.

If these steps are repeatedly executed, this leads to a bent state in a parallelized state illustrated in FIG. 41A. In this case, in step S134, the second convergence state during advance-retract movement is determined, and thus control of the convergence operation control section 215G proceeds to step S136.

Steps S131 to S135 constitute a parallelization step in which the optical axis become parallel to the reference axial line and which includes the locus acquisition step in which advance-retract movement of the arm portion is performed in a state in which an angle of the second redundant joint is fixed, the convergence determination amount calculation step, the convergence determination step, and the driving amount correction step in which a driving amount is obtained such that a deviation amount is further reduced and the first redundant joint is driven by the driving amount, and which is completed in a case where the second convergence state is determined to occur in the convergence determination step.

Steps S136 to S139 are the same as steps S21 to S24 (refer to FIG. 14) of the first modified example except that control is performed by the convergence operation control section 215G and the driving amount correction section 213G, the second joint 14 which is a first redundant joint is fixed to a certain position, and a driving amount of the first joint 12 which is a second redundant joint is corrected.

Therefore, if steps S136 to S139 are executed, a locus of the beam spot B is acquired and a diameter of the locus is computed in the parallelized state illustrated in FIG. 41A. A change amount of the diameter of the locus is determined.

Step S140 is a step which constitutes the driving amount correction step of the present modified example and in which driving amounts are obtained in which the first redundant joint and the second redundant joint are bent at the same angle in directions reverse to each other so that a distance between the optical axis OL and the reference axial line O is reduced in order to reduce a diameter of a locus, and the first redundant joint and the second redundant joint are driven by the driving amounts.

Specifically, as illustrated in FIG. 10, steps S151 to S156 are executed according to the flow shown in FIG. 10.

Steps S151 to S156 are the same as steps S91 to S96 of the fourth modified example (the modified example of the second embodiment) except that control is performed by the driving amount correction section 213Q and driving amounts of the first joint 12 and the second joint 14 are corrected in the same magnitude and in directions reverse to each other.

In step S152, test-driving amounts including appropriate magnitudes and driving directions reverse to each other are set in the first joint 12 and the second joint 14, and, in step S153, the first joint 12 and the second joint 14 are driven.

In steps S154 and S155, exactly the same operation as in steps S94 and S95 are performed.

Next, in step S156, driving amounts which are the same as the driving amounts in step S96 and include driving directions reverse to each other are set in the first joint 12 and the second joint 14.

For example, in the parallelized state illustrated in FIG. 41A, in step S156, as illustrated in FIG. 41B, driving amounts are set in which the first joint 12 is rotationally moved in an illustrated clockwise direction by $\Delta\theta$, and the second joint 14 is rotationally moved in an illustrated counterclockwise direction by $\Delta\theta$.

In step S153, as a result of the first joint 12 and the second joint 14 being driven by the driving amounts, as illustrated in FIG. 41B, a parallelized state is realized in which a distance between the reference axial line O and the arm axial line O13 is reduced. For this reason, it is determined that the locus is located inside the reference locus in step S155, step S140 of FIG. 42 is completed, and the flow proceeds to step S136.

Thus, if steps S136 to S140 are repeatedly executed, in the arm portion 78, a distance between the reference axial line O and the second arm 13 is gradually reduced while the parallelized state is maintained, and, as illustrated in FIG. 41C, an aligned state of the arm portion 78 is formed so that the arm axial lines O13 and O15 are aligned with the reference axial line O.

In this case, in step S139, the first convergence state during rotational movement is determined, and thus the initialization operation is finished.

Steps S136 to S140 constitute a linearization step which includes the locus acquisition step in which rotational movement of the arm portion is performed, the convergence determination amount calculation step, the convergence determination step, and the driving amount correction step in which driving amounts are obtained in which the first redundant joint and the second redundant joint are bent at the same angle in directions reverse to each other such that a distance between the optical axis and the reference axial line is reduced in order to reduce a diameter of a locus, and the first redundant joint and the second redundant joint are respectively driven by the driving amounts, and which is completed in a case where the first convergence state is determined to occur in the convergence determination step.

In steps S131 to S140, the parallelization step and the linearization step are executed in this order, and initialization of the pair of redundant joints is finished in a case where the locus has converged in the convergence determination step of the linearization step.

According to the surgery support robot 1G of the present modified example, since the arm portion 78 can be initialized as mentioned above, control can be started from a state in which a position and orientation of the arm portion 78 is known, accordingly, an intuitive operation can be performed.

The present embodiment is an example of an initialization operation in a case where the redundant joints are provided, and an offset amount is 0.

According to the initialization operation of the present embodiment, initialization can be performed while a parallelized state is maintained, and thus rapid convergence is possible. In addition, when compared with the third embodiment, a change in the bent state of the arm portion 78 is reduced, and thus a space required in initialization is reduced.

In the present modified example, as long as driving command values and the magnitude of a rotating amount of an actual operation in the first joint 12 and the second joint 14 substantially match each other (also including a case of matching each other), the initialization operation can be performed even if a relationship between the driving command values and the rotating amount of the actual operation is unclear.

Fourth Embodiment

Next, a medical manipulator and an initialization method for the medical manipulator of a fourth embodiment of the present invention will be described.

Figure 44A:
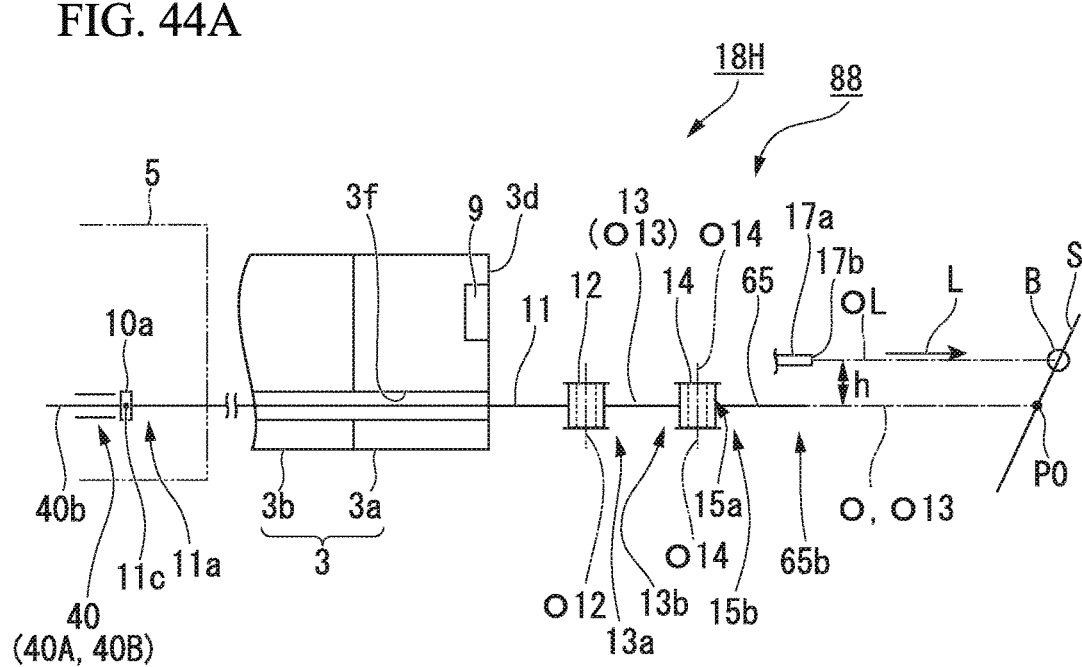
FIG. 44A is a schematic diagram of a front view illustrating configurations of main portions of a medical manipulator of a fourth embodiment of the present invention.
Figure 44B:
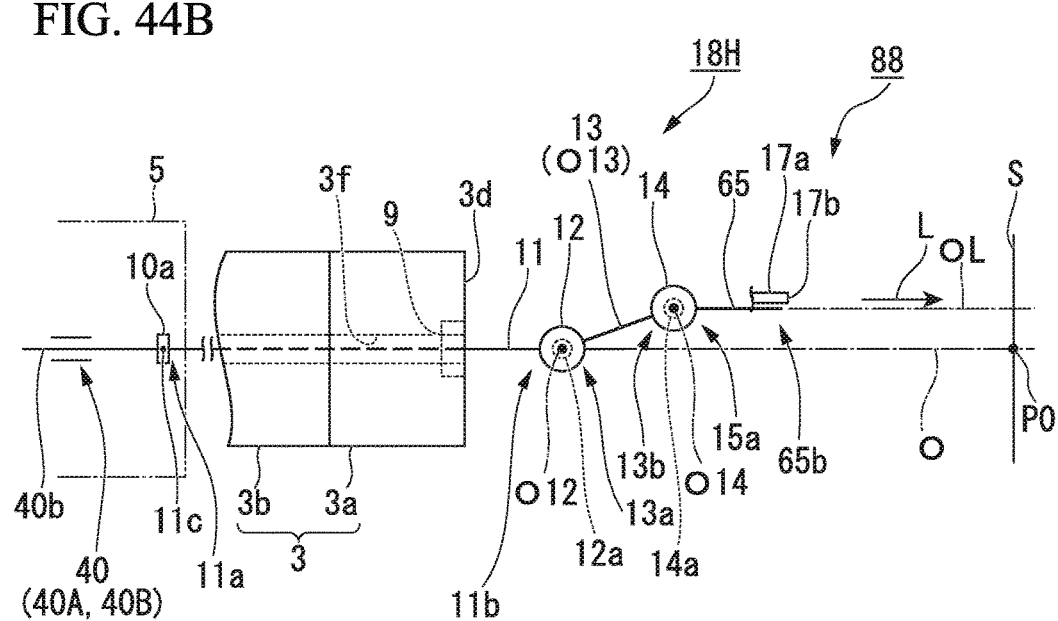
FIG. 44B is an operation explanatory diagram illustrating configurations of the main portions of the medical manipulator according to the fourth embodiment of the present invention.

FIGS. 44A and 44B are respectively a schematic diagram in a plan view and an operation explanatory diagram illustrating configurations of main portions of a medical manipulator of the fourth embodiment of the present invention.

As illustrated in FIG. 1, a surgery support robot 1H (medical manipulator) of the present embodiment includes a surgery instrument 18H and a control section 6H instead of the surgery instrument 18E and the control section 6E of the fourth modified example (the modified example of the second embodiment).

Hereinafter, a description will be made focusing on differences from the fourth modified example (the modified example of the second embodiment)

As main portions are schematically illustrated in FIGS. 44A and 44B, the surgery instrument 18H includes an arm portion 88 instead of the arm portion 68 of the fourth modified example.

The arm portion 88 is only different from the arm portion 78 in that the first joint 12 of the arm portion 68 of the fourth modified example is provided so that the first rotary shaft O12 is parallel to the second joint 14.

For this reason, a bent plane swept by the arm axial line O13 due to the first joint 12 and a bent plane swept by the arm axial line O15 due to the second joint 14 are the same plane (corresponding to the paper surface of FIG. 44B). Consequently, the third arm 65 is moved in the bent plane when the first joint 12 is driven, and has a redundant relationship with the first joint 12 and the second joint 14 in the present embodiment in the same manner as in the second embodiment.

On the basis of the configuration of the arm portion 88, the arm information supply section 11c of the present embodiment transmits configuration information of the arm portion 88 that "the number of bending joints is two", "there is a redundant joint", and "the magnitude of an offset amount is h and an offset direction is a rotary shaft direction offset".

As mentioned above, the arm portion 88 is configured so that the optical axis OL is formed to have a rotary shaft direction offset with respect to the arm axial line O13 by replacing the third arm 15 of the arm portion 78 of the third embodiment with the third arm 65.

For this reason, as illustrated in FIG. 44B, when the arm portion 88 is viewed from a direction along the first rotary shaft O12 and the second rotary shaft O14, a positional relationship between the first rotary shaft O12, the second rotary shaft O14, and the optical axis OL with respect to the reference axial line O is exactly the same as the positional relationship in the arm portion 78 (refer to FIG. 37).

As illustrated in FIG. 31, the control section 6H is different from the control section 6E of the fourth modified example in that an initialization control unit 201H is provided instead of the initialization control unit 201E of the fourth modified example.

As illustrated in FIG. 32, the initialization control unit 201H is different from the initialization control unit 201E of the fourth modified example in that a convergence operation control section 215H and a driving amount correction section 213H are provided instead of the convergence operation control section 215E and the driving amount correction section 213E of the first modified example.

The convergence operation control section 215H has functions of both of the convergence operation control section 215F of the third embodiment and the convergence operation control section 215G of the sixth modified example.

The driving amount correction section 213H has functions of both of the driving amount correction section 213F of the third embodiment and the driving amount correction section 213G of the sixth modified example.

Next, an operation of the surgery support robot 1H will be described focusing on an initialization method for the medical manipulator of the present modified example.

An offset of the arm portion 88 is a rotary shaft direction offset with respect to the redundant joint.

For this reason, as described in the example of a case of a single joint in the second embodiment, initialization can be performed in the same manner as in a case where an offset amount is 0 except that a locus during rotational movement converges to the minimum diameter instead of converging to one point.

Therefore, the arm portion 88 can be initialized in the same manner as in the case of the third embodiment or the sixth modified example in which the same two redundant joints are provided. Consequently, it is clear that an operation of the arm portion 88 in the operation explanatory diagrams (refer to FIGS. 39A, 39B, 39C, 40A, 40B, 40C, 41A, 41B, 41C, 43A, 43B, 43C and 43D) viewed from a direction perpendicular to the bent plane is exactly the same as the operation of the arm portion 78.

Therefore, the convergence operation control section 215H of the present embodiment selects the convergence operation of the third embodiment and the convergence operation of the sixth modified example through an input operation on the mode-switching switch 2e.

The convergence operation control section 215H executes steps S11 to S120 illustrated in FIG. 38 in a case of performing the initialization method of the third embodiment, and executes steps S131 to S140 illustrated in FIG. 42 in a case of performing the initialization method of the sixth modified example.

In the above-described way, the arm portion 88 can be initialized in the same manner as in the third embodiment or the sixth modified example.

According to the surgery support robot 1H of the present embodiment, since the arm portion 88 can be initialized as mentioned above, control can be started from a state in which a position and orientation of the arm portion 88 is known, accordingly, an intuitive operation can be performed.

The present embodiment is an example of an initialization operation in a case where the redundant joints are provided, and an offset amount is 0.

Seventh Modified Example

Next, a medical manipulator and an initialization method for the medical manipulator of a modified example (seventh modified example) of the fourth embodiment will be described.

Figure 45:
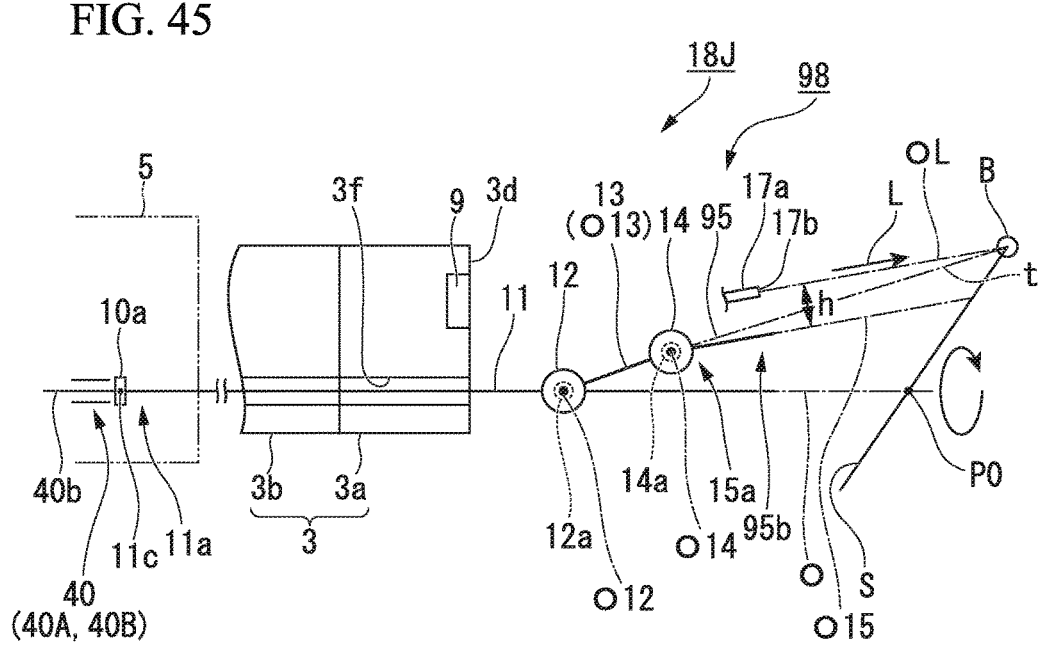
FIG. 45 is a schematic diagram of a front view illustrating configurations of main portions of a medical manipulator of a modified example (seventh modified example) of the fourth embodiment of the present invention.
Figure 46:
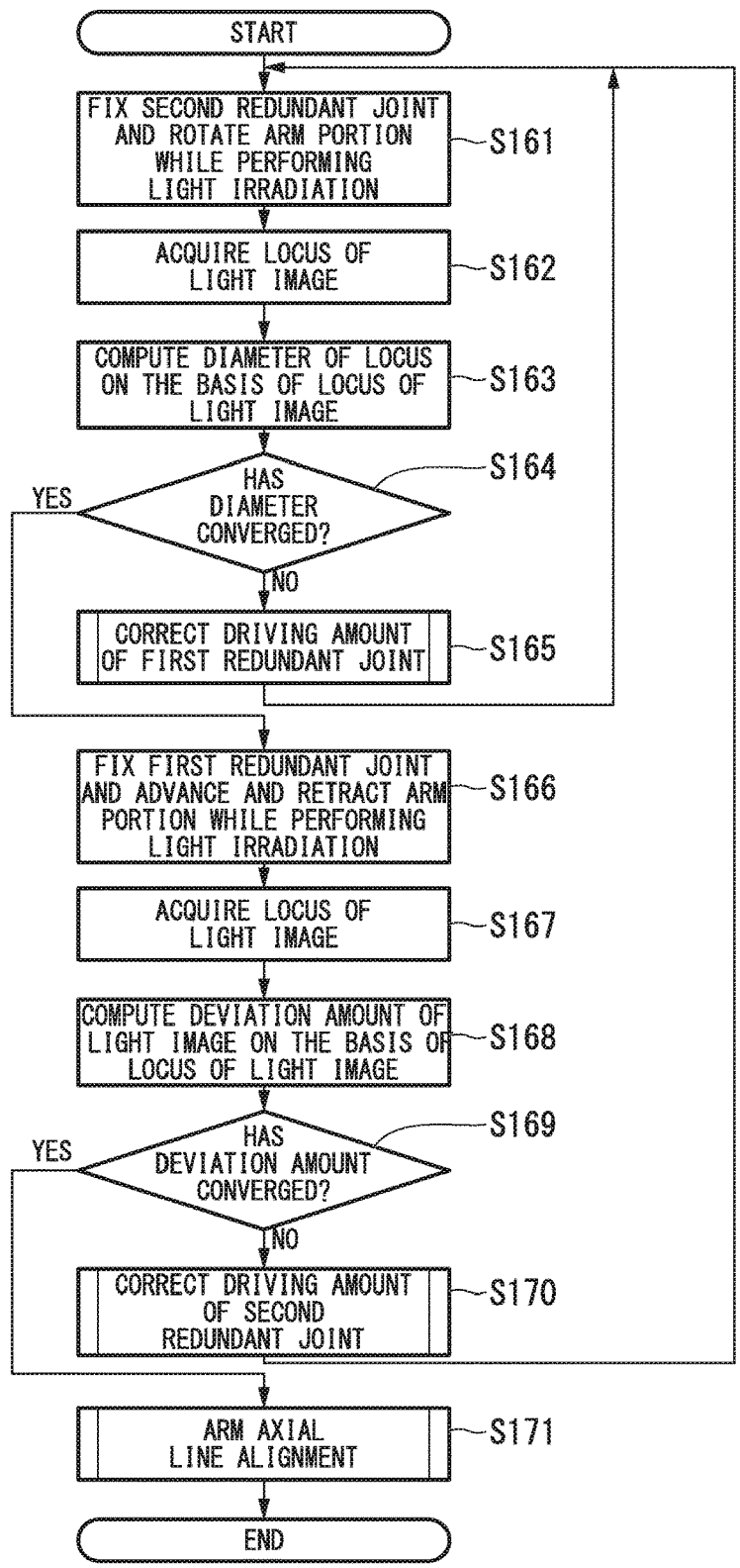
FIG. 46 is a flowchart illustrating a flow of an initialization method for a medical manipulator of the modified example (seventh modified example) of the fourth embodiment of the present invention.
Figure 47A:
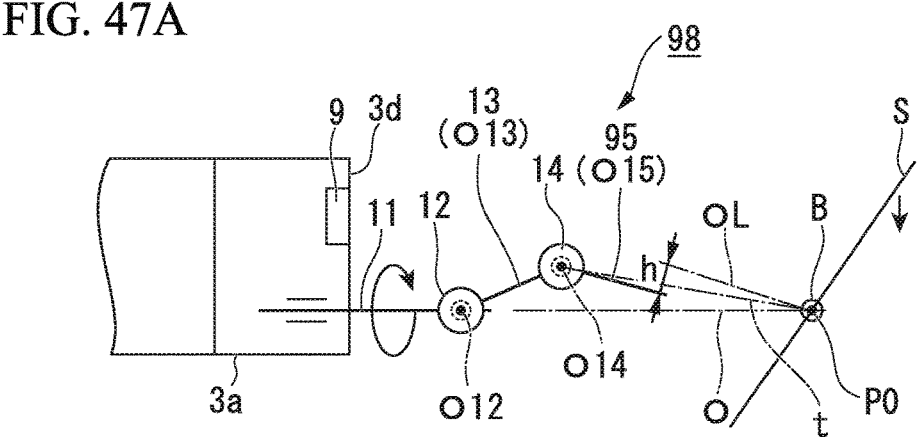
FIG. 47A is a schematic diagram for explaining an operation of initializing the medical manipulator of the modified example (seventh modified example) of the fourth embodiment of the present invention.
Figure 47B:
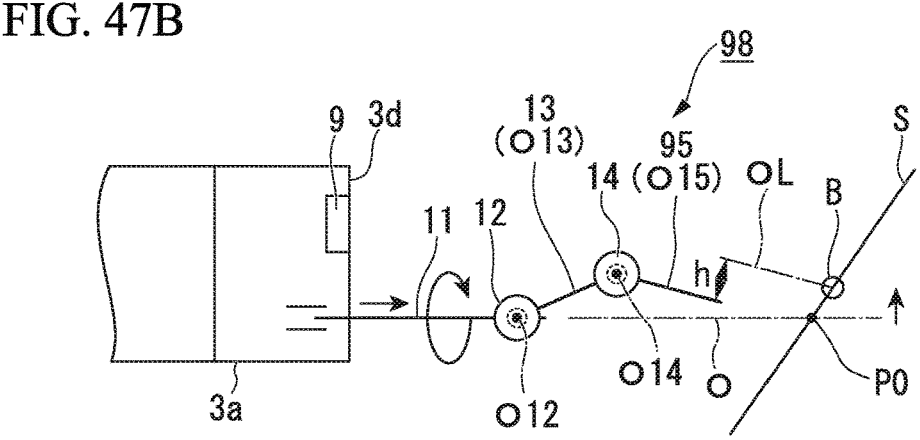
FIG. 47B is a schematic diagram for explaining an operation of initializing the medical manipulator of the modified example (seventh modified example) of the fourth embodiment of the present invention.
Figure 47C:
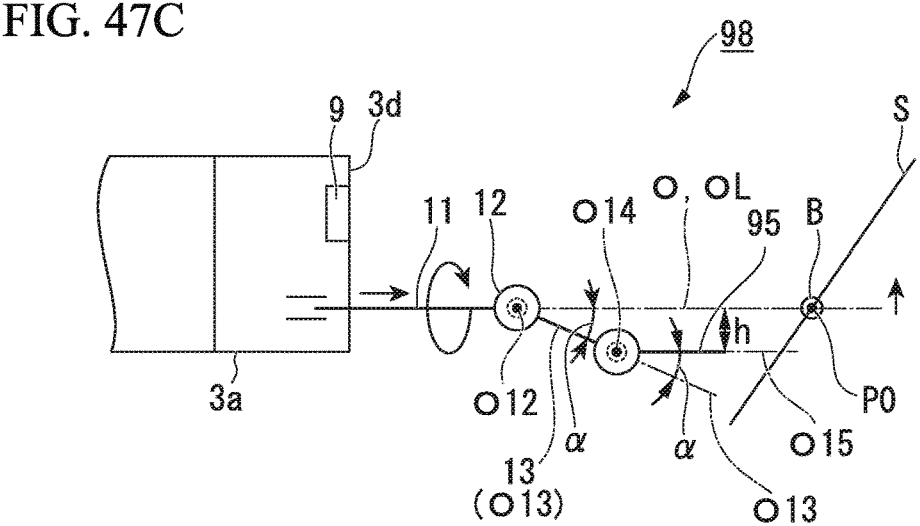
FIG. 47C is a schematic diagram for explaining an operation of initializing the medical manipulator of the modified example (seventh modified example) of the fourth embodiment of the present invention.
Figure 48:
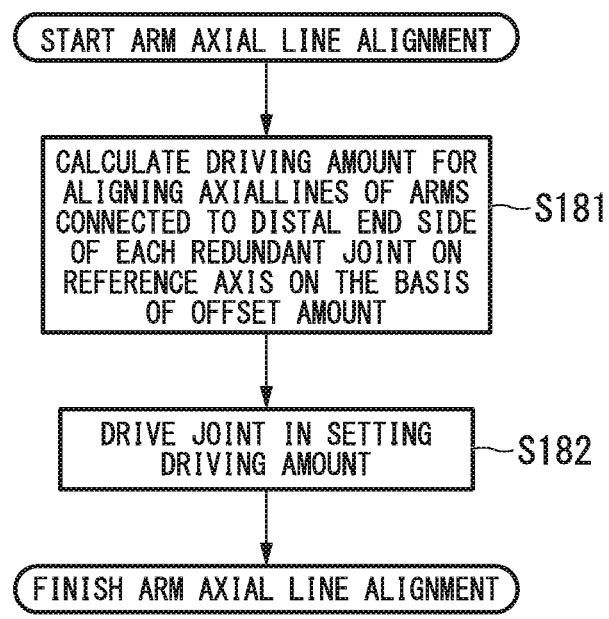
FIG. 48 is a flowchart illustrating a flow of an arm axis alignment step in the initialization method for the medical manipulator of the modified example (seventh modified example) of the fourth embodiment of the present invention.

FIG. 45 is a schematic diagram in a plan view illustrating configurations of main portions of a medical manipulator of a modified example (seventh modified example) of the fourth embodiment of the present invention. FIG. 46 is a flowchart illustrating a flow of an initialization method for a medical manipulator of the modified example (seventh modified example) of the fourth embodiment of the present invention. FIGS. 47A, 47B and 47C are schematic diagrams illustrating operations of initializing the medical manipulator of the modified example (seventh modified example) of the fourth embodiment of the present invention. FIG. 48 is a flowchart illustrating a flow of an arm axis alignment step in the initialization method for the medical manipulator of the modified example (seventh modified example) of the fourth embodiment of the present invention.

As illustrated in FIG. 1, a surgery support robot 1J (medical manipulator) of the present embodiment includes a surgery instrument 18J and a control section 6J instead of the surgery instrument 18H and the control section 6H of the fourth modified example of the fourth embodiment.

Hereinafter, a description will be made focusing on differences from the fourth embodiment.

As main portions are schematically illustrated in FIG. 45, the surgery instrument 18J includes an arm portion 98 instead of the arm portion 68 of the fourth modified example.

The arm portion 98 includes a third arm 95 (arm) instead of the third arm 65 of the arm portion 88 of the fourth embodiment.

In the third arm 95, there is only a difference in that the arm proximal end 15a of the third arm 95 is rotated around the arm axial line O13 by 90° and is connected to the second joint 14.

For this reason, the fiber end surface 17b of the third arm 95 is disposed in a positional relationship in which the fiber end surface 17b has a bent plane direction offset with respect to the second joint 14 as illustrated in FIG. 45. However, as illustrated in FIGS. 22A and 22B, a positional relationship in which the treatment portion 16 is on the reference axial line O and the fiber end surface 17b is moved in parallel by a distance h is the same as that in the arm portion 88.

On the basis of the configuration of the arm portion 98, the arm information supply section 11c of the present modified example transmits configuration information that "the number of bending joints is two", "there is a redundant joint", and "the magnitude of an offset amount is h and an offset direction is a bent plane direction offset".

As illustrated in FIG. 31, the control section 6J has a difference in that an initialization control unit 201J (initialization control unit) is provided instead of the initialization control unit 201H of the fourth embodiment.

As illustrated in FIG. 32, the initialization control unit 201J is different from the initialization control unit 201H of the fourth embodiment in that a convergence operation control section 215J and a driving amount correction section 213J are provided instead of the convergence operation control section 215H and the driving amount correction section 213H of the fourth embodiment.

Control performed by the convergence operation control section 215J and the driving amount correction section 213J will be described in descriptions of operations thereof.

Next, an operation of the surgery support robot 1J will be described focusing on an initialization method for the medical manipulator of the present modified example.

FIG. 46 is a flowchart illustrating a flow of an initialization method for a medical manipulator of the modified example (seventh modified example) of the fourth embodiment of the present invention. FIGS. 47A, 47B and 47C are schematic diagrams illustrating operations of initializing the medical manipulator of the modified example (seventh modified example) of the fourth embodiment of the present invention. FIG. 48 is a flowchart illustrating a flow of an arm axial line alignment step in the initialization method for the medical manipulator of the modified example (seventh modified example) of the fourth embodiment of the present invention.

In the present modified example, in order to initialize the arm portion 98, steps S161 to S171 illustrated in FIG. 46 are executed according to the flow shown in FIG. 46. Steps S161 to S165 are the first convergence step in which a driving amount is obtained such that a diameter of a locus acquired through rotational movement of the arm portion 98 is smaller while fixing an angle of the first joint 12, and the second joint 14 is driven by the driving amount, and which is completed in a case where the first convergence state is determined to occur. This step is executed in the same manner as the first convergence step of the third embodiment.

As described in the third embodiment, in a case where an offset amount is 0 as in the arm portion 78, even if two redundant joints are provided, a convergence operation can be performed in which the beam spot B converges to the point P0 by fixing one redundant joint to a certain point and acquiring a locus through rotational movement.

Since the arm portion 98 has the bent plane direction offset, the optical axis OL and the arm axial line O15 are moved in a bent plane and are maintained in a positional relationship of being parallel to each other. For this reason, as indicated by a two-dot chain line in FIG. 45, a straight line t connecting the second rotary shaft O14 to the beam spot B on the inner wall S is inclined with respect to the arm axial line O15.

Therefore, the arm portion 98 having such a positional relationship is equivalent to the arm portion 78 which has the optical axis OL on the straight line t and in which an offset amount is 0.

The initialization method of the third embodiment is a method in which convergence can be made to occur by repeatedly correcting a driving amount even if an angle of the bending joint is unclear, and thus the beam spot B can also be made to converge to the point P0 in the arm portion 98 in the same manner as in the arm portion 78.

Steps S161 to S165 are the same as steps S111 to S115 (refer to FIG. 38) of the third embodiment except that control is performed by the convergence operation control section 215J and the driving amount correction section 213J.

Through the above steps, for example, the arm portion 98 is brought into the first convergence state in which the beam spot B converges to the point P0 from a bent state illustrated in FIG. 45 as illustrated in FIG. 47A.

If the first convergence state is determined to occur in step S164, the convergence operation control section 215J proceeds to step S166.

Steps S166 to S170 are the second convergence step in which a driving amount is obtained such that a deviation amount of an optical image for a locus acquired through advance-retract movement of the arm portion 98 is further reduced while fixing an angle of the second joint 14, and the first joint 12 is driven by the driving amount, and which is completed in a case where the second convergence step is determined to occur. This step is executed in the same manner as the second convergence step of the third embodiment.

Steps S166 to S170 are the same as steps S116 to S120 (refer to FIG. 38) of the third embodiment except that control is performed by the convergence operation control section 215J and the driving amount correction section 213J.

In these steps, a driving amount of the first joint 12 is corrected such that the optical axis OL becomes parallel to the reference axial line O in the arm portion 98 on the basis of the locus acquired through advance-retract movement of the arm portion 98 until a deviation amount of the beam spot B is determined to converge and the second convergence state is determined to occur in step S169.

If these steps are repeatedly executed, a state in which the optical axis OL is parallel to the reference axial line O and the beam spot B converges to the point P0 in the same manner as in the third embodiment occurs. However, since the optical axis OL is located in an offset position, as illustrated in FIG. 47C, the arm portion 98 converges to a state (hereinafter, referred to as an "optical axis alignment state") in which the optical axis OL is aligned with the reference axial line O, and the arm axial line O15 is moved in parallel by the offset amount h from the reference axial line O.

Consequently, the second convergence state is determined in step S169, and the flow proceeds to step S171.

Steps S161 to S170 of the present embodiment constitute an optical axis alignment step in which the first convergence step and the second convergence step are repeatedly executed in this order, and which is completed in a case where a locus has converged in the convergence determination step and causes the optical axis to be aligned with the reference axial line.

Step S171 constitutes an arm axial line alignment step in which driving amounts for aligning the axial line of the arm connected to the distal end side of the first redundant joint and the axial line of the arm connected to the distal end side of the second redundant joint on the reference axial line by rotationally moved in directions reverse to each other from the optical axis alignment state are calculated on the basis of the offset amount, and the first redundant joint and the second redundant joint are respectively driven by the driving amounts. Specifically, the step is executed by executing steps S181 and S182 illustrated in FIG. 48 according to the flow shown in FIG. 48.

In step S181, driving amounts for aligning the arm axial lines O13 and O15 of the second arm 13 and the third arm 95 connected to the distal end sides of the first joint 12 and the second joint 14 on the reference axial line O are calculated on the basis of the offset amount h.

In the optical axis alignment state, the arm axial line O13 is separated from the reference axial line O by the distance h and is parallel to the reference axial line O. For this reason, as illustrated in FIG. 47C, if an angle formed between the reference axial line O and the arm axial line O13 is set to α, an angle formed between the arm axial lines O13 and O15 is a corresponding angle and is thus the same as the angle α.

Since the angle α is uniquely defined by a distance between the first rotary shaft O12 and the second rotary shaft O14 and the offset amount h, the driving amount correction section 213J acquires such information from the configuration information of the arm portion 98, and calculates the angle α so as to include a driving direction.

Through the operation, step S181 is completed.

Next, step S182 is executed. In this step, the first joint 12 and the second joint 14 are driven by the driving amounts set in step S181.

The driving amount correction section 213J sends driving command values corresponding to the set driving amounts to the first joint 12 and the second joint 14. Consequently, the first joint 12 and the second joint 14 are driven.

Through the operation, step S182 is completed. Consequently, step S171 is completed, and thus the initialization operation is finished.

According to the surgery support robot 1J of the present modified example, since the arm portion 98 can be initialized as mentioned above, control can be started from a state in which a position and orientation of the arm portion 98 is known, accordingly, an intuitive operation can be performed.

The present modified example is an example in which two redundant joints are provided, and initialization can be performed in a case where the optical axis OL has an offset in a bent plane direction with respect to the redundant joint on the distal end side.

Eighth Modified Example

Next, a medical manipulator and an initialization method for the medical manipulator of a modified example (eighth modified example) of the fourth embodiment will be described.

The present modified example is a modified example of the initialization method in the seventh modified example (a modified example of the fourth embodiment), and, as illustrated in FIG. 1, a surgery support robot 1K (medical manipulator) of the present embodiment includes a control section 6K instead of the control section 6J of the seventh modified example.

Hereinafter, a description will be made focusing on differences from the seventh modified example.

As illustrated in FIG. 31, the control section 6K includes an initialization control unit 201K instead of the initialization control unit 201J of the seventh modified example.

As illustrated in FIG. 32, the initialization control unit 201K includes a convergence operation control section 215K and a driving amount correction section 213K instead of the convergence operation control section 215J and the driving amount correction section 213J of the seventh modified example.

Control performed by the convergence operation control section 215K and the driving amount correction section 213K will be described in descriptions of operations thereof.

Next, an operation of the surgery support robot 1K will be described focusing on an initialization method for the medical manipulator of the present modified example.

Figure 49:
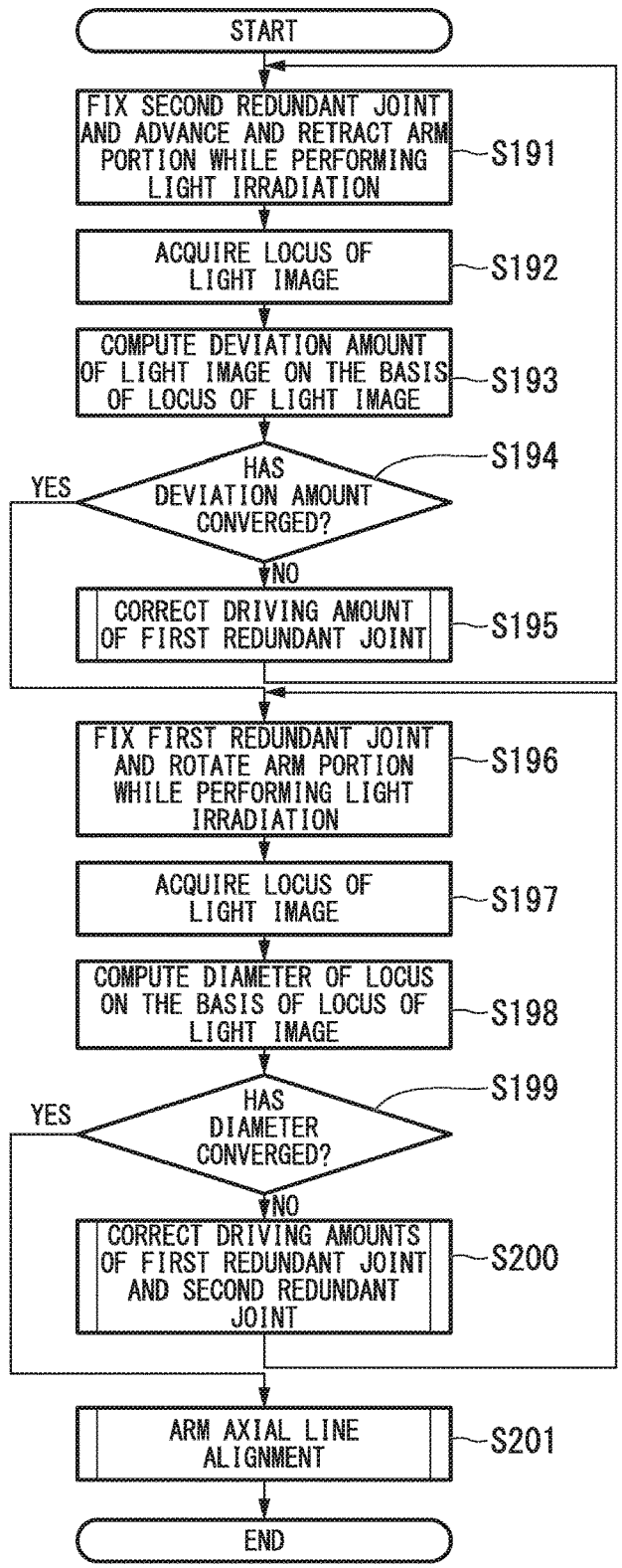
FIG. 49 is a flowchart illustrating a flow of an initialization method for a medical manipulator of a modified example (eighth modified example) of the fourth embodiment of the present invention.
Figure 50A:
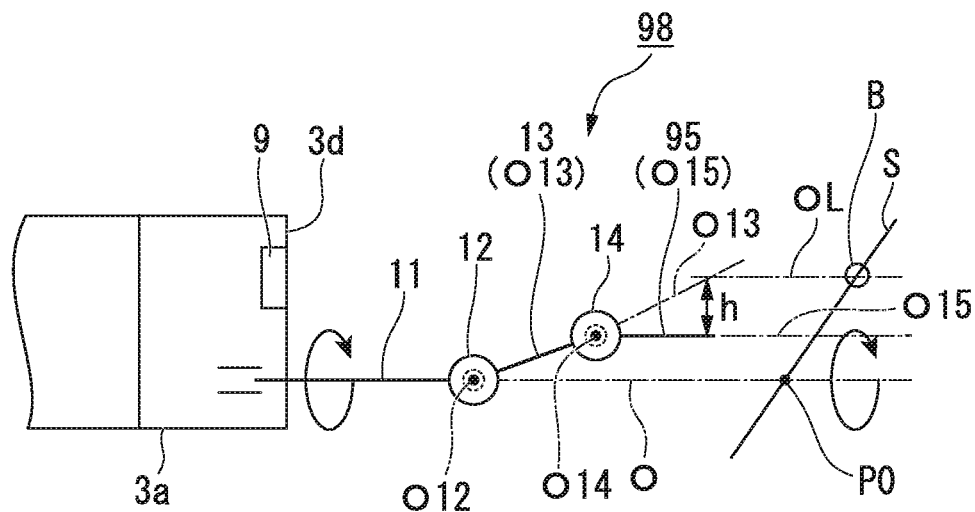
FIG. 50A is a schematic diagram for explaining an operation of initializing the medical manipulator of the modified example (eighth modified example) of the fourth embodiment of the present invention.
Figure 50B:
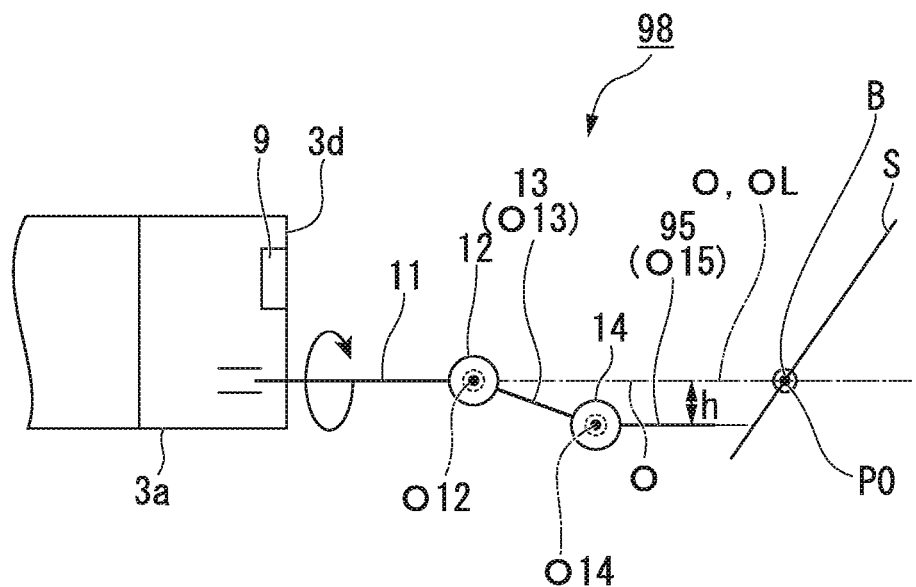
FIG. 50B is a schematic diagram for explaining an operation of initializing the medical manipulator of the modified example (eighth modified example) of the fourth embodiment of the present invention.

FIG. 49 is a flowchart illustrating a flow of an initialization method for a medical manipulator of the modified example (eighth modified example) of the fourth embodiment of the present invention. FIGS. 50A and 50B are schematic diagrams illustrating operations of initializing the medical manipulator of the modified example (eighth modified example) of the fourth embodiment of the present invention.

In the present modified example, in order to initialize the arm portion 98, steps S191 to S201 illustrated in FIG. 49 are executed according to the flow shown in FIG. 49.

Steps S191 to S195 are a parallelization step in which a driving amount is obtained such that a deviation amount of an optical image for a locus acquired through advance-retract movement of the arm portion 98 is further reduced while fixing an angle of the first joint 12, and the second joint 14 is driven by the driving amount, and which is completed in a case where the second convergence state is determined to occur which causes the optical axis OL to be parallel to the reference axial line O. This step is executed in the same manner as the parallelization step of the sixth modified example (a modified example of the third embodiment).

As described in the sixth modified example, in a case where an offset amount is 0 as in the arm portion 78, even if two redundant joints are provided, the optical axis OL can be made parallel to the reference axial line O by fixing one redundant joint to a certain point and acquiring a locus through advance-retract movement.

Since the arm portion 98 has the bent plane direction offset, the optical axis OL and the arm axial line O13 are moved in a bent plane and are maintained in a positional relationship of being parallel to each other.

For this reason, the optical axis OL and the reference axial line O can be brought into a parallelized state exactly in the same manner as in the sixth modified example.

Steps S191 to S195 are the same as steps S131 to S135 (refer to FIG. 42) of the sixth modified example except that control is performed by the convergence operation control section 215K and the driving amount correction section 213K.

Through the above steps, for example, the arm portion 98 is brought into the parallelized state in which the optical axis OL is parallel to the reference axial line O from a bent state illustrated in FIG. 45 as illustrated in FIG. 50A.

If the second convergence state is determined to occur in step S194, the convergence operation control section 215K proceeds to step S196.

Steps S196 to S200 are the optical axis alignment step in which an angle of the second joint 14 is fixed, driving amounts for bending the first joint 12 and the second joint 14 in directions reverse to each other by the same angle such that a diameter of a locus becomes smaller by performing rotational movement of the arm portion 98 while fixing an angle of the second joint 14 are obtained and the first joint 12 and the second joint 14 are driven by the driving amounts, and which is completed in a case where the first convergence state is determined to occur and which causes the optical axis OL is aligned with the reference axial line O. This step is executed in the same manner as the linearization step of the sixth modified example.

Steps S196 to S200 are the same as steps S136 to S140 (refer to FIG. 42) of the sixth modified example except that control is performed by the convergence operation control section 215K and the driving amount correction section 213K.

In these steps, driving amounts of the first joint 12 and the second joint 14 are corrected so that the optical axis OL becomes parallel to the reference axial line O in the arm portion 98 on the basis of the locus acquired through rotational movement of the arm portion 98 until it is determined that a diameter of the beam spot B converges and the first convergence state occurs in step S199.

If these steps are repeatedly executed, a state occurs in which the optical axis OL is parallel to the reference axial line O and the beam spot B converges to the point P0 in the same manner as in the sixth modified example. However, since the optical axis OL has an offset, as illustrated in FIG. 50B, the arm portion 98 converges to the same optical axis alignment state as in the seventh modified example.

Consequently, the second convergence state is determined in step S200, and the convergence operation control section 215K proceeds to step S201.

Step S201 constitutes the same arm axial line alignment step as in the seventh modified example, and is executed by executing steps S181 and S182 illustrated in FIG. 48 according to the flow in FIG. 48 specifically.

If step S182 is completed, step S201 is completed, and the initialization operation is finished.

According to the surgery support robot 1K of the present modified example, since the arm portion 98 can be initialized as mentioned above, control can be started from a state in which a position and orientation of the arm portion 98 is known, accordingly, an intuitive operation can be performed.

The present modified example is an example in which two redundant joints are provided, and initialization can be performed in a case where the optical axis OL has an offset in a bent plane direction with respect to the redundant joint on the distal end side.

Fifth Embodiment

Next, a medical manipulator and an initialization method for the medical manipulator of a fifth embodiment of the present invention will be described.

Figure 51A:
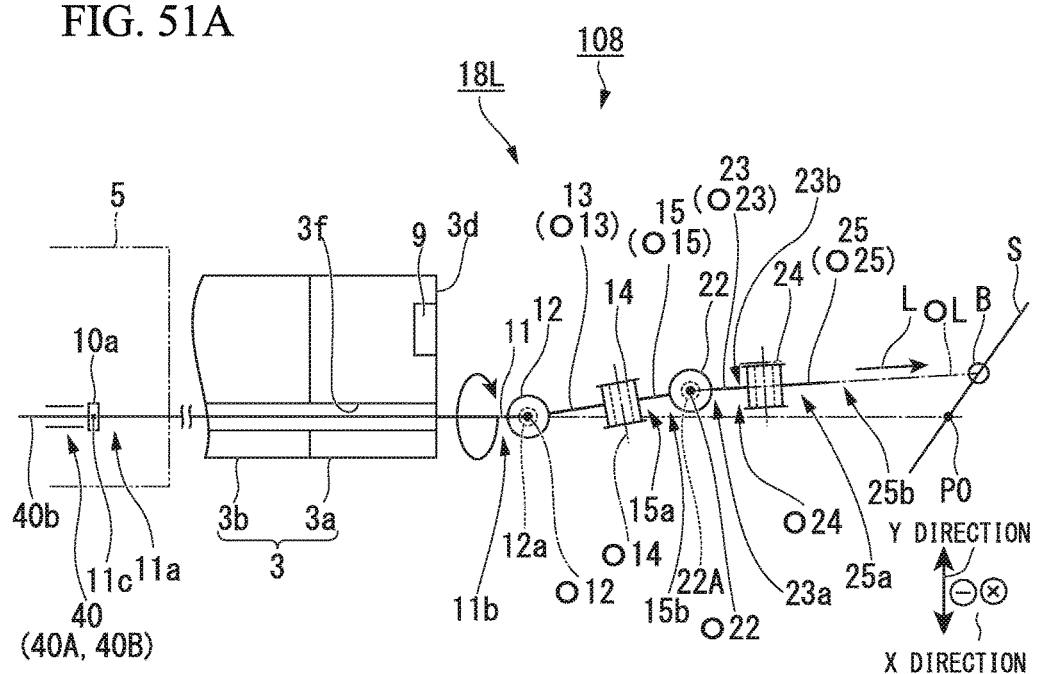
FIG. 51A is a schematic diagram of a front view of a bent state illustrating configurations of main portions of a medical manipulator of a fifth embodiment of the present invention.
Figure 51B:
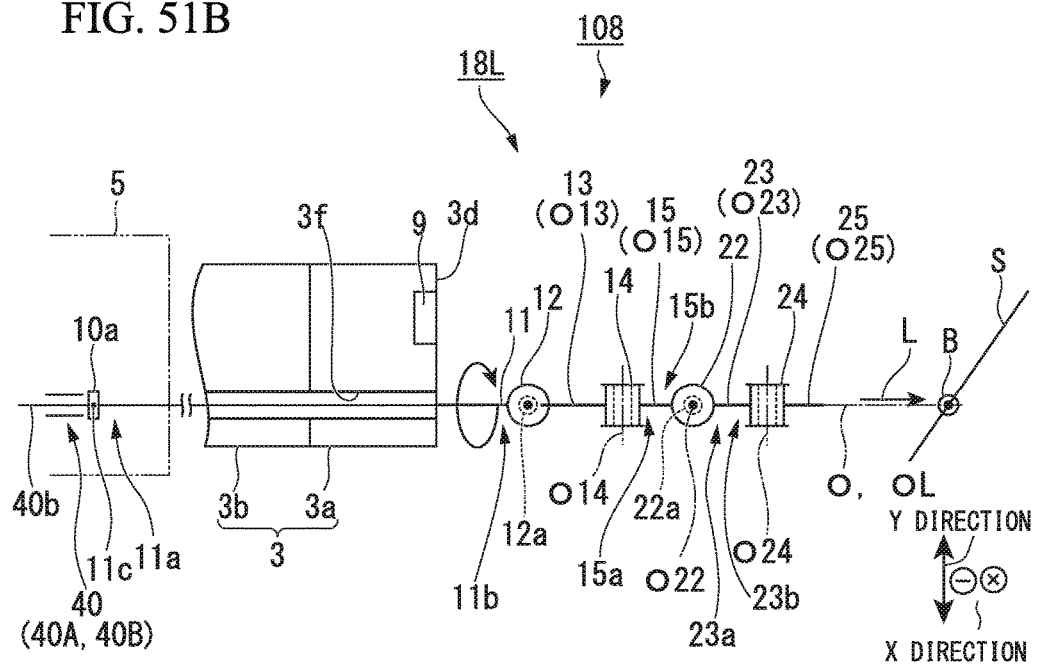
FIG. 51B is a schematic diagram of a front view of an aligned state illustrating configurations of the main portions of the medical manipulator according to the fifth embodiment of the present invention.
Figure 52:
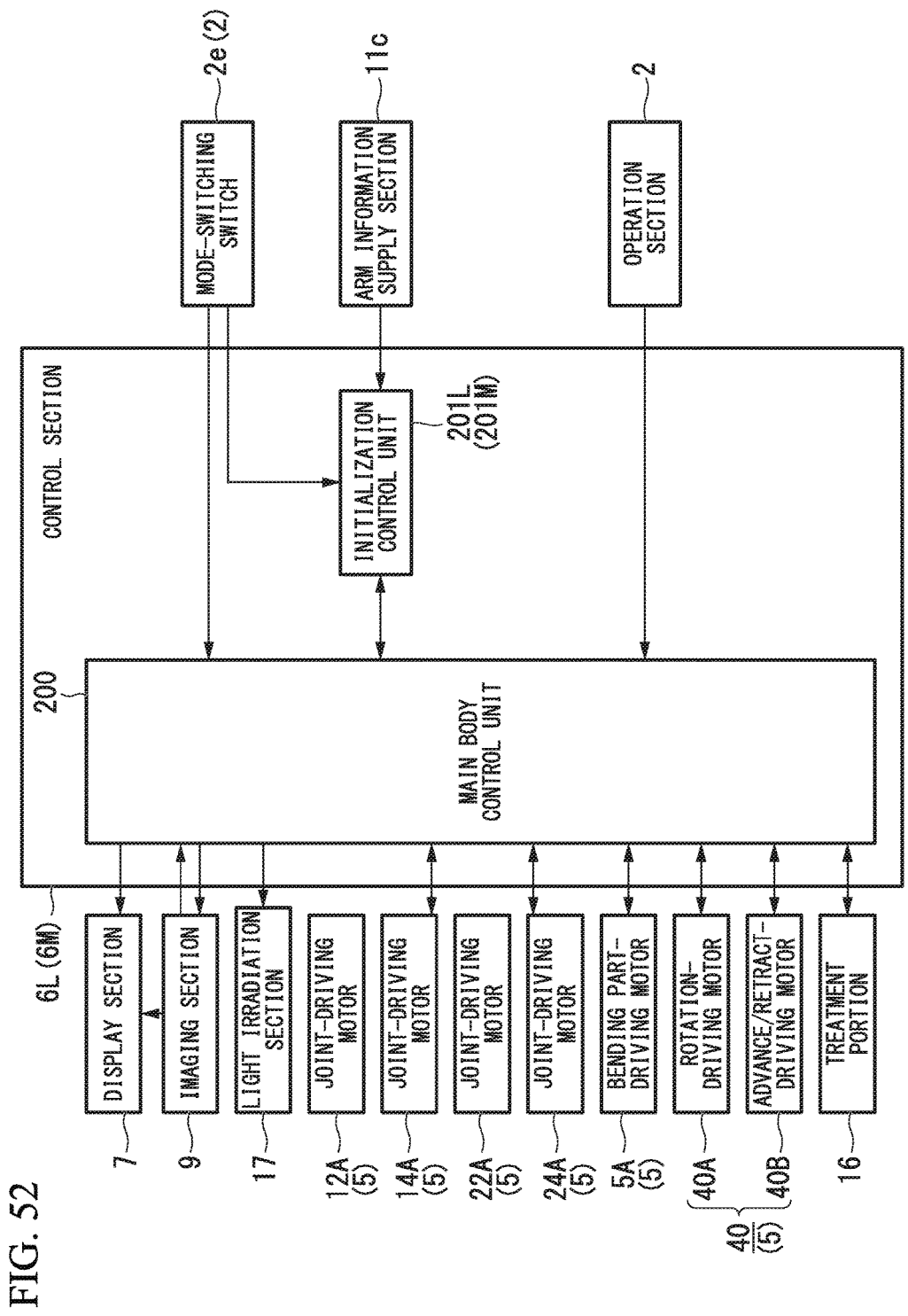
FIG. 52 is a functional block diagram illustrating a major functional configuration of a control section of the medical manipulator according to the fifth embodiment of the present invention.
Figure 53:
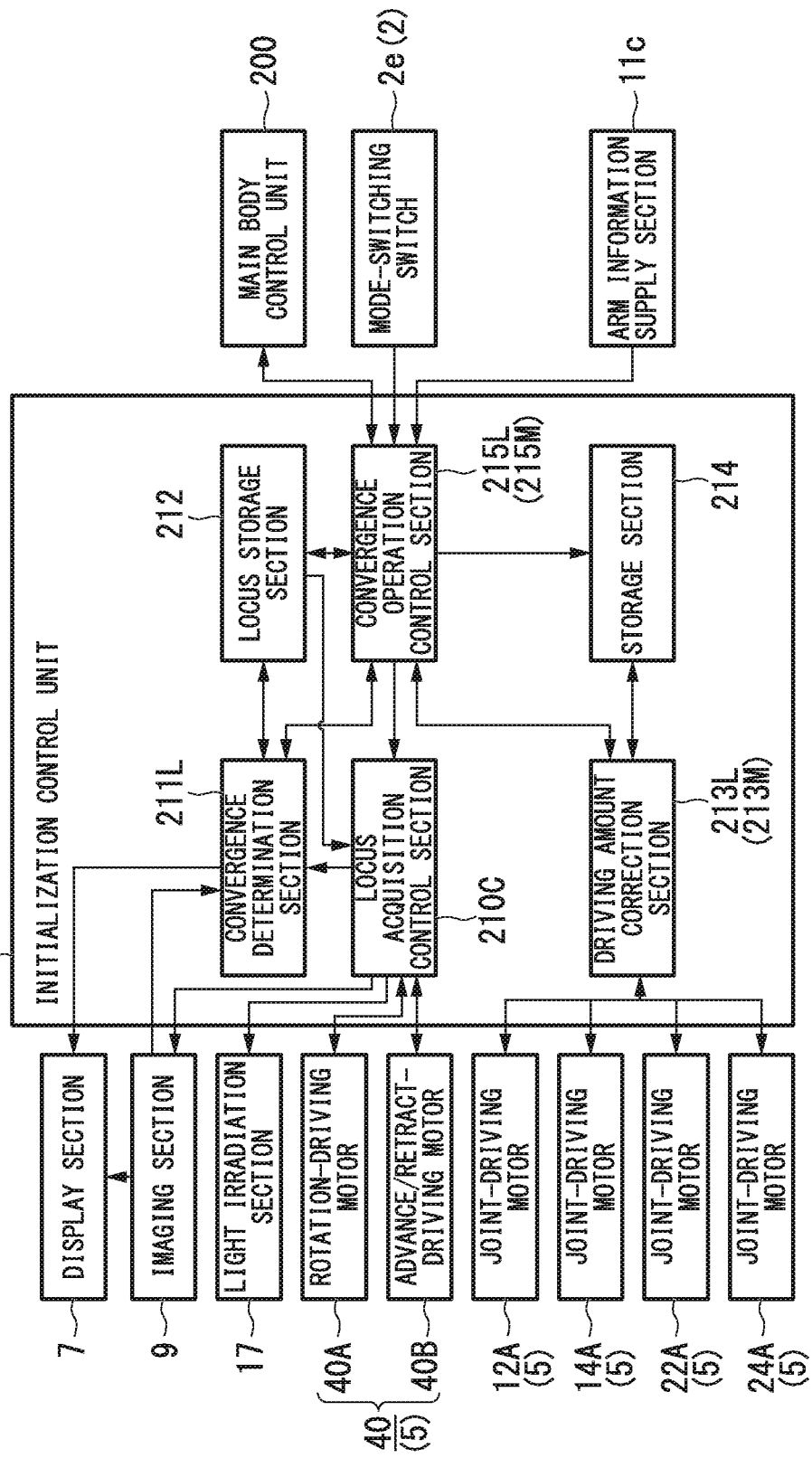
FIG. 53 is a functional block diagram illustrating a functional configuration of initialization control of the medical manipulator according to the fifth embodiment of the present invention.

FIGS. 51A and 51B are schematic diagrams of a bent state and an aligned state in a plan view illustrating configurations of main portions of a medical manipulator of the fifth embodiment of the present invention. FIG. 52 is a functional block diagram illustrating a major functional configuration of a control section of the medical manipulator according to the fifth embodiment of the present invention. FIG. 53 is a functional block diagram illustrating a functional configuration of initialization control of the medical manipulator according to the fifth embodiment of the present invention.

As illustrated in FIG. 1, a surgery support robot 1L (medical manipulator) of the present embodiment includes a surgery instrument 18L and a control section 6L instead of the surgery instrument 18F and the control section 6F of the third embodiment.

Hereinafter, a description will be made focusing on differences from the third embodiment.

As main portions are schematically illustrated in FIGS. 51A and 51B, the surgery instrument 18L includes an arm portion 108 instead of the arm portion 78 of the third embodiment.

The arm portion 108 corresponds to an example of a case of including redundant joints in two directions whereas the arm portion 78 of the third embodiment includes a pair of redundant joints. In this case, three or more pairs of redundant joints may be provided, but, hereinafter, as an example, a case of two pairs of redundant joints will be described.

The arm portion 108 includes the first arm 11, the first joint 12, the second arm 13, the second joint 14, the third arm 15, a third joint 22 (bending joint), a fourth arm 23 (arm), a fourth joint 24 (bending joint), and a fifth arm 25 (arm) in this order from the proximal end side toward the distal end side.

The arm portion 108 is an arm portion having an articulated structure in which the first arm 11, the second arm 13, the third arm 15, the fourth arm 23, and the fifth arm 25 (arm) can bent by the first joint 12, the second joint 14, the third joint 22, and the fourth joint 24 (refer to FIG. 51A), and are provided so as to be aligned on the reference axial line O (refer to FIG. 51B).

Hereinafter, in a case where mutual positional relationships are described, the description will be made assuming that the respective arms are in a state of being aligned with the reference axial line O (aligned state) unless otherwise mentioned.

The first arm 11, the first joint 12, and the second arm 13 have the same configurations as in the arm portion 78.

In the second joint 14, there is only a difference in that the second rotary shaft O14 is provided at a position of being rotated around the arm axial line O13 by 90°. For this reason, the first rotary shaft O12 and the second joint 14 have a positional relationship of being perpendicular to each other and are not in a redundant relationship.

In the third arm 15, there is a difference in that the treatment portion 16 and the fiber end surface 17b at the arm distal end 15b are removed, and the third joint 22 is connected to the arm distal end 15b.

The third joint 22 is a rotary joint having a rotation body which is rotationally moved around a third rotary shaft O22. A pulley 22a which transmits a rotation driving force from the proximal end side is provided at the rotation body of the third joint 22 on the same axis as that of the third rotary shaft O22.

A driving wire (driving force transmission wire material) (not illustrated) extending from the driving section 5 and inserted through the first arm 11, the first joint 12, the second arm 13, the second joint 14, and the third arm 15 is wound around the pulley 22a. The driving wire is routed inside the insertion portion 3 (the first arm 11) in a state of being inserted into, for example, a coil sheath or the like, and is connected to the driving section 5 (a joint-driving motor 22A which will be described later) on a proximal end side. For this reason, the driving wire is pushed and pulled by the driving section 5 (the joint-driving motor 22A which will be described later) in the longitudinal direction of the insertion portion 3 (the first arm 11), and the pulley 22a and the rotation body to which the pulley 22a is fixed are configured to be rotated by pushing and pulling the driving wire in the longitudinal direction of the insertion portion 3 (the first arm 11) by the driving section 5 (the joint-driving motor 22A which will be described later).

The rotation body provided with the pulley 22a is connected to the fourth arm 23.

The third joint 22 is connected to the arm distal end 15b of the third arm 15 with a positional relationship of being perpendicular to the reference axial line O and the second rotary shaft O14.

The fourth arm 23 is a member extending along an arm axial line O23. In the present embodiment, as an example, a cylindrical member in which the arm axial line O23 is in a central axial line is employed.

An arm proximal end 23a of the fourth arm 23 is connected to the third joint 22 such that the fourth arm 23 can rotate around the third rotary shaft O22 at an intersection between the arm axial line O15 and the third rotary shaft O22.

The fourth joint 24 is a rotary joint having a rotation body which is rotationally moved around a fourth rotary shaft O24. The same pulley (not illustrated) as the pulley 22a of the third joint 22 is provided at the rotation body of the fourth joint 24 on the same axis as that of the fourth rotary shaft O24. In the same manner as in the case of the pulley 22a, a driving wire (driving force transmission wire material) (not illustrated) whose distal end is connected to the driving section 5 (a joint-driving motor 24A which will be described later) and which extends from the driving section 5 (the joint-driving motor 24A which will be described later) to the fourth joint 24 is wound around the pulley.

For this reason, the driving wire is pushed and pulled by the driving section 5 (the joint-driving motor 24A which will be described later) in the longitudinal direction of the insertion portion 3 (the first arm 11), and the pulley and the rotation body to which the pulley is fixed are configured to be rotated by pushing and pulling the driving wire in the longitudinal direction of the insertion portion 3 (the first arm 11) by the driving section 5 (the joint-driving motor 24A which will be described later).

The rotation body provided with the pulley 22a is connected to the fifth arm 25.

The fourth joint 24 is connected to an arm distal end 23b of the fourth arm 23 with a positional relationship of being perpendicular to the reference axial line O and the third rotary shaft O22.

The fifth arm 25 is a member extending along an arm axial line O25. In the present embodiment, as an example, a cylindrical member in which the arm axial line O25 is in a central axial line is employed.

An arm proximal end 25a of the fifth arm 25 is connected to the fourth joint 24 such that the fifth arm 25 can rotate around the fourth rotary shaft O24 at an intersection between the arm axial line O23 and the fourth rotary shaft O24.

As illustrated in FIGS. 3A and 3B, the fiber end surface 17b and the treatment portion 16 are provided at an arm distal end 25b in the same positional relationship as at the arm distal end 15b of the arm portion 78 of the third embodiment.

The driving section 5 of the present embodiment is provided with the joint-driving motors 22A and 24A as motors for respectively supplying rotation driving forces to the third joint 22 and the fourth joint 24 as illustrated in FIG. 52. The joint-driving motors 22A and 24A are communicably connected to the main body control unit 200 (refer to FIG. 52) and an initialization control unit 201L (refer to FIG. 53).

In the arm portion 108 with such a configuration, in a case where axes of the respective arms are aligned on a straight line, the first joint 12 and the third joint 22 have the illustrated paper surface of FIG. 51B as a bent plane and thus have a redundant relationship. In addition, the second joint 14 and the fourth joint 24 have a plane perpendicular to the illustrated paper surface of FIG. 51B as a bent plane and thus have a redundant relationship.

On the basis of the configuration of the arm portion 108, the arm information supply section 11c of the present embodiment transmits configuration information of the arm portion 108 that "the number of bending joints is four", "redundant joints are two pairs of the first joint 12 and the third joint 22, and the second joint 14 and the fourth joint 24", and "an offset amount is 0".

As illustrated in FIG. 52, the control section 6L is different from the control section 6F of the third embodiment in that the initialization control unit 201L is provided instead of the initialization control unit 201F of the third embodiment.

As illustrated in FIG. 53, the initialization control unit 201L is different from the initialization control unit 201F of the third embodiment in that a convergence operation control section 215L, a driving amount correction section 213L, and a convergence determination section 211L (convergence determination amount calculation portion) are provided instead of the convergence operation control section 215F, the driving amount correction section 213F, and the convergence determination section 211C of the third embodiment.

Control performed by the convergence operation control section 215L, the driving amount correction section 213L, and the convergence determination section 211L will be described in descriptions of operations thereof.

Next, an operation of the surgery support robot 1L will be described focusing on an initialization method for the medical manipulator of the present modified example.

Figure 54:
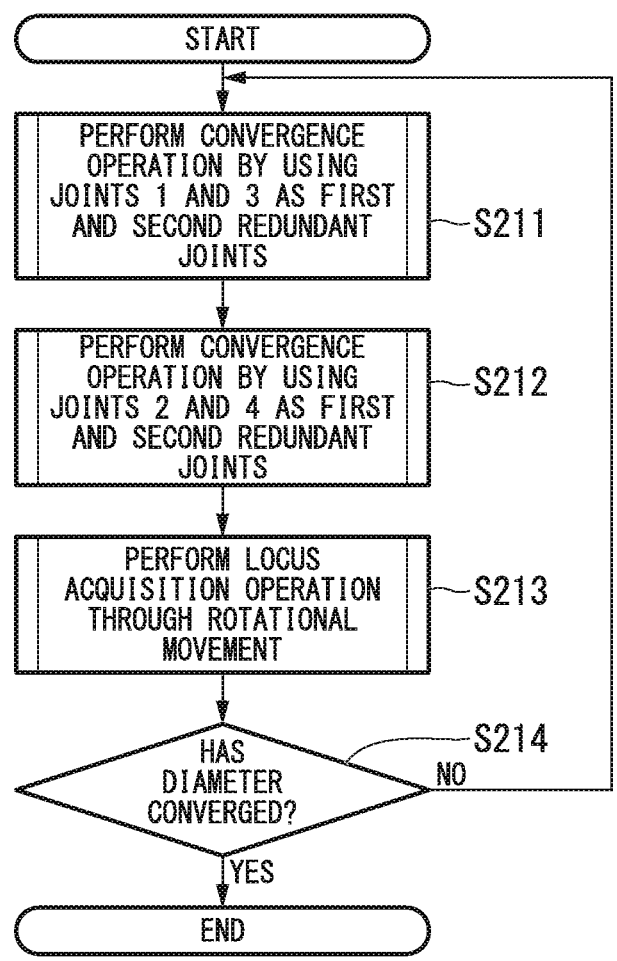
FIG. 54 is a flowchart illustrating a flow of an initialization method for the medical manipulator according to the fifth embodiment of the present invention.

FIG. 54 is a flowchart illustrating a flow of an initialization method for the medical manipulator according to the fifth embodiment of the present invention.

In the present embodiment, initialization is performed by repeatedly applying the initialization method of the third embodiment to bending joints having a relationship of redundant joints with each other.

Specifically, steps S211 to S214 illustrated in FIG. 54 are executed according to the flow shown in FIG. 54.

As long as an order of a convergence operation using rotational movement and a convergence operation using advance-retract movement is maintained of a pair of redundant joints, an execution order of the respective joints is not particularly limited.

Hereinafter, as an example, a case where a convergence operation is performed from a joint on the distal end side of the arm portion 108 will be described. In the flow of FIG. 54, the joints of the arm portion 108 are referred to as joints 1 to 4 from the distal end side to the proximal end side (hereinafter, the joints are represented in square brackets such as a [joint 1] so as to be differentiated from other reference numerals). A [joint 1] and a [joint 3] are respectively a first redundant joint and a second redundant joint in one pair of redundant joints. A [joint 2] and a [joint 4] are respectively a first redundant joint and a second redundant joint in the other pair of redundant joints.

In the present embodiment, the [joint 1] to the [joint 4] respectively correspond to the fourth joint 24, the third joint 22, the second joint 14, and the first joint 12.

In addition, hereinafter, for convenience of direction reference, a direction which is parallel to the first rotary shaft O12 is referred to as an X direction, and a direction which is perpendicular to the first rotary shaft O12 and the reference axial line O is referred to as a Y direction.

The X direction is a direction which is parallel to the first rotary shaft O12 and the third rotary shaft O22 in an aligned state of the arm portion 108.

The Y direction is a direction which is parallel to the second rotary shaft O14 and the fourth rotary shaft O24 in an aligned state of the arm portion 108.

In step S211, under the control of the convergence operation control section 215L, the redundant joints are aligned with each other so that an offset amount is 0 by using the fourth joint 24 ([joint 1]) as a first redundant joint and the second joint 14 ([joint 3]) as a second redundant joint in a state in which angles of the third joint 22 ([joint 2]) and the first joint 12 ([joint 4]) are fixed.

Specifically, step S211 is executed by executing the above steps S221 to S228, S229 and S230 illustrated in FIG. 38 according to the flow shown in FIG. 38.

Steps S221 to S228 are the same as steps S111 to S118 (refer to FIG. 38) of the third embodiment except for being executed under the control of the convergence operation control section 215L.

Step S229 is the same as the above step S119 except that the convergence determination section 211L determines convergence of a deviation amount on the basis of a deviation amount viewed from the Y direction, that is, an X direction component of the deviation amount.

Step S230 is the same as the above step S120 except that the driving amount correction section 213L determines a driving direction on the basis of a deviation direction in the X direction.

If step S211 is executed, driving amounts of the fourth joint 24 and the third joint 22 are corrected, and thus the arm axial lines O15, O23 and O25 viewed from the Y direction are aligned on a straight line.

Next, step S212 is executed. In this step, under the control of the convergence operation control section 215L, the redundant joints are aligned with each other so that an offset amount is 0 by using the third joint 22 ([joint 2]) as a first redundant joint and the first joint 12 ([joint 4]) as a second redundant joint in a state in which angles of the fourth joint 24 ([joint 1]) and the second joint 14 ([joint 3]) are fixed.

Specifically, step S212 is executed by executing the above steps S221 to S228, S229' and S230' illustrated in FIG. 38 according to the flow shown in FIG. 38.

Step S229' is the same as the above step S119 except that the convergence determination section 211L determines convergence of a deviation amount on the basis of a deviation amount viewed from the X direction, that is, an Y direction component of the deviation amount.

Step S230' is the same as the above step S120 except that the driving amount correction section 213L determines a driving direction on the basis of a deviation direction in the Y direction.

In the above-described way, if step S212 is executed, driving amounts of the third joint 22 and the first joint 12 are corrected, and thus the arm axial lines O11, O13, O15, O23 and O25 viewed from the X direction are aligned on a straight line.

Next, in step S213, under the control of the convergence operation control section 215L, a locus is acquired through rotational movement of the arm portion 108, and an aligned state of the arm portion 108 is checked.

Steps S213 and S214 are the same as steps S1 to S4 of the first embodiment except that control is performed by the convergence operation control section 215L and the convergence determination section 211L.

In a case where a diameter has not converged in step S214, the flow proceeds to step S211.

In a case where the diameter has converged, the second convergence state in the X direction and the Y direction has been achieved in steps S211 and S212, the first convergence state has been achieved in step S214, and thus the convergence determination section 211L determines that convergence has occurred. The convergence operation control section 215L is notified of the determination result and finishes the initialization operation.

In the above-described manner, the arm portion 108 is brought into an aligned state in which the arm axial lines O11, O13, O15, O23 and O25 are aligned with the reference axial line O, and is thus initialized.

According to the surgery support robot 1L of the present modified example, since the arm portion 108 can be initialized as mentioned above, control can be started from a state in which a position and orientation of the arm portion 108 is known, accordingly, an intuitive operation can be performed.

The present embodiment corresponds to an example of an initialization operation in a case where a plurality of pairs of redundant joints are provided, and an offset amount is 0.

In the present embodiment, after steps S211 and S212 in which convergence of a deviation amount in the X direction and convergence of a deviation amount in the Y direction are separately determined are completed, step S213 is executed so that a locus using rotational movement of the arm is acquired, and a convergence state is determined in step S214. In this case, steps S213 and S214 are steps in which convergence states in the X direction and the Y direction are simultaneously checked.

In this case, a locus using rotational movement is more easily enlarged and extracted from a deviation amount in an aligned state than from a deviation amount extracted through advance-retract movement, and thus a final aligned state can be checked with high accuracy.

However, in a case where an aligned state is easily determined on the basis of a deviation amount of an optical image using advance-retract movement depending on a condition such as inclination of the inner wall S, in the present embodiment, instead of steps S213 and S214, a step of acquiring a deviation amount through advance-retract movement in a state in which a rotating angle of each joint is fixed, and a step of determining whether or not the deviation amount converges may be used.

In this case, in a case where the deviation amount has not converged in a determination step, the flow proceeds to step S211 so that the respective steps are repeatedly executed until the deviation amount converges.

Ninth Modified Example

Next, an initialization method for a medical manipulator of a modified example (ninth modified example) of the fifth embodiment will be described.

Figure 55:
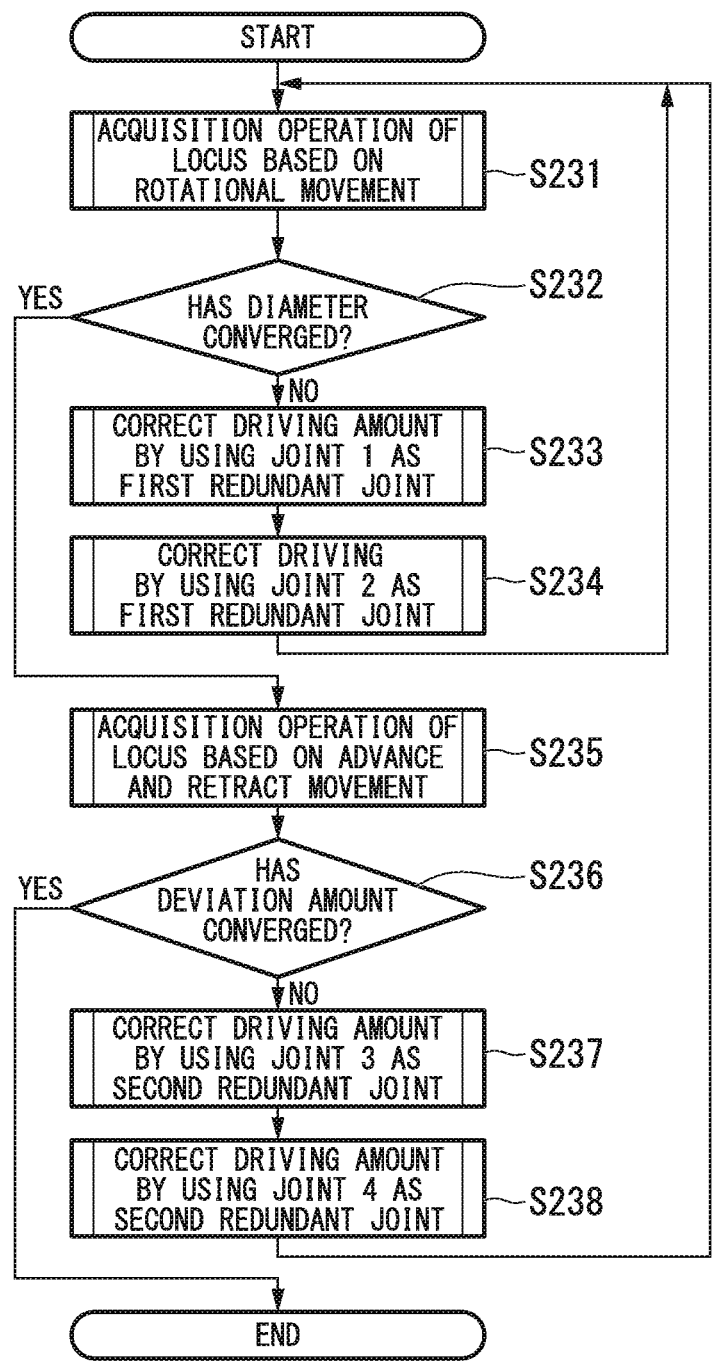
FIG. 55 is a flowchart illustrating a flow of an initialization method for a medical manipulator of a modified example (ninth modified example) of the fifth embodiment of the present invention.

FIG. 55 is a flowchart illustrating a flow of an initialization method for a medical manipulator of a modified example (ninth modified example) of the fifth embodiment of the present invention.

The initialization method for the medical manipulator of the present modified example is a modified example of the initialization method for the arm portion 108 of the fifth embodiment.

The initialization method of the fifth embodiment corresponds to an example of a case of performing serial operations in which the axial lines of the arms are aligned with each other when one pair of redundant joints is viewed from one direction according to a bending direction thereof, and then the axial lines of the arms are aligned with each other when the other pair of redundant joints is also viewed from one direction according to a bending direction thereof.

In contrast, the present modified example corresponds to an example of a case where a convergence operation using rotational movement is performed in each pair of redundant joints, and then a convergence operation using advance-retract movement is performed in each pair of redundant joints.

Specifically, steps S231 to S238 illustrated in FIG. 55 are executed according to the flow shown in FIG. 55.

However, the flow illustrated in FIG. 55 is only an example. In each pair, a method of allocating a joint to a first redundant joint or a second redundant joint is not particularly limited, and, between the respective pairs, which first redundant joint is first moved is not also particularly limited.

Steps S231 and S232 are the same as steps S213 and S214 of the fifth embodiment.

In a case where the diameter has not converged in step S232, the flow proceeds to step S233.

In a case where the diameter has converged, the flow proceeds to step S235.

Step S233 is a step in which the fourth joint 24 ([joint 1]) is used as a first redundant joint, and a driving amount of the fourth joint 24 is corrected in a state in which the other [joint 2] to [joint 4] are fixed to certain positions, and which is the same as step S225 of the fifth embodiment.

If step S233 is completed, the flow proceeds to step S234.

Step S234 is a step which is the same as the above step S233 except that a driving amount of the third joint 22 is corrected in a state in which the third joint 22 ([joint 2]) is used as a first redundant joint and the other [joint 1], [joint 3] and [joint 4] are fixed to certain positions, and which is the same as the above step S233.

If step S236 is completed, the flow proceeds to step S231.

Step S235 is the same as steps S226 to S228 (refer to FIG. 38) of the fifth embodiment.

Step S236 executed next is the same as step S229 of the fifth embodiment.

In a case where the deviation amount has not converged in step S236, the flow proceeds to step S237.

In a case where the deviation amount has converged, the first convergence state in the X direction and the Y direction has been achieved in step S232, and the second convergence state in the X direction and the Y direction has been achieved in step S236.

Therefore, the convergence determination section 211L determines that convergence has occurred. The convergence operation control section 215L is notified of the determination result and finishes the initialization operation.

In the above-described manner, the arm portion 108 is brought into an aligned state in which the arm axial lines O11, O13, O15, O23 and O25 are aligned with the reference axial line O, and is thus initialized.

Step S237 is the same as step S230 of the fifth embodiment. In other words, in this step, the second joint 14 ([joint 3]) is used as a second redundant joint, and a driving amount of the second joint 14 is corrected on the basis of a deviation amount of an optical image due to advance-retract movement in a state in which the other [joint 1], [joint 2] and [joint 4] are fixed to certain positions.

If step S237 is completed, the flow proceeds to step S238.

Step S238 is the same as step S229' of the fifth embodiment. In other words, in this step, the first joint 12 ([joint 4]) is used as a second redundant joint, and a driving amount of the first joint 12 is corrected on the basis of a deviation amount of an optical image due to advance-retract movement in a state in which the other [joint 1] to [joint 3] are fixed to certain positions.

If step S238 is completed, the flow proceeds to step S231, and steps S231 to S236 are repeatedly executed.

According to the surgery support robot 1L of the present modified example, since the arm portion 108 can be initialized as mentioned above, control can be started from a state in which a position and orientation of the arm portion 108 is known, accordingly, an intuitive operation can be performed.

The present embodiment corresponds to an example of an initialization operation in a case where a plurality of pairs of redundant joints are provided, and an offset amount is 0.

In addition, the present modified example has been described as an example of a case where a step of checking a final aligned state is omitted after step S236, but, in order to obtain an aligned state with higher accuracy, steps such as steps S213 and S214 may be executed after step S236 in the same manner as in the fifth embodiment. In a case where convergence has not occurred in step S214, the flow proceeds to step S231, and all the steps are repeatedly executed until convergence occurs.

Sixth Embodiment

Next, a medical manipulator and an initialization method for the medical manipulator of a sixth embodiment of the present invention will be described.

Figure 56A:
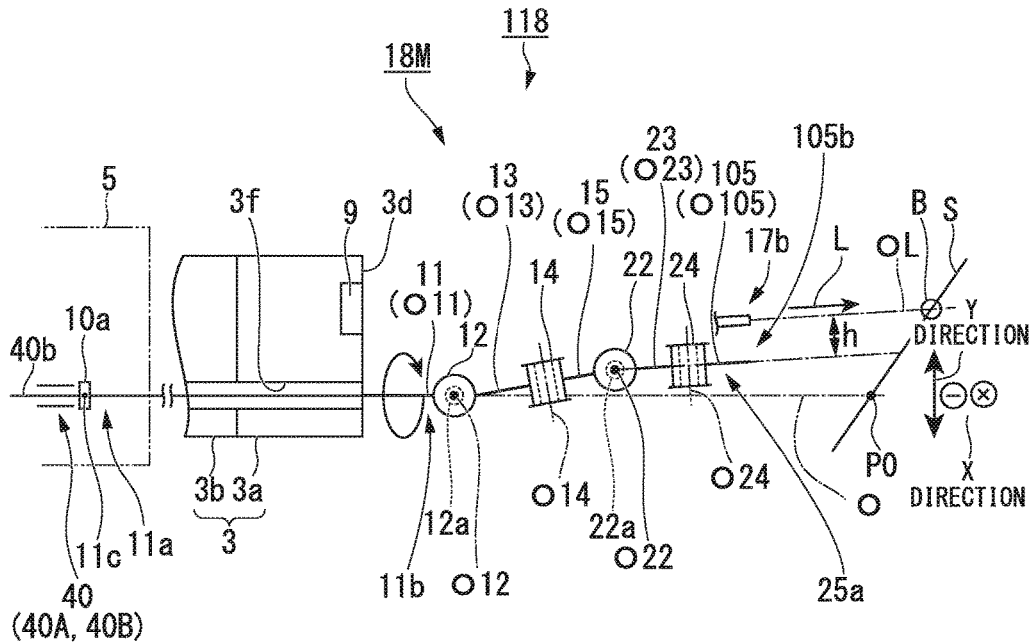
FIG. 56A is a schematic diagram of a front view of a bent state illustrating configurations of main portions of a medical manipulator of a sixth embodiment of the present invention.
Figure 56B:
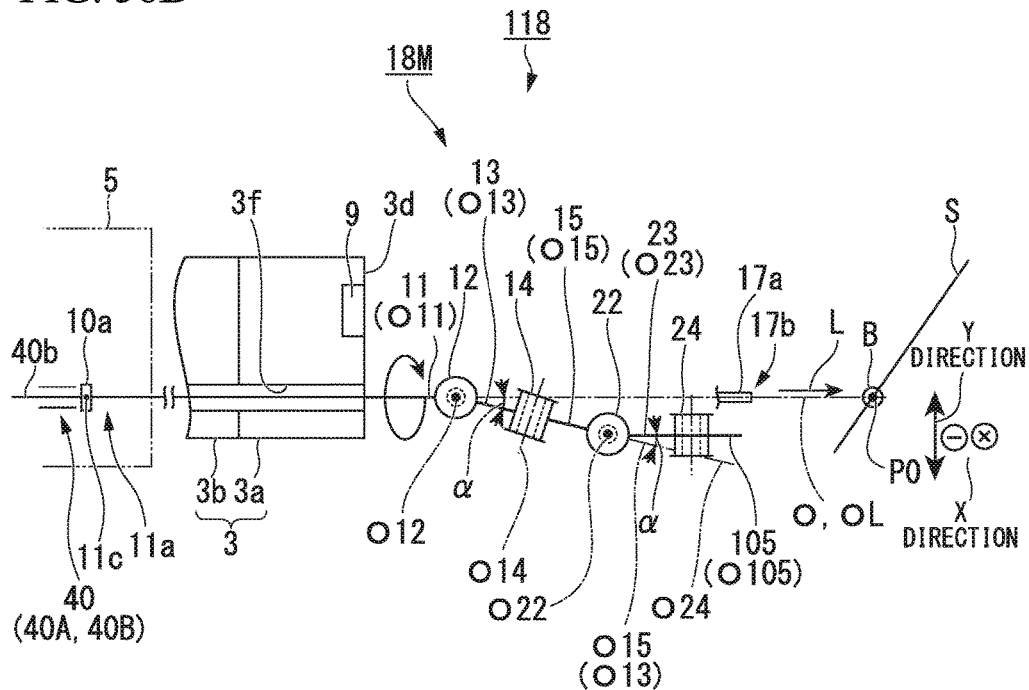
FIG. 56B is a schematic diagram of a front view of an aligned state illustrating configurations of the main portions of the medical manipulator according to the sixth embodiment of the present invention.

FIGS. 56A and 56B are schematic diagrams of a bent state and an aligned state in a plan view illustrating configurations of main portions of a medical manipulator of the sixth embodiment of the present invention.

As illustrated in FIG. 1, a surgery support robot 1M (medical manipulator) of the present embodiment includes a surgery instrument 18M and a control section 6M instead of the surgery instrument 18L and the control section 6L of the fifth embodiment.

Hereinafter, a description will be made focusing on differences from the fifth embodiment.

As main portions are schematically illustrated in FIGS. 56A and 56B, the surgery instrument 18M includes an arm portion 118 instead of the arm portion 108 of the fifth embodiment.

The arm portion 118 includes a fifth arm 105 (arm) instead of the fifth arm 25 of the arm portion 108 of the fifth embodiment.

The fifth arm 105 is only different from the fifth arm 25 in that an arm distal end 105b at which the fiber end surface 17b is disposed to be moved in parallel by a distance h (where h>0) is provided instead of the arm distal end 25b of the fifth arm 25.

As illustrated in FIGS. 22A and 22B, the optical axis OL of the fiber end surface 17b is moved in parallel by the distance h from the arm axial line O25 in the direction perpendicular to the opening and closing direction (refer to the arrow in FIG. 22A) of the treatment portion 16. Thus, an offset amount in the arm portion 118 is h.

As illustrated in FIGS. 56A and 56B, an offset direction is a direction along the fourth rotary shaft O24 of the fourth joint 24 which is a bending joint on the proximal end side which is closest to the fifth arm 105.

On the basis of the configuration of the arm portion 118, the arm information supply section 11c of the present embodiment transmits configuration information of the arm portion 118 that "the number of bending joints is four", "redundant joints are two pairs of the first joint 12 and the third joint 22, and the second joint 14 and the fourth joint 24", and "the magnitude of an offset amount is h, and an offset direction is a rotary shaft direction offset".

As illustrated in FIG. 52, the control section 6M is different from the control section 6L of the fifth embodiment in that an initialization control unit 201M is provided instead of the initialization control unit 201L of the fifth embodiment.

As illustrated in FIG. 53, the initialization control unit 201M is different from the initialization control unit 201M of the fifth embodiment in that a convergence operation control section 215M, and a driving amount correction section 213M are provided instead of the convergence operation control section 215L and the driving amount correction section 213L of the fifth embodiment.

Control performed by the convergence operation control section 215M and the driving amount correction section 213M will be described in descriptions of operations thereof.

Next, an operation of the surgery support robot 1M will be described focusing on an initialization method for the medical manipulator of the present modified example.

Figure 57:
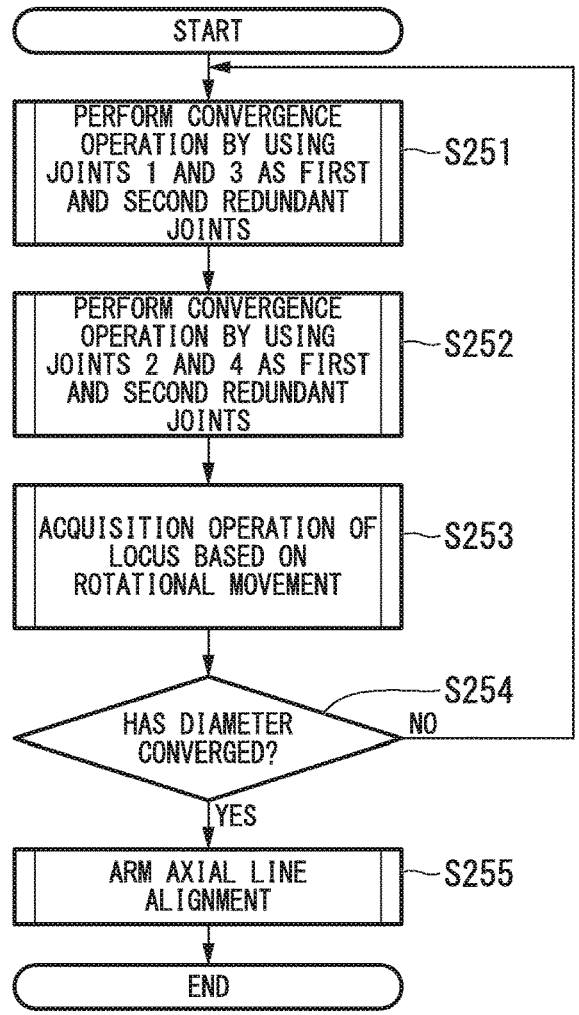
FIG. 57 is a flowchart illustrating a flow of an initialization method for the medical manipulator according to the sixth embodiment of the present invention.

FIG. 57 is a flowchart illustrating a flow of an initialization method for the medical manipulator according to the sixth embodiment of the present invention.

In the present embodiment, initialization is performed by executing the first convergence step and the second convergence step on each redundant joint in the same manner as in the fifth embodiment, and then executing the arm axial line alignment step in the same manner as in the seventh modified example (a modified example of the fourth embodiment).

Specifically, steps S251 to S255 illustrated in FIG. 57 are executed according to the flow shown in FIG. 57.

Also in the present embodiment, as long as an order of a convergence operation using rotational movement and a convergence operation using advance-retract movement is maintained of a pair of redundant joints, an execution order of the respective joints is not particularly limited.

Hereinafter, as an example, a case where a convergence operation is performed from a joint on the distal end side of the arm portion 118 will be described. In the flow of FIG. 57, the joints of the arm portion 118 are referred to as joints 1 to 4 from the distal end side to the proximal end side in the same manner as in the fifth embodiment.

In addition, hereinafter, for convenience of direction reference, a direction which is parallel to the first rotary shaft O12 is referred to as an X direction, and a direction which is perpendicular to the first rotary shaft O12 and the reference axial line O is referred to as a Y direction, in the same manner as in the fifth embodiment.

Steps S251 to S254 are the same as steps S211 to S214 (refer to FIG. 54) of the fifth embodiment except that the arm portion 118 is controlled by the control section 6M.

In a case where a diameter has not converged in step S254, the flow proceeds to step S251.

In a case where the diameter has converged, the second convergence state in the X direction and the Y direction has been achieved in steps S251 and S252, and the first convergence state has been achieved in step S254.

At this time, since the optical axis OL has the offset amount h, in the seventh modified example (a modified example of the fourth embodiment), as illustrated in FIG. 56B, the arm portion 118 converges to a state (hereinafter, referred to as an "optical axis alignment state") in which the optical axis OL is aligned with the reference axial line O, and an arm axial line O105 is moved in parallel by the offset amount h from the reference axial line O.

In other words, if an angle formed between the reference axial line O and the arm axial lines O13 and O15 is set to α, an angle formed between the arm axial lines O13 and O15 and the arm axial line O23 is a corresponding angle and is thus the same as the angle α.

The angle α is uniquely defined by a distance between the first rotary shaft O12 and the third joint 22, and the offset amount h.

Consequently, the convergence determination section 211L determines that convergence has occurred, and thus the flow proceeds to step S255.

Step S255 is a step which constitutes the arm axis alignment step in the present embodiment, and is the same as steps S181 and S182 (refer to FIG. 48) of the seventh modified example of the seventh modified example (a modified example of the fourth embodiment) except that the first joint 12 and the third joint 22 are respectively used as a first redundant joint and a second redundant joint.

In other words, the driving amount correction section 213M acquires information of the distance between the first rotary shaft O12 and the third joint 22 and the offset amount h from the configuration information of the arm portion 118, calculates the angle α so as to include a driving direction (step S181), and drives the first joint 12 and the third joint 22 in the same manner as in step S182.

In the above-described manner, the arm portion 118 is brought into an aligned state in which the arm axial lines O11, O13, O15, O23 and O105 are aligned with the reference axial line O, and is thus initialized.

According to the surgery support robot 1M of the present modified example, since the arm portion 118 can be initialized as mentioned above, control can be started from a state in which a position and orientation of the arm portion 118 is known, accordingly, an intuitive operation can be performed.

The present embodiment corresponds to an example of an initialization operation in a case where a plurality of pairs of redundant joints is provided, and an offset amount is h.

Tenth Modified Example

Next, an initialization method for a medical manipulator of a modified example (tenth modified example) of the sixth embodiment will be described.

Figure 58:
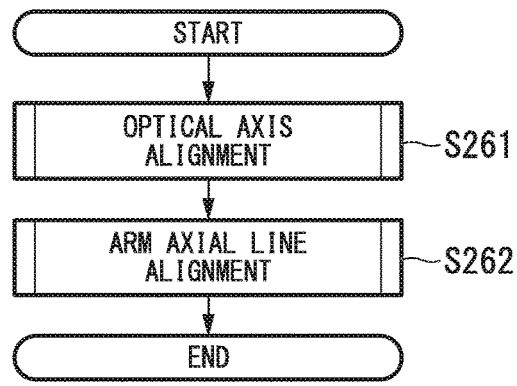
FIG. 58 is a flowchart illustrating a flow of an initialization method for a medical manipulator of a modified example (tenth modified example) of the sixth embodiment of the present invention.

FIG. 58 is a flowchart illustrating a flow of an initialization method for a medical manipulator of a modified example (tenth modified example) of the sixth embodiment of the present invention.

The initialization method for the medical manipulator of the present modified example is a modified example of the initialization method for the arm portion 118 of the sixth embodiment.

The initialization method of the sixth embodiment corresponds to an example of a case of performing serial operations in which the axial lines of the arms are aligned with each other when one pair of redundant joints is viewed from one direction according to a bending direction thereof, and then the axial lines of the arms are aligned with each other when the other pair of redundant joints is also viewed from one direction according to a bending direction thereof.

In contrast, the present modified example corresponds to an example of a case where a convergence operation using rotational movement is performed in each pair of redundant joints, and then a convergence operation using advance-retract movement is performed in each pair of redundant joints.

Specifically, steps S261 and S262 illustrated in FIG. 58 are executed according to the flow shown in FIG. 58.

Step S261 is a step in which the optical axis OL is aligned with the reference axial line O in the arm portion 118, and is the same as steps S231 to S238 (refer to FIG. 55) of the ninth modified example (a modified example of the fifth embodiment) except that control is performed by the control section 6M. However, since the arm portion 118 has an offset, the present modified example is different from the ninth modified example in that an optical axis alignment state illustrated in FIG. 56B occurs after step S238 is completed. For this reason, this step constitutes an optical axis alignment step in which the optical axis OL is aligned with the reference axial line O through the first convergence step and the second convergence step.

Step S262 is the same as step S255 of the sixth embodiment.

Consequently, the first rotary shaft O12 and the third joint 22 of the arm portion 118 are driven in the same manner as in step S255. As a result, the arm portion 118 is brought into an aligned state in which the arm axial lines O11, O13, O15, O23 and O105 are aligned with the reference axial line O, and is thus initialized.

However, in the same manner as in the sixth embodiment, the flow illustrated in FIG. 58 is only an example, and, in each pair, a method of allocating a joint to a first redundant joint or a second redundant joint is not particularly limited. In addition, between the respective pairs, which first redundant joint is first moved is not also particularly limited.

According to the surgery support robot 1M of the present modified example, since the arm portion 118 can be initialized as mentioned above, control can be started from a state in which a position and orientation of the arm portion 118 is known, accordingly, an intuitive operation can be performed.

Seventh Embodiment

Next, a medical manipulator and an initialization method for the medical manipulator of a seventh embodiment of the present invention will be described.

Figure 59:
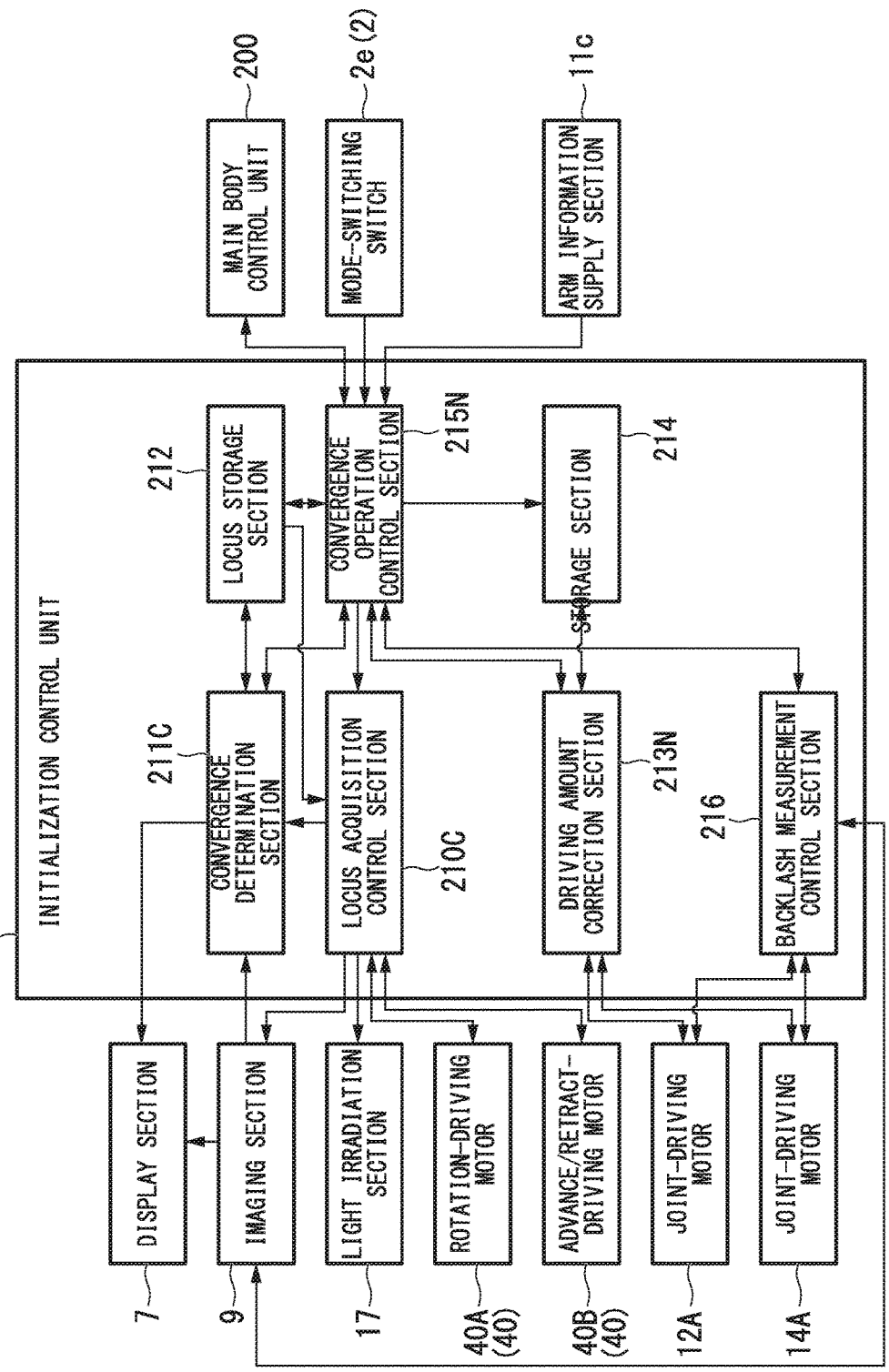
FIG. 59 is a functional block diagram illustrating a functional configuration of initialization control of a medical manipulator of a seventh embodiment of the present invention.

FIG. 59 is a functional block diagram illustrating a functional configuration of initialization control of a medical manipulator of the seventh embodiment of the present invention.

As illustrated in FIG. 1, a surgery support robot 1N (medical manipulator) of the present embodiment includes a control section 6N instead of the control section 6J of the seventh modified example (a modified example of the fourth embodiment).

Hereinafter, a description will be made focusing on differences from the seventh modified example.

As illustrated in FIG. 31, the control section 6N is different from the control section 6J of the seventh modified example in that an initialization control unit 201N is provided instead of the initialization control unit 201J of the seventh modified example.

As illustrated in FIG. 59, the initialization control unit 201N is different from the initialization control unit 201J of the seventh modified example in that a convergence operation control section 215N is provided instead of the convergence operation control section 215J of the seventh modified example, and a backlash measurement control section 216 is additionally provided.

Control performed by the convergence operation control section 215N will be described in descriptions of operations thereof.

The backlash measurement control section 216 drives a bending joint to perform a bending operation in which the bending joint reciprocates in a predetermined angle range while irradiating the laser luminous flux L from the light irradiation section 17, and measures a backlash amount of the bending joint on the basis of a relationship between a position of the beam spot B imaged by the imaging section 9 and a driving command value of the bending joint.

For this reason, the backlash measurement control section 216 is communicably connected to the convergence operation control section 215N, the joint-driving motors 12A and 14A, and the imaging section 9.

Next, an operation of the surgery support robot 1N will be described focusing on an initialization method for the medical manipulator of the present modified example.

Figure 60:
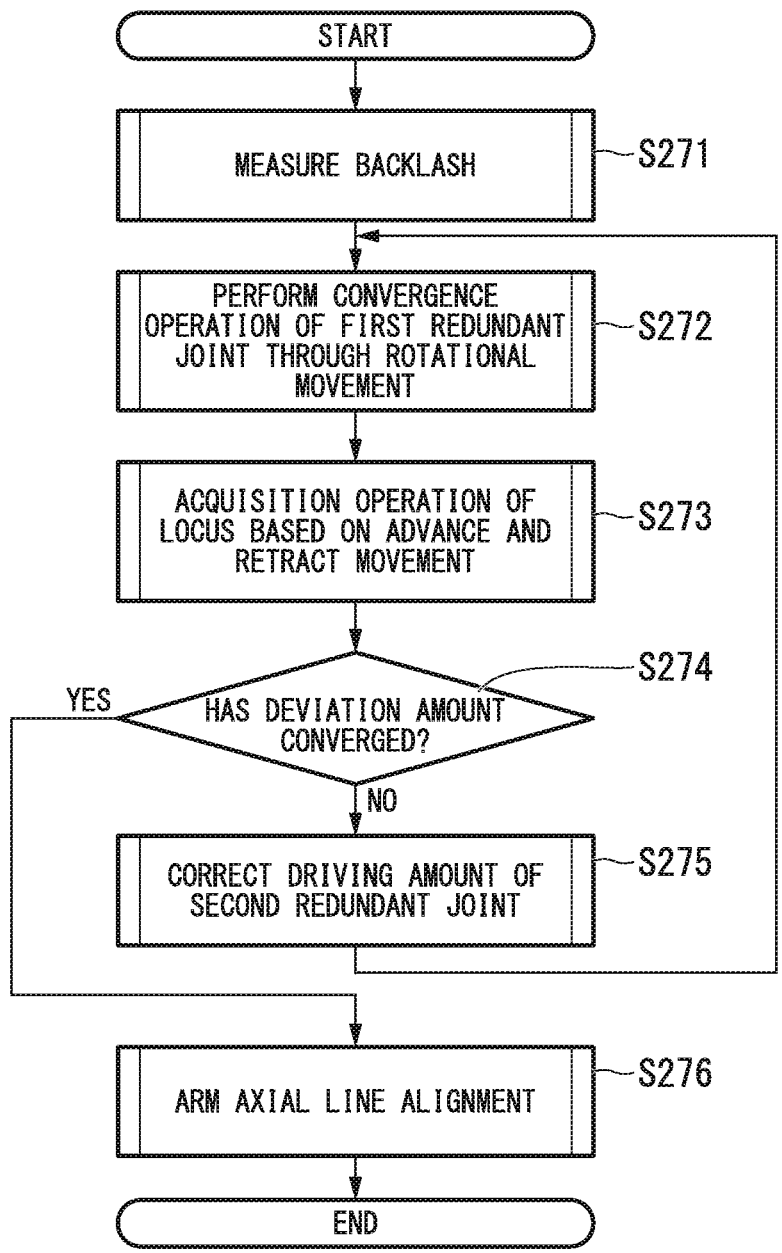
FIG. 60 is a flowchart illustrating a flow of an initialization method for the medical manipulator of the seventh embodiment of the present invention.
Figure 61:
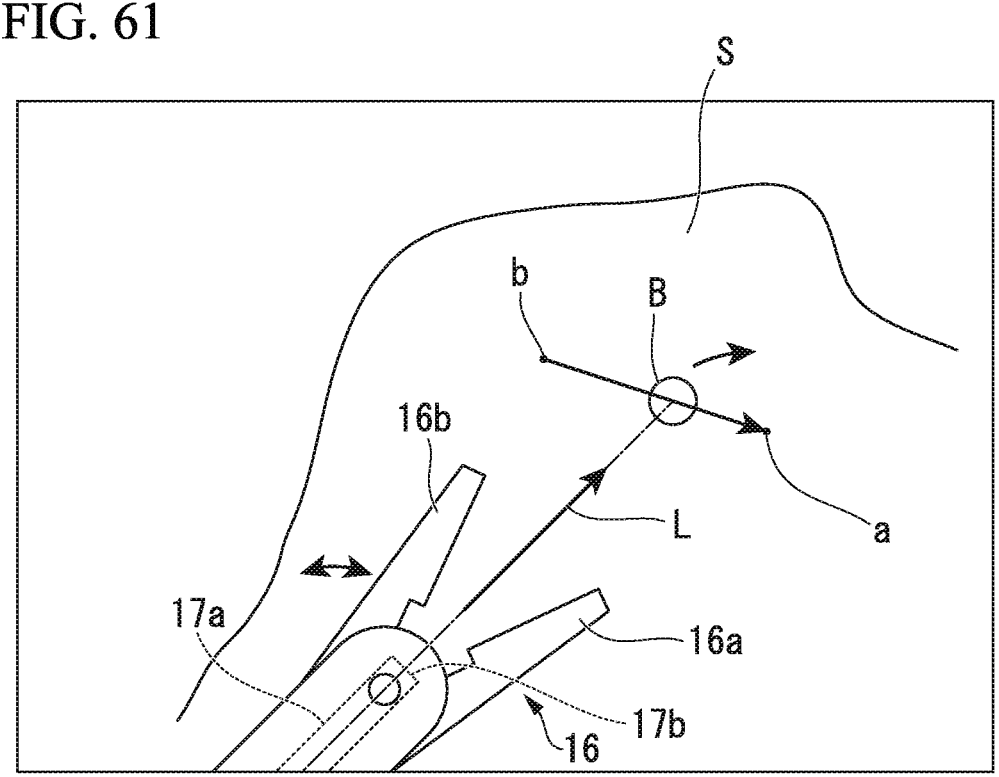
FIG. 61 is an operation explanatory diagram in the initialization method for the medical manipulator of the seventh embodiment of the present invention.
Figure 62:
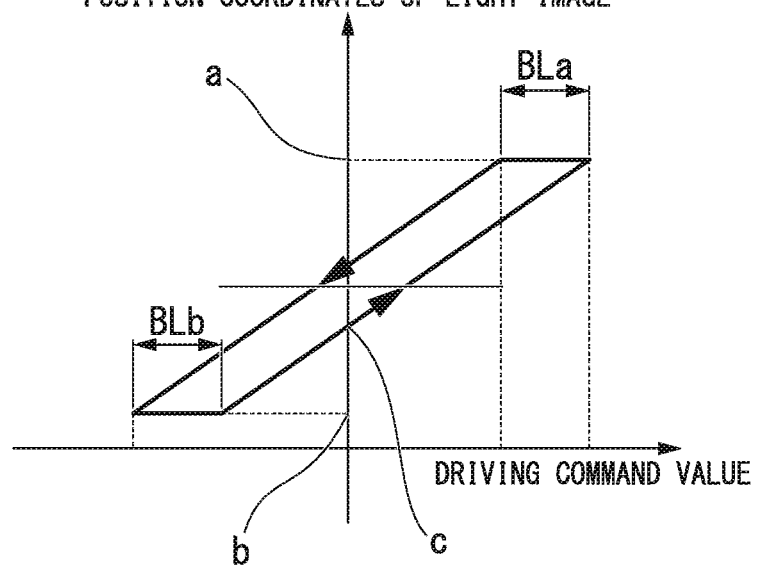
FIG. 62 is a schematic graph diagram for explaining a method of calculating a backlash.

FIG. 60 is a flowchart illustrating a flow of an initialization method for the medical manipulator of the seventh embodiment of the present invention. FIG. 61 is an operation explanatory diagram in the initialization method for the medical manipulator of the seventh embodiment of the present invention. FIG. 62 is a schematic graph diagram for explaining a method of calculating a backlash. A transverse axis expresses a driving command value, and a longitudinal axis expresses a position of an optical image.

An initialization method of the present embodiment is a modified example of the initialization method for the arm portion 98 according to the seventh modified example, and is different from the seventh modified example in that a backlash measurement step is executed before the first convergence step of the seventh modified example is executed.

Specifically, steps S271 to S276 illustrated in FIG. 60 are executed according to the flow shown in FIG. 60.

Step S271 constitutes a backlash measurement step of the present embodiment.

The convergence operation control section 215N turns on the light irradiation section 17, and sends a control signal to the backlash measurement control section 216 so as to start backlash measurement.

The backlash measurement control section 216 drives the joint-driving motor 12A so that a bending operation in which a joint reciprocates in a predetermined angle range is performed, and acquires images of the beam spot B captured by the imaging section 9 in a time series.

For example, as illustrated in FIG. 61, a bending operation is performed in which the joint reciprocates in an angle formed between a point a and a point b on the inner wall S.

The backlash measurement control section 216 calculates a central position of the beam spot B from the acquired image of the beam spot B, and obtains a relationship between movement coordinates of the beam spot B and a driving command value.

As illustrated in FIG. 62, in a case where driving is performed from an intermediate point c between the points a and b toward the point a, if there is a backlash in the joint-driving motor 12A, movement of the beam spot B is stopped according to an amount of the backlash after reaching the point a until returning to the point c side. The backlash measurement control section 216 drives the joint-driving motor 12A in the unit driving amount when the beam spot B reaches the point a and reverses its direction, and detects a position of the beam spot B from an image. The magnitude of the unit driving amount which is necessary until the beam spot B starts to move is obtained as a backlash amount BLa.

Similarly, a backlash amount BLb is also obtained for the point b side.

Next, backlash amounts BLa and BLb are also obtained in the same manner in relation to the joint-driving motor 14A.

The backlash amounts BLa and BLb are sent to the convergence operation control section 215N.

The convergence operation control section 215N sends the backlash amounts BLa and BLb to the driving amount correction section 213N. When changing driving directions of the joint-driving motors 12A and 14A, the driving amount correction section 213N generates driving command values in which the respective backlash amounts BLa and BLb are corrected, as driving command values.

Through the operation, step S271 is completed.

Next, steps S272 to S276 are executed.

Step S272 is the same as steps S161 to S165 (refer to FIG. 46) of the seventh modified example.

Step S273 executed next is the same as steps S166 to S168 (refer to FIG. 46) of the seventh modified example.

Steps S274 to S276 are the same as steps S169 to S171 (refer to FIG. 46) of the seventh modified example.

As mentioned above, steps S272 to S276 are the same as steps S161 to S171 of the seventh modified example. However, in each step, in a case where driving directions of the joint-driving motors 12A and 14A are changed, backlash amounts are corrected by the driving amount correction section 213N.

For this reason, there is no change in a driving amount due to a backlash, and thus a convergence operation is rapidly performed.

In addition, particularly, in step S276, an alignment error due to the backlash is removed, and thus it is possible to form an aligned state with higher accuracy.

In an arm portion of the related art, in a case where there is a change in a driving amount due to a backlash, if a control parameter is not appropriate, operations of an operation portion and the arm portion are brought into a non-matching correspondence relationship, and thus an intuitive operation may be damaged. However, according to the surgery support robot 1N of the present modified example, there is no change in a driving amount due to a backlash as described above. Consequently, since the arm portion 98 can be initialized as mentioned above, control can be started from a state in which a position and orientation of the arm portion 98 is known, accordingly, an intuitive operation can be performed.

In the above-described way, the respective embodiments and the respective modified examples of the present invention have been described, but the present invention is not limited to the embodiments and the modified examples. The present invention may be carried out by modifying, combining, or deleting all the constituent elements described above within the technical scope of the present invention.

Hereinafter, other modified examples which are applicable to the respective embodiments and the respective modified examples will be described.

In the description of the respective embodiments and the respective modified examples, as an example, a description has been made of a case where a reference locus using rotation driving of the arm portion is acquired, then the bending joint is driven in a state in which rotational movement is stopped, and thus a driving direction and a driving amount for reducing a diameter of a locus are determined. However, a driving direction and a driving amount may be changed without stopping rotational movement.

Figure 63A:
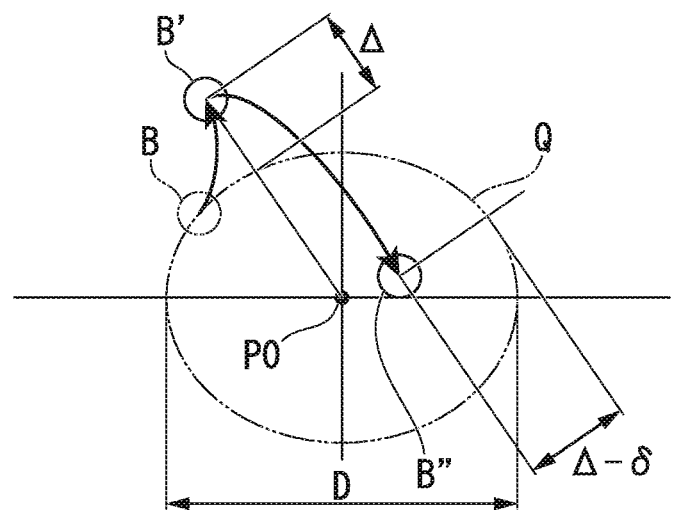
FIG. 63A is a schematic diagram illustrating an example of a locus of a optical image in an initialization method for a medical manipulator of a modified example of the first embodiment of the present invention.
Figure 63B:
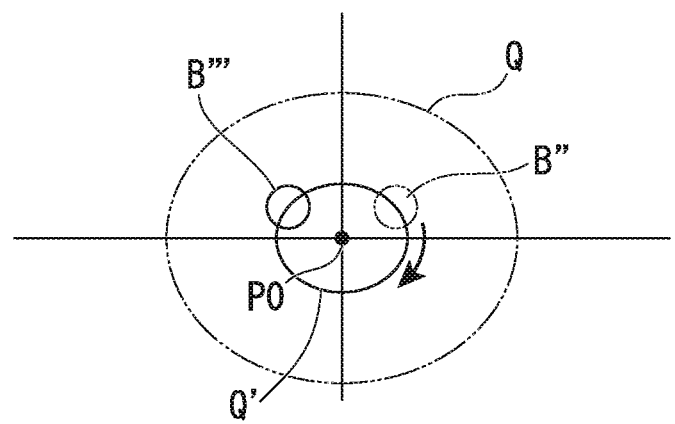
FIG. 63B is a schematic diagram illustrating an example of a locus of a optical image in the initialization method for the medical manipulator of the modified example of the first embodiment of the present invention.

FIGS. 63A and 63B are schematic diagrams illustrating an example of a locus of an optical image in an initialization method for a medical manipulator of a modified example of the first embodiment of the present invention.

For example, the following operation is possible.

As illustrated in FIG. 63A, in the first embodiment, the closed curve Q is acquired, then the first joint 12 is driven in a test-driving amount without stopping rotational movement of the arm portion 8, and thus a locus in which the beam spot B is moved to a beam spot B' is acquired. A distance Δ to the closed curve Q is calculated from an image. In addition, if the first joint 12 is driven in an opposite direction by Δ−δ while rotating the arm portion 8 so that the beam spot B' is moved as a beam spot B'', as illustrated in FIG. 63B, a locus based on rotational movement, drawn by the beam spot B'' is acquired while this angle is held, and a closed curve Q' is obtained. Such an operation is repeatedly performed, and is continued until the first convergence state is obtained.

Such a modified example of rotational movement is applicable to all embodiments and modified examples using rotational movement.

In the description of the respective embodiments and the respective modified examples, as an example, a description has been made of a case where a predetermined physical quantity computed on the basis of a locus in order to determine a convergence state of the locus is a diameter of the locus if rotational movement is performed by the movement portion, and is a deviation amount of an optical image if advance-retract movement is performed by the movement portion.

However, a predetermined physical quantity is not limited thereto. For example, a length of a locus based on rotational movement, or an area of a portion surrounded by a traced locus may be employed.

In the respective embodiments and the respective modified examples, as an example, a description has been made of a case where a locus of an optical image is acquired (locus acquisition step), a diameter of the locus or a deviation amount of the optical image which is a predetermined physical quantity for determining a convergence state of the locus is computed on the basis of the locus (convergence determination amount calculation step), a driving amount is corrected in a case where it is determined that the diameter of the locus or the deviation amount of the optical image has not converged in a convergence determination step (driving amount correction step), and the locus acquisition step, the convergence determination amount calculation step, the convergence determination step, and the driving amount correction step are repeatedly executed until the locus converges.

However, the convergence determination step and the driving amount correction step are not limited to the embodiments.

For example, a plurality of driving amounts are selected from a range including a driving amount leading to a convergence state, the bending joint is driven in the plurality of driving amounts, the locus acquisition step and the convergence determination amount calculation step are performed in respective driving states, and a plurality of loci and predetermined physical quantities are acquired. In addition, the minimum value of the plurality of physical quantities is subsequently obtained, and thus the convergence determination step of determining convergence of the locus is executed. Then, through the convergence determination step, the driving amount correction step of correcting a driving amount of the bending joint may be executed on the basis of a driving amount which is selected as the minimum value of the plurality of physical quantities calculated in the convergence determination amount calculation step.

Such a modified example will be described by exemplifying a case where a physical quantity is a diameter of a locus.

Figure 64:
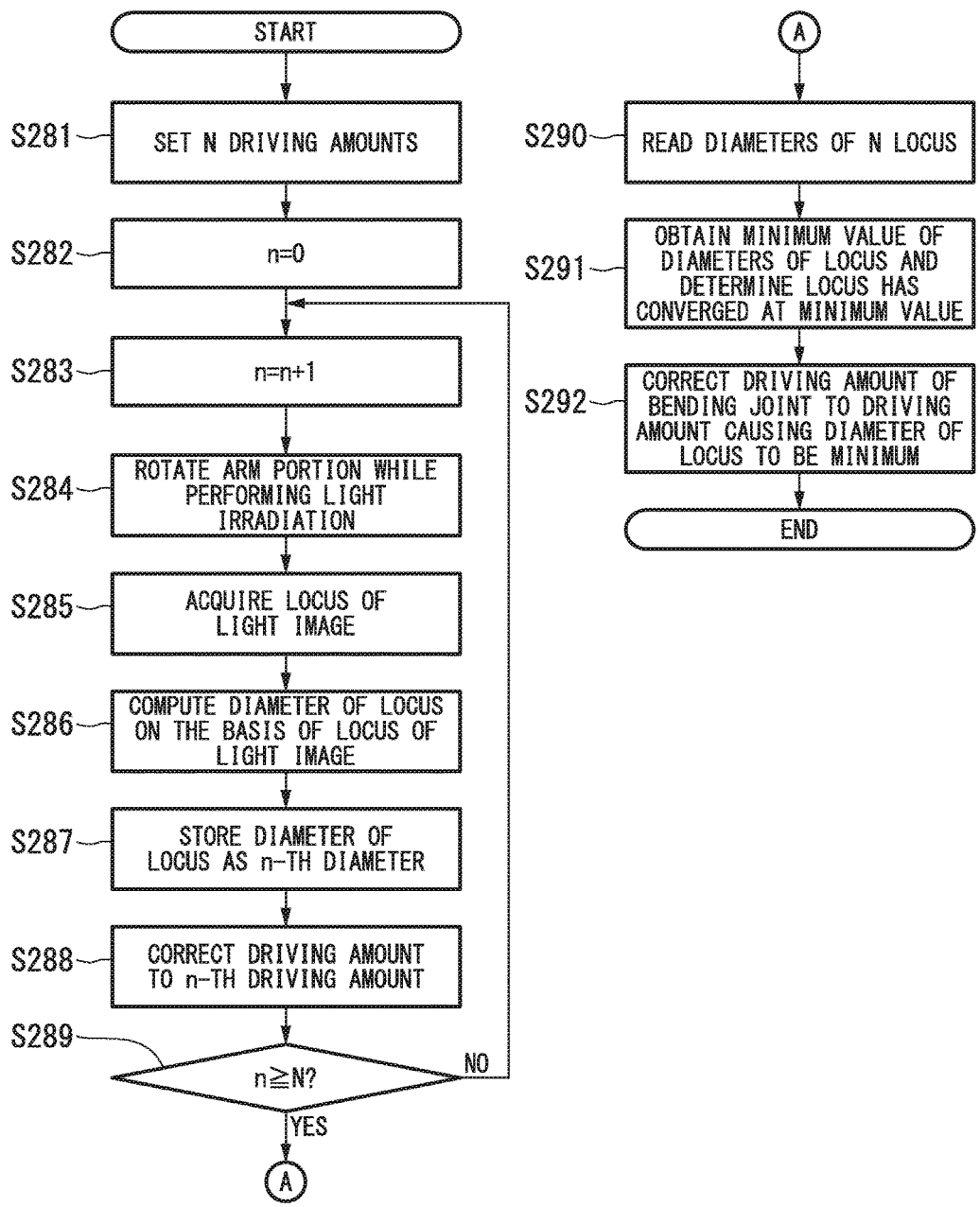
FIG. 64 is a flowchart illustrating a flow of a modified example (eleventh modified example) of a driving amount correction step and a convergence determination step which can be applied to the initialization method for the medical manipulator of the respective embodiments and the respective modified examples of the present invention.

FIG. 64 is a flowchart illustrating a flow of a modified example (eleventh modified example) of the driving amount correction step and the convergence determination step which can be applied to the initialization method for the medical manipulator of the respective embodiments and the respective modified examples of the present invention.

The present modified example corresponds to, for example, the flow illustrated in FIG. 8 of the first embodiment, and is performed by executing steps S281 to S292 illustrated in FIG. 64 according to the flow shown in FIG. 64.

In order to execute such a flow, for example, in the surgery support robot 1 of the first embodiment, a convergence determination section 211X (convergence determination amount calculation portion), a convergence operation control section 215X, and a driving amount correction section 213X, which performs the following operations, are provided instead of the convergence determination section 211, the convergence operation control section 215, and the driving amount correction section 213 (refer to FIG. 6).

Hereinafter, a description will be made focusing on differences from the first embodiment.

In step S281, the convergence operation control section 215X sets N (where N is an integer of 3 or greater) driving amounts.

As the N driving amounts, fixed values obtained by dividing a driving range which is necessary in initialization in appropriate driving steps may be stored in advance, and an operator may input driving ranges, driving steps, and the like via the operation section 2, and the convergence operation control section 215X may set values on the basis of such input values.

In either case, among the driving ranges, the N driving amounts are set on the basis of a driving range and driving steps which realize a highly accurate convergence state.

Next, step S282 is executed. In this step, the convergence operation control section 215X sets a counter n and assigns 0 thereto as an initial value.

Next, in step S283, the convergence operation control section 215X updates the counter n to n=n+1.

Next, steps S284 to S286 are executed. Steps S284 to S286 are the same as steps S1 to S3 illustrated in FIG. 8.

Next, step S287 is executed. In this step, the diameter of the locus computed in step S286 is stored in the locus storage section 212 as an n-th diameter.

Next, in step S288, a control signal is sent from the convergence operation control section 215X to the driving amount correction section 213X, and the joint-driving motor 12A is driven by the driving amount correction section 213X.

A driving amount at this time is an n-th driving amount among the N driving amounts.

Next, step S289 is executed. In this step, it is determined whether or not the counter n is equal to or greater than N.

In a case where n is smaller than N, the flow proceeds to step S283.

In a case where n is equal to or greater than N, the flow proceeds to step S290.

Consequently, steps S283 to S288 are repeatedly executed N times, and then the flow proceeds to step S290.

In step S290, the convergence determination section 211X reads diameters of N loci from the locus storage section 212.

Next, step S291 is executed. In this step, the convergence determination section 211X obtains the minimum value by comparing the diameters of N loci with each other, and determines that the locus has converged to the minimum value.

The convergence determination section 211X sends the counter value n at which the minimum value is obtained, to the convergence operation control section 215X.

Through the operation, step S291 is completed.

Next, the step S292 is executed. In this step, a driving amount of the bending joint is corrected to a driving amount in which the diameter of the locus is the minimum. In this step, a control signal is sent from the convergence operation control section 215X to the driving amount correction section 213X, and the joint-driving motor 12A is driven by the driving amount correction section 213X. A driving amount at this time is a driving amount corresponding to the counter value n sent in step S291.

Consequently, since the bending joint is driven by the driving amount in which it is determined that the locus has converged, in the surgery support robot 1, the second arm 13 is aligned with the reference axial line O.

In the present modified example, steps S284 and S285 constitute the locus acquisition step, step S286 constitutes the convergence determination amount calculation step, step S291 constitutes the convergence determination step, and the step S292 constitutes the driving amount correction step.

According to the present modified example, N loci are acquired so as to correspond to N driving amounts, and it is determined that the locus has converged in a case where a predetermined physical quantity computed on the basis of the loci is the smallest. Therefore, it is possible to determine a convergence state in a substantially constant period of time and thus to minimize a variation in time necessary in initialization.

In the above-described way, the present modified example has been described as a modified example of the first embodiment, but is only an example. The present modified example is applicable to the above-described respective embodiments and respective modified examples.

In addition, a predetermined physical quantity computed on the basis of a locus is not limited to a diameter of the locus, and may employ appropriate physical quantities as necessary.

In the respective embodiments and the respective modified examples, as an example, a description has been made of a case where the maximum diameter is computed as a diameter of a locus based on rotational movement, but is not limited thereto as long as convergence of a diameter can be determined.

For example, an average diameter may be used.

In addition, in a case where a locus may be approximated to a circular shape or an elliptical shape, a diameter of a circle or an ellipse by applying a curve thereto may be used.

The backlash measurement control section described in the seventh embodiment is applicable to the respective embodiments and the respective modified examples.

In the respective embodiments and the respective modified examples, as an example, a description has been made of a case where configuration information of the arm portion is transmitted from the arm information supply section 11c, but the arm information supply section 11c is not an essential constituent element. For example, when the arm portion is attached or detached, or is exchanged, configuration information of the arm portion may be input via the operation section 2. In this case, the operation section 2 constitutes an arm information supply section.

In addition, regarding configuration information of the arm portion, there may be a configuration in which all information of the arm portion which is attachable and detachable or exchangeable is stored in the storage section 214 as an arm portion information storage section in advance, and information corresponding to a transmission code which is transmitted from the arm information supply section 11c or the operation section 2 is selected.

In addition, in a case where the arm portion is not attached or detached, or is not exchanged, if configuration information of the attached arm portion is stored in the arm portion information storage section, the arm information supply section is not necessary.

Further, among the respective embodiments and the respective modified examples, ones including different device configurations may be combined with device configurations having appropriate functions, and thus a device configuration combined with functions of the respective embodiments and the respective modified examples can be realized.

For example, there may be a configuration in which a device configuration having the above-described functions is provided, and the corresponding initialization operation is performed according to configuration information of the arm portion.

In addition, the arm portion may be used as appropriate through exchange with an arm portion including a plurality of configurations.

In such a combined configuration, an initialization operation may be required to be changed or a plurality of initialization operations may be possible depending on configurations of the arm portion.

In this case, before initially executing the locus acquisition step in an initialization operation, the convergence operation control section may execute an operation setting step in which configuration information of the arm portion is acquired from the arm portion information storage section, and sets operations in the locus acquisition step, the convergence determination amount calculation step, the convergence determination step, and the driving amount correction step on the basis of the configuration information of the arm portion.

In the respective embodiments and the respective modified examples, as an example, a description has been made of a case where a joint is formed of only a bending joint, but the arm portion may include joints other than the bending joint.

For example, in the first embodiment, the intermediate part of the first arm 11 may be provided with a sliding joint which advances or retracts the arm distal end 11b along the arm axial line O11 with respect to the arm proximal end 11a, or a shaft rotation joint which rotates the arm distal end 11b around the arm axial line O11 with respect to the arm proximal end 11a.

The sliding joint and the shaft rotation joint do not bend the first arm 11, and thus a bent state of the arm portion 8 is not changed. For this reason, if driving of the sliding joint or the shaft rotation joint is stopped during an initialization operation of aligning the first arm 11 and the second arm 13 with the reference axial line O, an initialization operation can be performed exactly in the same manner as a case where the sliding joint or the shaft rotation joint is not provided.

This is also the same for the arms of the other embodiments and modified examples.

In the description of the first modified example, as an example, a description has been made of a case where an initialization operation is performed through only rotational movement in a case where the arm portion includes two bending joints and an offset amount is 0, but an initialization operation may also be performed through only advance-retract movement described in the second modified example.

In the description of the respective embodiments and the respective modified examples, as an example, a description has been made of a case where the arm proximal end 11a of the first arm 11 extends to the driving section 5 through the insertion portion 3, and the rotation-driving motors 10 and 40A, and the advance/retract-driving motors 30 and 40B are provided in the driving section 5 as a movement portion, but the movement portion may be fixed inside or outside the distal end rigid part 3a. In this case, the first arm 11 is entirely made of a rigid material.

In this configuration, the movement portion is also used as a support portion of the arm portion.

In the description of the second embodiment, as an example, a description has been made of a case where the arm portion 48 having an offset on the rotary shaft can also be initialized by using either one of locus acquisition through rotational movement and locus acquisition through advance-retract movement, and each operation can be selected via the operation section 2.

However, there may be a configuration in which either the rotation-driving motor 40A or the advance/retract-driving motor 40B is omitted, and an initialization operation is performed through only one locus acquisition.

In the description of the respective embodiments and the respective modified examples, as an example, a description has been made of a case where the light irradiation section 17 is provided separately from the treatment portion 16, but, in a case where a treatment portion performing laser light irradiation is provided, the treatment portion may also be used as a light irradiation section. In this case, in an initialization operation, a laser luminous flux with low intensity is irradiated, and thus the same light irradiation as in the laser luminous flux L is performed.

In this case, if an irradiation portion of a laser luminous flux is disposed on an axial line of an arm, this corresponds to a case where an offset amount is 0, and if the irradiation port is disposed to be deviated from the axial line of the arm, this corresponds to a case of having an offset amount.

In the description of the respective embodiments and the respective modified examples, the arm formed of a cylindrical member is schematically illustrated as a straight line, but this does not indicate that the arm is limited to an elongated cylindrical shape. The arm may be formed of a cylindrical member which can be said to be short and annular. As an example of such an arm, there may be a joint ring (piece) used in a so-called endoscope.

The present invention may be carried out by replacing all the constituent elements described in the respective embodiments and the respective modified examples with appropriate combinations or deleting the constituent elements within the scope of the technical spirit of the present invention.

In addition, although the preferred embodiments of the present invention have been described, the present invention is not limited to the embodiments. Addition, omission, replacement, and other changes of configurations are possible within the scope without departing from the spirit of the present invention. The present invention is not limited by the above description and is limited by only the accompanying claims.

What is claimed is:

1. A medical manipulator comprising:
   a proximal arm and a distal arm;
   a bending joint configured to connect the proximal arm and the distal arm to form an angle between the proximal arm and the distal arm;
   a light source configured to irradiate a luminous flux having an optical axis parallel to an axial line of the distal arm;
   an image sensor having an imaging optical axis;

a joint driving actuator configured to be controlled to drive the bending joint to change the angle between the proximal arm and the distal arm;

a proximal arm rotation actuator configured to be controlled to rotate the proximal arm around an axial line of the proximal arm; and a processor comprising hardware, wherein the processor is configured to:
- control the proximal arm rotation actuator to rotate the proximal arm around the axial line of the proximal arm while controlling the light source to irradiate the luminous flux to form an optical image on a surface, to thereby move the optical axis of the luminous flux relative to the imaging optical axis of the image sensor;
- control the image sensor to image a locus of the optical image as the optical axis of the luminous flux is moved relative to the imaging optical axis of the image sensor;
- determine a physical quantity of the locus;
- determine whether the physical quantity has converged to a predetermined value indicating a reference state of the proximal arm, the distal arm and the bending joint; and
- in response to determining that the physical quantity has not converged to the predetermined value, control the joint driving actuator to drive the bending joint to change the angle between the proximal arm and the distal arm.

2. The medical manipulator according to claim 1, wherein the processor is configured to determine that the physical quantity of the locus has converged to the predetermined value in a case where the physical quantity is the smallest.

3. The medical manipulator according to claim 2, wherein the processor is configured to, in response to determining that the physical quantity has not converged to the predetermined value, control the joint driving actuator to drive the bending joint to change the angle between the proximal arm and the distal arm so as to decrease the physical quantity of the locus.

4. The medical manipulator according to claim 3, wherein the processor is configured to:
- retrieve, from an arm portion information storage, configuration information comprising information of a presence or absence of a redundant joint in the bending joint, and information of an offset amount which is a distance between the axial line of the distal arm provided with an irradiation port from which the luminous flux is irradiated and the optical axis of the image sensor; and
- control the image sensor to image the locus of the optical image, determine the physical quantity of the locus, determine whether the physical quantity has converged to the predetermined value, and control the joint driving actuator on the basis of the configuration information.

5. The medical manipulator according to claim 4, wherein, in a case where the movement portion includes the rotational movement portion and the advance/retract movement portion, the arm portion supported at the support portion is not provided with a redundant joint, and the offset amount has a positive value in a direction parallel to a bent plane of the bending joint, the locus acquisition control section performs at least one of rotational movement of the arm portion by using the rotational movement portion and advance-retract movement of the arm portion by using the advance/retract movement portion, the convergence determination section determines whether or not a first convergence state occurs in which the physical quantity has converged in a case where the rotational movement portion rotationally moves the arm portion, and determines whether or not a second convergence state occurs in which the physical quantity has converged in a case where the advance/retract movement portion advances or retracts the arm portion, the convergence determination section determines that the locus has converged in a case where both of the first convergence state and the second convergence state are determined to occur, and the convergence operation control section performs, on one of the bending joints, a convergence operation in which a first convergence operation and a second convergence operation are performed until the convergence determination section determines that the locus has converged, the first convergence operation in which rotational movement of the arm portion by using the rotational movement portion and advance-retract movement of the arm portion by using the advance/retract movement portion are performed, and the bending joint is driven by the driving amount correction section according to a change amount of the physical quantity and a change direction of the physical quantity until the first convergence state is determined to occur by the convergence determination portion, and the second convergence operation in which advance-retract movement of the arm portion is performed by the advance/retract movement portion, and the bending joint is driven by the driving amount correction section until the second convergence state is determined to occur by the convergence determination portion, and the convergence operation is performed on all of the bending joints until the convergence determination section determines that the locus has converged.

6. The medical manipulator according to claim 4, wherein, in a case where the movement portion includes the rotational movement portion and the advance/retract movement portion, the arm portion supported at the support portion includes redundant joints, and the offset amount is 0, the locus acquisition control section performs rotational movement of the arm portion by using the rotational movement portion or advance-retract movement of the arm portion by using the advance/retract movement portion, the convergence determination section determines whether or not a first convergence state in which the physical quantity has converged in a case where the rotational movement portion rotationally moves the arm portion occurs, the convergence determination section determines whether or not a second convergence state in which the physical quantity has converged in a case where the advance/retract movement portion advances or retracts the arm portion occurs, and the convergence determination section determines that the locus has converged in a case where both of the first convergence state and the second convergence state are determined to occur, and when one of the redundant joints adjacent to each other is referred to as a first redundant joint, and the other redundant joint is referred to as a second redundant joint, the convergence operation control section performs a first convergence operation in which rotational movement of the arm portion by using the rotational movement portion is performed while fixing an angle of the second redundant joint, and the first redundant joint is driven in a driving amount of the first redundant joint obtained by the driving amount correction section until the convergence determination section determines the first convergence state occurs, the convergence operation control section consecutively performs a second convergence operation in which advance-retract movement of the arm portion by using the advance/retract movement portion is performed while fixing an angle of the first redundant joint, and the second redundant joint is driven in a driving amount of the second redundant joint obtained by the driving amount correction section until the convergence determination section determines the second convergence state occurs, and the convergence operation control section performs control for repeatedly performing the first convergence operation and the second convergence operation in this order until the convergence determination section determines the convergence operation control section during the second convergence operation.

7. The medical manipulator according to claim 4, wherein, in a case where the movement portion includes the rotational movement portion and the advance/retract movement portion, the arm portion supported at the support portion includes redundant joints, and the offset amount is 0, the locus acquisition control section performs rotational movement of the arm portion by using the rotational movement portion or advance-retract movement of the arm portion by using the advance/retract movement portion, the convergence determination section determines whether or not a first convergence state occurs in which the physical quantity has converged in a case where the rotational movement portion rotationally moves the arm portion, and determines whether or not a second convergence state occurs in which the physical quantity has converged in a case where the advance/retract movement portion advances or retracts the arm portion, and the convergence determination section determines that the locus has converged in a case where both of the first convergence state and the second convergence state are determined to occur, and when one of the redundant joints adjacent to each other is referred to as a first redundant joint, and the other redundant joint is referred to as a second redundant joint, the convergence operation control section performs a parallelization operation in which the optical axis is set parallel to the reference axial line by driving the first redundant joint by a driving amount of the first redundant joint obtained by the driving amount correction section until the convergence determination section determines the second convergence state occurs, and a linearization operation in which driving amounts for bending the first redundant joint and the second redundant joint at the same angle in directions reverse to each other by rotational movement of the arm portion by using the rotational movement portion so as to reduce a distance between the optical axis and the reference axial line thereby the physical quantity becoming smaller are obtained by the driving amount correction section until the first convergence state is determined to occur by the convergence determination section, and the first redundant joint and the second redundant joint are respectively driven by the driving amounts.

8. The medical manipulator according to claim 4, wherein, in a case where the movement portion includes the rotational movement portion and the advance/retract movement portion, the arm portion supported at the support portion includes redundant joints, and the offset amount has a positive value in a direction parallel to a bent plane of the bending joint, the locus acquisition control section performs rotational movement of the arm portion by using the rotational movement portion or advance-retract movement of the arm portion by using the advance/retract movement portion, the convergence determination section determines whether or not a first convergence state in which the physical quantity has converged in a case where the rotational movement portion rotationally moves the arm portion occurs, the convergence determination section determines whether or not a second convergence state occurs in which the physical quantity has converged in a case where the advance/retract movement portion advances or retracts the arm portion, and the convergence determination section determines that the locus has converged in a case where both of the first convergence state and the second convergence state are determined to occur, and wherein, when one of the redundant joints adjacent to each other is referred to as a first redundant joint, and the other redundant joint is referred to as a second redundant joint, the driving amount correction section calculates driving amounts of the first redundant joint and the second redundant joint on the basis of the offset amount, the driving amounts of the first redundant joint and the second redundant joint in which the first redundant joint and the second redundant joint are aligned with the reference axial line by deviating the optical axis by the offset amount on the basis of the offset amount in a case where the optical axis is aligned with the reference axial line, the convergence operation control section consecutively performs a first convergence operation in which rotational movement of the arm portion by using the rotational movement portion is performed while fixing an angle of the second redundant joint, and the first redundant joint is driven by the driving amount of the first redundant joint obtained by the driving amount correction section until the first convergence state is determined to occur by the convergence determination section, the convergence operation consecutively performs a second convergence operation in which advance-retract movement of the arm portion by using the advance/retract movement portion is performed while fixing an angle of the first redundant joint, and the second redundant joint is driven by the driving amount of the second redundant joint obtained by the driving amount correction section until the second convergence state is determined to occur by the convergence determination section, the convergence operation consecutively performs an optical axis alignment operation in which the optical axis is aligned with the reference axial line by repeatedly performing the first convergence operation and the second convergence operation until the convergence determination section determines that the locus has converged, and the convergence operation consecutively performs control for performing an arm axial line alignment operation in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other in a state in which the optical axis is aligned with the reference axial line are calculated on the basis of the offset amount by the driving amount correction section and the first redundant joint and the second redundant joint are respectively driven by the driving amounts.

9. The medical manipulator according to claim 4, wherein, in a case where the movement portion includes the rotational movement portion and the advance/retract movement portion, the arm portion supported at the support portion includes redundant joints, and the offset amount has a positive value in a direction parallel to a bent plane of the bending joint, the locus acquisition control section performs rotational movement of the arm portion by using the rotational movement portion or advance-retract movement of the arm portion by using the advance/retract movement portion, the convergence determination section determines whether or not a first convergence state occurs in which the physical quantity has converged in a case where the rotational movement portion rotationally moves the arm portion, the convergence determination section determines whether or not a second convergence state occurs in which the physical quantity has converged in a case where the advance/retract movement portion advances or retracts the arm portion, and the convergence determination section determines that the locus has converged in a case where both of the first convergence state and the second convergence state are determined to occur, and wherein, when one of the redundant joints adjacent to each other is referred to as a first redundant joint, and the other redundant joint is referred to as a second redundant joint, the convergence operation control section performs a parallelization operation in which advance-retract movement of the arm portion by using the advance/retract movement portion is performed while fixing an angle of the second redundant joint, and the first redundant joint is driven by the driving amount of the first redundant joint obtained by the driving amount correction section until the second convergence state is determined to occur by the convergence determination section thereby the optical axis is set parallel to the reference axial line, the convergence operation control section performs control for performing an optical axis alignment operation in which rotational movement of the arm portion by using the rotational movement portion is performed, driving amounts for bending the first redundant joint and the second redundant joint are bent at the same angle in directions reverse to each other such that a distance between the optical axis and the reference axial line become smaller and the physical quantity is further reduced are obtained by the driving amount correction section until the first convergence state is determined to occur by the convergence determination section, and the first redundant joint and the second redundant joint are respectively driven by the driving amounts thereby the optical axis is aligned with the reference axial line, and the convergence operation control section performs control for performing an arm axial line alignment operation in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other in a state in which the optical axis is aligned with the reference axial line are calculated on the basis of the offset amount by the driving amount correction section, and the first redundant joint and the second redundant joint are respectively driven by the driving amounts.

10. The medical manipulator according to claim 1, wherein the physical quantity comprises any one of a diameter of the locus, an area surrounded by the locus, and a length of the locus.

11. A method for controlling:

a proximal arm and a distal arm;

a bending joint configured to connect the proximal arm and the distal arm to form an angle between the proximal arm and the distal arm;

a light source configured to irradiate a luminous flux having an optical axis parallel to an axial line of the distal arm;

an image sensor having an imaging optical axis;

a joint driving actuator configured to be controlled to drive the bending joint to change the angle between the proximal arm and the distal arm; and a proximal arm rotation actuator configured to be controlled to rotate the proximal arm around an axial line of the proximal arm, wherein the method comprises:

controlling the proximal arm rotation actuator to rotate the proximal arm around the axial line of the proximal arm while controlling the light source to irradiate the luminous flux to form an optical image on a surface, to thereby move the optical axis of the luminous flux relative to the imaging optical axis of the image sensor;

controlling the image sensor to image a locus of the optical image as the optical axis of the luminous flux is moved relative to the imaging optical axis of the image sensor;

determining a physical quantity of the locus;

determining whether the physical quantity has converged to a predetermined value indicating a reference state of the proximal arm, the distal arm and the bending joint; and in response to determining that the physical quantity has not converged to the predetermined value, controlling the joint driving actuator to drive the bending joint to change the angle between the proximal arm and the distal arm.

12. The method according to claim 11,
wherein physical quantity of the locus is determined to have converged to the predetermined value in a case where the physical quantity is the smallest.

13. The method according to claim 12, comprising:
in response to determining that the physical quantity has not converged to the predetermined value, controlling the joint driving actuator to drive the bending joint to change the angle between the proximal arm and the distal arm so as to decrease the physical quantity of the locus.

14. The method according to claim 13, comprising:
retrieving, from arm portion information storage, configuration information comprising information of the presence or absence of a redundant joint in the bending joint, and information of an offset amount which is a distance between the axial line of the distal arm provided with an irradiation port from which the luminous flux is irradiated and the optical axis of the image sensor; and
controlling the image sensor to image the locus of the optical image, determine the physical quantity of the locus, determine whether the physical quantity has converged to the predetermined value, and control the joint driving actuator on the basis of the configuration information.

15. The initialization method for a medical manipulator according to claim 13,
wherein, in a case where the arm portion supported at the support portion is not provided with a redundant joint, and an offset amount which is a distance between the axial line of the arm provided with the irradiation port and the optical axis has a positive value in a direction parallel to a bent plane of the bending joint,
at least one of rotational movement and advance-retract movement of the arm portion is performed in the locus acquisition step, and
the convergence determination step determines whether or not a first convergence state in which the physical quantity has converged in a case where the locus acquisition step in which the arm portion is rotationally moved is executed occurs, determines whether or not a second convergence state occurs in which the physical quantity has converged in a case where the locus acquisition step in which the arm portion is advanced or retracted is executed, and determines that the locus has converged in a case where both of the first convergence state and the second convergence state are determined to occur,
wherein the initialization method further includes:
a first convergence step which includes the locus acquisition step in which rotational movement and advance-retract movement of the arm portion are performed, the convergence determination amount calculation step in which respective physical quantities are computed on the basis of loci acquired through the rotational movement and the advance-retract movement, the convergence determination step, and the driving amount correction step which is executed until the first convergence state is determined to occur in the convergence determination step and in which a driving amount is corrected on the basis of a change amount and a change direction of a physical quantity, and which is completed in a case where the first convergence state is determined to occur in the convergence determination step; and
a second convergence step which includes the locus acquisition step in which advance-retract movement of the arm portion is performed, the convergence determination amount calculation step, the convergence determination step, and the driving amount correction step which is executed until the second convergence state is determined to occur in the convergence determination step, and which is completed in a case where the second convergence state is determined to occur in the convergence determination step, and
wherein the first convergence step and the second convergence step are executed in this order, initialization of a single bending joint is completed in a case where the locus is determined to be converged in the convergence determination step, and the above respective steps are executed on all of the bending joints.

16. The initialization method for a medical manipulator according to claim 13,
wherein, in a case where the arm portion supported at the support portion includes redundant joints, and an offset amount which is a distance between the axial line of the arm provided with the irradiation port and the optical axis is 0,
rotational movement or advance-retract movement of the arm portion is performed in the locus acquisition step, and
the convergence determination step determines whether or not a first convergence state in which the physical quantity has converged in a case where the locus acquisition step in which the arm portion is rotationally moved is executed occurs, determines whether or not a second convergence state in which the physical quantity has converged in a case where the locus acquisition step in which the arm portion is advanced or retracted is executed occurs, and determines that the locus has converged in a case where both of the first convergence state and the second convergence state are determined to occur,
wherein, when one of the redundant joints adjacent to each other is referred to as a first redundant joint, and the other redundant joint is referred to as a second redundant joint,
the initialization method further includes:
a first convergence step which includes the locus acquisition step in which rotational movement of the arm portion is performed while fixing an angle of the second redundant joint, the convergence determination amount calculation step, the convergence determination step, and the driving amount correction step in which a driving amount of the first redundant joint is corrected, and which is completed in a case where the first convergence state is determined to occur in the convergence determination step; and
a second convergence step which includes the locus acquisition step in which advance-retract movement of the arm portion is performed while fixing an angle of the first redundant joint, the convergence determination amount calculation step, the convergence determination step, and the driving amount correction step in which a driving amount of the second redundant joint is corrected, and which is completed in a case where the second convergence state is determined to occur in the convergence determination step, and wherein the first convergence step and the second convergence step are repeatedly executed in this order, initialization of a pair of redundant joints is completed in a case where the locus is determined to be converged in the convergence determination step of the second convergence step, and the above respective steps are executed on all of the redundant joints.

17. The initialization method for a medical manipulator according to claim 13, wherein, in a case where the arm portion supported at the support portion includes redundant joints, and an offset amount which is a distance between the axial line of the arm provided with the irradiation port and the optical axis is 0, rotational movement or advance-retract movement of the arm portion is performed in the locus acquisition step, and the convergence determination step determines whether or not a first convergence state in which the physical quantity has converged in a case where the locus acquisition step in which the arm portion is rotationally moved is executed occurs, determines whether or not a second convergence state in which the physical quantity has converged in a case where the locus acquisition step in which the arm portion is advanced or retracted is executed occurs, and determines that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method further includes:
a parallelization step which includes the locus acquisition step in which advance-retract movement of the arm portion is performed while fixing an angle of the second redundant joint, the convergence determination amount calculation step, the convergence determination step, and the driving amount correction step in which a driving amount of the first redundant joint is corrected, and which is completed in a case where the second convergence state is determined to occur in the convergence determination step such that the optical axis is set parallel to the reference axial line; and a linearization step which includes the locus acquisition step in which rotational movement of the arm portion is performed, the convergence determination amount calculation step, the convergence determination step, and the driving amount correction step in which driving amounts for bending the first redundant joint and the second redundant joint at the same angle in directions reverse to each other such that a distance between the optical axis and the reference axial line become smaller thereby the physical quantity is reduced are obtained, and the first redundant joint and the second redundant joint are respectively driven by the driving amounts, and which is completed in a case where the first convergence state is determined to occur in the convergence determination step, and wherein the parallelization step and the linearization step are executed in this order, initialization of a pair of redundant joints is completed in a case where the locus is determined to be converged in the convergence determination step, and the above respective steps are executed on all of the redundant joints.

18. The initialization method for a medical manipulator according to claim 13 or 14, wherein, in a case where the arm portion supported at the support portion includes redundant joints, and an offset amount which is a distance between the axial line of the arm provided with the irradiation port and the optical axis has a positive value in a direction parallel to a bent plane of the bending joint, rotational movement or advance-retract movement of the arm portion is performed in the locus acquisition step, and the convergence determination step determines whether or not a first convergence state in which the physical quantity has converged in a case where the locus acquisition step in which the arm portion is rotationally moved is executed occurs, determines whether or not a second convergence state in which the physical quantity has converged in a case where the locus acquisition step in which the arm portion is advanced or retracted is executed occurs, and determines that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method further includes:
a first convergence step which includes the locus acquisition step in which rotational movement of the arm portion is performed while fixing an angle of the second redundant joint, the convergence determination amount calculation step, the convergence determination step, and the driving amount correction step in which a driving amount of the first redundant joint is corrected, and which is completed in a case where the first convergence state is determined to occur in the convergence determination step; and a second convergence step which includes the locus acquisition step in which advance-retract movement of the arm portion is performed while fixing an angle of the first redundant joint, the convergence determination amount calculation step, the convergence determination step, and the driving amount correction step in which a driving amount of the second redundant joint is corrected, and which is completed in a case where the second convergence state is determined to occur in the convergence determination step;

an optical axis alignment step in which the first convergence step and the second convergence step are performed in this order, and which is completed in a case where the locus is determined to be converged in the convergence determination step such that the optical axis is aligned with the reference axial line; and an arm axial line alignment step in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other from a state in which the optical axis is aligned with the reference axial line are calculated on the basis of the offset amount, and the first redundant joint and the second redundant joint are respectively driven by the driving amounts, and wherein the first convergence step, the second convergence step, the optical axis alignment step, and the arm axial line alignment step are executed in this order and initialization of a pair of redundant joints is completed, and the respective steps are executed on all of the redundant joints.

19. The initialization method for a medical manipulator according to claim 13 or 14, wherein, in a case where the arm portion includes redundant joints, and an offset amount which is a distance between the axial line of the arm provided with the irradiation port and the optical axis has a positive value in a direction parallel to a bent plane of the bending joint, rotational movement or advance-retract movement of the arm portion is performed in the locus acquisition step, and the convergence determination step determines whether or not a first convergence state in which the physical quantity has converged in a case where the locus acquisition step in which the arm portion is rotationally moved is executed occurs, determines whether or not a second convergence state in which the physical quantity has converged in a case where the locus acquisition step in which the arm portion is advanced or retracted is executed occurs, and determines that the locus has converged in a case where both of the first convergence state and the second convergence state are determined to occur, wherein, when one of the redundant joints adjacent to each other is referred to as a first redundant joint, and the other redundant joint is referred to as a second redundant joint, the initialization method further includes:

a parallelization step which includes the locus acquisition step advance-retract movement of the arm portion is performed while fixing an angle of the second redundant joint, the convergence determination amount calculation step, the convergence determination step, and the driving amount correction step in which a driving amount of the first redundant joint is corrected, and which is completed in a case where the second convergence state is determined to occur in the convergence determination step such that the optical axis is set parallel to the reference axial line;

an optical axis alignment step which includes the locus acquisition step in which rotational movement of the arm portion is performed, the convergence determination amount calculation step, the convergence determination step, and the driving amount correction step in which driving amounts for bending the first redundant joint and the second redundant joint at the same angle in directions reverse to each other such that a distance between the optical axis and the reference axial line is reduced such that the physical quantity become smaller are obtained, and the first redundant joint and the second redundant joint are respectively driven by the driving amounts, and which is completed in a case where the first convergence state is determined to occur in the convergence determination step thereby the optical axis is aligned with the reference axial line; and an arm axial line alignment step in which driving amounts causing an axial line of an arm connected to a distal end side of the first redundant joint and an axial line of an arm connected to a distal end side of the second redundant joint to be aligned with the reference axial line by rotationally moving the first redundant joint and the second redundant joint in directions reverse to each other from a state in which the optical axis is aligned with the reference axial line are calculated on the basis of the offset amount, and the first redundant joint and the second redundant joint are respectively driven by the driving amounts, and wherein the parallelization step, the optical axis alignment step, and the arm axial line alignment step are executed in this order and initialization of a pair of redundant joints is completed, and the respective steps are executed on all of the redundant joints.

20. The method according to claim 11, wherein the physical quantity comprises any one of a diameter of the locus, an area surrounded by the locus, and a length of the locus.

21. A medical manipulator comprising:

a processor comprising hardware for controlling:

a proximal arm and a distal arm;

a bending joint configured to connect the proximal arm and the distal arm to form an angle between the proximal arm and the distal arm;

a light source configured to irradiate a luminous flux having an optical axis parallel to an axial line of the distal arm;

an image sensor having an imaging optical axis;

a joint driving actuator configured to be controlled to drive the bending joint to change the angle between the proximal arm and the distal arm; and a proximal arm rotation actuator configured to be controlled to rotate the proximal arm around an axial line of the proximal arm, wherein the processor is configured to:

control the proximal arm rotation actuator to rotate the proximal arm around the axial line of the proximal arm while controlling the light source to irradiate the luminous flux to form an optical image on a surface, to thereby move the optical axis of the luminous flux relative to the imaging optical axis of the image sensor;

control the image sensor to image a locus of the optical image as the optical axis of the luminous flux is moved relative to the imaging optical axis of the image sensor;

determine a physical quantity of the locus;

determine whether the physical quantity has converged to a predetermined value indicating a reference state of the proximal arm, the distal arm and the bending joint; and in response to determining that the physical quantity has not converged to the predetermined value, control the joint driving actuator to drive the bending joint to change the angle between the proximal arm and the distal arm.

22. A computer-readable storage device storing instructions for controlling:

a proximal arm and a distal arm;

a bending joint configured to connect the proximal arm and the distal arm to form an angle between the proximal arm and the distal arm;

a light source configured to irradiate a luminous flux having an optical axis parallel to an axial line of the distal arm;

an image sensor having an imaging optical axis;

a joint driving actuator configured to be controlled to drive the bending joint to change the angle between the proximal arm and the distal arm; and a proximal arm rotation actuator configured to be controlled to rotate the proximal arm around an axial line of the proximal arm, wherein the instructions cause a computer to at least perform:

controlling the proximal arm rotation actuator to rotate the proximal arm around the axial line of the proximal arm while controlling the light source to irradiate the luminous flux to form an optical image on a surface, to thereby move the optical axis of the luminous flux relative to the imaging optical axis of the image sensor;

controlling the image sensor to image a locus of the optical image as the optical axis of the luminous flux is moved relative to the imaging optical axis of the image sensor;

determining a physical quantity of the locus;

determining whether the physical quantity has converged to a predetermined value indicating a reference state of the proximal arm, the distal arm and the bending joint; and in response to determining that the physical quantity has not converged to the predetermined value, controlling the joint driving actuator to drive the bending joint to change the angle between the proximal arm and the distal arm.

* * * * *